United States Patent
Salvino et al.

(10) Patent No.: US 11,267,817 B2
(45) Date of Patent: Mar. 8, 2022

(54) SUBSTITUTED PYRROLO[1,2-A]QUINOXALIN-4(5H)-ONES AS CX3CR1 ANTAGONISTS

(71) Applicant: Drexel University, Philadelphia, PA (US)

(72) Inventors: Joseph M. Salvino, Chester Springs, PA (US); Xin Feng, ChongQing (CN); Alessandro Fatatis, Penn Valley, PA (US); Fei Shen, Philadelphia, PA (US); Olimpia Meucci, Penn Valley, PA (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 16/610,450

(22) PCT Filed: May 1, 2018

(86) PCT No.: PCT/US2018/030462
§ 371 (c)(1),
(2) Date: Nov. 1, 2019

(87) PCT Pub. No.: WO2018/204370
PCT Pub. Date: Nov. 8, 2018

(65) Prior Publication Data
US 2020/0062768 A1    Feb. 27, 2020

Related U.S. Application Data

(60) Provisional application No. 62/578,154, filed on Oct. 27, 2017, provisional application No. 62/500,134, filed on May 2, 2017.

(51) Int. Cl.
| | |
|---|---|
| A61K 31/4985 | (2006.01) |
| C07D 487/04 | (2006.01) |
| A61P 35/00 | (2006.01) |
| C07D 519/00 | (2006.01) |
| A61K 31/337 | (2006.01) |
| A61K 31/704 | (2006.01) |

(52) U.S. Cl.
CPC ............ *C07D 487/04* (2013.01); *A61P 35/00* (2018.01); *C07D 519/00* (2013.01); *A61K 31/337* (2013.01); *A61K 31/704* (2013.01)

(58) Field of Classification Search
CPC .......................... A61K 31/4985; C07D 487/04
USPC ............................................ 514/250; 544/346
See application file for complete search history.

(56) References Cited

U.S. PATENT DOCUMENTS

| | | | |
|---|---|---|---|
| 3,939,159 | A | 2/1976 | Dornauer et al. |
| 5,405,847 | A | 4/1995 | Dieter et al. |
| 8,435,993 | B2 | 5/2013 | Salvino et al. |
| 2002/0010125 | A1 | 1/2002 | Carson et al. |
| 2006/0115834 | A1 | 6/2006 | Racila et al. |
| 2007/0142386 | A1 | 6/2007 | Nordvall et al. |
| 2008/0214578 | A1 | 9/2008 | Nordvall et al. |
| 2010/0069396 | A1 | 3/2010 | Zhang et al. |
| 2010/0105667 | A1 | 4/2010 | Furet et al. |
| 2010/0216726 | A1 | 8/2010 | Fuchino et al. |
| 2013/0156761 | A1 | 6/2013 | Fatatis et al. |
| 2014/0364420 | A1 | 12/2014 | Carson et al. |

FOREIGN PATENT DOCUMENTS

| | | |
|---|---|---|
| EP | 584487 A2 | 3/1994 |
| JP | 6076913 B2 | 2/2017 |
| WO | 0160406 A1 | 8/2001 |
| WO | 2004045526 A2 | 6/2004 |
| WO | 2005033115 A1 | 4/2005 |
| WO | 2005086971 A2 | 9/2005 |
| WO | 2008039139 A1 | 4/2008 |

(Continued)

OTHER PUBLICATIONS

Jordan, V. C. Nature Reviews: Drug Discovery, 2, 2003, 205.*

(Continued)

*Primary Examiner* — Douglas M Willis
(74) *Attorney, Agent, or Firm* — Saul Ewing Arnstein & Lehr LLP; Kathryn Doyle; Domingos J. Silva

(57) ABSTRACT

The disclosure provides compounds of formula (I) having the structure:

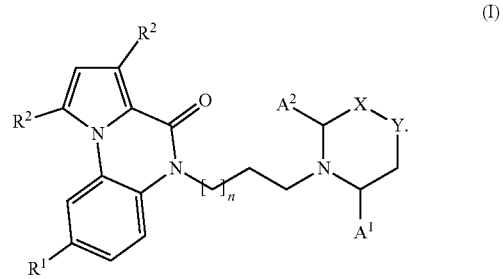

Compounds of formula (I) are fractalkine receptor agonists and useful in treating, preventing or minimizing metastasis in a subject diagnosed with cancer. The compounds of the invention are further useful in treating central nervous system diseases (such as, but not limited to, HIV Associated Neurocognitive Disorders (HAND), and/or Alzheimer's disease), pain, inflammation (such as, but not limited to, arthritis), cardiovascular disease (such as, but not limited to, undesired vascular smooth muscle proliferation, atherosclerosis, coronary vascular endothelial dysfunction, and/or coronary artery disease), and/or multiple sclerosis.

63 Claims, 36 Drawing Sheets

(56) References Cited

FOREIGN PATENT DOCUMENTS

| WO | 2009109616 | A2 | | 9/2009 | |
|---|---|---|---|---|---|
| WO | 2009120140 | A1 | | 10/2009 | |
| WO | 2011127333 | A2 | | 10/2011 | |
| WO | WO-2018204370 | A1 | * | 11/2018 | ............ A61K 31/506 |

OTHER PUBLICATIONS

Vippagunta, et al. Advanced Drug Delivery Reviews, 48, 2001, 18.*
"International Search Report and Written Opinion dated Sep. 18, 2018 for International Application No. PCT/US18/30462".
Trivedi, et al., "Chapter 17. Chemokines: Targets for Novel Therapeutics", Annual Reports in Medicinal Chemistry 35, Jan. 1, 2000, 191-200.
"International Search Report, issued in corresponding application, No. PCT/USII/63533 dated Jun. 12, 2012."
"Metastatic Cancer", (http://www.cancer.gov/ cancertopics/factsheet/Sites-Types/metastastic), 2014.
"Supplementary Partial European Search Report for 11847605.0 dated Oct. 1, 2015."
Aguirre-Ghiso, "Models, mechanisms and clinical evidence for cancer dormancy", Nature Reviews/Cancer, 7, Nov. 2007, 834-846.
Bazan, J. F., "A new class of membrane-bound chemokine with a CX3C motif", Nature, 1997, 385.
Bos, et al., "Modeling metastasis in the mouse", Current Opinion in Pharmacology, 10, 2010, 571-7.
Codding, Acta Cryst,, A61, C329, 2005, 08.08.6.
Coffey, et al., "Cancer surgery: risks and opportunities", BioEssays, 28, 2006, 433-437.
Coffey, et al., "Excisional surgery for cancer cure: therapy at a cost", Lancet Oncol, 4, Dec. 2003, 760-768.
Cook, et al., "Generation and analysis of mice lacking the chemokine fractalkine", Mol Cell Biol., 21, 2001, 3159-65.
Deng, et al., "CXCR6/CXCL16 functions as a regulator in metastasis and progression of cancer", Biochimica et Biophysica Acta, 1806, Feb. 2010, 42-49.
D'Haese, et al., "Fractalkine/CX3CR1: why a single chemokine-receptor duo bears a major and unique therapeutic potential", Expert Opin Ther Targets.;14, 2010, 207-19.
Eckhardt, et al., "Strategies for the discovery and development of therapies for metastatic breast cancer", Nature reviews Drug discovery 11, 2012, 479-97.
Fatatis, Kerberos Biopharmaceuticals Inc., Oct. 2014.
Gassmann, et al., "CXCR4 Regulates the Early Extravasation of Metastatic Tumor Cells In Vivo", Neoplasia, 11(7), Jul. 2009, 651-661.
Gassmann, et al., "The tumor cell-host organ interface in the early onset of metastatic organ colonisation", Clin Exp Metastasis, 25, 2008, 171-181.
Gkotzamanidou, et al., "Sclerostin: a possible target for the management of cancer-induced bone disease.", Expert Opin Ther Targets;16, 2012, 761-9.
Gruber, et al., "Disseminated tumor cells as a monitoring tool for adjuvant therapy in patients with primary breast cancer.", Breast Cancer Res Treat.;144, 2014, 353-60.
Hesselgesser, et al., "Identification and characterization of small molecule functional antagonists of the CCR1 chemokine receptor", J Biol Chem. 273(25), Jun. 1998, 15687-15692.
Huang, et al., "Chemokines and hepatocellular carcinoma", World J Gastroenterol, 16(15), Apr. 2010, 1832-1836.
Hulshof, et al., "Synthesis and pharmacological characterization of novel inverse agonists acting on the viral-encoded chemokine receptor US28", Bioorg Med Chem. 14(21), Nov. 1, 2006, 7213-7230.
Husemann, et al., "Systemic Spread is an Early Step in Breast Cancer", Cancer Cell, 13, Jan. 2018, 56-68.
Iami, et al., "Identification and molecular characterization of fractalkine Yeceptor CX3CR1, which mediates both leukocyte migration and adhesion", Cell.,91, 1997, 521-530.

Ignatiadis, et al., "Micrometastatic disease in breast cancer: clinical implications.", Eur J Cancer;44, 2008, 2726-36.
Izraely, et al., "Chemokine-chemokine receptor axes in melanoma brain metastasis", Immunology Letters, 130, 2010, 107-114.
Jamieson, et al., "CX3CR1 is Expressed by Prostate Epithelial Cells and Androgens Regulate the Levels of CX3CL1/Fractalkine in the Bone Marrow: Potential Role in Prostate Cancer Bone Tropism", Cancer Res, 68(6), Mar. 2008, 1715-1722.
Kim, et al., "In vivo structure/function and expression analysis of the CX3C chemokine fractalkine", Blood.;118, 2011, e156-67.
Koizumi, et al., "Role of CX3CL1/Fractalkine in Osteoclast Differentiation and Bone Resorption", J. Immunol. 183, Nov. 2009, 7825-7831.
Lin, et al., "Disseminated and circulating tumor cells: Role in effective cancer management", Critical reviews in oncology/hematology; 77, 2011, 1-11.
Liu, et al., "Interleukin-1β promotes skeletal colonization and progression of metastatic prostate cancer cells with neuroendocrine features", Cancer Res.; 73, 2013, 3297-305.
Mantovani, et al., "The chemokine system in cancer biology and therapy", Cytokine & Growth Factor Reviews, 21, 2010, 27-39.
Marchesi, et al., "The Chemokine Receptor CX3CR1 is Involved in the Neural Tropism and Malignant Behavior of Pancreatic Ductal Adenocarcinoma", Cancer Res. 68(21), Nov. 2008, 9060-9069.
Muhlbauer, et al., "Lack of association between the functional CX3CR1 polymorphism V249I and hepatocellular carcinoma", Oncol Rep. 13(5), (Abstract Only), May 2005, 957-963.
Nashan, et al., "Cutaneous metastases of visceral tumours: a review", J Cancer Res Clin Oncol. 135(1), Jan. 2009, 1-14.
Naya, et al., "Design, synthesis, and discovery of a novel CCR1 antagonist", J Med Chem. 44(9), Apr. 26, 2001, 1429-1435.
Nevo, et al., "The involvement of the fractalkine receptor in the transmigration of neuroblastoma cells through bone-marrow endothelial cells", Cancer Letters, 273, 2009, 127-139.
Ng, et al., "Discovery of Novel Non-Peptide CCR1 Receptor Antagonists", J. Med. Chem. 42, Jun. 1999, 4680-4694.
Onitilo, et al., "Breast cancer subtypes based on ER/PR and Her2 expression: comparison of clinicopathologic features and survival", Clinical Medicine & Research, 2009, 4-13.
Riethdorf, et al., "Review: Biological relevance of disseminated tumor cells in cancer patients", Int J Cancer.;123, 2008, 1991-2006.
Russell, et al., "Targeting the {alpha} receptor for platelet-derived growth factor as a primary or combination therapy in a preclinical model of prostate cancer skeletal metastasis", Clin Cancer Res;16, 2010, 5002-10.
Russell, et al., "The alpha-receptor for platelet-derived growth factor as a target for antibody-mediated inhibition of skeletal metastases from prostate cancer cells", Oncogene. 28(3), Jan. 22, 2009, 412-421.
Savarin-Vuaillat, et al., "Chemokines and Chemokine Receptors in Neurological Disease: Raise, Retain, or Reduce?", Neurotherapeutics: The Journal of the American Society for Experimental NeuroTherapeutics, 4, Oct. 2007, 590-601.
Schon, et al., J Natl Cancer Inst., 95(15), Aug. 2003, 1138-1149.
Shen, et al., "A small-molecule antagonist of CX3CR1 impairs homing and colonization of breast cancer cells in the skeleton", Proceedings of the 106th Annual Meeting of the American Association for Cancer Research; Apr. 18-22, 2015; Philadelphia, PA; Cancer Res. 75 (15 Suppl), 2015, Abstract.
Shiozawa, et al., "Hematopoietic stem cell niche is a potential therapeutic target for bone metastatic tumors", Clin Cancer Res.;17, 2011, 5553-8.
Shulby, et al., "CX3CR1-fractalkine expression regulates cellular mechanisms involved in adhesion, migration, and survival of human prostate cancer cells", Cancer Res. 64(14), Jul. 15, 2004, 4693-4698.
Stroke, et al., "Identification of CXCR3 receptor agonists in combinatorial small-molecule libraries", Biochemical and Biophysical Research Communications, 349, 2006, 221-228.
Stuelten, et al., "Acute Wounds Accelerate Tumorigenesis by a T Cell-Dependent Mechanism", Cancer Res. 68(18), Sep. 2008, 7278-7282.

(56) References Cited

OTHER PUBLICATIONS

Valastyan, et al., "Tumor metastasis: molecular insights and evolving paradigms", Cell. 147(2), Oct. 2011, 275-292.
Vandesompele, et al., "Accurate normalization of real-time quantitative RT-PCR data by geometric averaging of multiple internal control genes", Genome Biol. 3(7), 2002, 1-12.
Walters, et al., "Evaluation of a series of bicyclic CXCR2 antagonists", Bioorganic & Medicinal Chemistry Letters, 18, 2008, 798-803.
Yang, et al., "Synthesis and anti-leukemia activity mensuration of 1-phenethyl-4-hydroxy-4-substituted of bis[1-phenethyl-4-hydroxy-4-(3-flurophenyl) piperidinium hydrochloride] studied by X-ray and DFT methods", Journal of Molecular Structure 929, Jul. 16, 2009, 97-104.
Yonezawa, et al., "Anti-metastatic outcome of isoform-specific prolactin receptor targeting in breast cancer", Cancer Letters.; 366, 2015, 84-92.
Yu, et al., "Defective antitumor responses in CX3CR1-deficient mice", Int J Cancer. 121(2), Jul. 15, 2007, 316-22.
Zhu, et al., "Challenging role of Wnt5a and its signaling pathway in cancer metastasis (Review)", Exp Ther Med.;8, 2014, 3-8.

\* cited by examiner

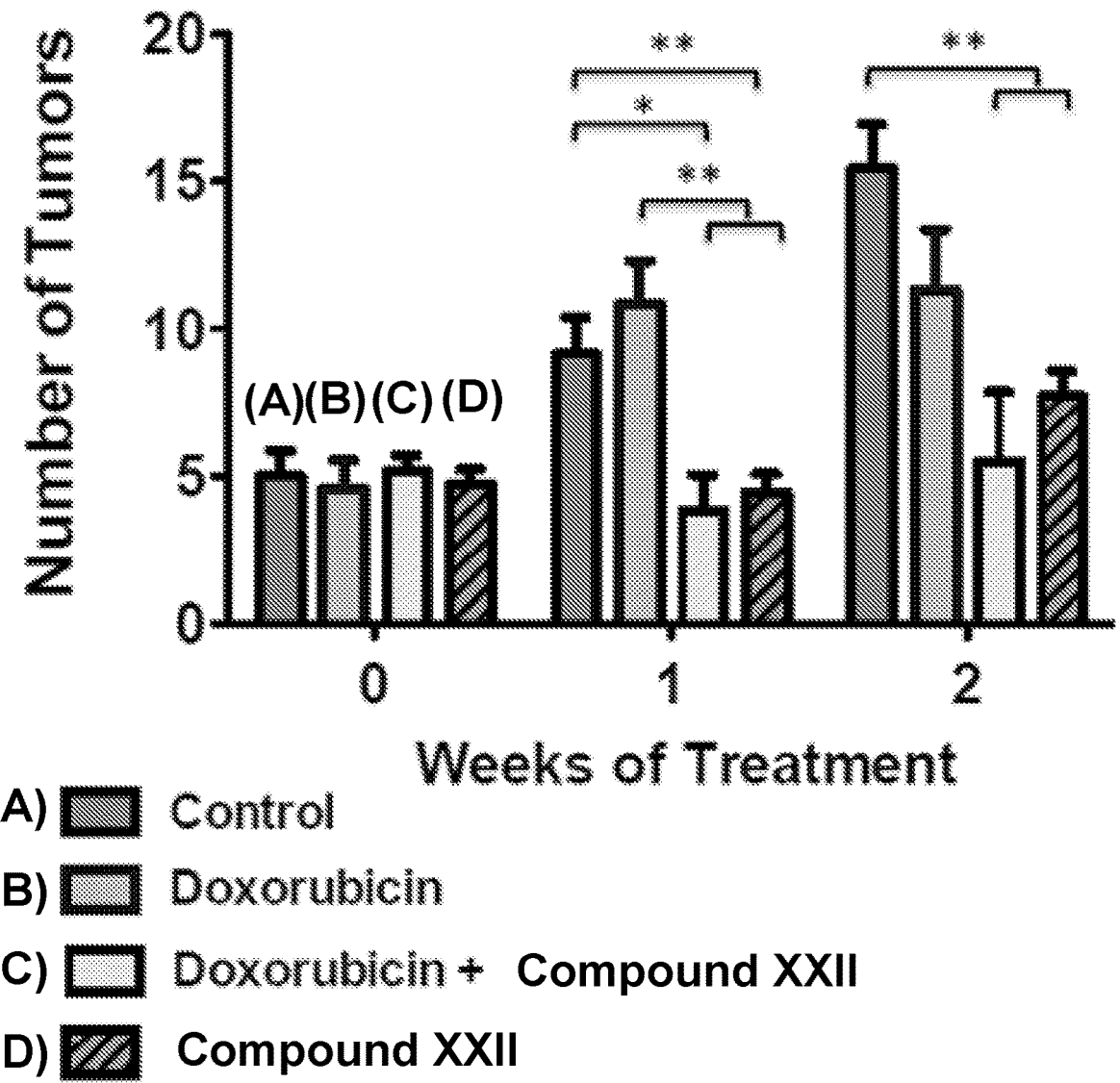

SUBSTITUTED PYRROLO[1,2-A]QUINOXALIN-4(5H)-ONES AS CX3CR1 ANTAGONISTS

CROSS-REFERENCE TO RELATED APPLICATIONS

The present application is a 35 U.S.C. § 371 national phase application of, and claims priority to, International Application No PCT/US2018/030462, filed May 1, 2018, which claims priority under 35 U.S.C. § 119(e) to U.S. Provisional Applications Nos. 62/500,134, filed May 2, 2017, and 62/578,154, filed Oct. 27, 2017, all of which applications are incorporated herein by reference in their entireties.

STATEMENT REGARDING FEDERALLY SPONSORED RESEARCH OR DEVELOPMENT

This invention was made with government support under grant number R21 CA178540-01A1 and grant number R43 CA183362-01A1 awarded by the National Institutes of Health. The government has certain rights in the invention.

BACKGROUND OF THE INVENTION

Cancer occurs after a single cell in a tissue is genetically damaged, thus forming a putative tumor-initiating cell (TCI). TCIs undergo uncontrolled abnormal mitosis, increasing the total number of cancer cells at that location. When the area of cancer cells at the originating site become clinically detectable, it is called primary tumor.

In aggressive tumors, cancer cells acquire the ability to penetrate the walls of lymphatic and/or blood vessels, after which they circulate through the bloodstream (circulating tumor cells) to other sites and tissues in the body. This process is known, respectively, as lymphatic or hematogenous spread. After the tumor cells reach the capillary bed of a distant organ, they can first adhere to the endothelial wall of the vessel and successively egress the blood circulation (extravasation), invade the surrounding tissue and continue to multiply, eventually generating another clinically detectable tumor (metastatic or secondary). Malignant tumors metastasize, although in varying degrees (e.g., basal cell carcinoma rarely metastasize).

Metastatic tumors are very common in the late stages of cancer. The most common places for the metastases to occur are the lungs, liver, brain, and bones. There is also a propensity for certain tumors to seed in particular organs. For example, prostate cancer usually metastasizes to the bones; colon cancer usually metastasizes to the liver; stomach cancer often metastasizes to the ovary in women; and breast tumor cells often metastasize to the bones. These tissue-selective metastasis processes are due to a combination of anatomic/mechanical routes and molecular mediators.

Only 6% of women first diagnosed with breast adenocarcinoma have metastases. Unfortunately, about 20-50% of them will eventually develop metastatic disease, with high mortality. About 70% of advanced breast cancer patients have skeletal metastases, which lead to considerable pain, spinal cord compression and pathological fractures. In addition, when breast cancer cells have disseminated to the skeleton, the resulting bone tumors can be treated only with palliative measures. The majority of patients develop metastases years after initial treatment of the primary breast tumor. The appearance of late metastases has been conventionally attributed to cancer cells that are disseminated to secondary tissues during different stages of primary tumor progression and remain dormant for variable periods of time. However, recent evidence shows that in patients with undetectable metastatic seeding, cancer cells residing in different organs continue to proliferate and recirculate in different tissues, eventually acquiring genetic traits increasing their propensity to successfully grow into full blown secondary tumors.

Breast cancer patients can undergo breast-conserving surgery (BCS) or lumpectomy, which minimizes the physical and psychological impact of breast surgery. However, following lumpectomy, only 37% of breasts are found to be tumor-free, and between 22% and 59% of patients will need re-intervention because positive or close margins are detected. In general, reexcision or adjuvant therapies, such as local irradiation or chemotherapy, are started several weeks or even months after primary surgery to allow for complete patient's recovery and improve post-operatory aesthetic results. However, the stroma at the site of tumor removal has altered angiogenesis, immune cells infiltration and activation of cancer-associated fibroblasts. These events may potentially promote perioperative proliferation and motility of residual cancer cells, thereby allowing their escape into the circulation. Even in the presence of dormant cancer cells already lodged into distant sites, the additional spreading of these cells would produce new waves of micrometastases.

The arrest of circulating cancer cells to the skeleton is highly dependent on specific adhesive interactions with the endothelial cells lining the marrow sinusoids. The required step is the extravasation of adherent cancer cells drawn by chemoattractant cues generated by the surrounding stroma. Similarities between cancer cell dissemination and leukocyte trafficking pointed to chemokines as crucial players in both sets of events.

$CX_3C$ chemokine receptor 1 ($CX_3CR1$), also known as the fractalkine receptor or G-protein coupled receptor 13 (GPR13), is a protein encoded by the $CX_3CR1$ gene in humans. This receptor binds the chemokine $CX_3CL1$ (also called neurotactin, fractalkine or FKN), which is a transmembrane protein that can be cleaved into a soluble chemoattractant molecule. In its membrane-bound form, FKN can establish strong and stable adhesive interactions with its receptor $CX_3CR1$, and does not require downstream signaling to induce activation of additional adhesion molecules. Prostate cancer cells express $CX_3CR1$, and under dynamic-flow conditions adhere to human bone marrow endothelial cells in a FKN-dependent manner. Further evidence for the involvement of FKN/$CX_3CR1$ pair in metastasis includes: $CX_3CR1$ is expressed in a high percentage of prostate cancer tissues and human bone marrow supernatants contain soluble FKN, which is released from bone stroma cells through an androgen-regulated mechanism; $CX_3CR1$ expression in primary breast tumors correlates with clinical metastases; $CX_3CR1$ expression in pancreatic tumor cells promotes infiltration of the central nervous system; and FKN and $CX_3CR1$ are involved in adhesion of neuroblastoma cells to the bone at least in vitro.

$CX_3CR1$ is present in the epithelial compartment of normal and malignant human prostate gland tissues. FKN is present both in the soluble fraction of human bone marrow and on the surface of human bone marrow endothelial cells. Human breast cancer cells are also often positive for $CX_3CR1$ expression. Because of the high propensity shown by several solid tumors, including breast cancer, to target the skeleton, these results support the idea that functional interactions between bone's FKN and cancer cells' $CX_3CR1$ are involved in skeletal metastasis. Unfortunately, there is not a validated and effective approach to minimize the development of metastasis in patients afflicted with primary tumors.

Further, $CX_3CR1/FKN$ has been linked to other kinds of cancers in mammals. The $CX_3CR1/FKN$ axis is overexpressed in, for example, gliomas, renal cell carcinoma, epithelial ovarian cancer, pancreatic ductal adenocarcinoma, prostate cancer, stomach cancer, gastric carcinoma, colorectal cancer, and the four major subtypes of breast cancer (in both primary tumors and metastases). $CX_3CR1$ and/or FKN overexpression is inversely correlated with overall survival in gliomas, renal cell carcinoma and pancreatic ductal adenocarcinoma. $CX_3CR1$ overexpression is associated with more tumor perineural infiltration (PNI) and local and earlier tumor recurrence in pancreatic ductal adenocarcinoma. Further, $CX_3CR1$ overexpression is associated with lymph node metastasis, higher clinical stage and larger tumor size in stomach cancer, and a $CX_3CR1$ variant is associated with increased survival in gliomas.

There is a need in the art for novel compounds that can prevent, delay or minimize the development of secondary tumors (metastases) in patients, such as but not limited to metastatic bone cancer associated with primary prostate or breast cancers. There is also a need in the art for compounds that can label or identify metastatic cells in vitro or in vivo. There is also a need in the art for compounds that treat other diseases, such as central nervous system diseases, pain, cardiovascular disease, and/or multiple sclerosis. The present invention addresses these needs.

BRIEF SUMMARY OF THE INVENTION

The invention provides a compound, or a salt or solvate thereof. The invention further provides a pharmaceutical composition comprising at least one compound of the invention, or a pharmaceutically acceptable salt or solvate thereof. The invention further provides a method of preventing or treating metastasis in a subject diagnosed with cancer. The invention further provides a method of detecting a $CX_3R1$-expressing cell in a biological sample of a subject diagnosed with cancer. The invention further provides a method of identifying a subject diagnosed with cancer that is to be administered a $CX_3R1$ antagonist to treat or prevent metastasis in the subject. The invention further provides a method of treating or preventing a central nervous system (CNS) disease in a subject in need thereof. The invention further provides a method of treating or preventing pain in a subject in need thereof. The invention further provides a method of treating or preventing inflammation in a subject in need thereof. The invention further provides a method of treating or preventing cardiovascular disease in a subject in need thereof. The invention further provides a method of treating or preventing multiple sclerosis in a subject in need thereof. The invention further provides a kit for identifying a subject diagnosed with cancer that is to be administered a $CX_3R1$ antagonist to treat or prevent metastasis in the subject. The invention further provides a composition comprising a compound of structure

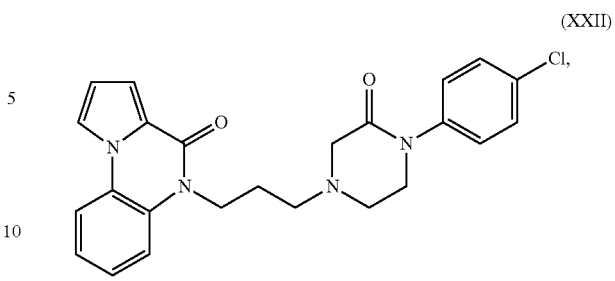

(XXII)

and at least one chemotherapeutic agent selected from the group of taxanes and anthracyclines; or a pharmaceutically acceptable salt or solvate thereof.

In certain embodiments, the compound is selected from the group consisting of:

(i) a compound of Formula (I):

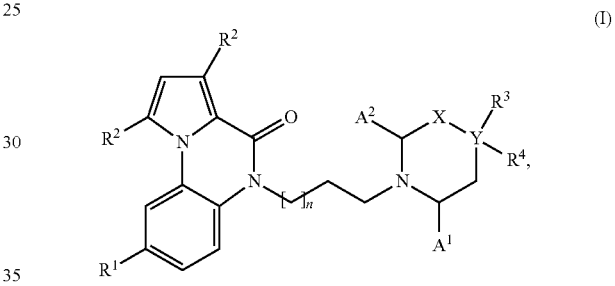

(I)

wherein in (I):

$A^1$ and $A^2$ are independently selected from the group consisting of H and $C_1$-$C_6$ alkyl; or one selected from the group consisting of $A^1$ and $A^2$ combines with the carbon atom to which it is bound to form a —C(=O)— group, and the other selected from the group consisting of $A^1$ and $A^2$ is selected from the group consisting of H and $C_1$-$C_6$ alkyl; or $A^1$ and $A^2$ combine to form a divalent radical selected from the group consisting of methanediyl, ethane-1,2-diyl, and propane-1,3-diyl;

X is selected from the group consisting of $CH_2$ and C(=O), and Y is selected from the group consisting of N and C; wherein: if Y is N, then $R^3$ is selected from the group consisting of phenyl, substituted phenyl, heteroaryl, and substituted heteroaryl, and $R^4$ is null; if Y is C and X is C(=O), then $R^3$ is selected from the group consisting of phenyl, substituted phenyl, heteroaryl, and substituted heteroaryl, and $R^4$ is selected from the group consisting of H and OH, or $R^3$ and $R^4$ combine with Y to form an optionally substituted 5-6 membered heterocycle; if Y is C and X is $CH_2$, then $R^3$ and $R^4$ combine with Y to form an optionally substituted 5-6 membered heterocycle;

$R^1$ is selected from the group consisting of H, halo, $C_1$-$C_3$ haloalkyl, and $OR^5$;

each occurrence of $R^2$ is independently selected from the group consisting of H, halo, and $CH_3$;

$R^5$ is selected from the group consisting of H, $C_1$-$C_6$ alkyl, —$(CH_2)_{2-5}NH_2$,

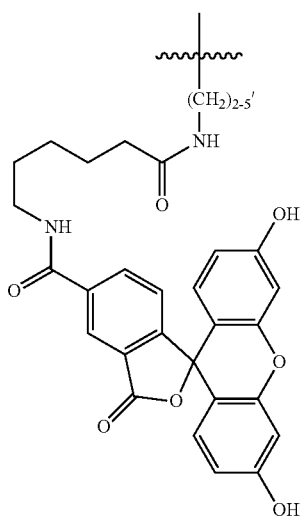
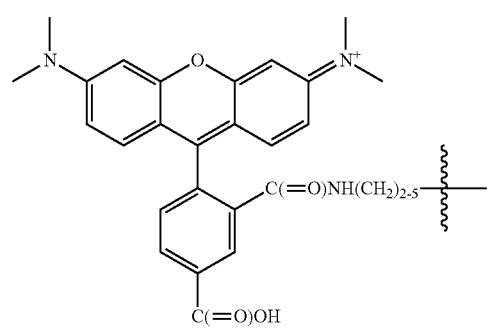
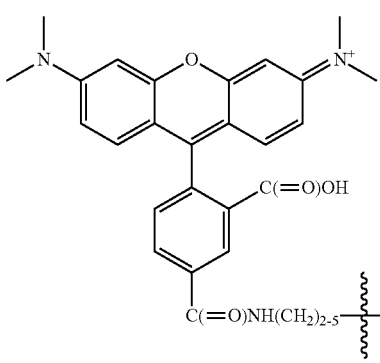
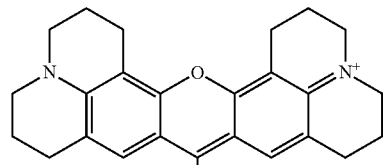
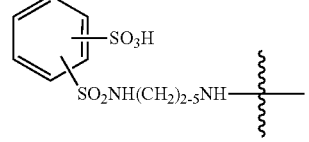
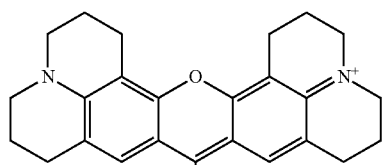
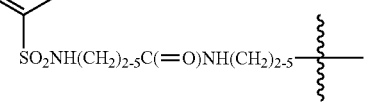

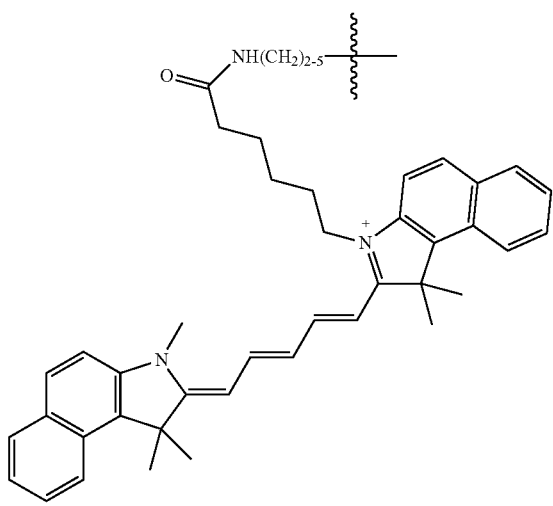

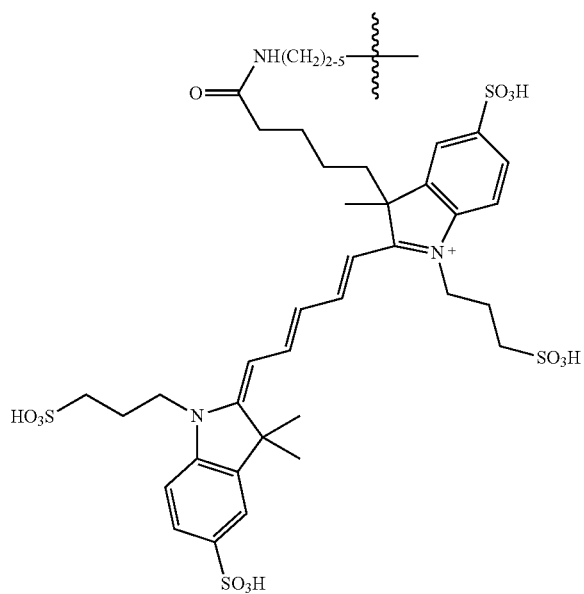

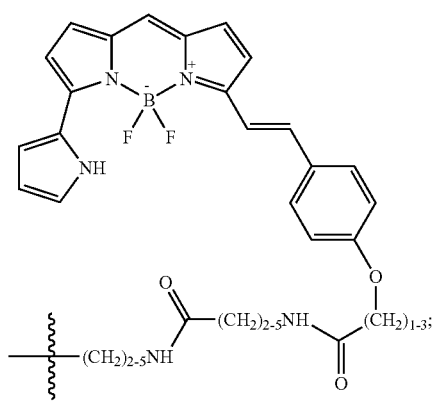

and
n is 1, 2 or 3;
and
(ii) a compound of Formula (II):

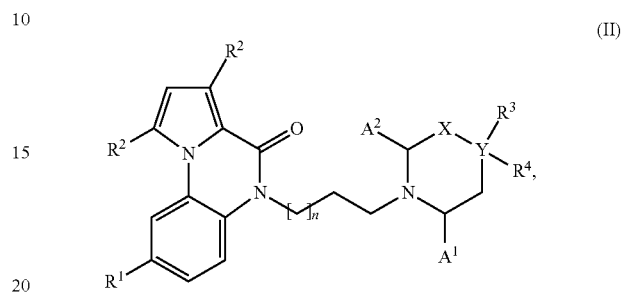

wherein in (II):

$A^1$ and $A^2$ are both H, or $A^1$ and $A^2$ combine to form a divalent radical selected from the group consisting of methanediyl, ethane-1,2-diyl, and propane-1,3-diyl;

X is $CH_2$;

Y is C;

$R^3$ is selected from the group consisting of phenyl, substituted phenyl, heteroaryl, and substituted heteroaryl, and $R^4$ is selected from the group consisting of H and OH;

$R^1$ is selected from the group consisting of H, halo, $C_1$-$C_3$ haloalkyl, and $OR^5$;

each occurrence of $R^2$ is independently selected from the group consisting of H, Cl, and $CH_3$; with the proviso that, if both occurrences of $R^2$ are H, then $R^1$ is $OR^5$ and $R^5$ is not H;

$R^5$ is selected from the group consisting of H, $—(CH_2)_{2-5}NH_2$,

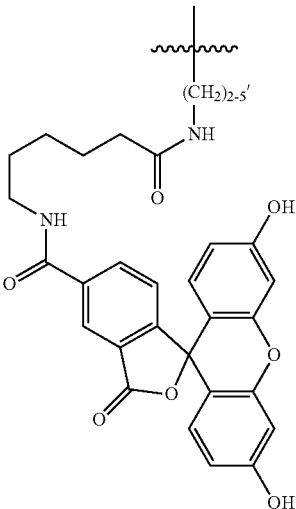

-continued
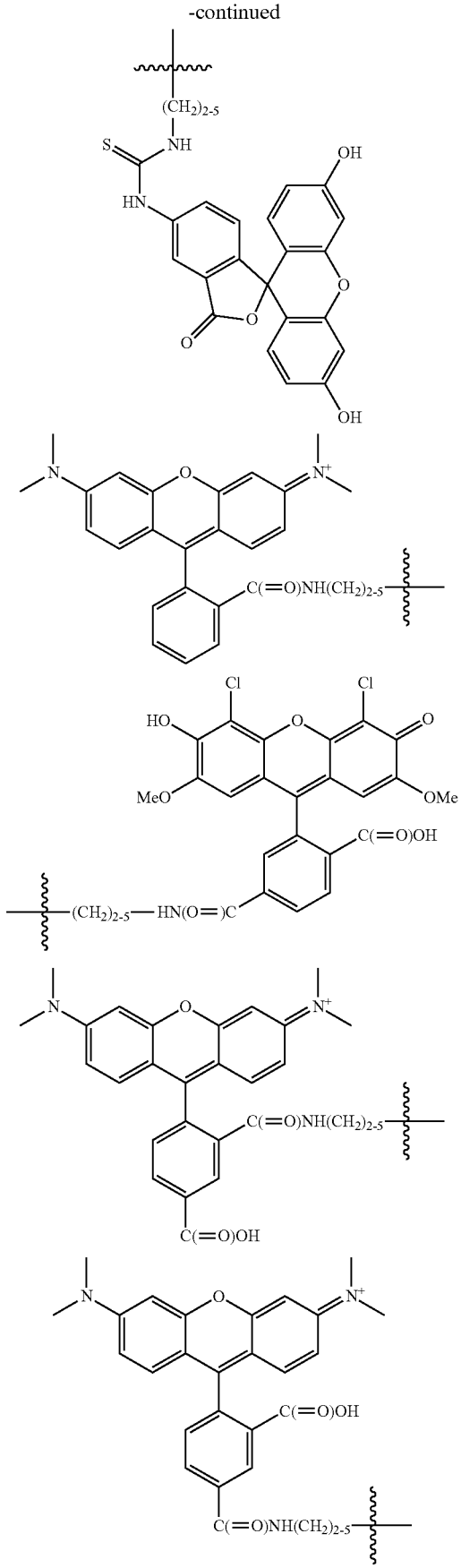
-continued
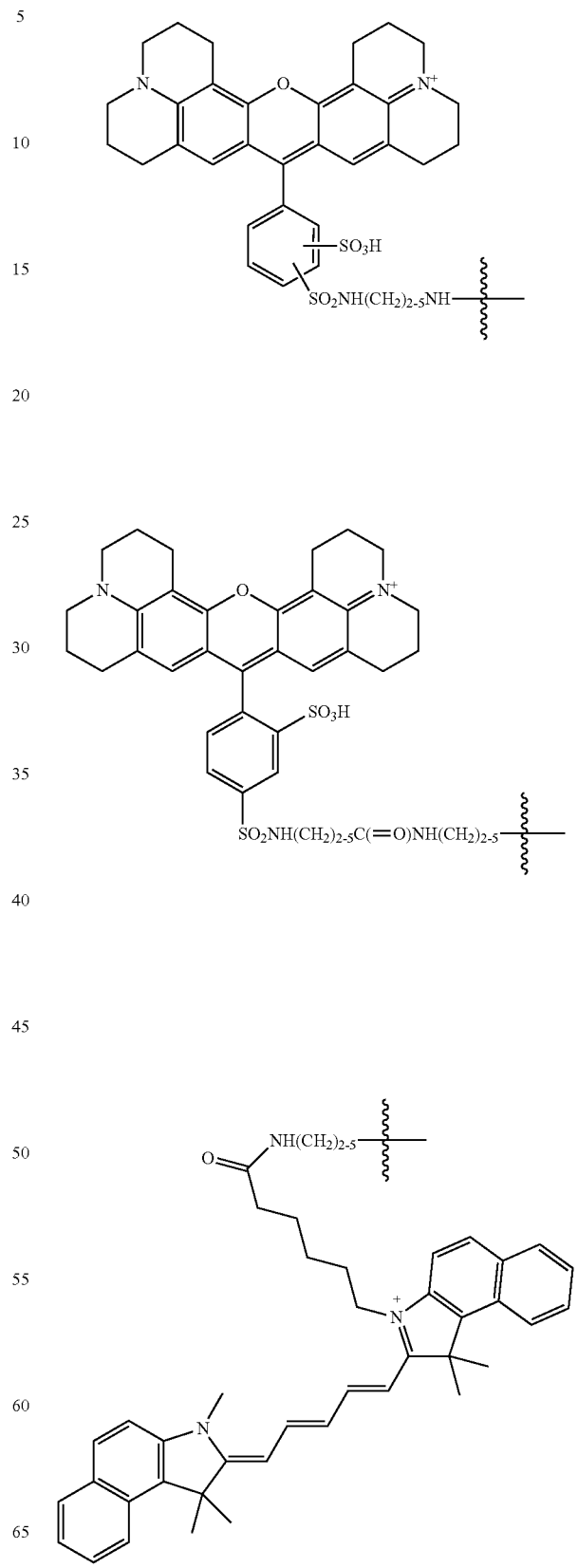

-continued

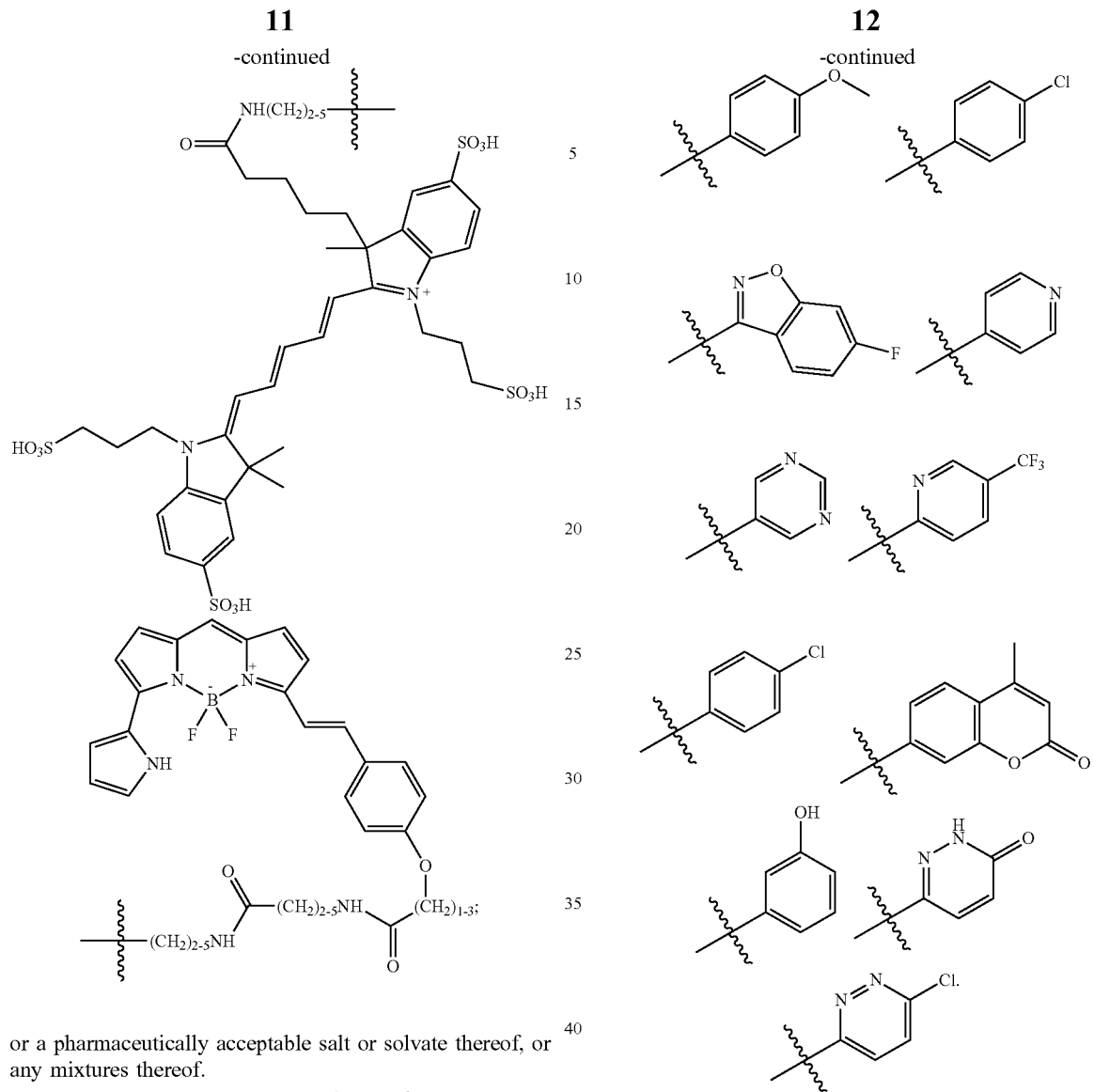

or a pharmaceutically acceptable salt or solvate thereof, or any mixtures thereof.

In certain embodiments, in (I) $A^1$ and $A^2$ are both H. In other embodiments, in (II) $A^1$ and $A^2$ are both H.

In certain embodiments, in (I) X is $CH_2$ and Y is N; X is $CH_2$ and Y is C; X is C(=O) and Y is C; or X is C(=O) and Y is N. In other embodiments, in (I) Y is N and $R^3$ is optionally substituted fluorescent phenyl or heteroaryl. In yet other embodiments, in (I) Y is C, X is C(=O) and $R^3$ is optionally substituted fluorescent phenyl or heteroaryl.

In certain embodiments, $R^3$ is optionally substituted 2-oxo-2H-chromen-7-yl. In other embodiments, in (II) $R^3$ is optionally substituted fluorescent phenyl or heteroaryl. In yet other embodiments, $R^3$ is optionally substituted 2-oxo-2H-chromen-7-yl. In yet other embodiments, in (I) or (II) $R^3$ is selected from the group consisting of:

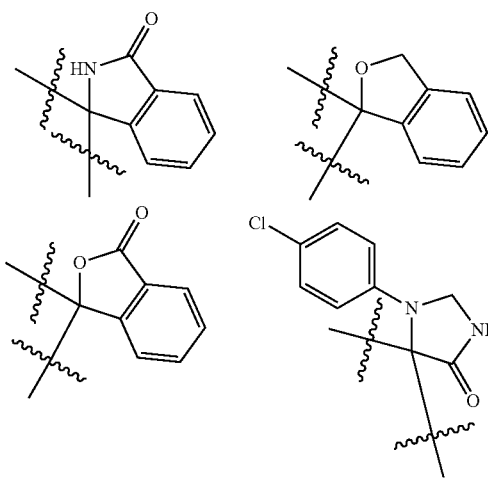

In certain embodiments, in (I) or (II) $R^3$ and $R^4$ combine with Y to form at least one of the following groups:

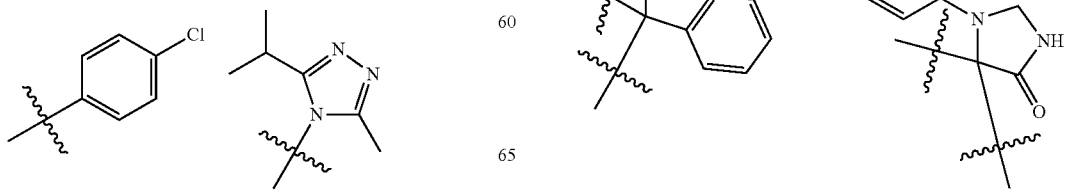

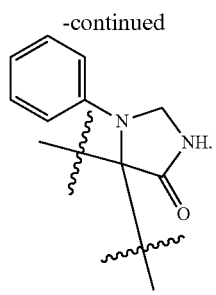

In certain embodiments, the compound of Formula (I) is selected from the group consisting of: 5-(3-(4-(3-hydroxyphenyl)piperazin-1-yl)propyl)pyrrolo[1,2-a]quinoxalin-4(5H)-one; 5-(3-(4-(pyridin-4-yl)piperazin-1-yl)propyl)pyrrolo[1,2-a]quinoxalin-4(5H)-one; 8-chloro-5-(3-(4-(pyridin-4-yl)piperazin-1-yl)propyl)pyrrolo[1,2-a]quinoxalin-4(5H)-one; 8-fluoro-5-(3-(4-(pyridin-4-yl)piperazin-1-yl)propyl)pyrrolo[1,2-a]quinoxalin-4(5H)-one; 8-fluoro-1-methyl-5-(3-(4-(pyridin-4-yl)piperazin-1-yl)propyl)pyrrolo[1,2-a]quinoxalin-4(5H)-one; 5-(3-(4-(pyridin-4-yl)piperazin-1-yl)propyl)-8-(trifluoromethyl)pyrrolo[1,2-a]quinoxalin-4(5H)-one; 5-(3-(4-(4-methyl-2-oxo-2H-chromen-7-yl)piperazin-1-yl)propyl)pyrrolo[1,2-a]quinoxalin-4(5H)-one; 5-(3-(4-(6-oxo-1,6-dihydropyridazin-3-yl)piperazin-1-yl)propyl)pyrrolo[1,2-a]quinoxalin-4(5H)-one; 8-chloro-5-(3-(4-(6-oxo-1,6-dihydropyridazin-3-yl)piperazin-1-yl)propyl)pyrrolo[1,2-a]quinoxalin-4(5H)-one; 5-(3-(4-(6-oxo-1,6-dihydropyridazin-3-yl)piperazin-1-yl)propyl)-8-(trifluoromethyl)pyrrolo[1,2-a]quinoxalin-4(5H)-one; 8-fluoro-5-(3-(4-(6-oxo-1,6-dihydropyridazin-3-yl)piperazin-1-yl)propyl)pyrrolo[1,2-a]quinoxalin-4(5H)-one; 8-fluoro-1-methyl-5-(3-(4-(6-oxo-1,6-dihydropyridazin-3-yl)piperazin-1-yl)propyl)pyrrolo[1,2-a]quinoxalin-4(5H)-one; 5-(3-(4-(5-(trifluoromethyl)pyridin-2-yl)piperazin-1-yl)propyl)pyrrolo[1,2-a]quinoxalin-4(5H)-one; 5-(3-(4-(pyrimidin-5-yl)piperazin-1-yl)propyl)pyrrolo[1,2-a]quinoxalin-4(5H)-one; 8-methoxy-5-(3-(4-(pyrimidin-5-yl)piperazin-1-yl)propyl)pyrrolo[1,2-a]quinoxalin-4(5H)-one; 5-(3-(4-(6-chloropyridazin-3-yl)piperazin-1-yl)propyl)pyrrolo[1,2-a]quinoxalin-4(5H)-one; 5-(3-(4-(4-chlorophenyl)-3-oxopiperazin-1-yl)propyl)pyrrolo[1,2-a]quinoxalin-4(5H)-one; 5-(3-(4-(4-chlorophenyl)-3-oxopiperazin-1-yl)propyl)-8-methoxypyrrolo[1,2-a]quinoxalin-4(5H)-one; 5-(3-(4-(4-chlorophenyl)-3-oxopiperazin-1-yl)propyl)-8-fluoropyrrolo[1,2-a]quinoxalin-4(5H)-one; 5-(3-(4-(4-chlorophenyl)-3-oxopiperazin-1-yl)propyl)-8-fluoro-1-methylpyrrolo[1,2-a]quinoxalin-4(5H)-one; 8-chloro-5-(3-(4-(4-chlorophenyl)-3-oxopiperazin-1-yl)propyl)pyrrolo[1,2-a]quinoxalin-4(5H)-one; 5-(3-(4-(4-chlorophenyl)-3-oxopiperazin-1-yl)propyl)-8-(trifluoromethyl)pyrrolo[1,2-a]quinoxalin-4(5H)-one; 5-chloro-1'-(3-(4-oxopyrrolo[1,2-a]quinoxalin-5(4H)-yl)propyl)-3H-spiro[isobenzofuran-1,4'-piperidin]-3-one; 5-(3-(4-oxo-1-phenyl-1,3,8-triazaspiro[4.5]decan-8-yl)propyl)pyrrolo[1,2-a]quinoxalin-4(5H)-one; 5-(3-(1-(4-chlorophenyl)-4-oxo-1,3,8-triazaspiro[4.5]decan-8-yl)propyl)pyrrolo[1,2-a]quinoxalin-4(5H)-one; 5-(3-(1-(4-fluorophenyl)-4-oxo-1,3,8-triazaspiro[4.5]decan-8-yl)propyl)pyrrolo[1,2-a]quinoxalin-4(5H)-one; 1'-(3-(4-oxopyrrolo[1,2-a]quinoxalin-5(4H)-yl)propyl)spiro[isoindoline-1,4'-piperidin]-3-one; and 5-(3-(3H-spiro[isobenzofuran-1,4'-piperidin]-1'-yl)propyl)pyrrolo[1,2-a]quinoxalin-4(5H)-one.

In certain embodiments, the compound of Formula (II) is selected from the group consisting of: 5-(3-(4-(4-chlorophenyl)piperidin-1-yl)propyl)-8-fluoro-1-methylpyrrolo[1,2-a]quinoxalin-4(5H)-one; 8-fluoro-5-(3-((1R,5S)-3-(3-isopropyl-5-methyl-4H-1,2,4-triazol-4-yl)-8-azabicyclo[3.2.1]octan-8-yl)propyl)-1-methylpyrrolo[1,2-a]quinoxalin-4(5H)-one; 8-(3-aminopropoxy)-5-(3-(4-(4-chlorophenyl)piperidin-1-yl)propyl)pyrrolo[1,2-a]quinoxalin-4(5H)-one; 8-(4-aminobutoxy)-5-(3-(4-(4-chlorophenyl)piperidin-1-yl)propyl)pyrrolo[1,2-a]quinoxalin-4(5H)-one; N-(6-((3-((5-(3-(4-(4-chlorophenyl)piperidin-1-yl)propyl)-4-oxo-4,5-dihydropyrrolo[1,2-a]quinoxalin-8-yl)oxy)propyl)amino)-6-oxohexyl)-3',6'-dihydroxy-3-oxo-3H-spiro[isobenzofuran-1,9'-xanthene]-5-carboxamide; 1-(3-((5-(3-(4-(4-chlorophenyl) piperidin-1-yl)propyl)-4-oxo-4,5-dihydropyrrolo[1,2-a]quinoxalin-8-yl)oxy)propyl)-3-(3',6'-dihydroxy-3-oxo-3H-spiro[isobenzofuran-1,9'-xanthen]-5-yl)thiourea; and 1-(4-((5-(3-(4-(4-chlorophenyl)piperidin-1-yl)propyl)-4-oxo-4,5-dihydropyrrolo[1,2-a]quinoxalin-8-yl)oxy)butyl)-3-(3',6'-dihydroxy-3-oxo-3H-spiro[isobenzofuran-1,9'-xanthen]-5-yl)thiourea.

In certain embodiments, the method comprises administering to the subject a therapeutically effective amount of at least one compound of the invention, or a pharmaceutically acceptable solvate or salt thereof.

In certain embodiments, the method comprises administering to the subject: a therapeutically effective amount of a compound of structure (XXII):

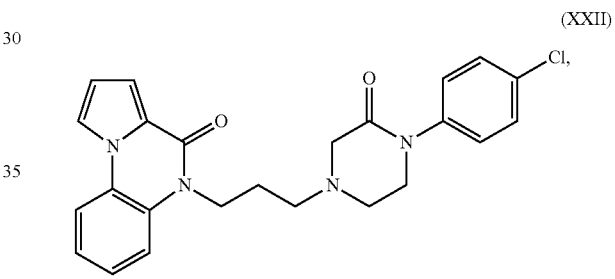

(XXII)

and a therapeutically effective amount of at least one chemotherapeutic agent selected from the group of taxanes and anthracyclines; or a pharmaceutically acceptable solvate or salt thereof.

In certain embodiments, the subject is subjected to primary surgery related to the cancer. In other embodiments, administration of the compound takes place before, during or after the primary surgery. In yet other embodiments, administration takes place at a time selected from the group consisting of: at least 6 months before the primary surgery; at least 3 months before the primary surgery; at least 1 month before the primary surgery; within 1 week after the surgery. In yet other embodiments, the cancer includes breast cancer or prostate cancer. In yet other embodiments, the metastasis includes bone metastasis. In yet other embodiments, the compound is administered by an inhalational, oral, rectal, vaginal, parenteral, topical, transdermal, pulmonary, intranasal, buccal, ophthalmic, intrathecal, or intravenous route of administration. In yet other embodiments, the subject is a mammal. In yet other embodiments, the mammal is human.

In certain embodiments, the detecting method comprises contacting the biological sample with a fluorescent compound of the invention, under conditions whereby, if any $CX_3R1$-expressing cell is present in the sample, the fluorescent compound binds to the $CX_3R1$-expressing cell, thus forming a first system. In other embodiments, the detecting method comprises removing any unbound fluorescent compound from the first system. In yet other embodiments, the detecting method comprises detecting if there is any cell-bound fluorescent compound in the first system, wherein, if a cell-bound fluorescent compound is detected in the first system, the biological sample comprises a $CX_3R1$-expressing cell.

In certain embodiments, the identifying method comprises contacting a biological sample of the subject with a fluorescent compound of the invention, under conditions whereby, if any $CX_3R1$-expressing cell is present in the sample, the fluorescent compound binds to the $CX_3R1$-expressing cell, thus forming a first system. In other embodiments, the identifying method comprises removing any unbound fluorescent compound from the first system. In yet other embodiments, the identifying method comprises detecting if there is any cell-bound fluorescent compound in the first system, wherein, if a cell-bound fluorescent compound is detected in the first system, the biological sample comprises a $CX_3R1$-expressing cell, whereby the subject is instructed to be administered a therapeutically effective amount of a $CX_3R1$ antagonist to treat or prevent metastasis in the subject.

In certain embodiments, the sample is in vitro, in vivo, or ex vivo. In other embodiments, the cell comprises a CTC. In yet other embodiments, the sample comprises blood or lymphatic fluid.

In certain embodiments, the subject is further administered a therapeutically effective amount of a $CX_3R1$ antagonist. In other embodiments, the $CX_3R1$ antagonist comprises at least one compound of the invention.

In certain embodiments, the CNS disease comprises at least one selected from the group consisting of HIV Associated Neurocognitive Disorders (HAND) and Alzheimer's disease. In certain embodiments, the inflammation comprises arthritis. In certain embodiments, the cardiovascular disease comprises at least one selected from the group consisting of undesired vascular smooth muscle proliferation, atherosclerosis, coronary vascular endothelial dysfunction, and coronary artery disease.

In certain embodiments, the kit comprises at least one fluorescent compound of the invention. In other embodiments, the kit comprises instructional material describing a method of identifying a subject diagnosed with cancer that is to be administered a $CX_3R1$ antagonist to treat or prevent metastasis in the subject.

In certain embodiments, the at least one chemotherapeutic agent is selected from the group consisting of cabazitaxel, paclitaxel, nab-paclitaxel, docetaxel, doxorubicin, and epirubicin. In other embodiments, administration of the at least one chemotherapeutic agent takes place before, during or after the primary surgery. In yet other embodiments, administration of the at least one chemotherapeutic agent takes place at a time selected from the group consisting of: at least 6 months before the primary surgery; at least 3 months before the primary surgery; at least 1 month before the primary surgery; within 1 week after the surgery. In yet other embodiments, the compound and the at least one chemotherapeutic agent are coformulated in a pharmaceutical composition.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 6A shows human (SKBR3) breast cancer cells, FIG. 6B shows murine (4T-1) breast cancer cells and FIG. 6C shows human prostate cancer cells (PC3ML).

FIG. 7C is a set of images of mice which were inoculated with MDA-231 cells, monitored weekly by bioluminescence imaging and allowed to develop small tumors for one week, prior to administration of either vehicle or Compound XXII for the entire duration of the experiment. The number of tumors (FIG. 7D) and total tumor burden (FIG. 7E) in Compound XXII treated animals were both strongly reduced by the CX3CR1 antagonist as compared to controls (7 mice/group; Tumor numbers: *P=0.014, P=0.009, *P=0.002, paired Studen's t-test; tumor burden: ***P=0.0002, One-way Anova with Dunnett's post-test. FIG. 7F is a Kaplan-Meier curve showing increase in overall survival with Compound XXII treatment (11 mice/group, Log-rank test: $\chi^2$=19.95, P<0.0001).

FIG. 8A is a set of images showing that AMD3100 was used to forcefully mobilize CTCs from disseminated tumors in mice, above steady-state levels measured without treatment. FIG. 8B shows that Compound XXII does not mobilize cancer cells back into circulation. FIG. 8C is a graph of CTCs enumerated at different time points following administration of AMD-3100 alone or combined with Compound XXII. The area under the curve was 345 for AMD-3100 alone and 781 for AMD-3100+ Compound XXII (3 mice/group; *P=0.04 **P=0.02, paired t-test. FIG. 8D is a schematic of AMD3100 and Compound XXII administration to tumor-bearing mice. FIG. 8E is a graph showing percentage of apoptotic CTCs following mobilization by AMD-3100 in the absence or presence of Compound XXII as compared to steadystate levels (dotted line).

FIG. 9A is scheme comprising images of MDA-231 cells, stably expressing GFP, labeled with the red dye CM-Dil to distinguish re-seeded cells from dormant cells in mice harboring skeletal and soft-tissue tumors. Highly proliferating cancer cells in tumors and re-seeded cancer cells lacked red fluorescence, which was detected in non-proliferating, dormant cancer cells. FIG. 9B is a graph showing re-seeded cells detected in bone and lungs of animals treated with AMD-3100 in combination with Compound XXII were significantly fewer as compared to AMD-3100 alone (2 mice/data point).

FIG. 10A is a scheme outlining a procedure wherein CTCs collected from three mice harboring multiple tumors in skeleton and soft-tissues were collected and re-inoculated. Tumors were detected in one out of three recipient mice within 2 weeks. FIG. 10B is a schematic of the experiment aimed to assess the metastatic potential of CTCs and the protective effect of CX3CR1 antagonism. FIG. 10C is a set of images of mice harboring disseminated tumors reproducing early metastatic disease and treated as shown in FIG. 10B. The mice were monitored by in vivo bioluminescence imaging at two weeks for initial lesions and three weeks later for additional lesions. FIG. 10D is a graph showing that AMD-3100 doubled the number of additional lesions as compared to control animals, an effect that was counteracted by co-treatment with Compound XXII. (Control 11 mice, Treated 7 mice/group; ***P=0.0008, unpaired t-test).

FIGS. 11A-11G comprise graphs and images showing the obstruction of the reseeding of CTCs by Compound XXII in combination with Doxorubicin and Docetaxel. FIGS. 11A-11B are graphs showing a two-week treatment with Doxorubicin did not reduce tumor number and burden in mice with disseminated tumors, as compared to Compound XXII alone. Combination of these two compounds improved control of tumor burden at 1 week of treatment when compared to Compound XXII alone. FIGS. 11C-11D show that retaining CTCs in the blood by administering Compound XXII increased the exposure to Doxorubicin, as measured by the percentage of cells showing red fluorescence emitted by the drug. Arrows show two cancer cells that did not incorporate Doxorubicin (3 mice/group; *P=0.03, One-way Anova with Dunnett's post-test. FIGS. 11E-11G are graphs showing that treatment with docetaxel significantly suppressed tumor growth and combined therapy (docetaxel+Compound XXII) showed significantly lower tumor burden and fewer lesions. It was observed that administration of Compound XXII alone demonstrated comparable efficacy in lowering total tumor burden when compared to administration of docetaxel alone.

DETAILED DESCRIPTION OF THE INVENTION

Figure 1A:
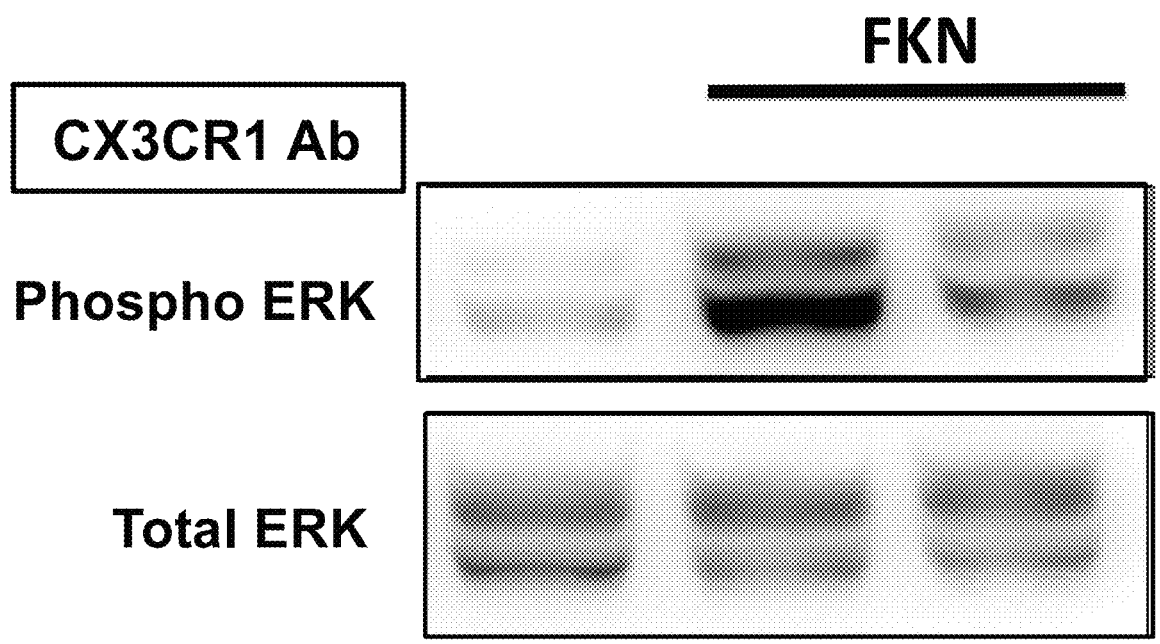
FIG. 1A comprises a set of images of representative Western blot assays illustrating that a neutralizing antibody directed against CX3CR1 can block ERK phosphorylation in SKBR3 human breast cancer cells induced by soluble FKN.

The present invention relates in part to the discovery that metastatic dissemination can take place after a primary surgical intervention. In one aspect, the metastatic dissemination is caused by cancer cells departing from residual tumor or tumor recurrences. Thus, emergence of metastatic disease may be prevented or minimized by therapeutic intervention around the time of the primary surgery.

In certain embodiments, local surgery on the primary mammary tumor induces the production of a plethora of wound factors that profoundly affect cancer cell proliferation and cells that were not eliminated by surgical excision. Prior to re-intervention, a fertile stromal environment may induce dissemination of residual cancer cells in patients with positive resection margins. This process would produce secondary waves of micrometastases with at least equal probability of developing into macroscopic tumors as those seeded years earlier.

In certain embodiments, the compounds of the invention are useful in treating, preventing or minimizing metastasis in a subject diagnosed with cancer. In other embodiments, the subject is subjected to primary surgery related to cancer. In yet other embodiments, the cancer is any kind of cancer or tumor. In yet other embodiments, the cancer is a solid cancer or tumor. In yet other embodiments, the cancer is breast or prostate cancer or tumor. In yet other embodiments, the cancer is selected from the group consisting of glioma, renal cell carcinoma, epithelial ovarian cancer, pancreatic ductal adenocarcinoma, gastric cancer, colorectal cancer.

In certain embodiments, the compounds of the invention are useful in detecting circulating tumor cells in vitro, ex vivo or in vivo. In other embodiments, the compounds of the invention can be used to identify metastatic tumors, which can be removed as needed. In yet other embodiments, the compounds of the invention can be used in assays that aim to identify novel $CX_3CR1$ small molecule modulators.

In certain embodiments, the compounds of the invention are useful in treating diseases, such as central nervous system diseases (such as, but not limited to, HIV Associated Neurocognitive Disorders (HAND), and/or Alzheimer's disease), pain, inflammation (such as, but not limited to, arthritis), cardiovascular disease (such as, but not limited to, undesired vascular smooth muscle proliferation, atherosclerosis, coronary vascular endothelial dysfunction, and/or coronary artery disease), and/or multiple sclerosis.

Due to the lack of qualified surrogate measures of clinical benefit, there is a need for new clinically relevant biomarkers to monitor disease progression. For example, there is a need to develop a therapeutic approach focused on preventing $CX_3CR1$-expressing circulating tumor cells (CTCs) from homing and extravasating into the stroma and becoming disseminated tumor cells (DTCs). CTCs are rare cells that are found in the blood of cancer patients and are shed by both primary and metastatic tumors that mediate the hematogenous spread of cancer to distant sites, including bone, lung, brain, and liver, by providing the seeds for distal metastases. CTCs are a potential source of cells derived from metastatic cancers, and may be analyzed repeatedly. Thus, CTCs represent an important biomarker in the clinical management of advanced disease.

As described herein, in certain embodiments, the compounds of the invention are small molecule fluorescent probes that can be used to identify $CX_3CR1$ expression on circulating tumor cells (CTCs) derived from patient's blood. In certain embodiments, the compounds of the invention allow for rapid and facile measurement of $CX_3CR1$ CTC expression, in conjunction with, as non-limiting examples, Abnova's ClearCell® CX-Label-Free, CTC Microfiltration System and/or the CellSearch system (Janssen Diagnostics). The methods of the invention help identify patients most likely to benefit from $CX_3CR1$ therapy, thus improving translational accuracy. In certain embodiments, the invention provides a companion biomarker that can be used clinically to optimize the therapeutic potential of anti-metastasis $CX_3CR1$ antagonist treatment. In other embodiments, the compounds of the invention allow for the development of a robust binding assay in $CX_3CR1$ stably expressing cells to identify $CX_3CR1$ antagonists. In yet other embodiments, the compounds of the invention specifically bind $CX_3CR1$-expressing CTCs, and thus can be used to analyze CTCs.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e., to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

By the term "applicator," as the term is used herein, is meant any device including, but not limited to, a hypodermic syringe, a pipette, and the like, for administering the compounds and compositions of the invention.

As used herein, the term "arrest" refers to the recruitment and/or immobilization of circulating cancer cells to an immobilized biological target, such as an organ, for example, a bone.

"Circulating tumor cells" or "CTCs" refers to cancerous cells that are shed by primary and/or metastatic tumors and mediate hematogenous spread of cancer to distant sites, including, but not limited to, bones, lungs, brain, and/or liver by providing the "seeds" for distal metastases.

As used herein, a "disease" is a state of health of an animal wherein the animal cannot maintain homeostasis, and wherein if the disease is not ameliorated then the animal's health continues to deteriorate.

As used herein, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "effective amount" or "therapeutically effective amount" or "pharmaceutically effective amount" of a compound are used interchangeably to refer to the amount of the compound that is sufficient to provide a beneficial effect to the subject to which the compound is administered. The term to "treat," as used herein, means reducing the frequency with which symptoms are experienced by a patient or subject or administering an agent or compound to reduce the severity with which symptoms are experienced. An appropriate therapeutic amount in any individual case may be determined by one of ordinary skill in the art using routine experimentation.

As used herein "endogenous" refers to any material from or produced inside an organism, cell, tissue or system.

As used herein, the term "exogenous" refers to any material introduced from or produced outside an organism, cell, tissue or system.

The terms "inhibit" and "antagonize", as used herein, mean to reduce a molecule, reaction, interaction, gene, mRNA, and/or protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

"Instructional material," as that term is used herein, includes a publication, a recording, a diagram, or any other medium of expression which can be used to communicate the usefulness of the composition and/or compound of the invention in a kit. The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

"Naturally occurring" as applied to an object refers to the fact that the object can be found in nature. For example, a polypeptide or polynucleotide sequence that is present in an organism (including viruses) that can be isolated from a source in nature and that has not been intentionally modified by man is a naturally occurring sequence.

As used herein, the term "pharmaceutical composition" refers to a mixture of at least one compound useful within the invention with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

The language "pharmaceutically acceptable carrier" includes a pharmaceutically acceptable salt, pharmaceutically acceptable material, composition or carrier, such as a liquid or solid filler, diluent, excipient, solvent or encapsulating material, involved in carrying or transporting a compound(s) of the present invention within or to the subject such that it may perform its intended function. Typically, such compounds are carried or transported from one organ, or portion of the body, to another organ, or portion of the body. Each salt or carrier must be "acceptable" in the sense of being compatible with the other ingredients of the formulation, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; diluent; granulating agent; lubricant; binder; disintegrating agent; wetting agent; emulsifier; coloring agent; release agent; coating agent; sweetening agent; flavoring agent; perfuming agent; preservative; antioxidant; plasticizer; gelling agent; thickener; hardener; setting agent; suspending agent; surfactant; humectant; carrier; stabilizer; and other non-toxic compatible substances employed in pharmaceutical formulations, or any combination thereof. As used herein, "pharmaceutically acceptable carrier" also includes any and all coatings, antibacterial and antifungal agents, and absorption delaying agents, and the like that are compatible with the activity of the compound, and are physiologically acceptable to the subject. Supplementary active compounds may also be incorporated into the compositions.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof.

"Polypeptide" refers to a polymer composed of amino acid residues, related naturally occurring structural variants, and synthetic non-naturally occurring analogs thereof linked via peptide bonds. Synthetic polypeptides can be synthesized, for example, using an automated polypeptide synthesizer. The term "protein" typically refers to large polypeptides. The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus. As used herein, a "peptidomimetic" is a compound containing non-peptidic structural elements that is capable of mimicking the biological action of a parent peptide. A peptidomimetic may or may not comprise peptide bonds.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease. Disease and disorder are used interchangeably herein.

By the term "specifically bind" or "specifically binds," as used herein, is meant that a first molecule (e.g., an antibody) preferentially binds to a second molecule (e.g., a particular antigenic epitope), but does not necessarily bind only to that second molecule.

A "subject", as used therein, can be a human or non-human mammal. Non-human mammals include, for example, livestock and pets, such as ovine, bovine, porcine, canine, feline and murine mammals. Preferably, the subject is human.

As used herein, the term "treatment" or "treating" is defined as the application or administration of a therapeutic agent, i.e., a compound useful within the invention (alone or in combination with another pharmaceutical agent), to a subject, or application or administration of a therapeutic agent to an isolated tissue or cell line from a subject (e.g., for diagnosis or ex vivo applications), who has cancer, a symptom of cancer or the potential to develop cancer, with the purpose to cure, heal, alleviate, relieve, alter, remedy, ameliorate, improve or affect cancer, the symptoms of cancer or the potential to develop cancer. Such treatments may be specifically tailored or modified, based on knowledge obtained from the field of pharmacogenomics.

As used herein, the term "alkyl," by itself or as part of another substituent means, unless otherwise stated, a straight or branched chain hydrocarbon having the number of carbon atoms designated (i.e. $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$) alkyl, particularly ethyl, methyl, isopropyl, isobutyl, n-pentyl, n-hexyl and cyclopropylmethyl.

As used herein, the term "cycloalkyl," by itself or as part of another substituent means, unless otherwise stated, a cyclic chain hydrocarbon having the number of carbon atoms designated (i.e. $C_3$-$C_6$ means a cyclic group comprising a ring group consisting of three to six carbon atoms) and includes straight, branched chain or cyclic substituent groups. Examples include cyclopropyl, cyclobutyl, cyclopentyl, cyclohexyl, cycloheptyl, and cyclooctyl. Most preferred is ($C_3$-$C_6$)cycloalkyl, particularly cyclopropyl, cyclobutyl, cyclopentyl and cyclohexyl.

As used herein, the term "alkenyl," employed alone or in combination with other terms, means, unless otherwise stated, a stable mono-unsaturated or di-unsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by —$CH_2$—CH=$CH_2$.

As used herein, the term "alkynyl," employed alone or in combination with other terms, means, unless otherwise stated, a stable straight chain or branched chain hydrocarbon group with a triple carbon-carbon bond, having the stated number of carbon atoms. Examples include ethynyl and propynyl, and the higher homologs and isomers.

As used herein, the term "substituted alkyl," "substituted cycloalkyl," "substituted alkenyl" or "substituted alkynyl" means alkyl, cycloalkyl, alkenyl or alkynyl, as defined above, substituted by one, two or three substituents selected from the group consisting of halogen, —OH, alkoxy, —$NH_2$, —$N(CH_3)_2$, —C(=O)OH, trifluoromethyl, —C≡N, —C(=O)O($C_1$-$C_4$)alkyl, —C(=O)$NH_2$, —C(=O)NH($C_1$-$C_4$)alkyl, —C(=O)N(($C_1$-$C_4$)alkyl)$_2$, —$SO_2NH_2$, —C(=NH)$NH_2$, and —$NO_2$, preferably containing one or two substituents selected from halogen, —OH, alkoxy, —$NH_2$, trifluoromethyl, —$N(CH_3)_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$) alkoxy, particularly ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$ As used herein, the term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—$CH_3$, —CH=CH—$CH_2$—OH, —$CH_2$—CH=N—$OCH_3$, —CH=CH—N($CH_3$)—$CH_3$, and —$CH_2$—CH=CH—$CH_2$—SH.

As used herein, the term "aromatic" refers to a carbocycle or heterocycle with one or more polyunsaturated rings and having aromatic character, i.e. having (4n+2) delocalized π(pi) electrons, where n is an integer.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. Preferred are phenyl and naphthyl, most preferred is phenyl.

As used herein, the term "aryl-($C_1$-$C_3$)alkyl" means a functional group wherein a one to three carbon alkylene chain is attached to an aryl group, e.g., —$CH_2CH_2$-phenyl. Preferred is aryl-$CH_2$— and aryl-CH($CH_3$)—. The term "substituted aryl-($C_1$-$C_3$)alkyl" means an aryl-($C_1$-$C_3$)alkyl functional group in which the aryl group is substituted. Preferred is substituted aryl($CH_2$)—. Similarly, the term "heteroaryl-($C_1$-$C_3$)alkyl" means a functional group wherein a one to three carbon alkylene chain is attached to a heteroaryl group, e.g., —$CH_2CH_2$-pyridyl. Preferred is heteroaryl-($CH_2$)—. The term "substituted heteroaryl-($C_1$-$C_3$) alkyl" means a heteroaryl-($C_1$-$C_3$)alkyl functional group in which the heteroaryl group is substituted. Preferred is substituted heteroaryl-($CH_2$)—.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "substituted" means that an atom or group of atoms has replaced hydrogen as the substituent attached to another group.

For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two. In yet another embodiment, the substituents are independently selected from the group consisting of $C_{1-6}$ alkyl, —OH, $C_{1-6}$ alkoxy, halo, amino, acetamido and nitro. In yet another embodiment, the substituents are independently selected from the group consisting of $C_{1-6}$ alkyl, $C_{1-6}$ alkoxy, halo, acetamido, and nitro. As used herein, where a substituent is an alkyl or alkoxy group, the carbon chain may be branched, straight or cyclic, with straight being preferred.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compositions

In one aspect, the composition useful in the methods of the invention comprises a compound of Formula (I):

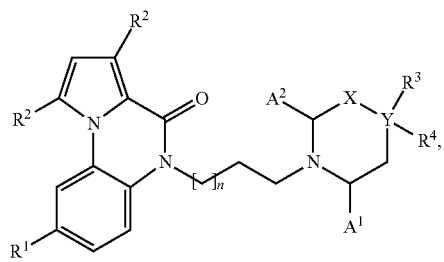

(I)

wherein in (I):

$A^1$ and $A^2$ are independently selected from the group consisting of H and $C_1$-$C_6$ alkyl; or one selected from the group consisting of $A^1$ and $A^2$ combines with the carbon atom to which it is bound to form a —C(=O)— group, and the other selected from the group consisting of $A^1$ and $A^2$ is selected from the group consisting of H and $C_1$-$C_6$ alkyl; or $A^1$ and $A^2$ combine to form a divalent radical selected from the group consisting of methanediyl, ethane-1,2-diyl, and propane-1,3-diyl;

X is selected from the group consisting of $CH_2$ and C(=O), and Y is selected from the group consisting of N and C; wherein: if Y is N, then $R^3$ is selected from the group consisting of benzyl, substituted benzyl, phenyl, substituted phenyl, heteroaryl, and substituted heteroaryl, and $R^4$ is null; if Y is C and X is C(=O), then $R^3$ is selected from the group consisting of phenyl, substituted phenyl, heteroaryl, and substituted heteroaryl, and $R^4$ is selected from the group consisting of H and OH, or $R^3$ and $R^4$ combine with Y to form an optionally substituted 5-6 membered heterocycle; if Y is C and X is $CH_2$, then $R^3$ and $R^4$ combine with Y to form an optionally substituted 5-6 membered heterocycle;

$R^1$ is selected from the group consisting of H, halo, $C_1$-$C_3$ haloalkyl, and $OR^5$;

each occurrence of $R^2$ is independently selected from the group consisting of H, halo (such as F, Cl, Br and I), and $CH_3$;

$R^5$ is selected from the group consisting of H, $C_1$-$C_6$ alkyl, —$(CH_2)_{2-5}NH_2$,

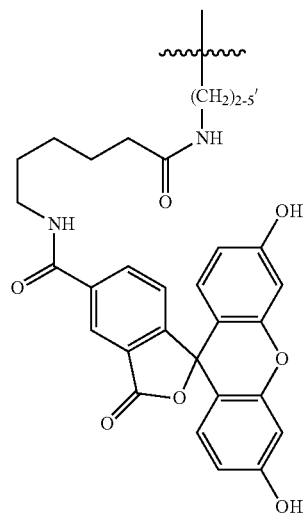

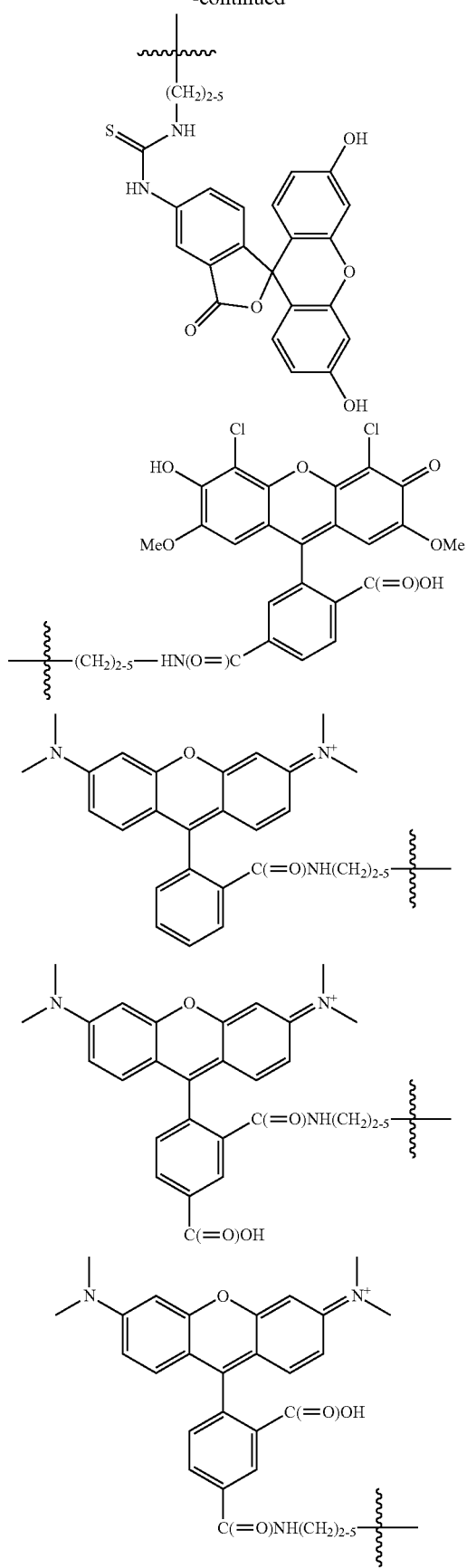
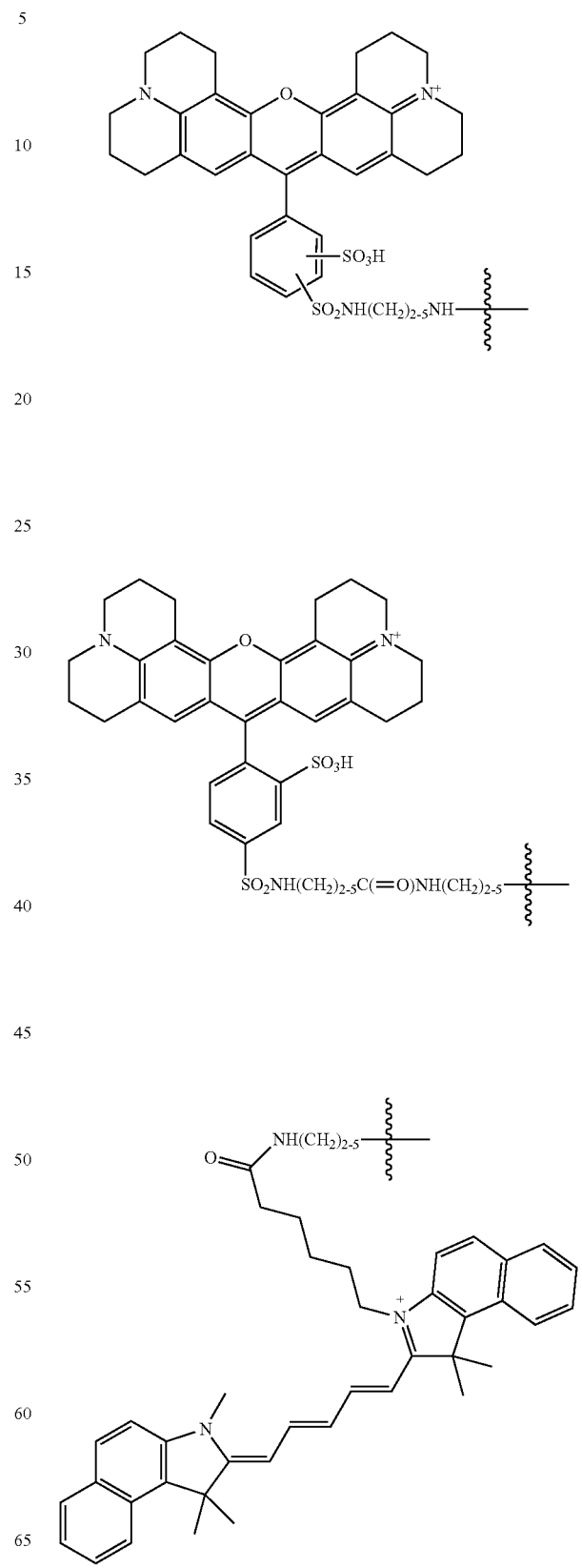

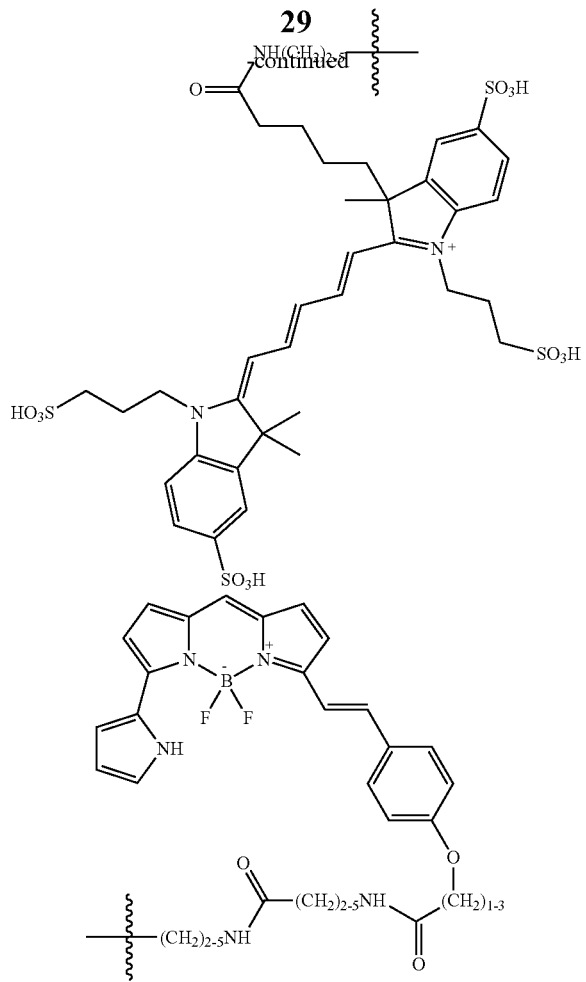

and n is 1, 2 or 3;

or a salt or solvate thereof.

In one aspect, the composition useful in the methods of the invention comprises a compound of Formula (II):

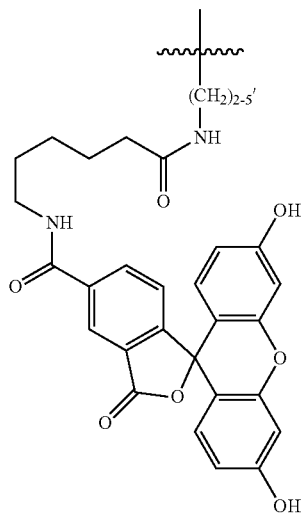

wherein in (II):

$A^1$ and $A^2$ are independently selected from the group consisting of H and $C_1$-$C_6$ alkyl; or one selected from the group consisting of $A^1$ and $A^2$ combines with the carbon atom to which it is bound to form a —C(=O)— group, and the other selected from the group consisting of $A^1$ and $A^2$ is selected from the group consisting of H and $C_1$-$C_6$ alkyl; or $A^1$ and $A^2$ combine to form a divalent radical selected from the group consisting of methanediyl, ethane-1,2-diyl, and propane-1,3-diyl;

X is $CH_2$;

Y is C;

$R^3$ is selected from the group consisting of phenyl, substituted phenyl, heteroaryl, and substituted heteroaryl, and $R^4$ is selected from the group consisting of H and OH;

$R^1$ is selected from the group consisting of H, halo, $C_1$-$C_3$ haloalkyl, and $OR^5$;

each occurrence of $R^2$ is independently selected from the group consisting of H, halo, and $CH_3$; with the proviso that, if both occurrences of $R^2$ are H, then $R^1$ is $OR^5$ and $R^5$ is not H;

$R^5$ is selected from the group consisting of H, —$(CH_2)_{2-5}NH_2$,

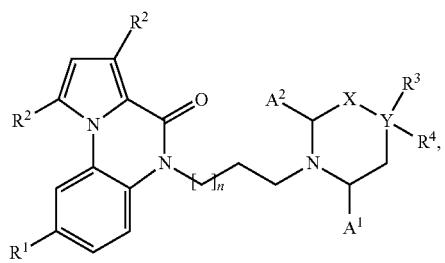

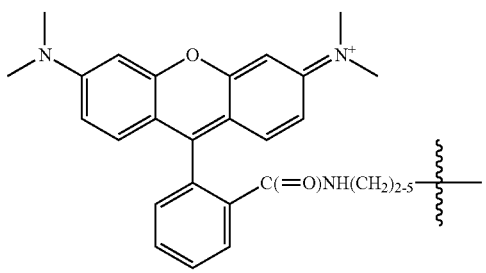

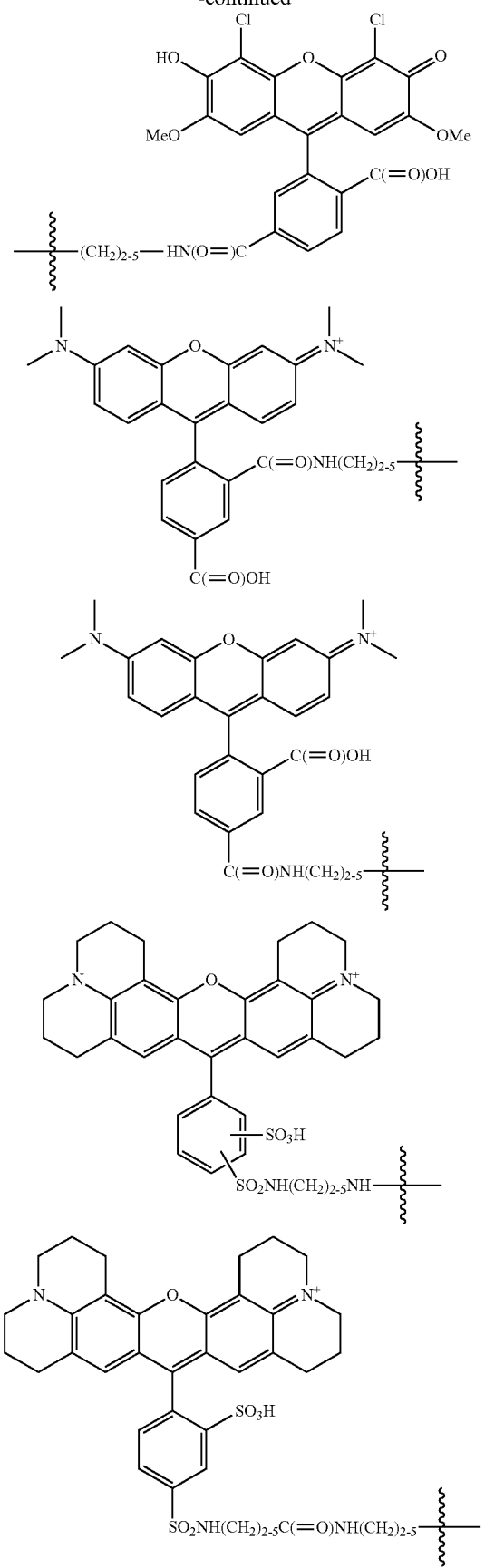
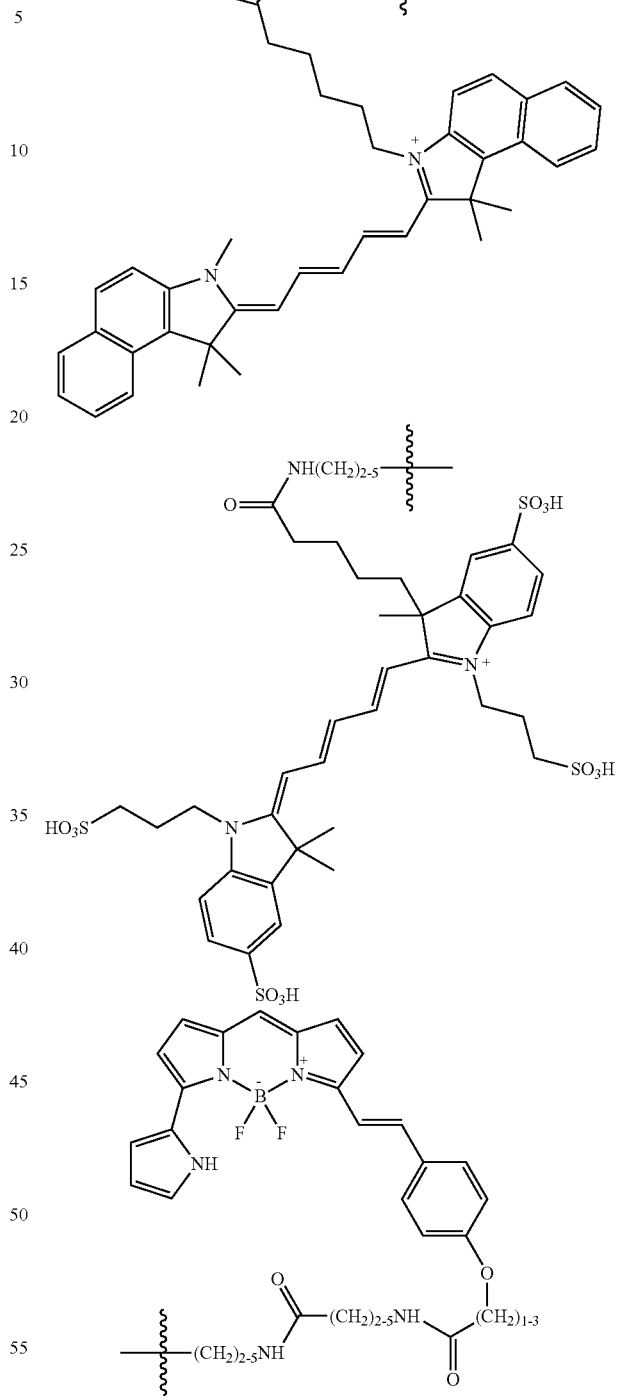

or a salt or solvate thereof.

In certain embodiments, in (I) $A^1$ and $A^2$ are both H.

In certain embodiments, in (II) $A^1$ and $A^2$ are both H.

In certain embodiments, in (I) X is $CH_2$ and Y is N. In other embodiments, in (I) X is $CH_2$ and Y is C. In yet other embodiments, in (I) X is C(=O) and Y is C. In yet other embodiments, in (I) X is C(=O) and Y is N.

In certain embodiments, in (I) Y is N and $R^3$ is an optionally substituted fluorescent phenyl or heteroaryl. In other embodiments, in (I) Y is C, X is C(=O) and $R^3$ is an optionally substituted fluorescent phenyl or heteroaryl. In yet other embodiments, $R^3$ is optionally substituted 2-oxo-2H-chromen-7-yl. In yet other embodiments, $R^3$ is an optionally substituted fluorescent phenyl or heteroaryl, and $R^1$ is selected from the group consisting of H, halo, $C_1$-$C_3$ haloalkyl, OH, $C_1$-$C_6$ alkoxy, and —$O(CH_2)_{2-5}NH_2$.

In certain embodiments, in (II) $R^3$ is an optionally substituted fluorescent phenyl or heteroaryl. In other embodiments, in (II) $R^3$ is optionally substituted 2-oxo-2H-chromen-7-yl. In yet other embodiments, $R^3$ is an optionally substituted fluorescent phenyl or heteroaryl, and $R^1$ is selected from the group consisting of H, halo, $C_1$-$C_3$ haloalkyl, OH, and —$O(CH_2)_{2-5}NH_2$.

In certain embodiments, $R^3$ is selected from the group consisting of:

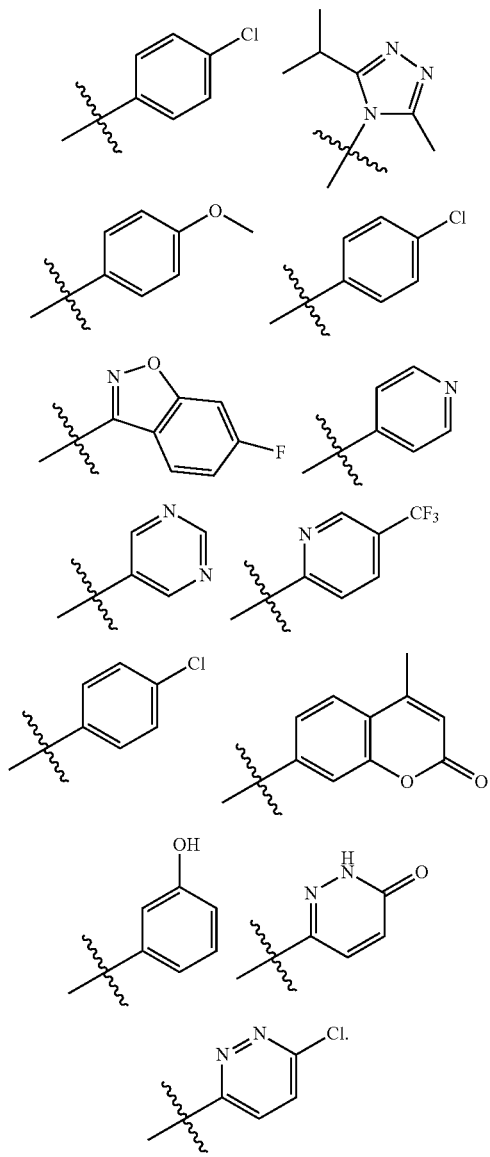

In certain embodiments, in (I) $R^3$ and $R^4$ combine with Y to form at least one of the following groups:

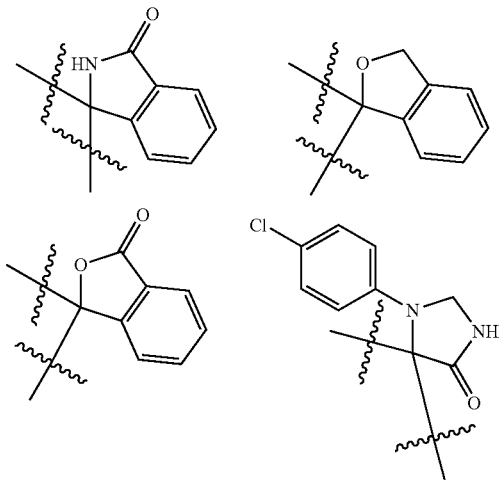

In certain embodiments, the compound of Formula (I) is selected from the group consisting of:

5-(3-(4-(3-hydroxyphenyl)piperazin-1-yl)propyl)pyrrolo[1,2-a]quinoxalin-4(5H)-one

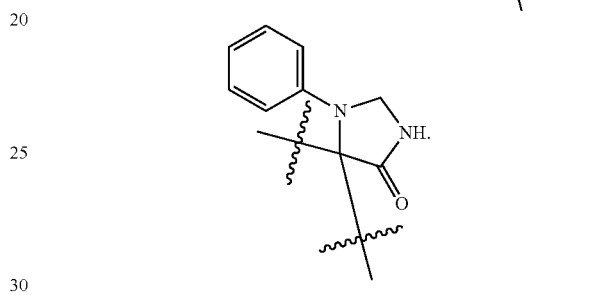

5-(3-(4-(pyridin-4-yl)piperazin-1-yl)propyl)pyrrolo[1,2-a]quinoxalin-4(5H)-one

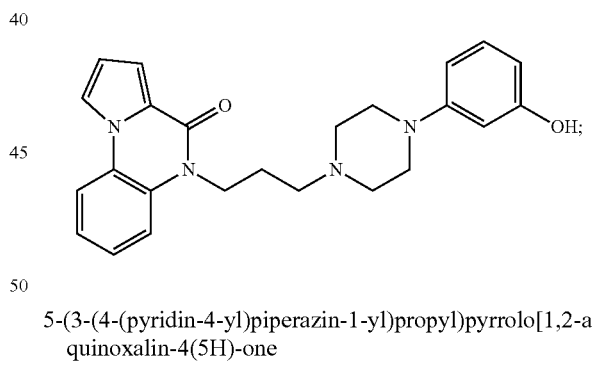

35

8-chloro-5-(3-(4-(pyridin-4-yl)piperazin-1-yl)propyl)pyrrolo[1,2-a]quinoxalin-4(5H)-one

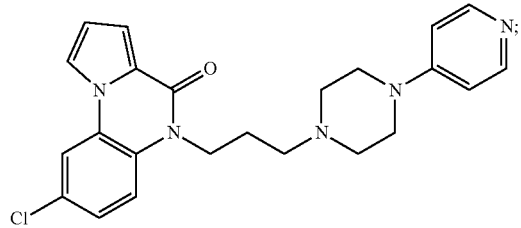 [SMILES: O=c1c2cccn2c2cc(Cl)ccc2n1CCCN1CCN(c2ccncc2)CC1]

8-fluoro-5-(3-(4-(pyridin-4-yl)piperazin-1-yl)propyl)pyrrolo[1,2-a]quinoxalin-4(5H)-one

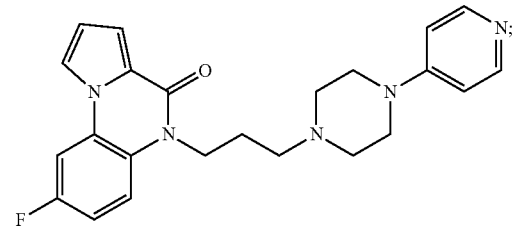 [SMILES: O=c1c2cccn2c2cc(F)ccc2n1CCCN1CCN(c2ccncc2)CC1]

8-fluoro-1-methyl-5-(3-(4-(pyridin-4-yl)piperazin-1-yl)propyl)pyrrolo[1,2-a]quinoxalin-4(5H)-one

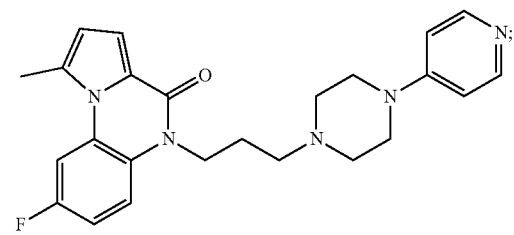 [SMILES: Cc1ccc2c(=O)n(CCCN3CCN(c4ccncc4)CC3)c3ccc(F)cc3n12]

5-(3-(4-(pyridin-4-yl)piperazin-1-yl)propyl)-8-(trifluoromethyl)pyrrolo[1,2-a]quinoxalin-4(5H)-one

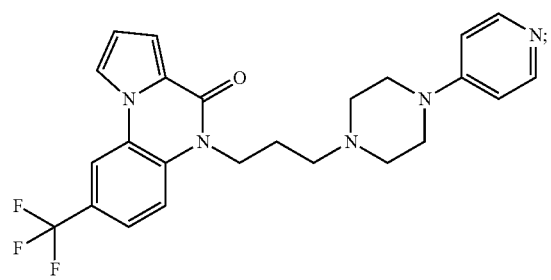 [SMILES: O=c1c2cccn2c2cc(C(F)(F)F)ccc2n1CCCN1CCN(c2ccncc2)CC1]

36

5-(3-(4-(4-methyl-2-oxo-2H-chromen-7-yl)piperazin-1-yl)propyl)pyrrolo[1,2-a]quinoxalin-4(5H)-one

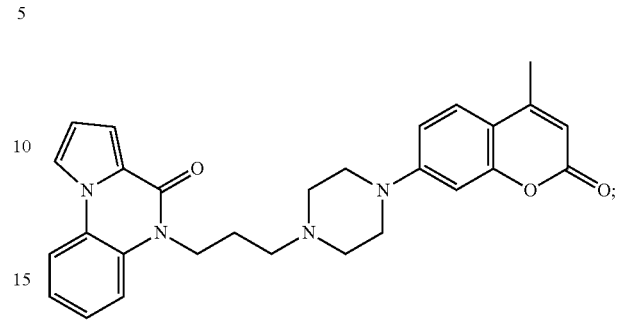

5-(3-(4-(6-oxo-1,6-dihydropyridazin-3-yl)piperazin-1-yl)propyl)pyrrolo[1,2-a]quinoxalin-4(5H)-one

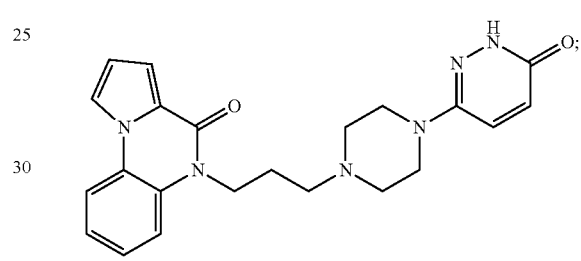

8-chloro-5-(3-(4-(6-oxo-1,6-dihydropyridazin-3-yl)piperazin-1-yl)propyl)pyrrolo[1,2-a]quinoxalin-4(5H)-one

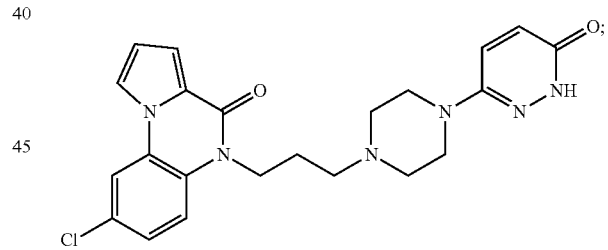

5-(3-(4-(6-oxo-1,6-dihydropyridazin-3-yl)piperazin-1-yl)propyl)-8-(trifluoromethyl)pyrrolo[1,2-a]quinoxalin-4(5H)-one

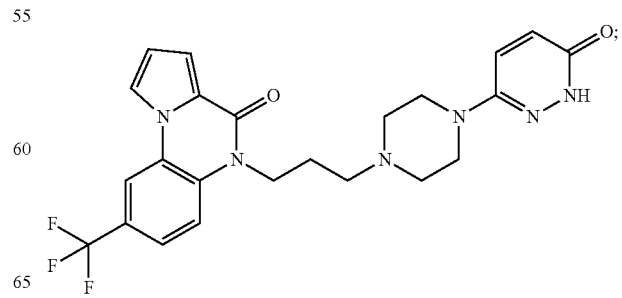

| 37 | 38 |
|---|---|
| 8-fluoro-5-(3-(4-(6-oxo-1,6-dihydropyridazin-3-yl)piperazin-1-yl)propyl)pyrrolo[1,2-a]quinoxalin-4(5H)-one | 8-methoxy-5-(3-(4-(pyrimidin-5-yl)piperazin-1-yl)propyl)pyrrolo[1,2-a]quinoxalin-4(5H)-one |

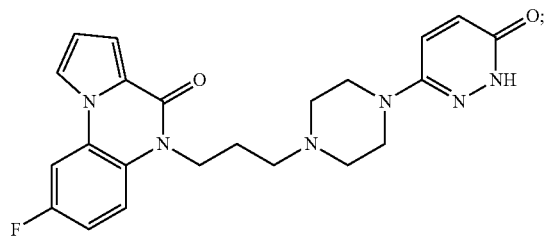 [SMILES: O=c1ccc(N2CCN(CCCn3c(=O)c4cccn4c4cc(F)ccc43)CC2)n[nH]1] 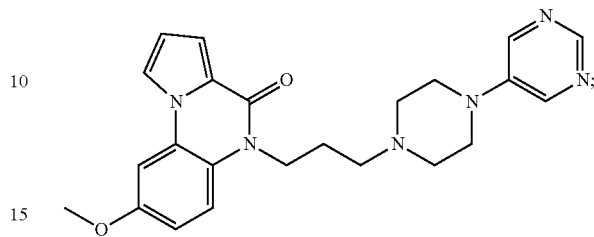

8-fluoro-1-methyl-5-(3-(4-(6-oxo-1,6-dihydropyridazin-3-yl)piperazin-1-yl)propyl)pyrrolo[1,2-a]quinoxalin-4(5H)-one 5-(3-(4-(6-chloropyridazin-3-yl)piperazin-1-yl)propyl)pyrrolo[1,2-a]quinoxalin-4 (5H)-one

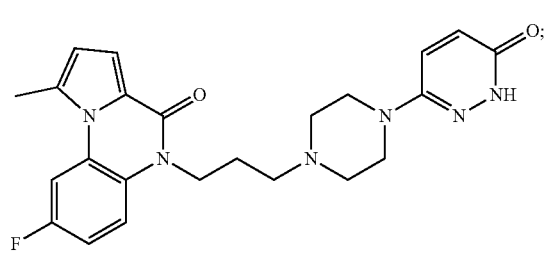 [SMILES: Cc1ccc2c(=O)n(CCCN3CCN(c4ccc(=O)[nH]n4)CC3)c3ccc(F)cc3n12] 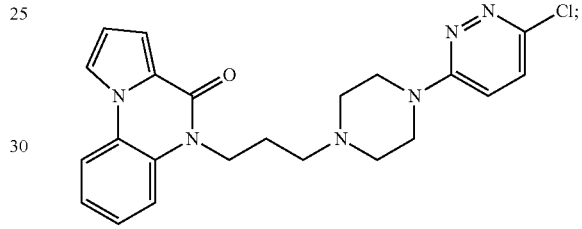

5-(3-(4-(5-(trifluoromethyl)pyridin-2-yl)piperazin-1-yl)propyl)pyrrolo[1,2-a]quinoxalin-4(5H)-one 5-(3-(4-(4-chlorophenyl)-3-oxopiperazin-1-yl)propyl)pyrrolo[1,2-a]quinoxalin-4(5H)-one

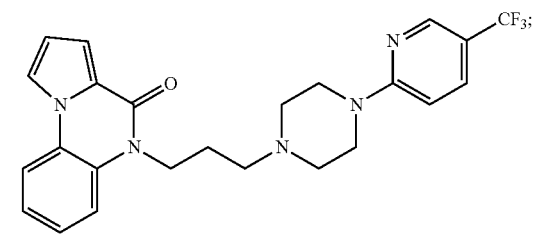 [SMILES: O=c1c2cccn2c2ccccc2n1CCCN1CCN(c2ccc(C(F)(F)F)cn2)CC1] 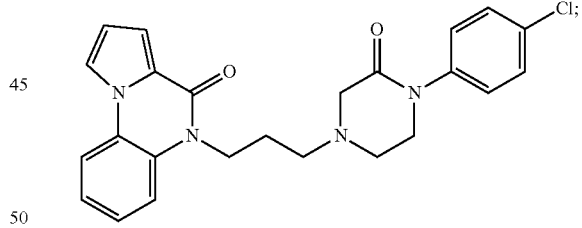

5-(3-(4-(pyrimidin-5-yl)piperazin-1-yl)propyl)pyrrolo[1,2-a]quinoxalin-4(5H)-one 5-(3-(4-(4-chlorophenyl)-3-oxopiperazin-1-yl)propyl)-8-methoxypyrrolo[1,2-a]quinoxalin-4(5H)-one

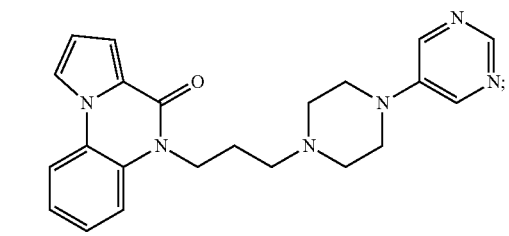 [SMILES: O=c1c2cccn2c2ccccc2n1CCCN1CCN(c2cncnc2)CC1] 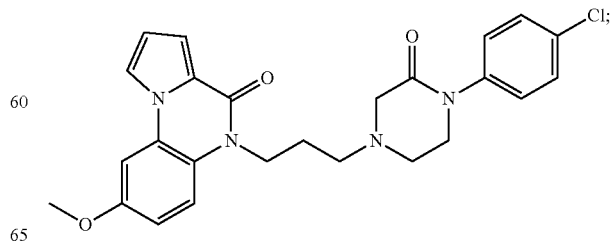

5-(3-(4-(4-chlorophenyl)-3-oxopiperazin-1-yl)propyl)-8-fluoropyrrolo[1,2-a]quinoxalin-4(5H)-one

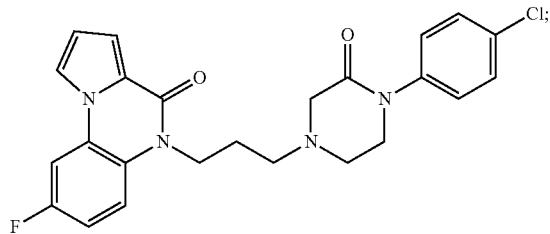 [SMILES: O=C1CN(CCCn2c(=O)c3cccn3c3cc(F)ccc32)CCN1c1ccc(Cl)cc1]

5-(3-(4-(4-chlorophenyl)-3-oxopiperazin-1-yl)propyl)-8-fluoro-1-methylpyrrolo[1,2-a]quinoxalin-4(5H)-one

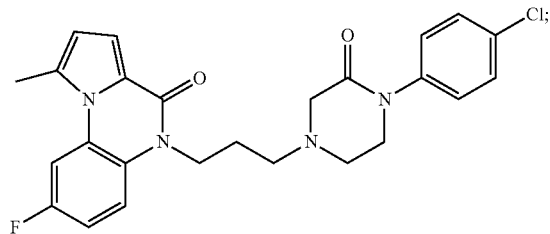 [SMILES: Cc1ccc2c(=O)n(CCCN3CCN(c4ccc(Cl)cc4)C(=O)C3)c3ccc(F)cc3n12]

8-chloro-5-(3-(4-(4-chlorophenyl)-3-oxopiperazin-1-yl)propyl)pyrrolo[1,2-a]quinoxalin-4(5H)-one

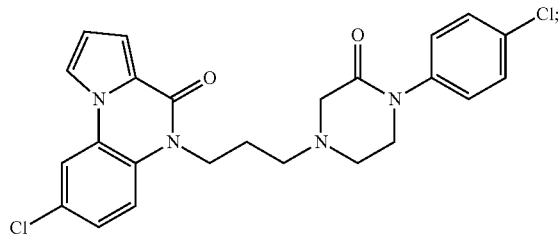 [SMILES: O=C1CN(CCCn2c(=O)c3cccn3c3cc(Cl)ccc32)CCN1c1ccc(Cl)cc1]

5-(3-(4-(4-chlorophenyl)-3-oxopiperazin-1-yl)propyl)-8-(trifluoromethyl)pyrrolo[1,2-a]quinoxalin-4(5H)-one

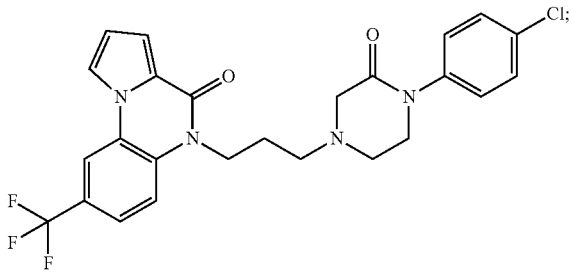 [SMILES: O=C1CN(CCCn2c(=O)c3cccn3c3cc(C(F)(F)F)ccc32)CCN1c1ccc(Cl)cc1]

5-chloro-1'-(3-(4-oxopyrrolo[1,2-a]quinoxalin-5(4H)-yl)propyl)-3H-spiro[isobenzofuran-1,4'-piperidin]-3-one

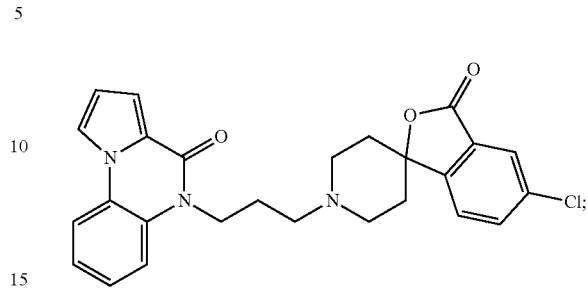

5-(3-(4-oxo-1-phenyl-1,3,8-triazaspiro[4.5]decan-8-yl)propyl)pyrrolo[1,2-a]quinoxalin-4(5H)-one

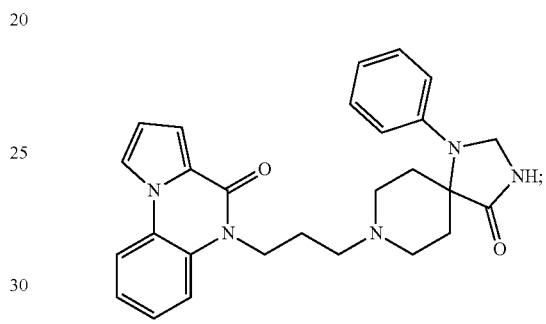

5-(3-(1-(4-chlorophenyl)-4-oxo-1,3,8-triazaspiro[4.5]decan-8-yl)propyl)pyrrolo[1,2-a]quinoxalin-4(5H)-one

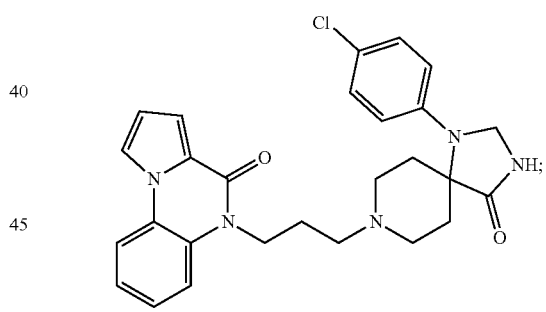

5-(3-(1-(4-fluorophenyl)-4-oxo-1,3,8-triazaspiro[4.5]decan-8-yl)propyl)pyrrolo[1,2-a]quinoxalin-4(5H)-one

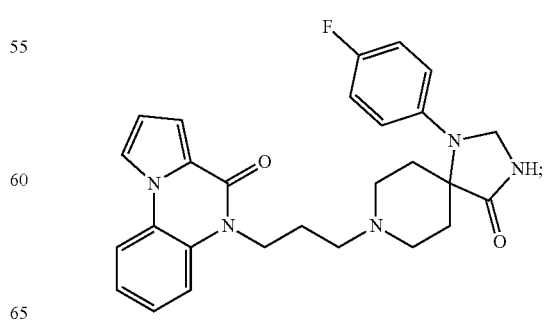

1'-(3-(4-oxopyrrolo[1,2-a]quinoxalin-5(4H)-yl)propyl)spiro[isoindoline-1,4'-piperidin]-3-one

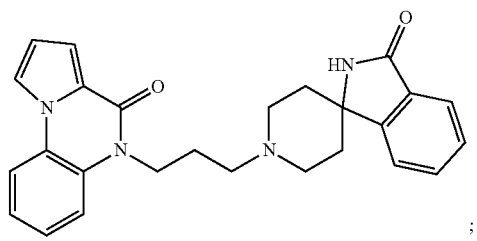 [SMILES: O=C1NC2(CCN(CCCn3c(=O)c4cccn4c4ccccc43)CC2)c2ccccc21]

and
5-(3-(3H-spiro[isobenzofuran-1,4'-piperidin]-1'-yl)propyl)pyrrolo[1,2-a]quinoxalin-4(5H)-one

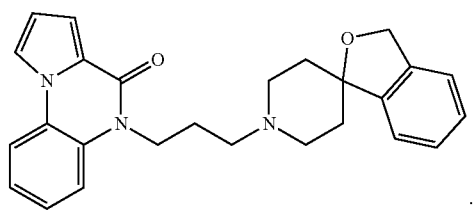 [SMILES: O=c1c2cccn2c2ccccc2n1CCCN1CCC2(CC1)OCc1ccccc12]

In certain embodiments, the compound of Formula (II) is selected from the group consisting of:

5-(3-(4-(4-chlorophenyl)piperidin-1-yl)propyl)-8-fluoro-1-methylpyrrolo[1,2-a]quinoxalin-4(5H)-one

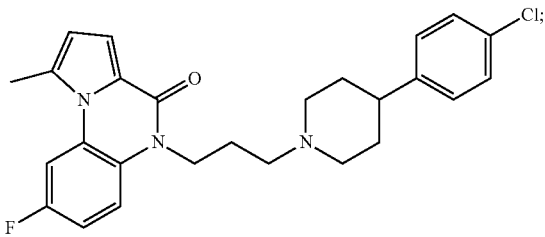 [SMILES: Cc1ccc2c(=O)n(CCCN3CCC(c4ccc(Cl)cc4)CC3)c3ccc(F)cc3n12]

8-fluoro-5-(3-(((1R,5S)-3-(3-isopropyl-5-methyl-4H-1,2,4-triazol-4-yl)-8-azabicyclo[3.2.1]octan-8-yl)propyl)-1-methylpyrrolo[1,2-a]quinoxalin-4(5H)-one

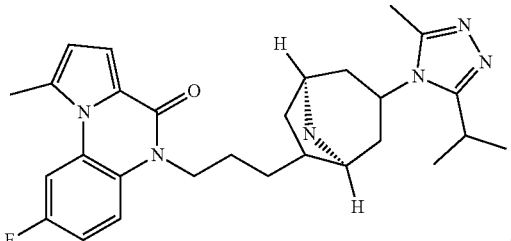

8-(3-aminopropoxy)-5-(3-(4-(4-chlorophenyl)piperidin-1-yl)propyl)pyrrolo[1,2-a]quinoxalin-4(5H)-one

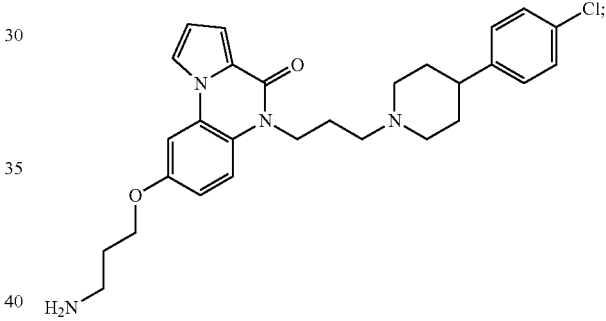

8-(4-aminobutoxy)-5-(3-(4-(4-chlorophenyl)piperidin-1-yl)propyl)pyrrolo[1,2-a]quinoxalin-4(5H)-one

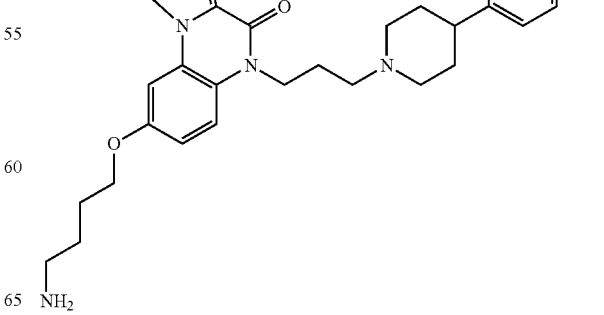

N-(6-((3-((5-(3-(4-(4-chlorophenyl)piperidin-1-yl)propyl)-4-oxo-4,5-dihydropyrrolo[1,2-a]quinoxalin-8-yl)oxy)propyl)amino)-6-oxohexyl)-3',6'-dihydroxy-3-oxo-3H-spiro[isobenzofuran-1,9'-xanthene]-5-carboxamide
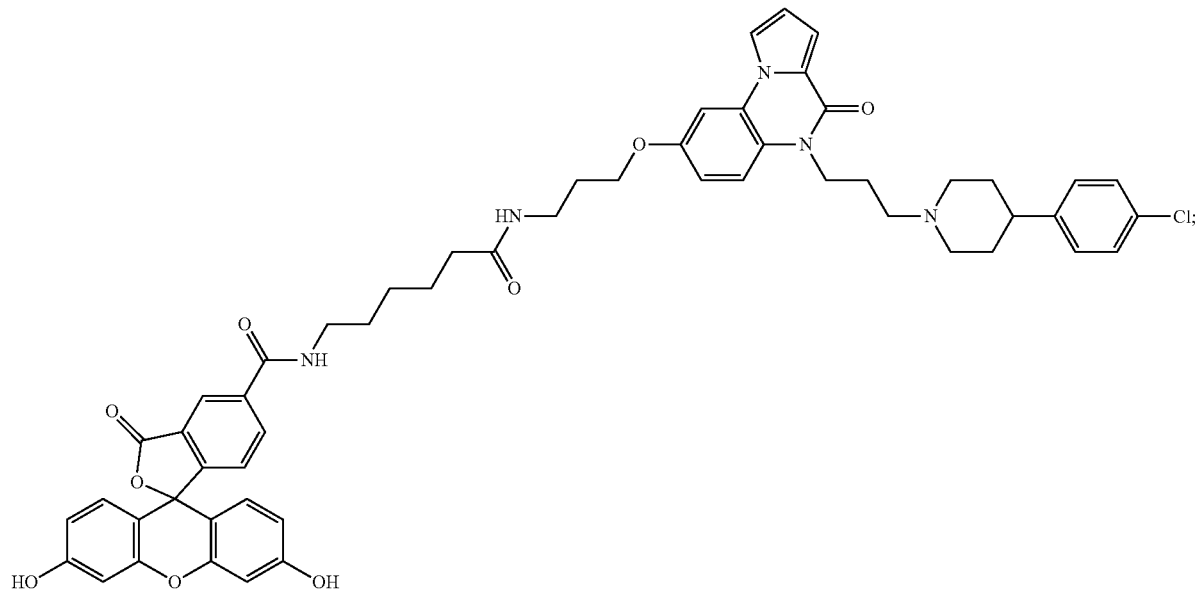 [SMILES: O=C(CCCCCNC(=O)c1ccc2c(c1)C(=O)OC21c2ccc(O)cc2Oc2cc(O)ccc21)NCCCOc1ccc2c(c1)n1cccc1c(=O)n2CCCN1CCC(c2ccc(Cl)cc2)CC1]
1-(3-((5-(3-(4-(4-chlorophenyl)piperidin-1-yl)propyl)-4-oxo-4,5-dihydropyrrolo[1,2-a]quinoxalin-8-yl)oxy)propyl)-3-(3',6'-dihydroxy-3-oxo-3H-spiro[isobenzofuran-1,9'-xanthen]-5-yl)thiourea
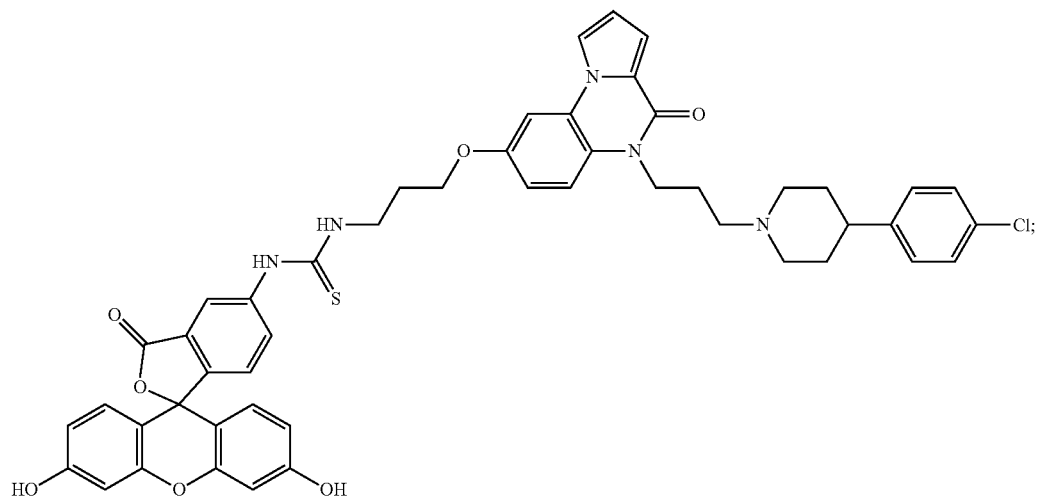 [SMILES: O=C1OC2(c3ccc(O)cc3Oc3cc(O)ccc32)c2ccc(NC(=S)NCCCOc3ccc4c(c3)n3cccc3c(=O)n4CCCN3CCC(c4ccc(Cl)cc4)CC3)cc21]

and 1-(4-((5-(3-(4-(4-chlorophenyl)piperidin-1-yl)propyl)-4-oxo-4,5-dihydropyrrolo[1,2-a]quinoxalin-8-yl)oxy)butyl)-3-(3',6'-dihydroxy-3-oxo-3H-spiro[isobenzofuran-1,9'-xanthen]-5-yl)thiourea In certain embodiments, each occurrence of alkyl, alkylenyl, or cycloalkyl is independently optionally substituted with at least one substituent selected from the group consisting of $C_1$-$C_6$ alkyl, halo, —OR", phenyl (thus yielding, in non-limiting examples, optionally substituted phenyl-($C_1$-

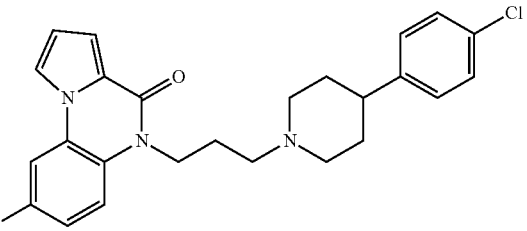
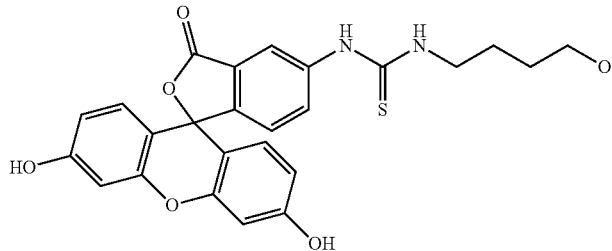

The chromophores useful within the invention should not be construed to be limited to those exemplified here, but rather encompass any chromophore known in the art, such as UV-active or fluorescent chromophores. In certain embodiments, the chromophore comprises at least one selected from the group consisting of coumarin, quantum dots (Xing, et al., 2007, Nature Protocols 2(5): 1152, incorporated herein in its entirety), 6-(2,4-dinitrophenyl) aminohexanoic acid, the ALEXA FLUOR® class of dyes (such as ALEXA FLUOR® 350, ALEXA FLUOR® 405, ALEXA FLUOR® 430, ALEXA FLUOR® 488, ALEXA FLUOR® 514, ALEXA FLUOR® 532, ALEXA FLUOR® 546 carboxylic acid), BODIPY class of dyes (such as 4,4-difluoro-5-(4-phenyl-1,3-butadienyl)-4-bora-3a,4a-diaza-s-indacene-3-propionic acid, BODIPY® 581/591, BODIPY® TMR-X, BODIPY® 493/503, and BODIPY® FL), Lissamine Rhodamine B, Malachite Green, Oregon Green 488, 5-(and -6) carboxynapthofluorescein, and PyMPO (1-(3-(succinimidyloxycarbonyl)benzyl)-4-(5-(4-methoxyphenyl)oxazol-2-yl) pyridinium bromide, available from Molecular Probes, Invitrogen, Life Technologies).

In certain embodiments, an activated carboxylic acid derivative, or a thioisocyanate, of a chromophore is reacted with a free amine of a compound of the invention, giving rise to a labelled compound of the invention. In other embodiments, the activated carboxylic acid is selected from the group consisting of acyl chloride, symmetric or mixed acid anhydride, vinyl ester, cyanomethyl ester, S-phenyl thioester, piperidino ester, pyrid-3-yl ester, p-nitrophenyl ester, 2,4,6-trichlorophenyl ester, 2,3,4,5,6-pentachlorophenyl ester, 2,3,4,5,6-pentafluorophenyl ester, tetrafluorophenyl ester, phtalimido ester, succinimido ester, 4-oxo-3,4-dihydrobenzotriazin-3-yl ester, and benzotriazolyl ester.

In certain embodiments, a chromophore is linked to a compound of the invention through a linker. In other embodiments, the linker comprises $C_1$-$C_{20}$ alkylene, $C_3$-$C_{20}$ cycloalkylene, $(CH_2CH_2O)_n$, $(CH_2CH(CH_3)O)_n$, an amino acid, or a peptide, wherein n=1-10, and the alkylene and cycloalkylene groups are independently optionally substituted with one or more substituents selected from the group consisting of $C_1$-$C_6$ alkyl, aryl, heteroaryl, heterocyclyl, hydroxyl, alkoxy and halo.

$C_3$ alkyl), such as, but not limited to, benzyl or substituted benzyl), and —N(R")(R"), wherein each occurrence of R" is independently H, $C_1$-$C_6$ alkyl or $C_3$-$C_8$ cycloalkyl.

In certain embodiments, each occurrence of aryl or heteroaryl is independently optionally substituted with at least one substituent selected from the group consisting of $C_1$-$C_6$ alkyl, $C_1$-$C_6$ haloalkyl, $C_1$-$C_6$ haloalkoxy, halo, —CN, —OR", —N(R")(R"), —NO_2, —S(=O)_2N(R")(R"), acyl, and $C_1$-$C_6$ alkoxycarbonyl, wherein each occurrence of R" is independently H, $C_1$-$C_6$ alkyl or $C_3$-$C_8$ cycloalkyl.

In certain embodiments, each occurrence of aryl or heteroaryl is independently optionally substituted with at least one substituent selected from the group consisting of $C_1$-$C_6$ alkyl, $C_1$-$C_6$ haloalkyl, $C_1$-$C_6$ haloalkoxy, halo, —CN, —OR", —N(R")(R"), and $C_1$-$C_6$ alkoxycarbonyl, wherein each occurrence of R" is independently H, $C_1$-$C_6$ alkyl or $C_3$-$C_8$ cycloalkyl.

The compounds of the invention may possess one or more stereocenters, and each stereocenter may exist independently in either the (R) or (S) configuration. In certain embodiments, compounds described herein are present in optically active or racemic forms. The compounds described herein encompass racemic, optically active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically active starting materials, chiral synthesis, or chromatographic separation using a chiral stationary phase. A compound illustrated herein by the racemic formula further represents either of the two enantiomers or mixtures thereof, or in the case where two or more chiral center are present, all diastereomers or mixtures thereof.

In certain embodiments, the compounds of the invention exist as tautomers. All tautomers are included within the scope of the compounds recited herein.

Compounds described herein also include isotopically labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2$H, $^3$H, $^{11}$C, $^{13}$C, $^{14}$C, $^{36}$Cl, $^{18}$F, $^{123}$I, $^{125}$I, $^{13}$N, $^{15}$N, $^{15}$O, $^{17}$O, $^{18}$O, $^{32}$P, and $^{35}$S. In certain embodiments, substitution with heavier isotopes such as deuterium affords greater chemical stability. Isotopically labeled compounds are prepared by any suitable method or by processes using an appropriate isotopically labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

In all of the embodiments provided herein, examples of suitable optional substituents are not intended to limit the scope of the claimed invention. The compounds of the invention may contain any of the substituents, or combinations of substituents, provided herein.

Salts

The compounds described herein may form salts with acids or bases, and such salts are included in the present invention. The term "salts" embraces addition salts of free acids or bases that are useful within the methods of the invention. The term "pharmaceutically acceptable salt" refers to salts that possess toxicity profiles within a range that affords utility in pharmaceutical applications. In certain embodiments, the salts are pharmaceutically acceptable salts. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (or pamoic), methanesulfonic, ethanesulfonic, benzenesulfonic, pantothenic, sulfanilic, 2-hydroxyethanesulfonic, trifluoromethanesulfonic, p-toluenesulfonic, cyclohexylaminosulfonic, stearic, alginic, β-hydroxybutyric, salicylic, galactaric, galacturonic acid, glycerophosphonic acids and saccharin (e.g., saccharinate, saccharate). Salts may be comprised of a fraction of one, one or more than one molar equivalent of acid or base with respect to any compound of the invention.

Suitable pharmaceutically acceptable base addition salts of compounds of the invention include, for example, ammonium salts and metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (or N-methylglucamine) and procaine. All of these salts may be prepared from the corresponding compound by reacting, for example, the appropriate acid or base with the compound.

Preparation of Compounds

The compounds useful within the methods of the invention may be prepared using methods known to those skilled in the art.

The following intermediates can be prepared according to the non-limiting reaction schemes herein (see further details in PCT Application Publication Nos. WO 2008/84300, WO 2010/23161, WO 2007/25978, and WO 2010/23161; and U.S. Application Publication Nos. US 2007/117796, US 2007/179158, US 2009/62334, US 2007/21978, and US 2008/62332):

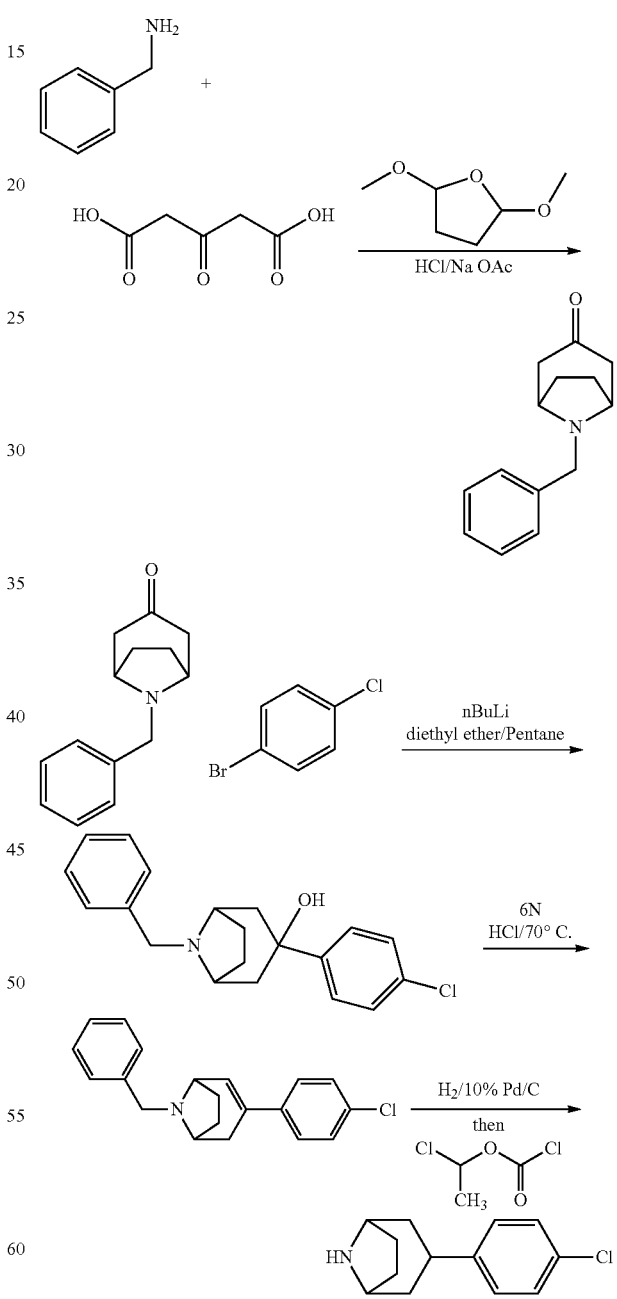

In a non-limiting example, compounds of the invention can be prepared using the non-limiting chemistry illustrated herein. The intermediate pyrrolo[1,2-a]quinoxalin-4(5H)-one may be obtained from commercial sources or synthesized according to literature procedures (Campiani, et al., 1991, Synth. Commun. 21:1567-1576; Prunier, et al., 1997, J. Med. Chem. 40:1808-1819).
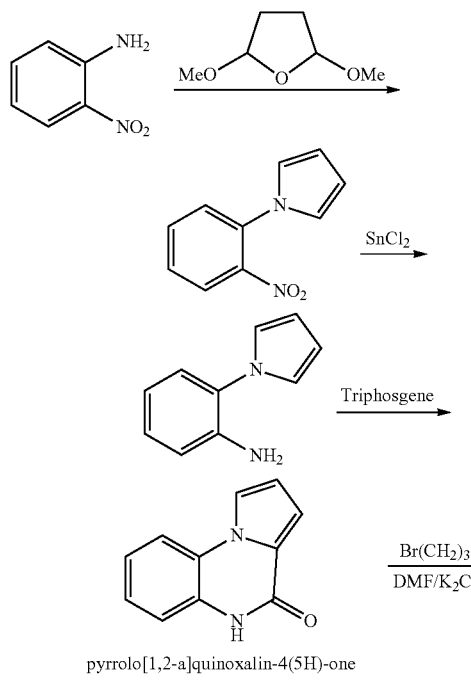
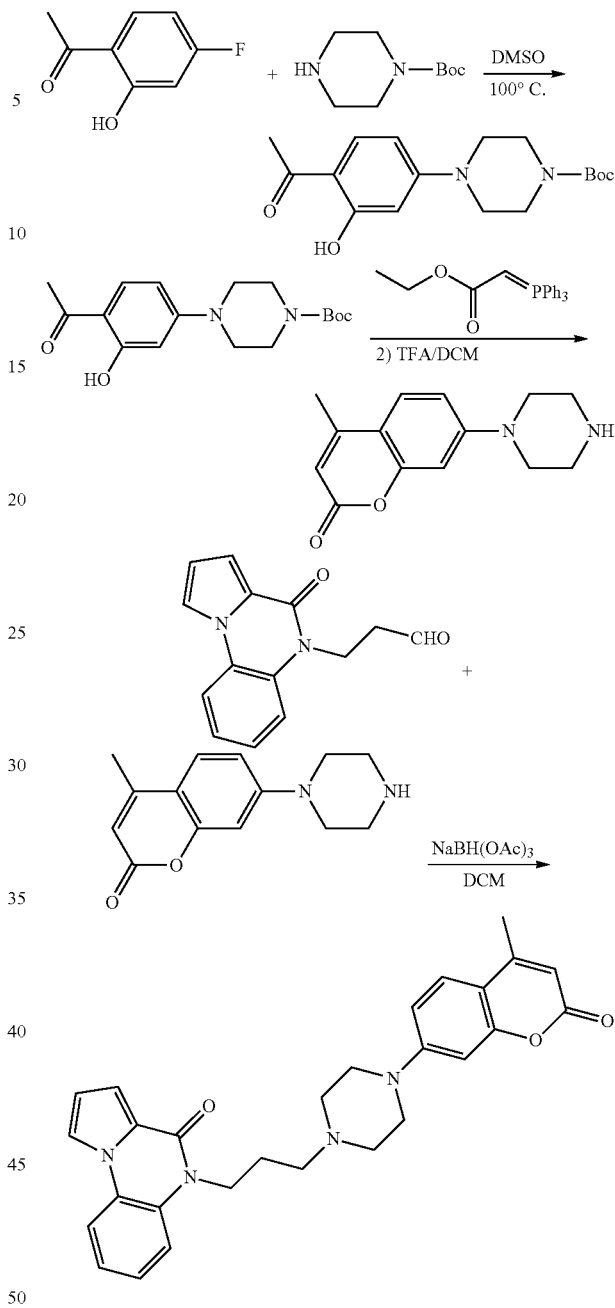
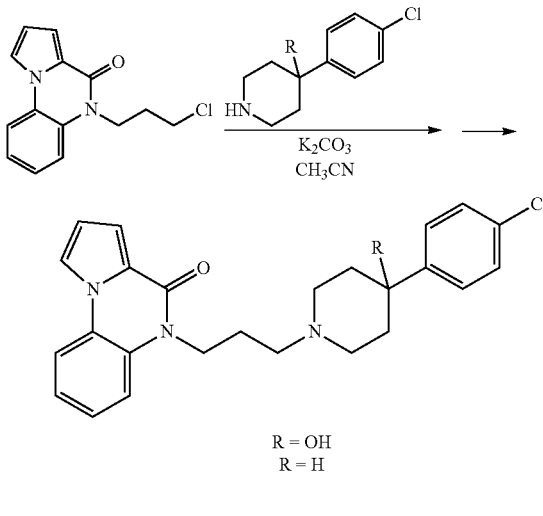
R = OH
R = H
In a non-limiting example, compounds of the invention can be prepared using the methodology illustrated in the scheme below:
In a non-limiting example, compounds of the invention can be prepared using the methodology illustrated in the scheme below:
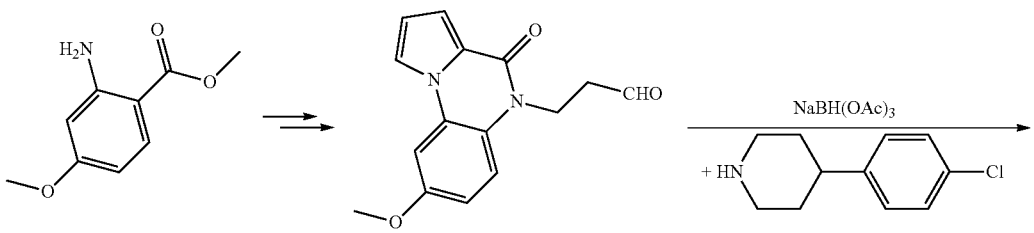

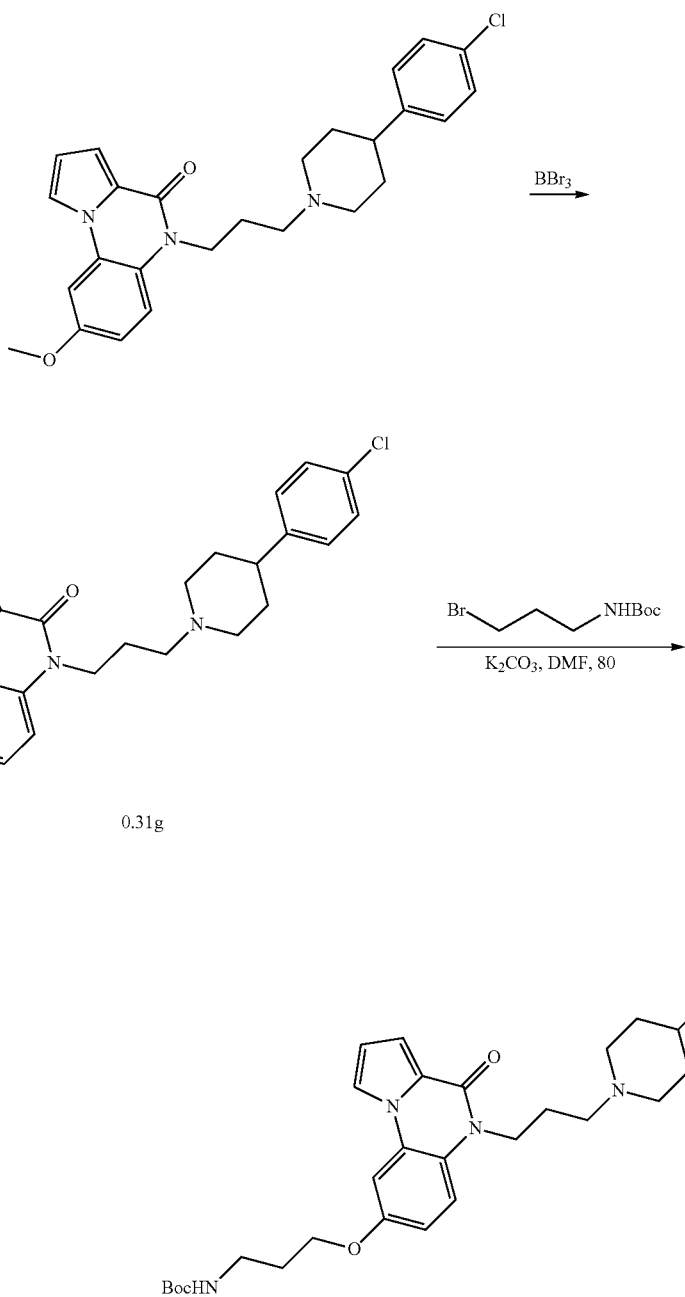
In a non-limiting example, compounds of the invention can be prepared using the methodology illustrated in the scheme below:
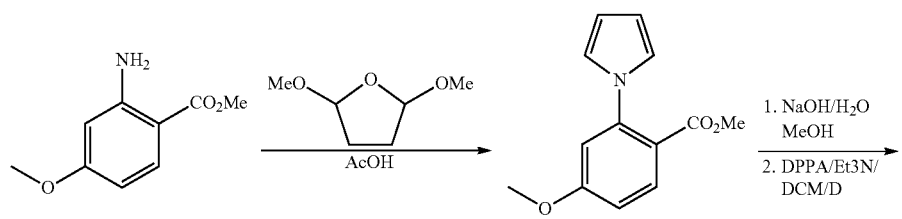

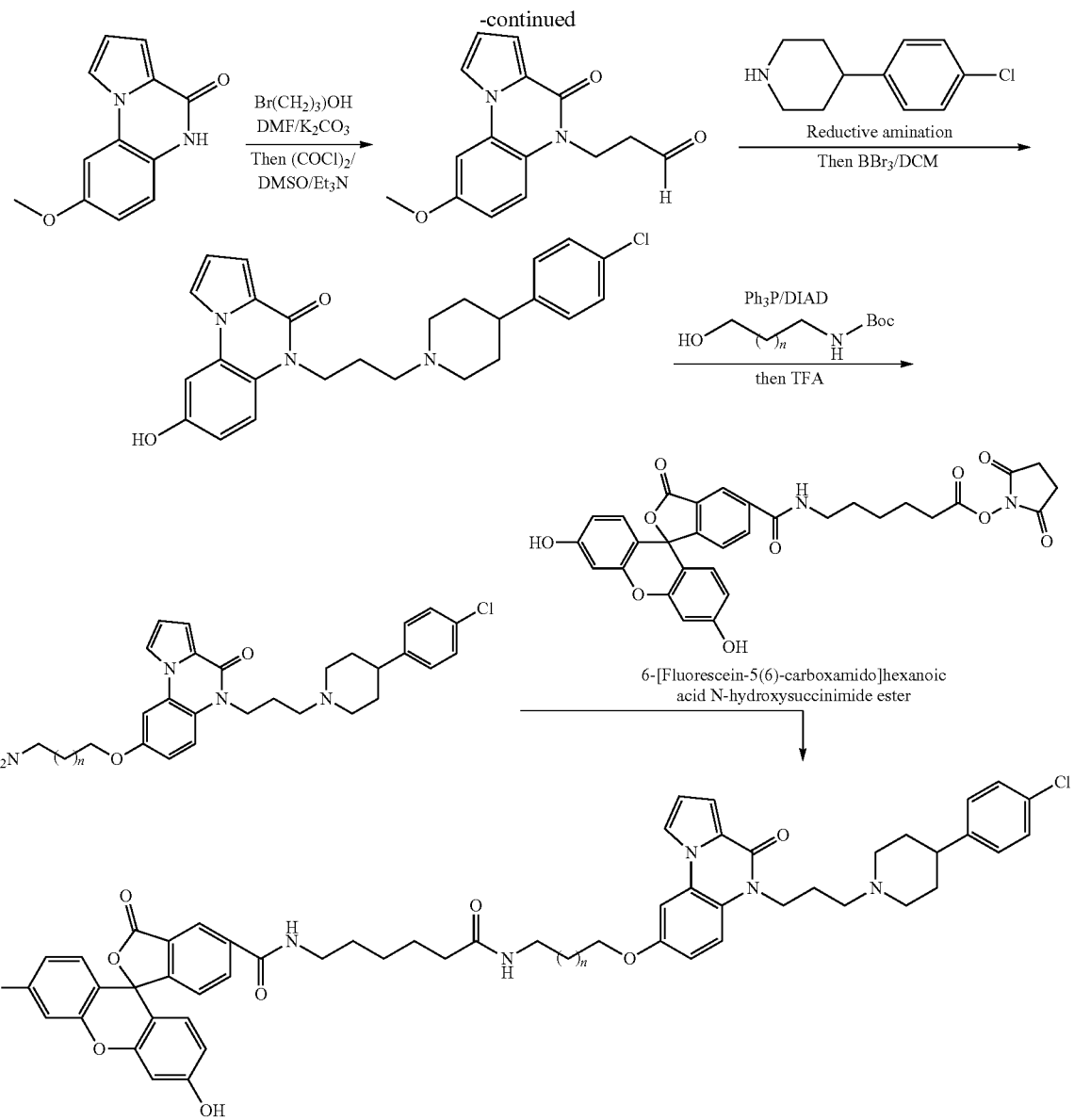

Methods of the Invention

The invention includes a method of preventing or treating metastasis in a subject diagnosed with cancer. The method comprises administering to the subject in need thereof an effective amount of at least one compound of the invention.

The invention further includes a method of detecting a $CX_3R1$-expressing cell in a sample of a subject diagnosed with cancer. The invention further includes a method of identifying a subject diagnosed with cancer that is to be administered a $CX_3R1$ antagonist to treat or prevent metastasis in the subject.

The invention further includes a method of preventing or treating a disease or disorder in a subject. The method comprises administering to the subject in need thereof an effective amount of at least one compound of the invention. In certain embodiments, the disease or disorder comprises central nervous system diseases (such as, but not limited to, HIV Associated Neurocognitive Disorders (HAND), and/or Alzheimer's disease), pain, inflammation (such as, but not limited to, arthritis), cardiovascular disease (such as, but not limited to, undesired vascular smooth muscle proliferation, atherosclerosis, coronary vascular endothelial dysfunction, and/or coronary artery disease), and/or multiple sclerosis.

In certain embodiments, the method comprises contacting a biological sample of a subject diagnosed with cancer with a fluorescent compound of the invention, under conditions whereby, if any $CX_3R1$-expressing cell is present in the sample, the fluorescent compound binds to the $CX_3R1$-expressing cell, thus forming a first system. In other embodiments, any unbound fluorescent compound is removed from the first system. In yet other embodiments, detecting if there is any cell-bound fluorescent compound in the first system, wherein, if a cell-bound fluorescent compound is detected in the first system, the biological sample comprises a $CX_3R1$-expressing cell. In yet other embodiments, the sample is in vitro. In yet other embodiments, the sample is in vivo. In yet other embodiments, the sample is ex vivo. In yet other embodiments, the cell comprises a CTC. In yet other embodiments, the biological sample comprises blood or lymphatic fluid.

In certain embodiments, the subject is subjected to primary surgery related to the cancer. In other embodiments, administration of the compound takes place before, during or after the primary surgery. In yet other embodiments, the cancer includes breast cancer or prostate cancer. In yet other embodiments, the metastasis includes bone metastasis. In yet other embodiments, the administration starts at least 6 months before the primary surgery. In yet other embodiments, the administration starts at least 3 months before the primary surgery. In yet other embodiments, the administration starts at least 1 month before the primary surgery. In yet other embodiments, the administration starts within 1 week after the surgery.

In certain embodiments, the compound is administered by an inhalational, oral, rectal, vaginal, parenteral, topical, transdermal, pulmonary, intranasal, buccal, ophthalmic, intrathecal, or intravenous route of administration. In other embodiments, the subject is a mammal. In yet other embodiments, the mammal is human.

In certain embodiments, fluorescent probe compounds of the invention, once bound to $CX_3CR1$, provide a facile means to rapidly develop binding assays for drug development, high throughput screening, and commercialization of assay kits to expand this field of chemokine research. Currently, only radio-labeled peptide ligands are available for binding assays. These assess only peptide interaction sites that are not necessarily relevant to putative transmembrane binding small molecule antagonists. In addition, $CX_3CR1$ small molecule fluorescent probes act as tools that target $CX_3CR1$ expressing circulating tumor cells (CTCs) and form the basis of assays with significant potential clinical impact on the diagnosis, prognosis, treatment, and monitoring of CTCs as biomarkers drug response in the treatment of metastatic disease.

Combination Therapies

The compounds identified using the methods described here are useful in the methods of the invention in combination with one or more additional compounds useful for treating cancer. These additional compounds may comprise compounds identified herein or compounds, e.g., commercially available compounds, known to treat, prevent, or reduce the symptoms of cancer and/or metastasis.

In one aspect, the present invention contemplates that the agents useful within the invention may be used in combination with a therapeutic agent such as an anti-tumor agent, including but not limited to a chemotherapeutic agent, an anti-cell proliferation agent or any combination thereof. For example, any conventional chemotherapeutic agents of the following non-limiting exemplary classes are included in the invention: alkylating agents; nitrosoureas; antimetabolites; antitumor antibiotics; plant alkyloids; taxanes; hormonal agents; and miscellaneous agents.

Alkylating agents add alkyl groups to many electronegative groups under conditions present in cells, thereby interfering with DNA replication to prevent cancer cells from reproducing. Most alkylating agents are cell cycle non-specific. In specific aspects, they stop tumor growth by cross-linking guanine bases in DNA double-helix strands. Non-limiting examples include busulfan, carboplatin, chlorambucil, cisplatin, cyclophosphamide, dacarbazine, ifosfamide, mechlorethamine hydrochloride, melphalan, procarbazine, thiotepa, and uracil mustard.

Anti-metabolites prevent incorporation of bases into DNA during the synthesis (S) phase of the cell cycle, prohibiting normal development and division. Non-limiting examples of antimetabolites include drugs such as 5-fluorouracil, 6-mercaptopurine, capecitabine, cytosine arabinoside, floxuridine, fludarabine, gemcitabine, methotrexate, and thioguanine.

Antitumor antibiotics generally prevent cell division by interfering with enzymes needed for cell division or by altering the membranes that surround cells. Included in this class are the anthracyclines, such as doxorubicin, which act to prevent cell division by disrupting the structure of the DNA and terminate its function. These agents are cell cycle non-specific. Non-limiting examples of antitumor antibiotics include dactinomycin, daunorubicin, doxorubicin, idarubicin, mitomycin-C, and mitoxantrone.

Plant alkaloids inhibit or stop mitosis or inhibit enzymes that prevent cells from making proteins needed for cell growth. Frequently used plant alkaloids include vinblastine, vincristine, vindesine, and vinorelbine. However, the invent ion should not be construed as being limited solely to these plant alkaloids.

The taxanes affect cell structures called microtubules that are important in cellular functions. In normal cell growth, microtubules are formed when a cell starts dividing, but once the cell stops dividing, the microtubules are disassembled or destroyed. Taxanes prohibit the microtubules from breaking down such that the cancer cells become so clogged with microtubules that they cannot grow and divide. Non-limiting exemplary taxanes include cabazitaxel, paclitaxel, nab-paclitaxel, Hongdoushan A, Hongdoushan B, Hongdoushan C, and docetaxel.

Hormonal agents and hormone-like drugs are utilized for certain types of cancer, including, for example, leukemia, lymphoma, and multiple myeloma. They are often employed with other types of chemotherapy drugs to enhance their effectiveness. Sex hormones are used to alter the action or production of female or male hormones and are used to slow the growth of breast, prostate, and endometrial cancers. Inhibiting the production (aromatase inhibitors) or action (tamoxifen) of these hormones can often be used as an adjunct to therapy. Some other tumors are also hormone dependent. Tamoxifen is a non-limiting example of a hormonal agent that interferes with the activity of estrogen, which promotes the growth of breast cancer cells. Treatment of prostate cancer may also involve hormone treatment (also called androgen deprivation therapy or androgen suppression therapy). Prostate cancer may grow when exposed to the male hormone testosterone and its related hormones, called androgens. Hormone treatment for prostate cancer stops the production of testosterone and all androgens either temporarily or permanently. Drugs can stop the testicles from producing testosterone and protect cells from any other androgens that remain in the body. Hormone medications may include: various hormones such as estrogen to counter the effects of testosterone; drugs that lower testosterone levels or block the activity of male hormones in the body, such as antiandrogen agents, lutenizing hormone-releasing hormone (LHRH) analogs, or agonists, and agents that block the production of androgens by the adrenal glands; combined hormone therapy that decreases testosterone production from the testicles, as well as from glands located on the kidneys, called adrenal glands, that produce hormones. Hormone treatment may also include surgical removal of the testicles (called orchiectomy) where testosterone is produced. This prevents male hormones from further stimulating the growth of the prostate cancer.

Miscellaneous agents include chemotherapeutics such as bleomycin, hydroxyurea, L-asparaginase, and procarbazine that are also useful in the invention.

An anti-cell proliferation agent can further be defined as an apoptosis-inducing agent or a cytotoxic agent. The apoptosis-inducing agent may be a granzyme, a Bcl-2 family member, cytochrome C, a caspase, or a combination thereof. Exemplary granzymes include granzyme A, granzyme B, granzyme C, granzyme D, granzyme E, granzyme F, granzyme G, granzyme H, granzyme I, granzyme J, granzyme K, granzyme L, granzyme M, granzyme N, or a combination thereof. In other specific aspects, the Bcl-2 family member is, for example, Bax, Bak, Bcl-Xs, Bad, Bid, Bik, Hrk, Bok, or a combination thereof. In additional aspects, the caspase is caspase-1, caspase-2, caspase-3, caspase-4, caspase-5, caspase-6, caspase-7, caspase-8, caspase-9, caspase-10, caspase-11, caspase-12, caspase-13, caspase-14, or a combination thereof. In specific aspects, the cytotoxic agent is TNF-α, gelonin, Prodigiosin, a ribosome-inhibiting protein (RIP), *Pseudomonas exotoxin, Clostridium difficile* Toxin B, *Helicobacter pylori* VacA, *Yersinia enterocolitica* YopT, Violacein, diethylenetriaminepentaacetic acid, irofulven, Diptheria Toxin, mitogillin, ricin, botulinum toxin, cholera toxin, saporin 6, or a combination thereof.

In certain embodiments, the methods of the invention further comprise administration of at least one chemotherapeutic agents selected from the group consisting of taxanes (such as but not limited to cabazitaxel, paclitaxel, nab-paclitaxel, Hongdoushan A, Hongdoushan B, Hongdoushan C, and docetaxel), anthracyclines (such as but not limited to doxorubicin (Adriamycin) and epirubicin), 5-fluorouracil, cyclophosphamide, carboplatin, cisplatin, vinorelbine, capecitabine, gemcitabine, ixabepilone, and eribulin. In certain embodiments, administering both a compound of the invention and at least one chemotherapeutic agent allows for a lower dose of the chemotherapeutic agent while maintaining overall efficacy. In other embodiments, the lower dose of the chemotherapeutic agent reduces the cytotoxic side effects of the chemotherapeutic agent.

In certain embodiments, the compounds of the invention can be co-administered with the one or more agents useful for treating cancer. In other embodiments, the compounds of the invention can be co-formulated with the one or more agents useful for treating cancer. In yet other embodiments, the compounds of the invention can be administered to a subject before the one or more agents useful for treating cancer are administered to the subject. In yet other embodiments, the compounds of the invention can be administered to the subject after the one or more agents useful for treating cancer are administered to the subject.

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Pharmaceutical Compositions and Formulations

The invention also encompasses the use of pharmaceutical compositions of at least one compound of the invention or a salt thereof to practice the methods of the invention.

Such a pharmaceutical composition may consist of at least one compound of the invention or a salt thereof, in a form suitable for administration to a subject, or the pharmaceutical composition may comprise at least one compound of the invention or a salt thereof, and one or more pharmaceutically acceptable carriers, one or more additional ingredients, or some combination of these. The at least one compound of the invention may be present in the pharmaceutical composition in the form of a physiologically acceptable salt, such as in combination with a physiologically acceptable cation or anion, as is well known in the art.

In certain embodiments, the pharmaceutical compositions useful for practicing the method of the invention may be administered to deliver a dose of between 1 ng/kg/day and 100 mg/kg/day. In other embodiments, the pharmaceutical compositions useful for practicing the invention may be administered to deliver a dose of between 1 ng/kg/day and 500 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for inhalational, oral, rectal, vaginal, parenteral, topical, transdermal, pulmonary, intranasal, buccal, ophthalmic, intrathecal, intravenous or another route of administration. Other contemplated formulations include projected nanoparticles, liposomal preparations, resealed erythrocytes containing the active ingredient, and immunologically-based formulations. The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In one embodiment, the compositions of the invention are formulated using one or more pharmaceutically acceptable excipients or carriers. In one embodiment, the pharmaceutical compositions of the invention comprise a therapeutically effective amount of at least one compound of the invention and a pharmaceutically acceptable carrier. Pharmaceutically acceptable carriers, which are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it may include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A non-limiting preservative is a combination of about 0.5% to 2.0% benzyl alcohol and 0.05% to 0.5% sorbic acid.

The composition preferably includes an antioxidant and a chelating agent which inhibit the degradation of the compound. Exemplary antioxidants for some compounds are BHT, BHA, alpha-tocopherol and ascorbic acid in the preferred range of about 0.01% to 0.3%, for example BHT in the range of 0.03% to 0.1% by weight by total weight of the composition. The chelating agent may be present in an amount of from 0.01% to 0.5% by weight by total weight of the composition. Exemplary chelating agents include edetate salts (e.g. disodium edetate) and citric acid in the weight range of about 0.01% to 0.20%, for example in the range of 0.02% to 0.10% by weight by total weight of the composition. The chelating agent is useful for chelating metal ions in the composition which may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethyl cellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Administration/Dosing

The regimen of administration may affect what constitutes an effective amount. The therapeutic formulations may be administered to the patient either prior to or after surgical intervention related to cancer. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat cancer in the patient. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.01 and 50 mg/kg of body weight/per day. One of ordinary skill in the art would be able to study the relevant factors and make the determination regarding the effective amount of the therapeutic compound without undue experimentation.

The compound can be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, the type and age of the animal, etc.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of cancer in a patient.

In one embodiment, the compositions of the invention are administered to the patient in dosages that range from one to five times per day or more. In another embodiment, the compositions of the invention are administered to the patient in range of dosages that include, but are not limited to, once every day, every two, days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physical taking all other factors about the patient into account.

Compounds of the invention for administration may be in the range of from about 1 mg to about 7,500 mg, about 20 mg to about 7,000 mg, about 40 mg to about 6,500 mg, about 80 mg to about 6,000 mg, about 100 mg to about 5,500 mg, about 200 mg to about 5,000 mg, about 400 mg to about 4,000 mg, about 800 mg to about 3,000 mg, about 1 mg to about 2,500 mg, about 2 mg to about 2,000 mg, about 5 mg to about 1,000 mg, about 10 mg to about 750 mg, about 20 mg to about 600 mg, about 30 mg to about 500 mg, about 40 mg to about 400 mg, about 50 mg to about 300 mg, about 60 mg to about 250 mg, about 70 mg to about 200 mg, about 80 mg to about 150 mg, and any and all whole or partial increments therebetween.

In some embodiments, the dose of a compound of the invention is from about 0.5 mg and about 5,000 mg. In some embodiments, a dose of a compound of the invention used in compositions described herein is less than about 5,000 mg, or less than about 4,000 mg, or less than about 3,000 mg, or less than about 2,000 mg, or less than about 1,000 mg, or less than about 800 mg, or less than about 600 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of cancer in a patient.

The term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing cancer in a patient.

Routes of Administration

Routes of administration of any of the compositions of the invention include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin. Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

Topical Administration

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

Buccal Administration

A pharmaceutical composition of the invention may be prepared, packaged, or sold in a formulation suitable for buccal administration. Such formulations may, for example, be in the form of tablets or lozenges made using conventional methods, and may contain, for example, 0.1 to 20% (w/w) of the active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein. The examples of formulations described herein are not exhaustive and it is understood that the invention includes additional modifications of these and other formulations not described herein, but which are known to those of skill in the art.

Rectal Administration

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

Controlled- or sustained-release formulations of a pharmaceutical composition of the invention may be made using conventional technology. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gelcaps, and caplets, which are adapted for controlled-release are encompassed by the present invention.

Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood level of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water, or other physiological conditions or compounds. The term "controlled-release component" in the context of the present invention is defined herein as a compound or compounds, including, but not limited to, polymers, polymer matrices, gels, permeable membranes, liposomes, or microspheres or a combination thereof that facilitates the controlled-release of the active ingredient.

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In a preferred embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Materials and Methods
Materials

Unless otherwise noted, all starting materials and resins were obtained from commercial suppliers and used without purification.

Cell Lines and Cell Cultures

MDA-MB-231 (MDA-231) human and 4T-1 murine breast cancer cell lines were purchased from ATCC and cultured in Dulbecco's Modified Eagle Medium (DMEM, Invitrogen) or RPMI-1640, respectively, supplemented with 10% fetal bovine serum (Hyclone) and 0.1% gentamicin (Invitrogen). All cell lines were cultured at 37° C. and 5% $CO_2$. Starting from the original vials from ATCC, each cell line was expanded and frozen in different aliquots that were used for not more than 10 passages and not longer than 2 months following resuscitation. Control for Mycoplasma contamination and cell authentication by Single Tandem Repeat were performed by IDEXX Radil. Each cell line was genetically engineered to stably express Green Fluorescent Protein (GFP) by transduction with a proprietary lentiviral vector (Addgene) in DMEM for 24 hours.

SDS-PAGE and Western Blotting

Cell lysates were obtained using a single detergent lysis buffer containing DTT, phosphatase inhibitor cocktail (Calbiochem), protease inhibitor cocktail (Calbiochem) and Igepal CA-630 (Sigma-Aldrich). Protein concentrations of cellular lysates were determined using a BCA protein assay (Pierce). Samples containing equivalent amounts of protein were resolved by SDS-PAGE using 10% polyacrylamide gels and then transferred onto Immobilon PVDF membranes (Millipore Corporation). Membranes were blocked for one hour at room temperature with 0.1% Tween-20/TBS with 5% (w/v) powdered milk. CX3CR1 was detected using a primary antibody (AB8021, Abcam) used at 0.5 mg/ml, diluted in 0.1% Tween-20, 5% dry milk in TBS and incubated overnight at 4° C. A secondary, HRP-conjugated antibody (Pierce) was used at 10 ng/ml. Blotted membranes were processed with SuperSignal Femto chemiluminescence substrates (Pierce) and visualized using a FluorChem imaging system (ProteinSimple).

Pharmacokinetic Studies for Compound XXII

Figure 6A:
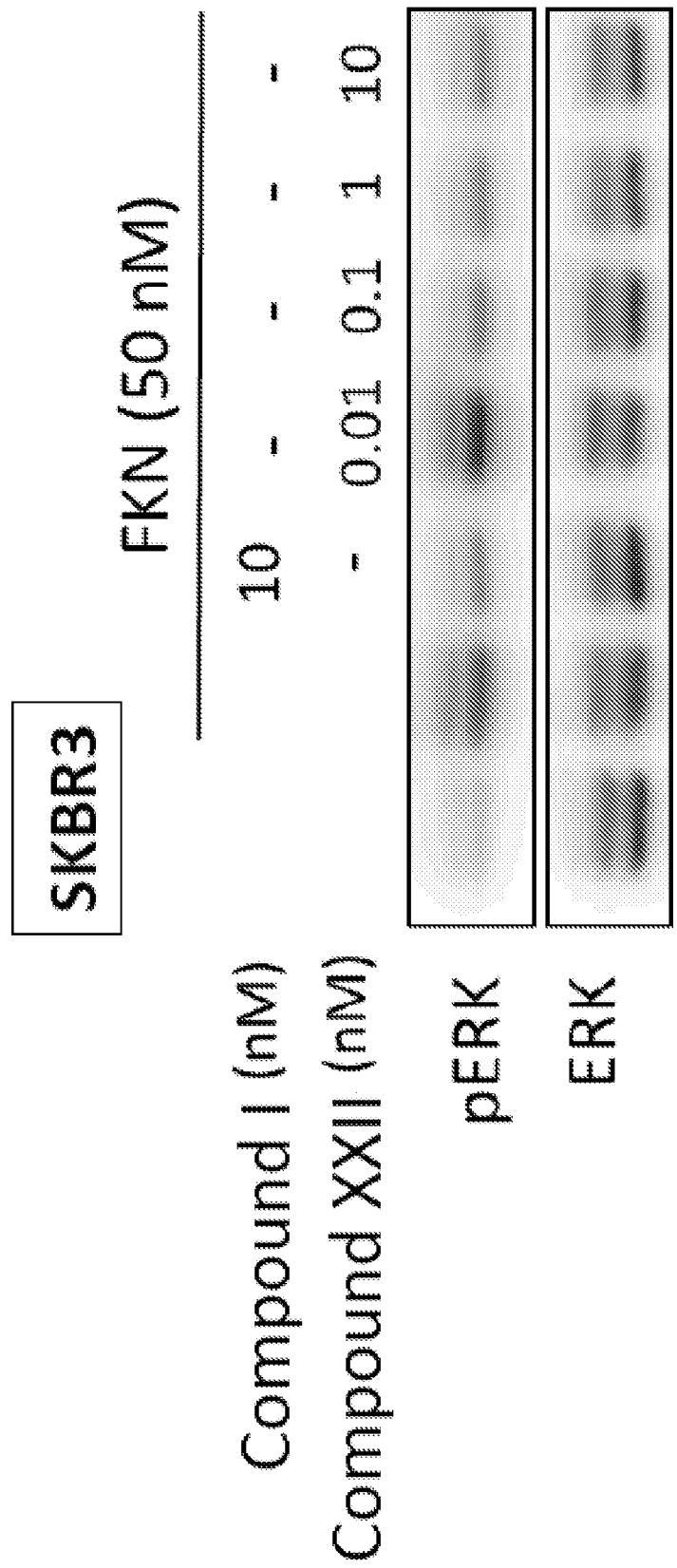
FIGS. 6A-6C comprise Western blots showing inhibition by Compounds I and XXII of ERK phosphorylation induced by soluble FKN.
Figure 6B:
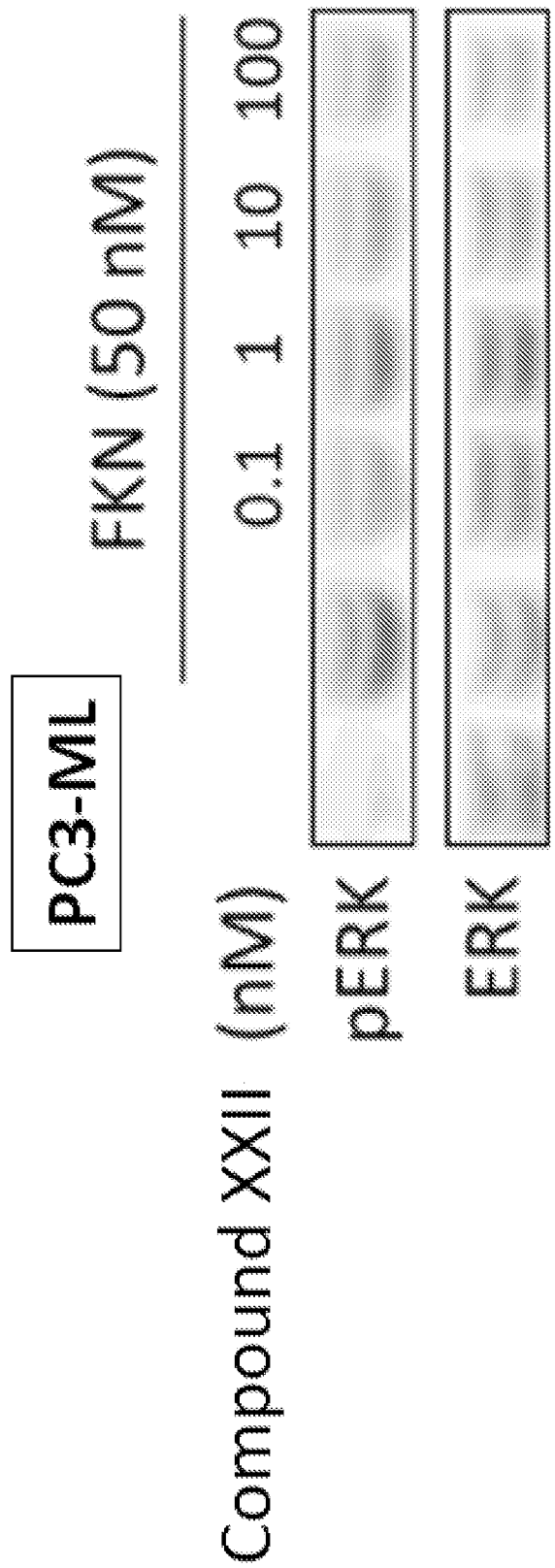
Figure 6C:
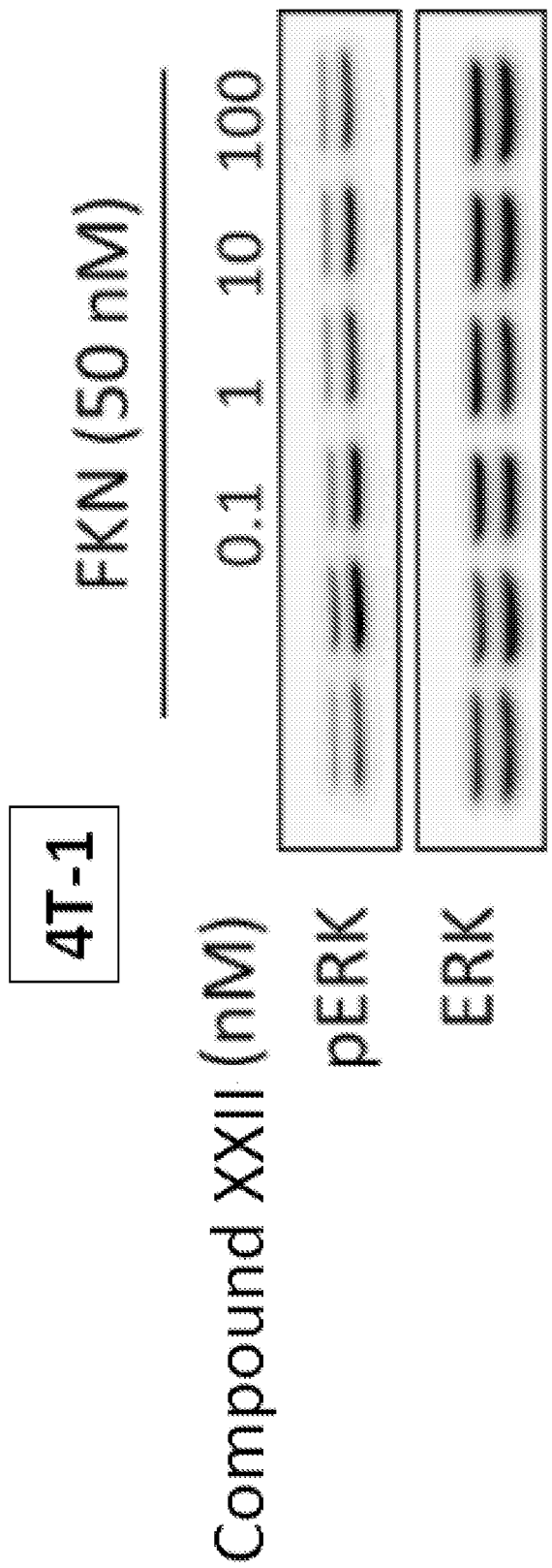

The $EC_{50}$ for Compound XXII—as measured by inhibition of MAPK activation induced by cell stimulation with 50 nM Fractalkine and assessed by Western Blotting analysis—was found similar to that reported for Compound I (FIGS. 6A-6C). For pharmacokinetic studies, mice were administered via intraperitoneal (i.p.) route with 10 mg/kg of Compound XXII in 10% dimethylacetamide (DMAC), 10% tetraethylene glycol and 10% Solutol HS15 in sterile ddH2O. Animals were then anesthetized as described above and 300 µl of blood samples were collected by cardiac puncture at the designated time points and transferred in K2EDTA tubes. Blood samples were placed on ice and tested after dilution. The measurement of Compound XXII concentrations in blood was outsourced to Alliance Pharma. The results showed that this compound reached a plasma concentration of ~200 ng/ml one hour after administration, which declined to 60 ng/ml at six hours. These concentrations are in the high micromolar range for this compound, several folds above its measured EC50 in vitro.

Animal Models of Metastasis

Female SCID mice (Taconic CB17-SCRF, ~20 g body weight) were housed in a germfree barrier. At 6 weeks of age, mice were anesthetized with a mixture of ketamine (80 mg/kg) and xylazine (10 mg/kg). Tumor cells (2.5×104 MDA-231 or 5×103 4T-1) were delivered as a 100 µl suspension of serum-free culture medium by carefully accessing the left ventricle of the heart through the chest with an insulin syringe mounting a 30-gauge needle. After intracardiac injection, the experimenter distributed each animal in unlabeled cages. Each cage was randomly assigned to different treatment groups by a second experimenter.

Model of Tumor Seeding

Animals were treated i.p. with Compound XXII dissolved in 4% DMSO, 4% Cremophor EL (Kolliphor E L, Sigma-Aldrich, MO) in sterile PBS or vehicle one-hour prior and three hours after being injected with cancer cells. The dosing regimen was selected based on results from pharmacokinetic analyses. Mice were sacrificed 24 hours post-injection. Validation of the intracardiac delivery of cancer cells was performed as previously described 10. For the detection and enumeration of single cancer cells, the experimenter was not blinded but was assisted by the Nuance FX multiplex imaging software (see below). A fluorescence image was acquired for each tissue section analyzed, approximately 36 serial sections spanning the entire width of each knee-joint. The identification and enumeration of single cells was obtained by three different experimenters, including the Principal Investigator, and occasional discrepancies reconciled prior to compiling the final data.

Model of Metastatic Disease

One week after intracardiac injection, animals were randomly assigned to control and treated group and then imaged for tumors in the skeleton and soft-tissue organs. Vehicle or Compound XXII (10 mg/kg) were administered i.p. twice/day, for the entire duration of the study and animals were imaged weekly. Doxorubicin was purchased from LEK Laboratories (D5794), dissolved in PBS at 1 mg/ml and stored at −20° C. before use. All experiments were performed in agreement with NIH guidelines for the humane use of animals. The Drexel University College of Medicine Committee approved all protocols involving the use of animals for the Use and Care of Animals.

Labeling of Cancer Cells with CM-Dil

The CellTracker™ CM-Dil (ThermoFisher Scientific) was diluted as 50 µg in 50 µl of DMSO to prepare a stock solution. Immediately before use, the stock solution was diluted with D-PBS to a 1 µM working solution. Cells were exposed to the working solution at 37° C. for 5 minutes and then at 4° C. for 15 minutes and then washed with PBS followed by F-12 cell culture medium.

In Vivo Bioluminescence Imaging

MDA-231 cells were stably transduced with the pLeGo-IG2-Luc2 vector. Prior to imaging, animals were injected i.p. with 150 mg/kg of D-luciferin (ViVoGlo, Promega) and anesthetized using 3% isoflurane. Animals were then transferred to the chamber of an IVIS Lumina XR (PerkinElmer) where they received 2% isoflurane throughout the image acquisition. Fifteen minutes after injection of the substrate, five-minute exposures of both dorsal and ventral views were obtained and quantification and analysis of bioluminescence was performed using the Living Image software.

Processing of Animal Tissues

Bones and soft-tissue organs were collected and fixed in 4% paraformaldehyde solution (Electron Microscopy Sciences) for 24 hours and then transferred into fresh formaldehyde for additional 24 hours. Soft-tissue organs were then placed either in 30% sucrose for cryoprotection or 1% paraformaldehyde for long-term storage. Bones were decalcified in 0.5M EDTA (Fisher Scientific) for 7 days followed by incubation in 30% sucrose. Tissues were maintained at 4° C. for all aforementioned steps and frozen in O.C.T. medium (Sakura Finetek) by placement over dry-ice chilled 2-methyl butane. Soft-tissue organs as well as knee joints (femora and tibiae) were processed to obtain serial frozen sections, 80 µm in thickness, using a Microm HM550 cryostat 44. All sections spanning the entire bone width of femur and tibia were inspected to obtain either accurate enumeration of DTCs or visualization and measurement of tumor foci in the inoculated animals.

Fluorescence Microscopy and Morphometric Analysis of Metastases

Fluorescent images of tumor cells and skeletal metastases were acquired using an Axio Scope.A1 microscope (Zeiss) connected to a Nuance Multispectral Imaging System (PerkinElmer). Digital images were analyzed and processed using the Nuance Software (v. 2.4). Microscope and software calibration for size measurement is regularly performed using a TS-M2 stage micrometer (Oplenic Optronics).

Enumeration and Collection of CTCs from Mouse Blood

Blood was withdrawn by cardiac puncture. AMD-3100 was purchased from Selleckchem (S8030) dissolved in PBS at 1 mg/ml and at −20° C. before use. Tumor-bearing animals were anesthetized as described above and 200-250 μl of systemic blood was collected at the designated time points and transferred in K2EDTA tubes. Blood samples were placed on ice, diluted using a saline buffer (0.5% BSA, 2% EDTA in PBS) at a 1:8 ratio and then filtered through a 70 μm cell strainer immediately prior to achieve a label-free, microfluidic isolation of CTCs. For enumeration, the Captor® system (Clearbridge Biomedics, Singapore) was used, which allows visualization of individual CTCs trapped into crescent-shape microwells. Following complete flowing of the diluted blood, the CTChip® was transferred to the stage of an inverted fluorescent microscope and all trapped CTCs were counted. For the recovery of fully viable CTCs we used the ClearCell® FX system (Clearbridge Biomedics, Singapore), which employs the CTChip® FR1 to isolate cancer cells from blood cells based on size, deformability and inertia through a Dean Flow Fractionation process.

qRT-PCR for Viability Assessment of CTCs

CTCs were lysed on the same microfluidic chip used for capture using an ice-cooled RNA lysis buffer (Norgen Bioteck Corp.). TaqMan RNA-to-Ct 1-step kit (cat.4392653) was used with an Applied Biosystem 7900HT Fast Real-Time PCR system. Genespecific primers and probe sets were purchased from Applied Biosystem.

Statistical Analysis

One-way Anova with Dunnett's post-test was used to compare multiple experimental groups. Student's t-test with Welch's correction (GraphPad Prism 5.0) was used to compare two experimental groups assuming no equal variance. Log-rank (Mantel-Cox) test was used for comparison of survival curves.

Example 1: Inhibition of CX3CR1 Signaling In Vitro

In a first set of experiments, SKBR3 human breast cancer cells were incubated with 15 μg/ml of a neutralizing antibody for CX3CR1 (TP-502, Torrey Pines Biolabs) or to different concentrations of Compound I (5-(3-(4-(4-chlorophenyl)piperidin-1-yl)propyl)pyrrolo[1,2-a]quinoxalin-4(5H)-one) for 30 minutes at 37° C. prior to be exposed to human recombinant Fractalkine (50 nM) for 5 minutes.

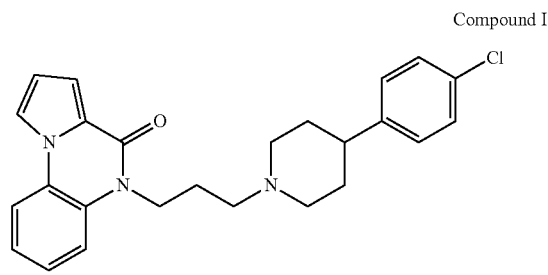 [SMILES: O=c1c2cccn2c2ccccc2n1CCCN1CCC(c2ccc(Cl)cc2)CC1]

Compound I

At the end of the experiment, total cell lysates were obtained using a single detergent lysis buffer containing DTT, phosphatase inhibitor cocktail (Calbiochem), protease inhibitor cocktail (Calbiochem) and Igepal CA-630 (Sigma-Aldrich). Protein concentrations of cellular lysates were determined using a BCA protein assay (Pierce). Samples containing equivalent amounts of protein were resolved by SDS-PAGE using 10% polyacrylamide gels and then transferred onto Immobilon PVDF membranes (Millipore Corporation). Membranes were blocked for one hour at room temperature with 0.1% Tween-20/TBS with 5% (w/v) powdered milk. The activation of the ERK signaling pathway was detected with rabbit phospho-ERK and total-ERK antibodies (Cell Signaling Technology) used at 10 ng/ml. Primary antibodies were diluted in 0.1% Tween-20/TBS and incubated overnight at 4° C. A secondary, HRP-conjugated antibody (Pierce) was used at 10 ng/ml. Blotted membranes were processed with SuperSignal Femto chemiluminescence substrates (Pierce) and visualized using a FluorChem imaging system (ProteinSimple).

Figure 1B:
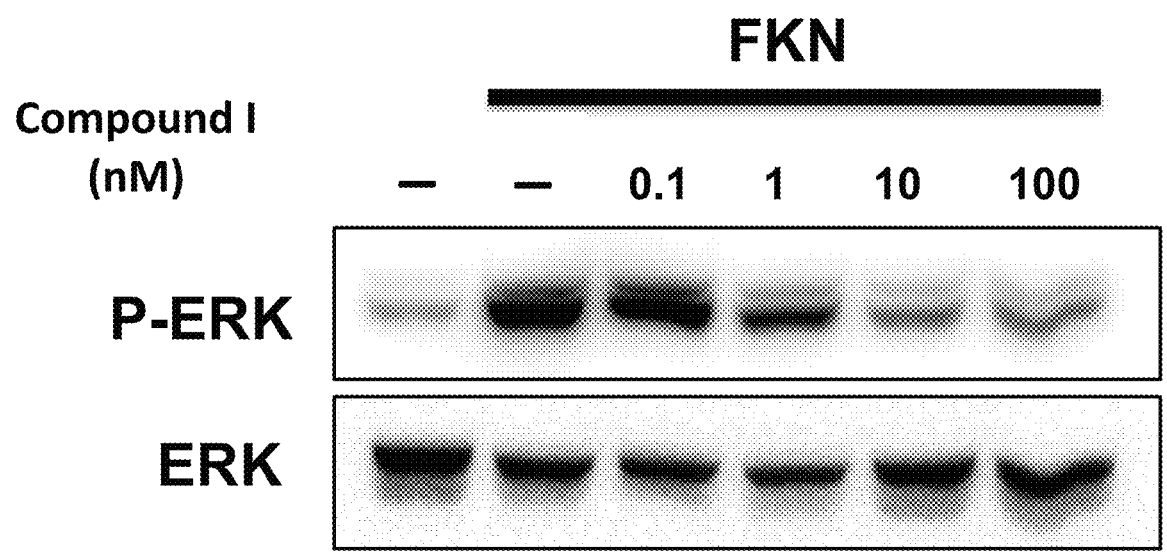
FIG. 1B comprises a set of images of representative Western blot assays illustrating that Compound I caused a dose-dependent inhibition of ERK phosphorylation in SKBR3 breast cancer cells exposed to 50 nM FKN.

FIGS. 1A-1B illustrate that in human breast cancer cells the CX3CR1 neutralizing antibody clearly inhibited downstream signaling from the chemokine receptor to the ERK pathway (FIG. 1A); similarly, Compound I showed a dose-dependent inhibition of the same pathway (FIG. 1B).

Example 2: Effects of CX3CR1 Inhibition Measured In Vivo

Effects of CX3CR1 Inhibition of Tumor Seeding.

When cancer cells spread from a primary tumor or an existing metastatic tumor to other sites, they re-enter the blood circulation thus becoming Circulating Tumor Cells (CTCs) and upon seeding in a tissue they convert into Disseminated Tumot Cells (DTCs). For the pre-clinical experiments evaluating how $CX_3CR1$ inhibition would affect the number of DTCs in the skeleton, $CX_3CR1$ was targeted with three different approaches: a) A neutralizing antibody pre-incubated with human breast cancer cells prior to their grafting into experimental animals; b) genetic silencing of $CX_3CR1$ based on CRISPRi technology using a deactivated Cas9; c) administration of Compound I via the intraperitoneal route before and after the grafting of human cancer cells.

For the experiment, MDA-231 human breast cancer cells were genetically engineered to stably express Green Fluorescent Protein (GFP) by transduction with a proprietary lentiviral vector (Addgene) in DMEM for 24 hours. The stable silencing of $CX_3CR1$ in the same cells was achieved as follows: $CX_3CR1$-specific sgRNAs were expressed using a lentiviral U6-based expression vector carrying a puromycin-resistant gene (Addgene, 52963). The sgRNA expression plasmids were cloned by inserting annealed CX3CR1 oligos (5'-CACCGCTGCACGGTCCGGTTGTTCA-3', SEQ ID NO: 1; and 3'-CGACGTGCCAGGCCAACAAGT-5', SEQ ID NO:2) into the lentiviral expression vector that was digested by BsmBI. Lentiviral expression vector of the human codon-optimized, nuclease-deficient Cas9 (dCas9) protein fused with transcription suppressor KRAB domain was purchased from Addgene (Addgene, 46911).

Animal Model of Tumor Seeding:

SCID mice (Taconic CB17-SCRF, ~25 g body weight) were housed in a germ-free barrier. At 6 weeks of age, mice were anesthetized with a mixture of ketamine (80 mg/kg) and xylazine (10 mg/kg). Tumor cells were delivered as a 100 µl suspension of serum-free culture medium by carefully accessing the left ventricle of the heart through the chest with an insulin syringe mounting a 30-gauge needle. MDA-231 cells in suspension were exposed to either a $CX_3CR1$ neutralizing antibody (15 µg/ml, Torrey Pines Biolabs) or Compound I (10 nM in 0.1% DMSO) for 30 minutes (10 minutes at room temperature plus 20 minutes on ice), before being delivered to mice in the same preincubation suspension to maximize target engagement. Species- and class-matched irrelevant immunoglobulins (Rabbit IgG, 15 µg/ml, Jackson ImmunoResearch) or DMSO were used for the control groups. For the experiments requiring administration of Compound I, animals were then treated i.p. with the $CX_3CR1$ antagonist dissolved in 4% DMSO, 4% Cremophor EL (Kolliphor E L, Sigma-Aldrich, MO) in sterile $ddH_2O$ or just vehicle twice, one-hour prior and three hours after being injected with cancer cells. The dosing regimen was selected based on results from pharmacokinetic analyses. Mice were killed 24 hours post-injection. Blue-fluorescent beads, 10 µm-polystyrene in diameter (Invitrogen-Molecular Probes) were included in the injection medium and visualized by fluorescence microscopy to validate injection efficiency. Mice showing non-homogenous distribution of or lacking fluorescent beads in tissue sections of lungs and kidneys were removed from the study. Finally, for the experiments with human breast cancer cells with CX3CR1 stably silenced, the animals were grafted with the cell suspension via the intracardiac route and sacrificed 24 hours later without any additional treatment.

Processing of Mouse Tissues.

Figure 2:
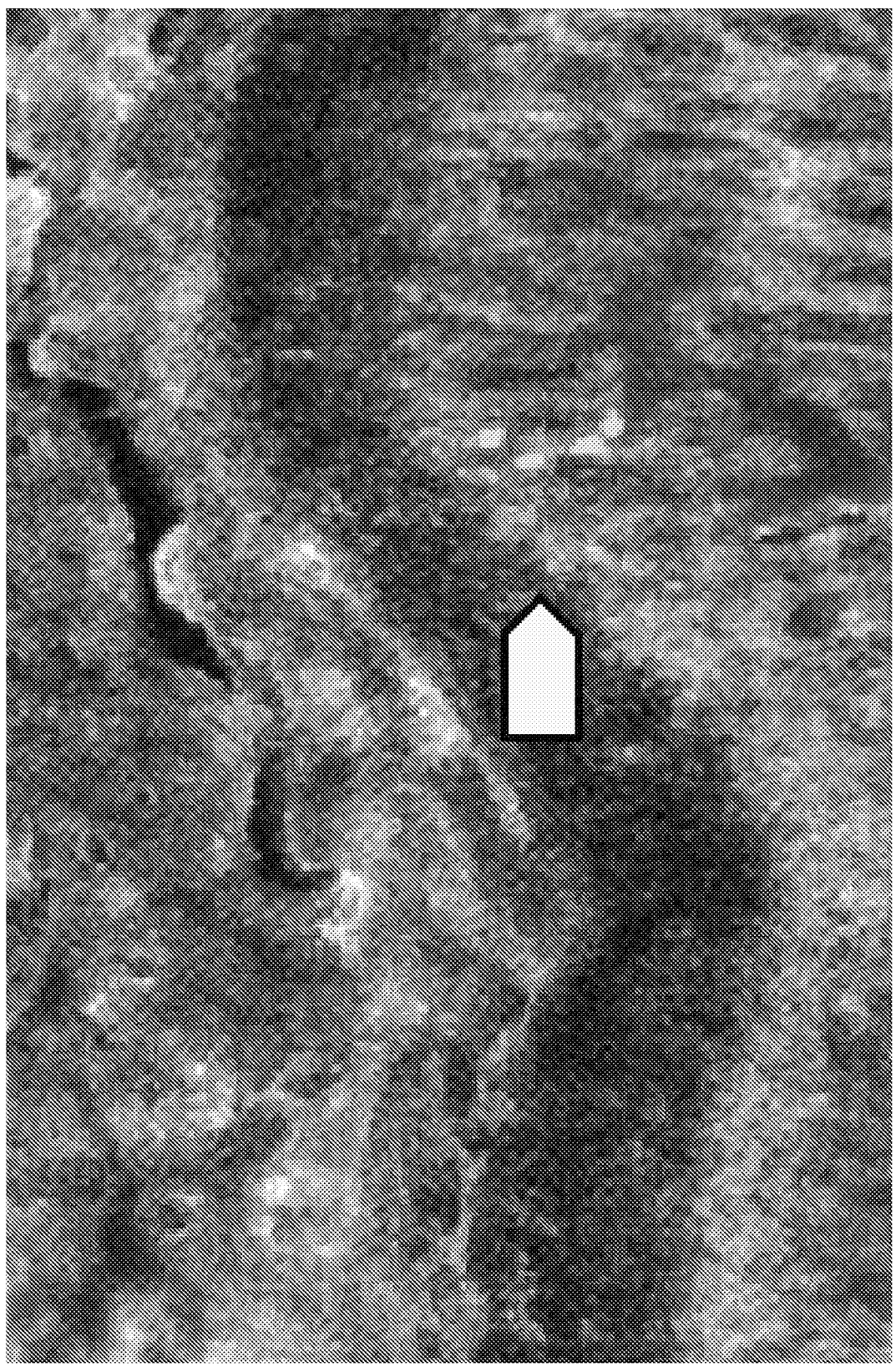
FIG. 2 comprises an image depicting a cluster of single breast cancer cells disseminated to the skeleton of mice and detected by multispectral fluorescence microscopy of bone tissue sections.

Bones and soft-tissue organs were collected and fixed in 4% paraformaldehyde solution (Electron Microscopy Sciences) for 24 hours and then transferred into fresh formaldehyde for additional 24 hours. Soft-tissue organs were then placed either in 30% sucrose for cryoprotection or 1% paraformaldehyde for long-term storage. Bones were decalcified in 0.5M EDTA (Fisher Scientific) for 7 days followed by incubation in 30% sucrose. Tissues were maintained at 4° C. for all aforementioned steps and frozen in O.C.T. medium (Sakura Finetek) by placement over dry-ice chilled 2-methylbutane. Soft-tissue organs as well as knee joints (femora and tibiae) were processed to obtain serial frozen sections, 80 m in thickness, using a Microm HM550 cryostat. All sections spanning the entire bone width (approximately 32 for femur and tibia) were inspected to obtain the accurate enumeration of DTCs and visualization and measurement of tumor foci in the inoculated animals (FIG. 2).

Fluorescence Microscopy and Morphometric Analysis of Isolated Tumor Cells and Tumors.

Fluorescent images of skeletal metastases were acquired using an Axio Scope.A1 microscope (Zeiss) connected to a Nuance Multispectral Imaging System (PerkinElmer). Digital images were analyzed and processed using the Nuance Software (v. 2.4). Microscope and software calibration for size measurement is regularly performed using a TS-M2 stage micrometer (Oplenic Optronics).

Figure 3A:
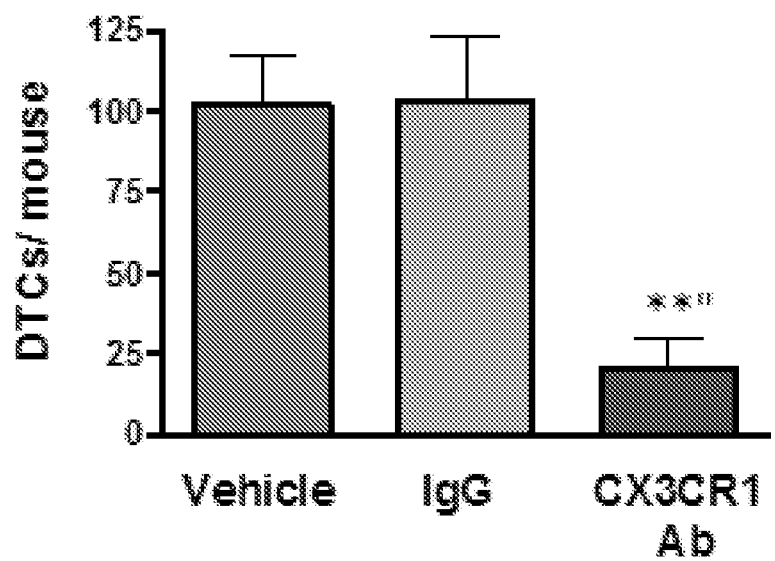
FIG. 3A comprises a bar graph illustrating that pre-incubation of cells with a neutralizing antibody, the same one tested in FIG. 1A, prior to IC inoculation in mice dramatically reduced the number of fluorescent MDA-231 cells detected in the knee joints 24 hours post-inoculation, as compared to animals that received cells pre-incubated with either vehicle or an irrelevant immunoglobulin (Vehicle: n=6; IgG: n=7; CX3CR1-Ab: n=6. **p<0.01).
Figure 3B:
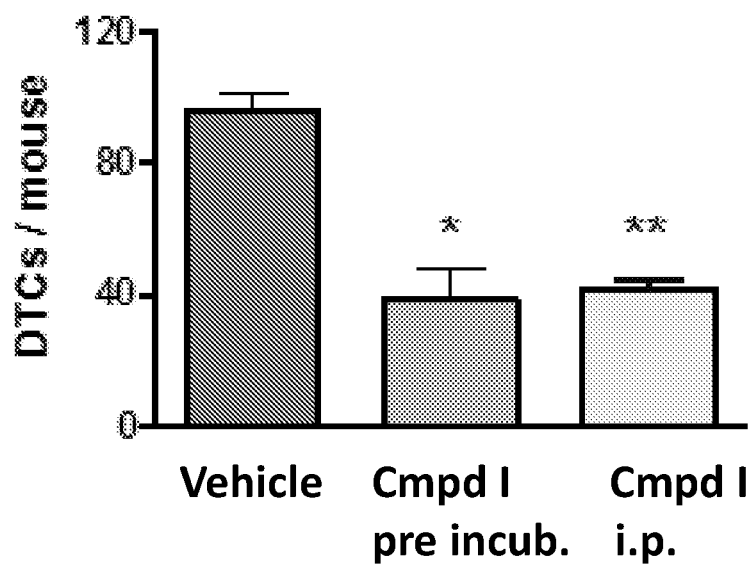
FIG. 3B comprises a bar graph illustrating MDA-231 cells either pre-incubated with 10 nM Compound I prior to IC inoculation in mice or inoculated in animals administered with the same compound at 10 mg/Kg i.p. Both pre-incubation and i.p. administration of Compound I showed comparable and significant decrease in skeletal disseminated breast tumor cells as detected 24 hours after IC inoculation (Vehicle: n=8; Compound I pre-incubation: n=7; Compound I i.p.: n=8. *p=0.0001;  p<0.0001).
Figure 3C:
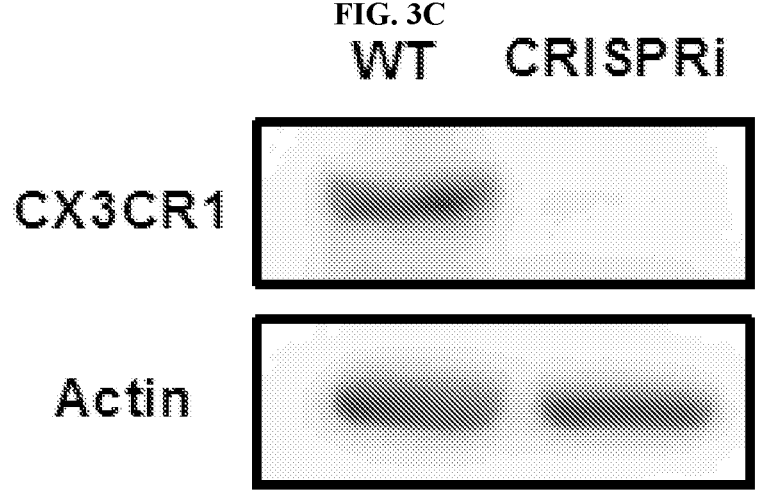
FIG. 3C comprises a set of images illustrating the effective silencing of CX3CR1 in MDA-231 cells by CRISPRi and confirmed by Western blotting.
Figure 3D:
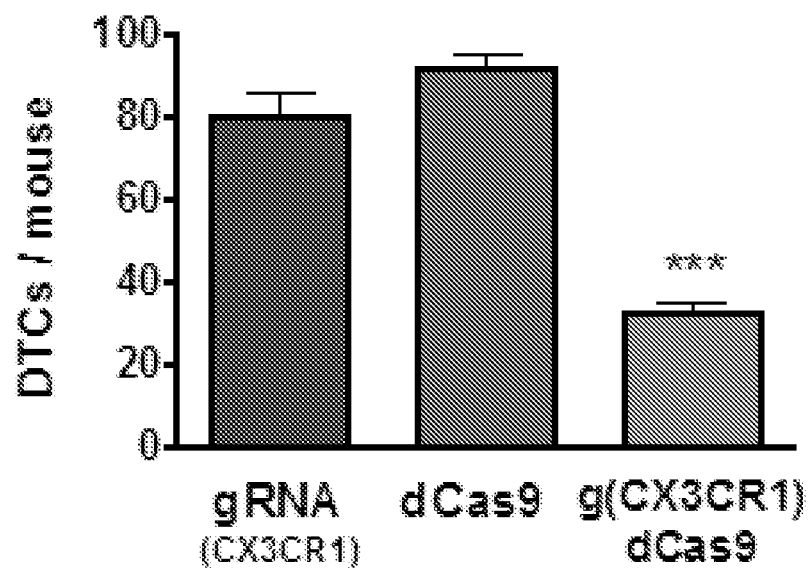
FIG. 3D comprises a bar graph illustrating that when CX3CR1-silenced cells were inoculated in mice, the number of disseminated breast tumor cells detected in bone was significantly reduced (gRNA: n=3; dCas9: n=3; g(CX3CR1)dCas9: n=5. * p<0.001).

Blocking $CX_3CR1$ with the neutralizing antibody reduced DTCs in the skeleton of inoculated animals by approximately 80% as compared to the same cells exposed to either vehicle or a species- and isotype-matched irrelevant immunoglobulin (FIG. 3A). Pharmacokinetic evaluation of Compound I administered to mice at a dose of 10 mg/Kg (i.p.) produced drug levels of 89 ng/ml (210 nM) in blood measured one hour after dosing, which corresponds to a 20-fold increase over the lowest fully effective dose of this compound in vitro (10 nM). Thus, a first group of mice received MDA-231 cancer cells pre-incubated with 10 nM Compound I, whereas a second group of animals was dosed with Compound I (10 mg/Kg; i.p.) twice, one hour prior and three hours after the IC inoculation of cancer cells, to maximize target engagement. Remarkably, both experimental groups showed a reduction in DTCs of approximately 60% as compared to control animals treated with vehicle (FIG. 3B). As final target validation, $CX_3CR1$ transcription was silenced in MDA-231 cells by CRISPRi, which completely abrogated CX3CR1 protein expression in vitro (FIG. 3C). When these cells were injected in mice via the IC route, the reduction in skeletal DTCs observed was fully comparable to that previously obtained with the antibody-neutralization of CX3CR1 (FIG. 3D). Control cells expressing only the guidance RNA (gRNA) or a deactivated Cas9 (dCAS9) disseminated to the skeleton with efficacy comparable to wild-type MDA-231 cells (compare with FIG. 3A-3B).

Effects of $CX_3CR1$ Inhibition on the Cross-Seeding of Existing Metastatic Tumors to Other Sites and on the Growth of Established Metastases.

Figure 4A:
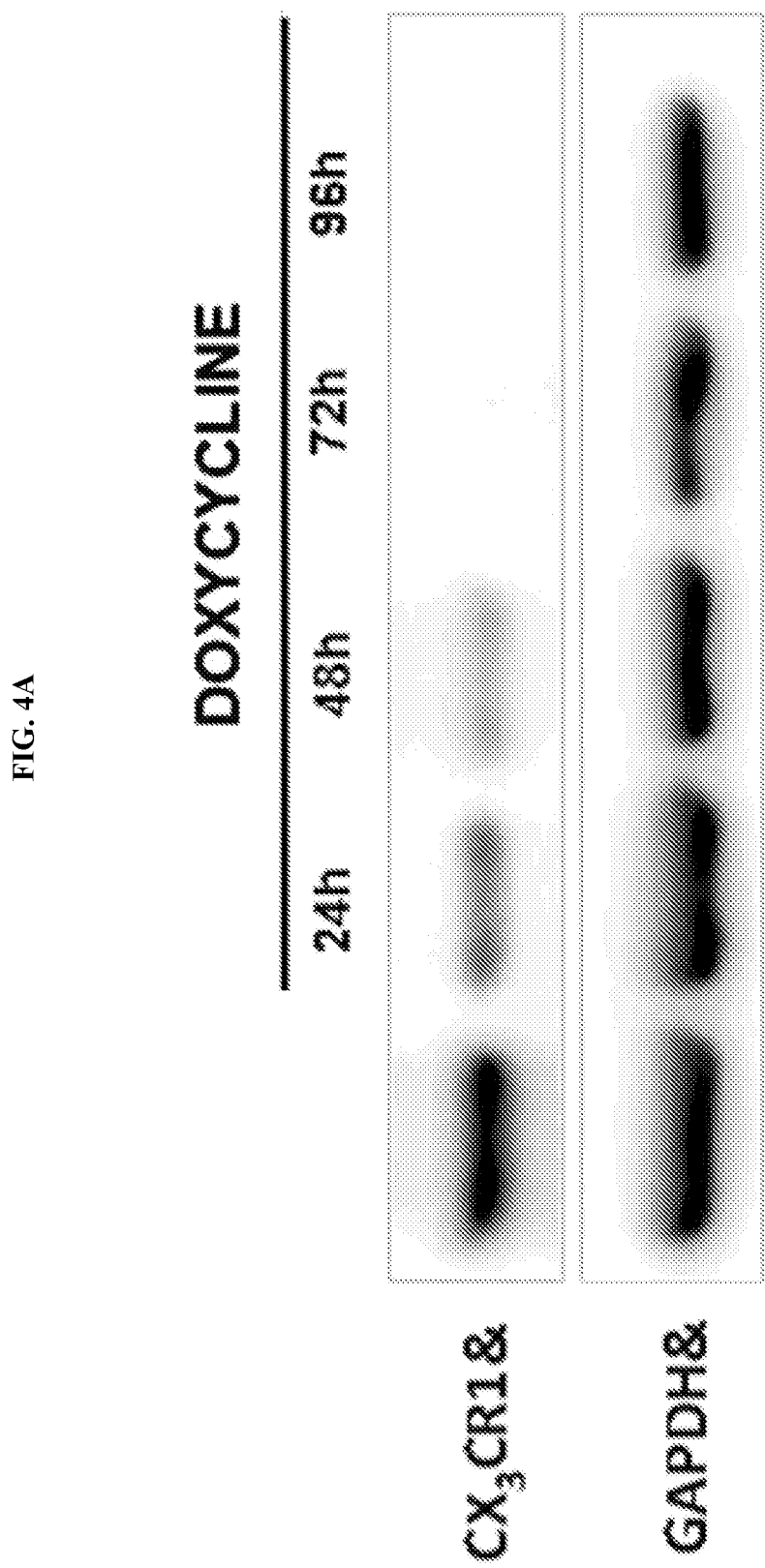
FIG. 4A comprises a set of images depicting a Western blot illustrating the conditional silencing of CX3CR1 by an inducible-CRISPRi system. Complete protein repression was achieved 72 hours after exposing cells to 2 µg/ml of doxycycline in vitro.

With these experiment, it was sought to replicate a common clinical scenario in which breast cancer patients present with early metastatic lesions, years after successful treatment of their primary tumor by local modalities. Despite treatment, these patients eventually and inevitably progress, presenting with a surge in tumor burden due to multiplication of metastatic lesions by cross-seeding. To this end, mice were IC injected with MDA-231 cells expressing a regulatable CRISPRi system for $CX_3CR1$, established as follows: A Tet-regulatable dCas9-KRAB lentiviral expression vector carrying a neomycin-resistant gene was also purchased from Addgene (Addgene Plasmid 50917). HEK293T cells were maintained in Dulbecco's Modified Eagle Medium supplemented with 10% fetal bovine serum. For lentivirus generation, HEK293T cells were split and plated at $1.3 \times 10^5$ cells/$cm^2$. The following day, packaging plasmids (pCMV R8.74; pMD2.G) and dCas9-, Tet-regulatable dCas9 or sgRNA-coding plasmids were transfected using lipofectamine 2000 in Opti-MEM according to the manufacturer's instructions. Viruses were harvested 48 hours after transfection and incubated with MDA-231 cells expressing both GFP and luciferase in the presence of polybrene. Transduced cells were selected using G418 (1000 µg/ml) or puromycin (1.5 µg/ml) for 3 weeks. Tet-regulatable dCas9 expression was induced in vitro by adding 2 µg/ml doxycycline to complete culture medium. This system was first validated in vitro, providing a complete ablation of protein expression by 72 hours after administration of doxycycline (FIG. 4A). To replicate the onset of metastatic disease observed in the clinic, animals were inoculated with human breast cancer cells via the intracardiac route and the left untreated until one week later, when bioluminescence imaging showed small tumors in skeleton and soft-tissues. At this stage, animals were randomly assigned to control or CRISPRi groups and received vehicle or doxycycline in the diet, respectively. Imaging continued weekly for the following 21 days before euthanasia.

Figure 4B:
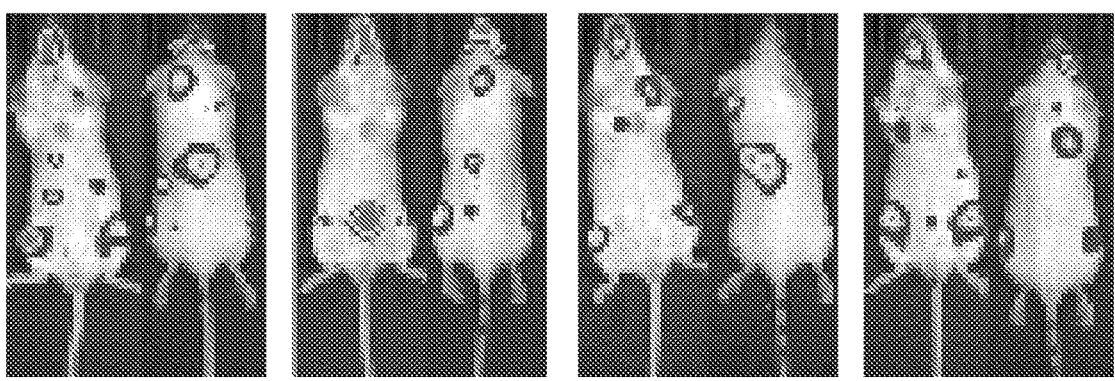
FIG. 4B comprises a set of images illustrating mice that were inoculated via the left cardiac ventricle with MDA-231 cells carrying the CX3CR1-silencing inducible CRISPRi system, stably expressing both GFP and luciferase. Animals were left untreated for one week after the inoculation of cancer cells; then, a doxycycline-containing diet was administered to the treatment group for the next following 3 weeks before euthanasia. Tumor progression was monitored weekly by in vivo bioluminescence imaging. Mice in both control and treatment groups imaged at 4 weeks are shown.
Figure 4B:
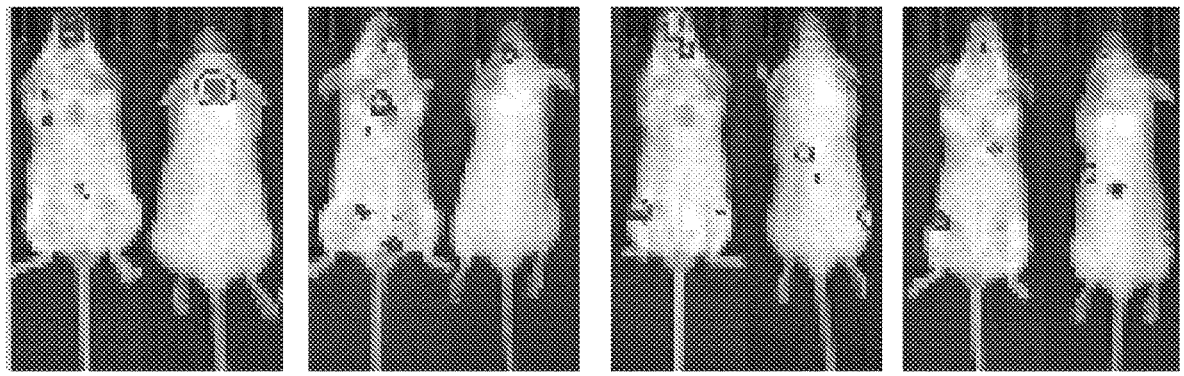
Figure 4C:
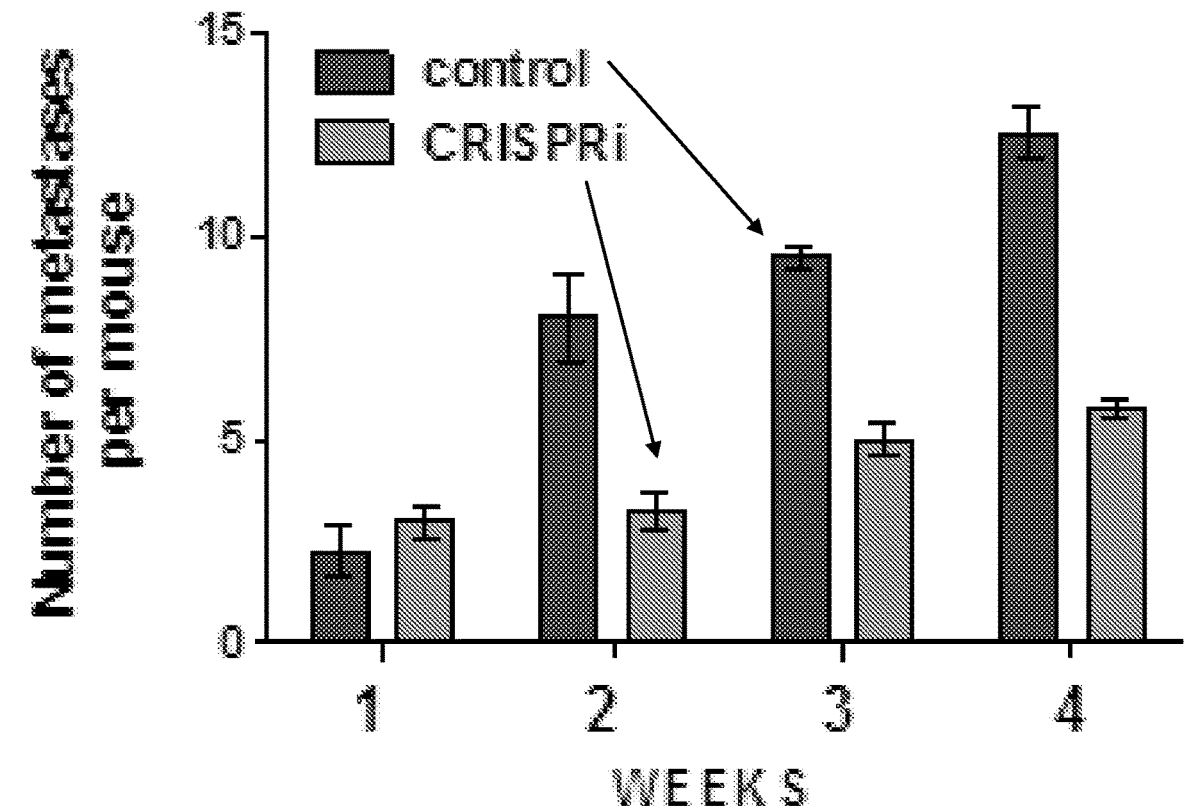
FIG. 4C comprises a bar graph illustrating the quantification of the number of metastatic lesions and overall tumor burden based on the detection of bioluminescent signal in both control and CRISPRi groups described in FIG. 4B.
Figure 4C:
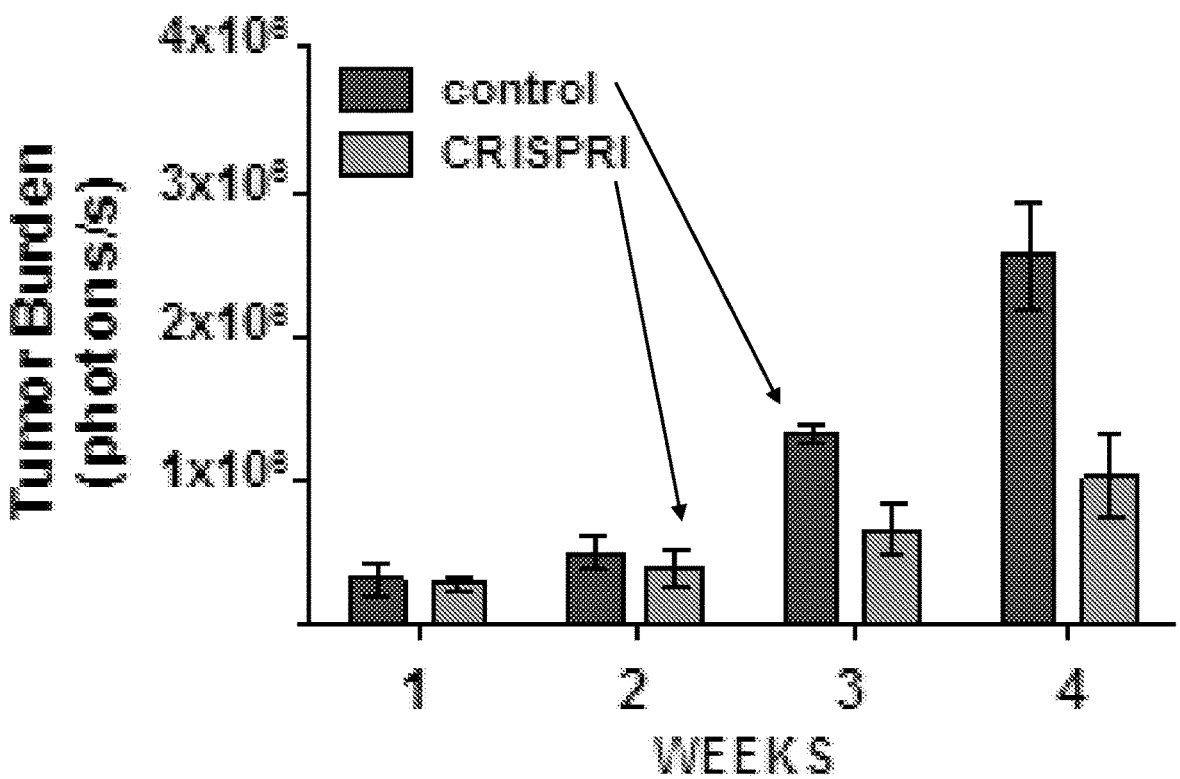

As shown, down-regulation of CX$_3$CR1 expression significantly reduced both the number of total lesions/animal and the overall tumor burden (FIGS. 4B-4C). The effective down-regulation of CX$_3$CR by CRISPRi was confirmed by harvesting tumor tissues from different lesions by Laser Capture Microdissection (LCM) and performing qRT-PCR analysis.

Figure 5A:
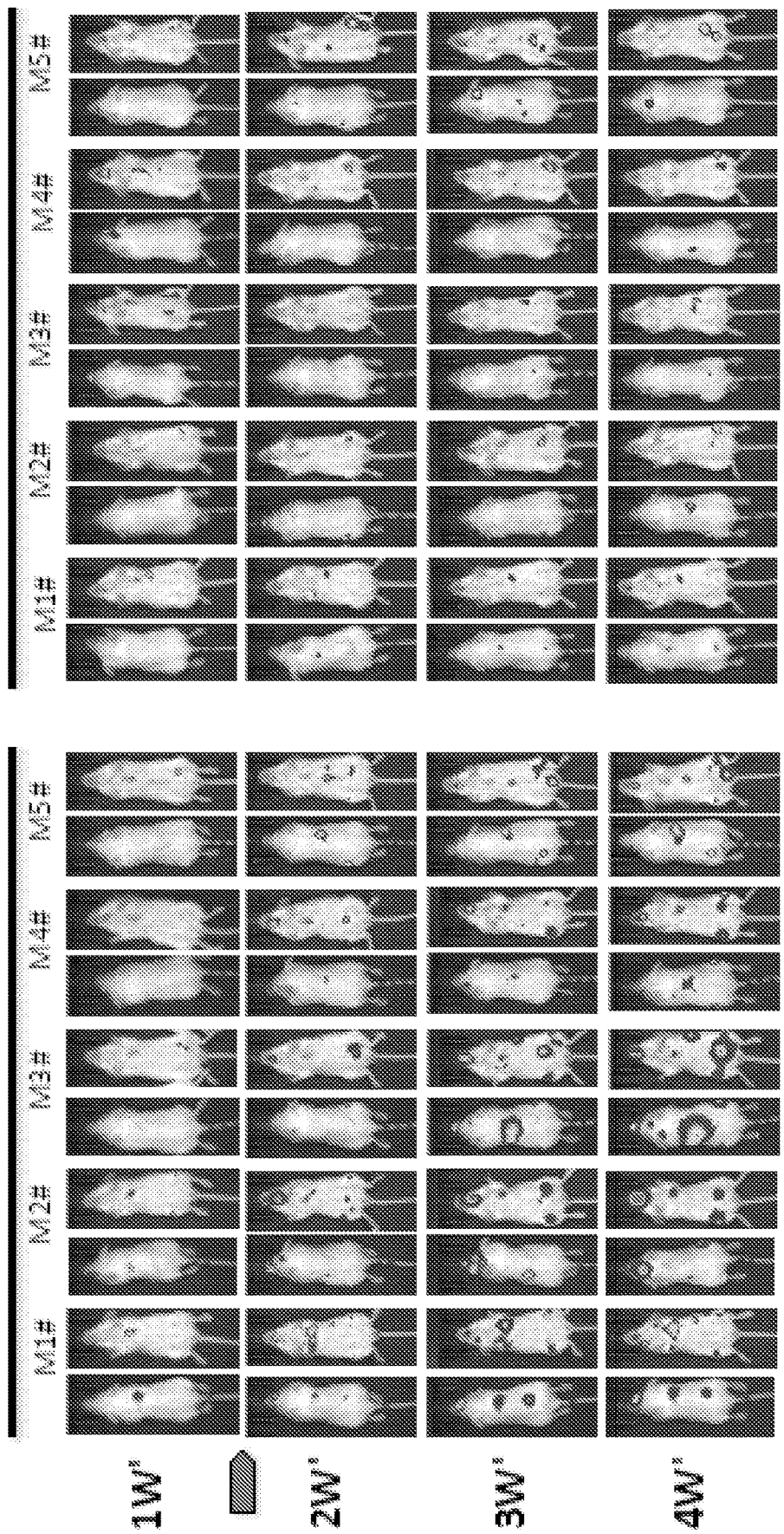
FIG. 5A comprises a set of images illustrating mice bearing one-week tumors in bones and soft-tissues that were treated daily with Compound I (10 mg/kg—i.p. twice a day) for the next following 3 weeks before euthanasia. Control animals received only vehicle.
Figure 5B:
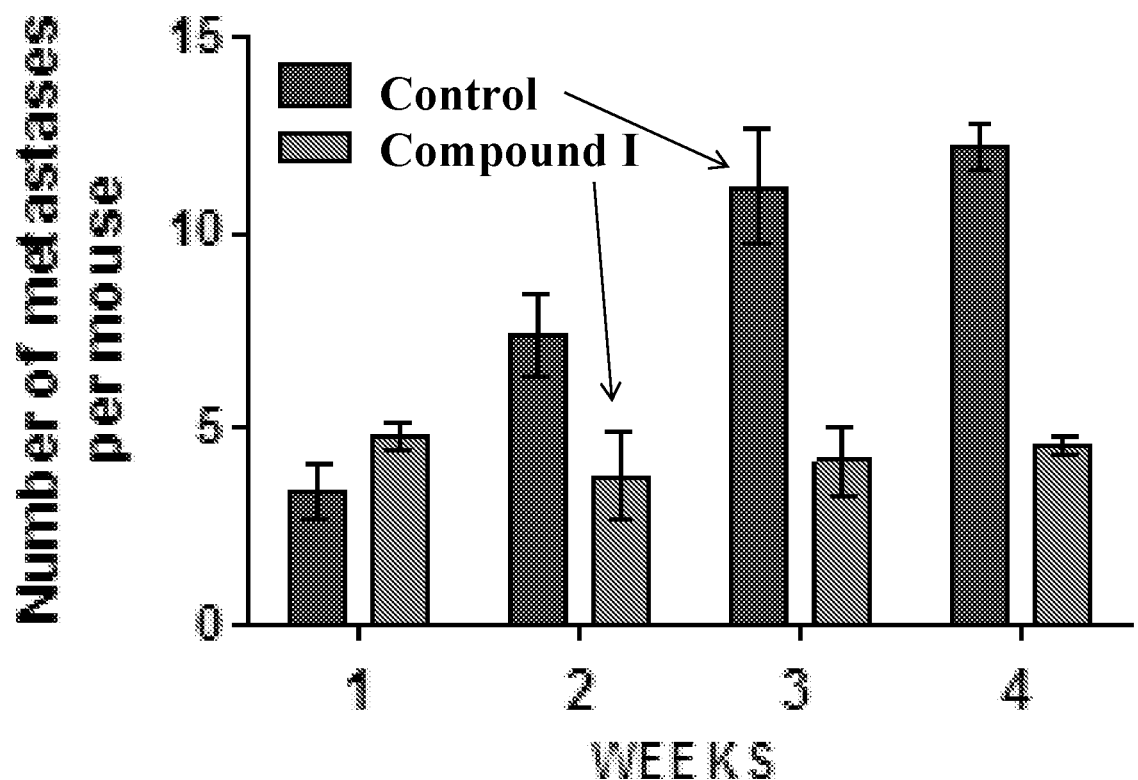
FIG. 5B comprises a set of bar graphs illustrating the quantification of the number of metastatic lesions and overall tumor burden based on bioluminescent signal in both control and Compound I treated groups.
Figure 5B:
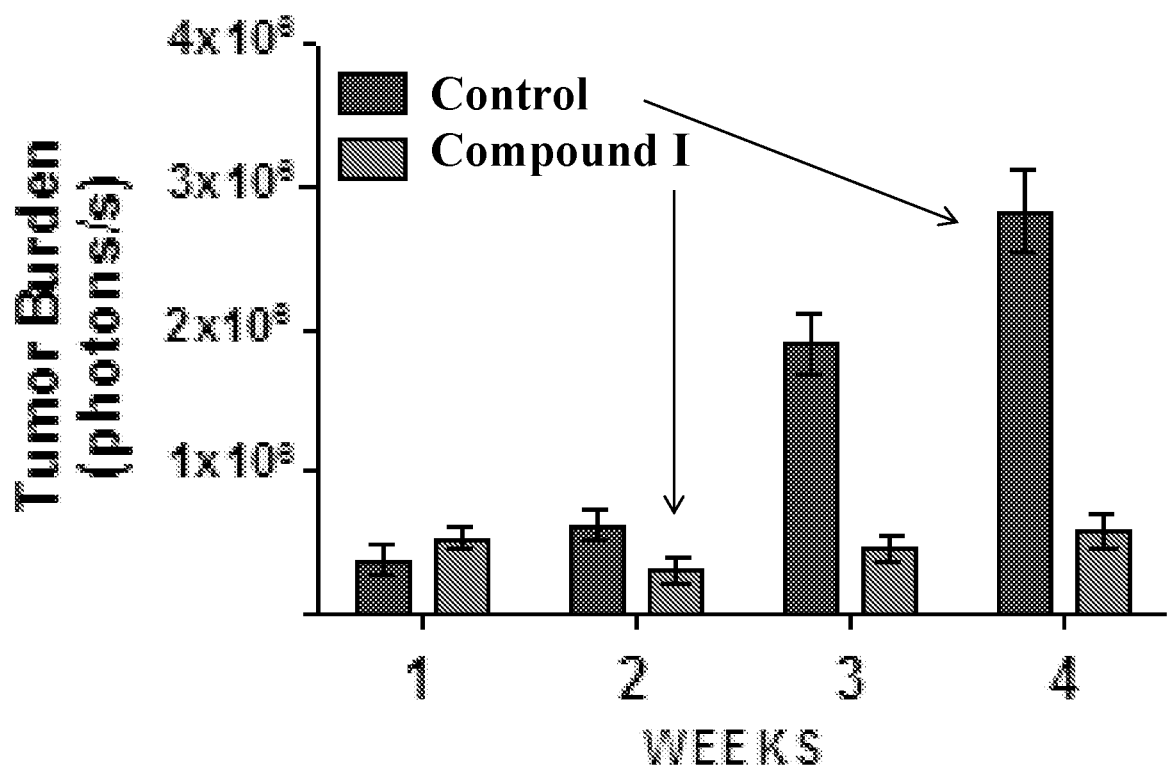

To determine whether the pharmacologic targeting of CX3CR1 with Compound I would produce similar effects, mice were grafted with MDA-231 cells and at the first week post-IC injection were randomized and administered with either vehicle or 10 mg/Kg Compound I i.p. twice daily for three weeks, based on pharmacokinetics studies with this compound. Animals were imaged weekly before being euthanized, and treatment with Compound I led to a reduction in the number of tumor foci and overall tumor burden, at least as effectively as observed using CRISPRi (FIGS. 5A-5B). Taken together, these results point towards a crucial role of CX$_3$CR1 in dictating seeding, colonization and progression of disseminated breast cancer cells and the highly promising therapeutic use of CX$_3$CR1 inhibitors to counteract the progression of metastatic disease.

Example 3: Synthesis of Compound I Analogue Precursors

A solution of compound 1 (1 eq) and compound 2 (1 eq) in acetic acid were stirred under microwave at 200° C. After 5 minutes, the mixture was diluted with EtOAc, washed with brine, dried over Na$_2$SO$_4$ and concentrated. The residue was purified by flash chromatography on silica gel (petroleum ether/EtOAc=20:1) to give compound 3 as a colorless oil (96% yield).

To a solution of 3 in MeOH was added 10% NaOH$_{aq}$ at 50° C. After 3 hours, the reaction was monitored by TLC analysis. Concentrated HCl was added to this mixture then diluted with EtOAc, washed with brine, dried over Na$_2$SO$_4$ and concentrated. The residue was purified by flash chromatography on silica gel (AcOEt/petroleum ether=1:3) gave compound 4 as a colorless oil (90% yield).

A solution of compound 4 (1 eq) and DIPEA (3 eq) in DCM were stirred at RT, DPPA (2 eq) was added slowly to this mixture, then heated to 50° C. for 3 h. The reaction was monitored by TLC analysis, then diluted with EtOAc, washed with 1N HCl, dried over Na$_2$SO$_4$ and concentrated. The residue was purified by flash chromatography on silica gel (AcOEt/petroleum ether=1:1) gave compound 5 as a yellow solid (71% yield).

To a solution of 5 (1 eq) and 3-bromo-1-propanol (1.2 eq) in DMF was added K$_2$CO$_3$ (2 eq) at 50° C. After overnight, the mixture was diluted with EtOAc, washed with brine, dried over Na$_2$SO$_4$ and concentrated. The residue was purified by flash chromatography on silica gel (petroleum ether/EtOAc=1:1) to give compound 6 as a yellow solid (82% yield).

A solution of oxalyl chloride (2 eq) in dry CH$_2$Cl$_2$ was cooled to −78° C., and DMSO (3 eq) was carefully added under nitrogen atmosphere. After stirring for 30 min, a solution of compound 6 in CH$_2$Cl$_2$ and Et$_3$N (4 eq) were added successively. The cooling bath was removed, and the reaction mixture was allowed to warm to room temperature and stirred for 2.5 h. The solvent was removed under reduced pressure, and the residue was extracted with ethyl acetate. The extract was washed with brine, dried over Na$_2$SO$_4$ and concentrated. The residue was purified by flash chromatography on silica gel (petroleum ether/EtOAc=1:1) to give compound 7 as a yellow solid (78% yield).

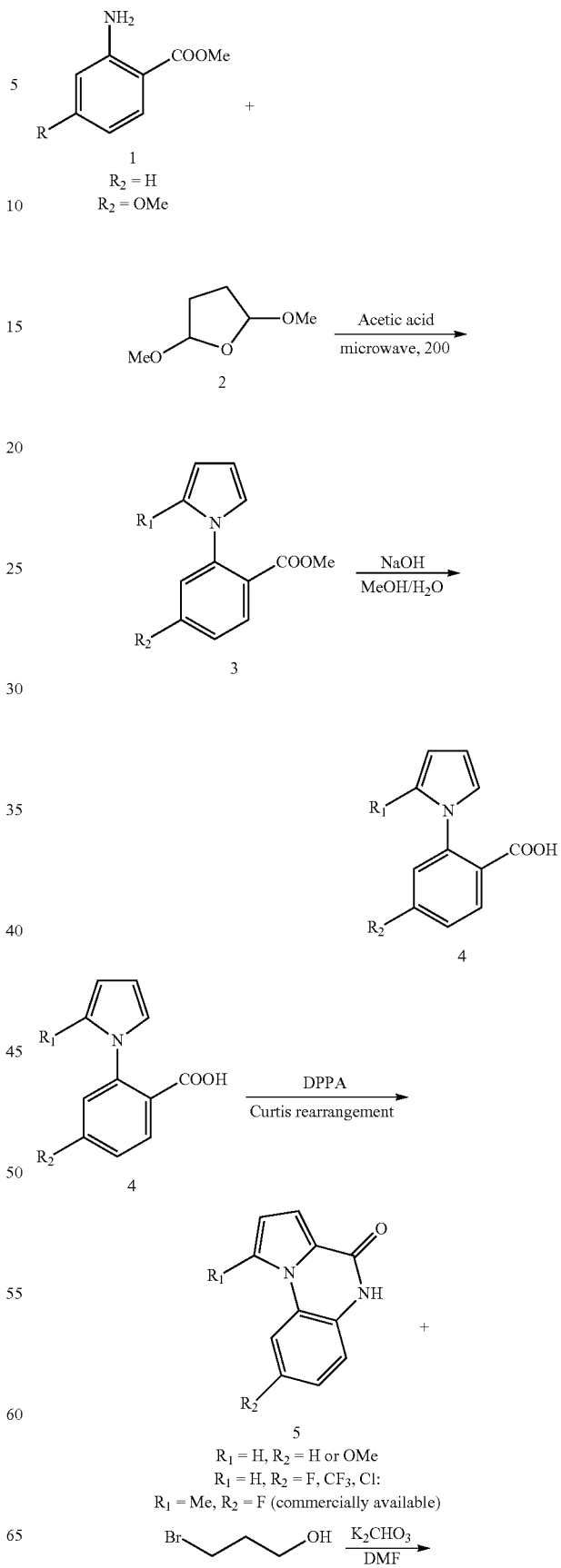

-continued

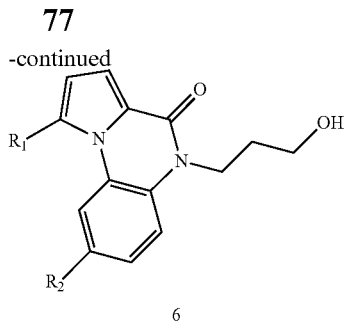

6

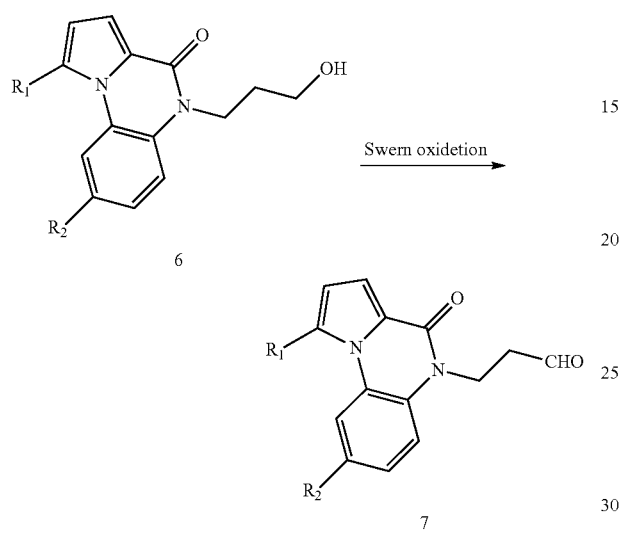

Example 4: Synthesis of Compound I Analogues

Certain analogues can be prepared using the following exemplary method:

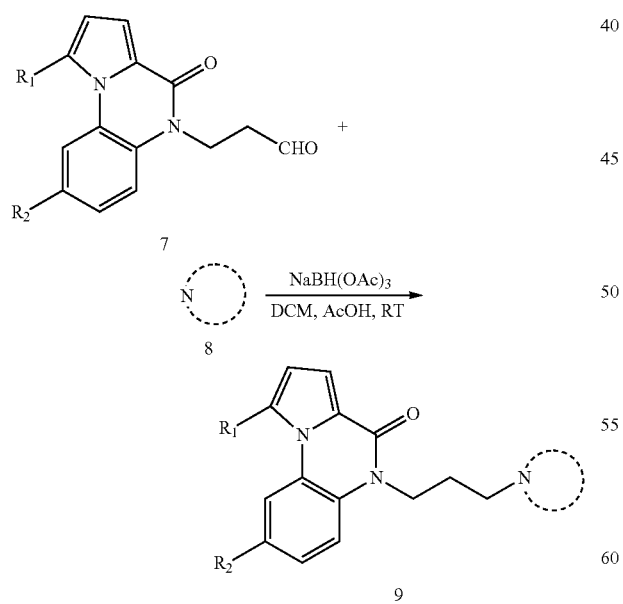

A solution of compound 7 (1 eq), second arylamine 8 (1.2 eq), AcOH (0.02 eq) and NaBH(OAc)$_3$ (2 eq) in dry DCM were stirred at RT until consumption of 7, which was monitored by TLC analysis. Purification by flash chroma- tography on silica gel (EtOAc/petroleum ether and DCM/MeOH) gave the desired product,

Example 5: Synthesis of Compound I Analogues

Certain analogues can be prepared using the following exemplary method:

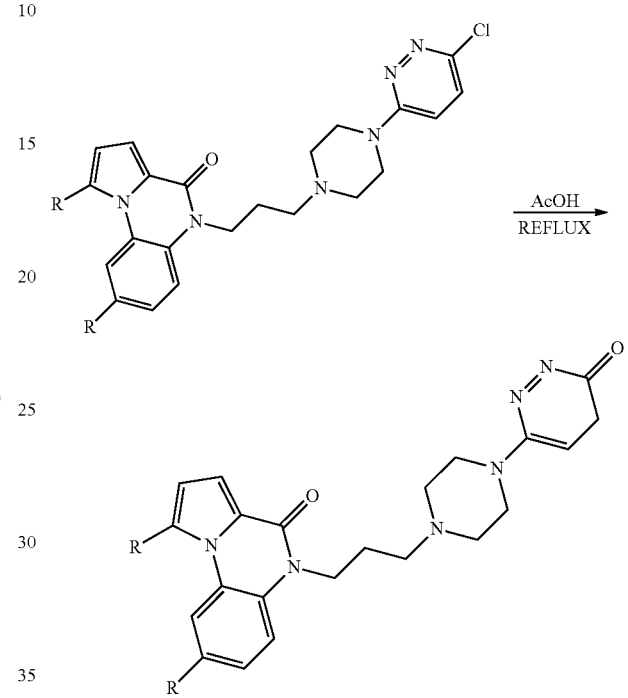

The corresponding compound was dissolved in AcOH, and heated to reflux until consumption of material, which was monitored by TLC analysis. Purification by flash chromatography on silica gel (EtOAc/petroleum ether and DCM/MeOH) gave the desired product.

Example 6

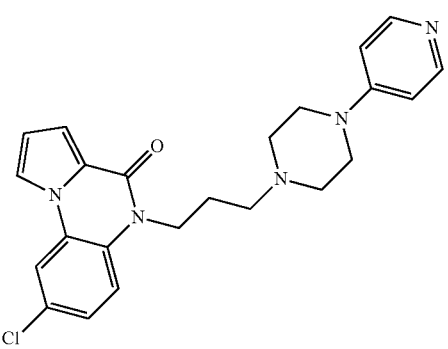 [SMILES: O=c1c2cccn2c2cc(Cl)ccc2n1CCCN1CCN(c2ccncc2)CC1]

Compound III—64% yield; $^1$H NMR (400 MHz, CDCl$_3$): δ (ppm) 8.25-8.23 (m, 2H), 7.64-7.60 (m, 2H), 7.39-7.21 (m, 4H), 6.65-6.63 (m, 2H), 4.36 (t, J=8.0 Hz, 2H), 3.39-3.37 (m, 4H), 2.60-2.57 (m, 6H), 1.98-1.91 (m, 2H); ESI-HRMS: calcd. for $C_{23}H_{25}ClN_5O$+H: 422.17421, found 422.17452.

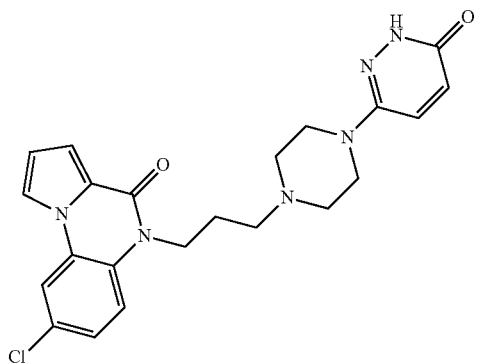 [SMILES: O=c1ccc(N2CCN(CCCn3c(=O)c4cccn4c4cc(Cl)ccc43)CC2)n[nH]1]
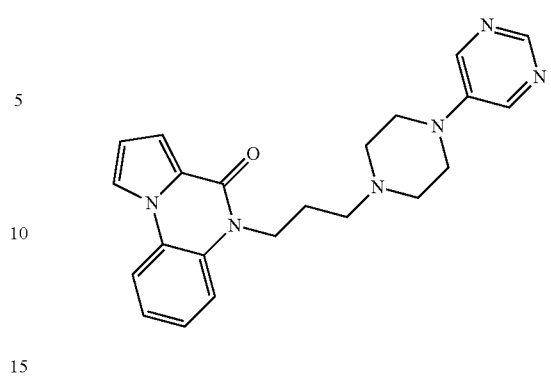

Compound V—51% yield; $^1$H NMR (400 MHz, CDCl$_3$): δ (ppm) 7.66-7.51 (m, 2H), 7.44-7.18 (m, 5H), 6.88-6.81 (m, 1H), 6.65-6.62 (m, 1H), 4.36-4.24 (m, 2H), 3.36-3.26 (m, 4H), 2.60-2.47 (m, 6H), 1.96-1.89 (m, 2H); ESI-HRMS: calcd. for C$_{22}$H$_{24}$ClN$_6$O$_2$+H: 439.16438, found 439.16456.

Compound IX—59% yield; $^1$H NMR (400 MHz, CDCl$_3$): δ (ppm) 8.70-8.68 (m, 1H), 8.36-8.35 (m, 2H), 7.72-7.65 (m, 2H), 7.45-7.42 (m, 1H), 7.34-7.22 (m, 3H), 6.66 (s, 1H), 4.37 (t, J=8 Hz, 2H), 3.26-3.24 (m, 4H), 2.64-2.55 (m, 6H), 2.05-1.95 (m, 2H); ESI-HRMS: calcd. for C$_{22}$H$_{25}$N$_6$O+H: 389.20844, found 389.20869.

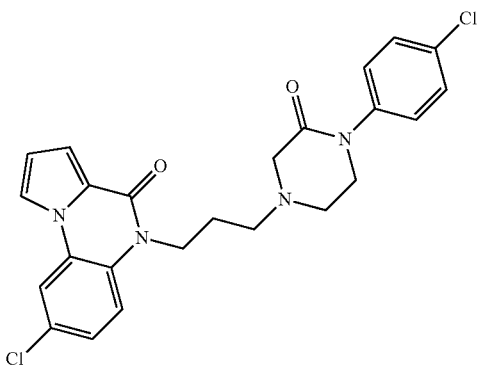 [SMILES: O=C1CN(CCCn2c(=O)c3cccn3c3cc(Cl)ccc32)CCN1c1ccc(Cl)cc1]
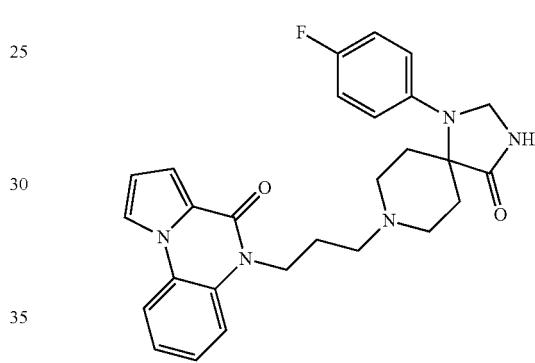

Compound VI—76% yield; $^1$H NMR (400 MHz, CDCl$_3$): δ (ppm) 7.71-7.53 (m, 2H), 7.38-7.08 (m, 7H), 6.71-6.60 (m, 1H), 4.38-4.34 (m, 2H), 3.66-3.60 (m, 2H), 3.30-3.24 (m, 2H), 2.88-2.72 (m, 2H), 2.60-2.56 (m, 2H), 1.98-1.88 (m, 2H); ESI-HRMS: calcd. for C$_{24}$H$_{23}$Cl$_2$N$_4$O$_2$+H: 469.11926, found 469.11942.

Compound X—80% yield; $^1$H NMR (400 MHz, CDCl$_3$): δ (ppm) 7.71-7.65 (m, 2H), 7.45-7.43 (m, 1H), 7.34-7.21 (m, 4H), 7.00-6.94 (m, 5H), 6.64 (s, 1H), 4.68 (s, 2H), 4.36-4.30 (m, 2H), 3.18-3.10 (m, 4H), 2.76-2.71 (m, 2H), 2.65-2.56 (m, 2H), 2.14-2.08 (m, 2H), 1.82-1.76 (m, 2H); ESI-HRMS: calcd. for C$_{27}$H$_{29}$FN$_5$O$_2$+H: 474.22998, found 474.22975.

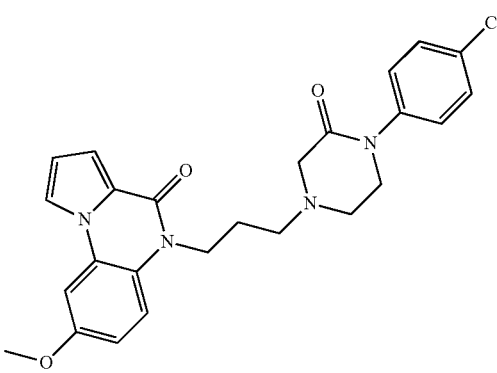
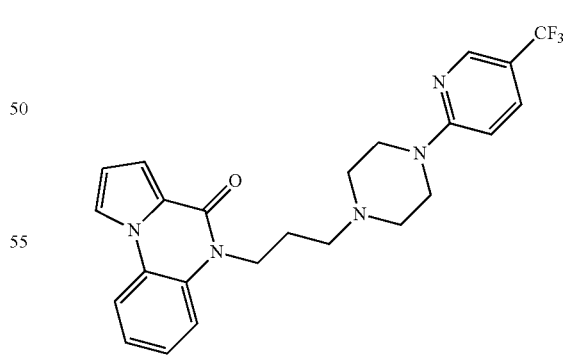

Compound VII—78% yield; $^1$H NMR (400 MHz, CDCl$_3$): δ (ppm) 7.59 (s, 1H), 7.37-7.21 (m, 7H), 6.91-6.88 (m, 1H), 6.68-6.60 (m, 1H), 4.38-4.34 (m, 2H), 3.88 (s, 3H), 3.68-3.66 (m, 2H), 3.33-3.31 (m, 2H), 2.87-2.82 (m, 2H), 2.65-2.60 (m, 2H), 2.01-1.98 (m, 2H); ESI-HRMS: calcd. for C$_{25}$H$_{26}$Cl$_2$N$_4$O$_3$+H: 465.16879, found 465.16856.

Compound XII—51% yield; $^1$H NMR (400 MHz, CDCl$_3$): δ (ppm) 8.39 (s, 1H), 7.65-7.60 (m, 3H), 7.42-7.41 (m, 1H), 7.26-7.20 (m, 3H), 6.63-6.59 (m, 2H), 4.35 (t, J=8 Hz, 2H), 3.62-3.58 (m, 4H), 2.58-2.46 (m, 6H), 1.98-1.95 (m, 2H); ESI-HRMS: calcd. for C$_{24}$H$_{25}$F$_3$N$_5$O+H: 456.20057, found 456.20043.

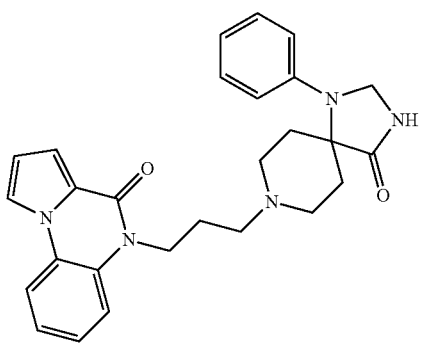 [SMILES: O=C1NCN(c2ccccc2)C12CCN(CCCn1c(=O)c3cccn3c3ccccc31)CC2]

Compound XIII—81% yield; ¹H NMR (400 MHz, CDCl₃): δ (ppm) 7.86-7.84 (m, 1H), 7.76-7.63 (m, 2H), 7.46-7.42 (m, 1H), 7.38-7.19 (m, 4H), 6.95-6.62 (m, 5H), 4.68 (s, 2H), 4.38-4.36 (m, 2H), 3.24-3.19 (m, 4H), 2.98-2.88 (m, 4H), 2.18-2.15 (m, 2H), 1.78-1.70 (m, 2H); ESI-HRMS: calcd. for $C_{27}H_{30}N_5O_2$+H:456.23940, found 456.23932.

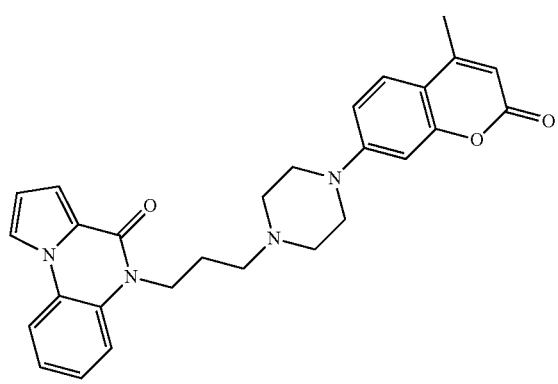 [SMILES: Cc1cc(=O)oc2cc(N3CCN(CCCn4c(=O)c5cccn5c5ccccc54)CC3)ccc12]

Compound XIV—76% yield; ¹H NMR (400 MHz, CDCl₃): δ (ppm) 7.72-7.68 (m, 1H), 7.65-7.64 (m, 1H), 7.43-7.39 (m, 2H), 7.33-7.29 (m, 1H), 7.25-7.21 (m, 2H), 6.81-6.77 (m, 1H), 6.67-6.65 (m, 2H), 6.03 (s, 1H), 4.35 (t, J=8 Hz, 2H), 3.31-3.29 (m, 4H), 2.63-2.57 (m, 6H), 2.04 (s, 3H), 2.01-1.96 (m, 2H); ESI-HRMS: calcd. for $C_{28}H_{29}N_4O_3$+H:469.22342, found 469.22345.

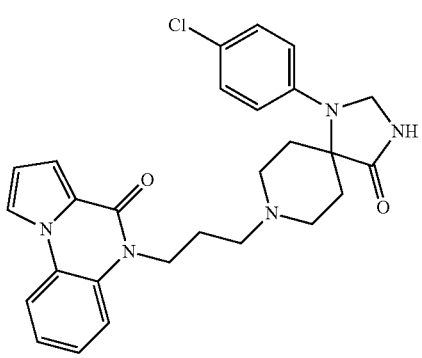 [SMILES: O=C1NCN(c2ccc(Cl)cc2)C12CCN(CCCn1c(=O)c3cccn3c3ccccc31)CC2]

Compound XV—84% yield; ¹H NMR (400 MHz, CDCl₃): δ (ppm) 8.73 (s, 1H), 8.23-8.22 (m, 1H), 8.17-8.14 (m, 1H), 7.69-7.66 (m, 1H), 7.38-7.24 (m, 4H), 7.07-7.05 (m, 1H), 6.90-6.87 (m, 2H), 6.72-6.69 (m, 1H), 4.59 (s, 2H), 4.32-4.28 (m, 2H), 3.18-3.17 (m, 2H), 2.88-2.73 (m, 3H), 2.52-2.49 (m, 3H), 1.88-1.87 (m, 2H), 1.67-1.59 (m, 2H); ESI-HRMS: calcd. for $C_{27}H_{29}ClN_5O_2$+H:490.20043, found 490.20050.

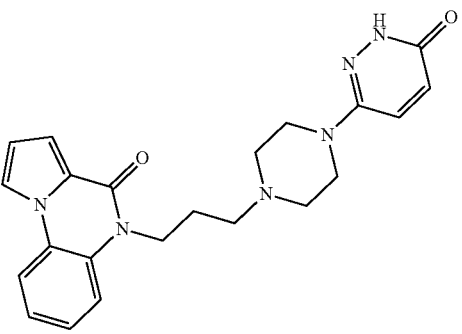 [SMILES: O=c1ccc(N2CCN(CCCn3c(=O)c4cccn4c4ccccc43)CC2)n[nH]1]

Compound XVI—53% yield; ¹H NMR (400 MHz, CDCl₃): δ (ppm) 12.18 (s, 1H), 8.22-8.15 (m, 2H), 7.64-7.28 (m, 4H), 7.06-7.04 (m, 1H), 6.79-6.68 (m, 2H), 4.31-4.28 (m, 2H), 4.06-4.00 (m, 1H), 3.18-3.10 (m, 5H), 2.52-2.50 (m, 2H), 1.88-1.60 (m, 3H), 1.20-1.18 (m, 1H); ESI-HRMS: calcd. for $C_{22}H_{25}N_6O_2$+H: 405.20335, found 405.20311.

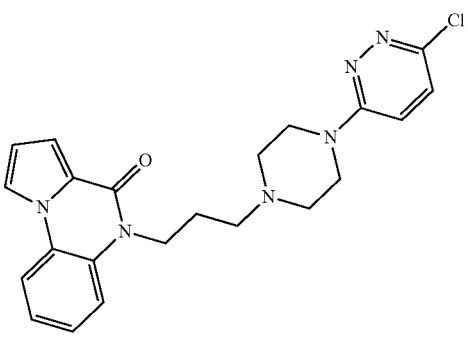 [SMILES: O=c1c2cccn2c2ccccc2n1CCCN1CCN(c2ccc(Cl)nn2)CC1]

Compound XVII—66% yield; ¹H NMR (400 MHz, CDCl₃): δ (ppm) 7.71-7.65 (m, 2H), 7.44-7.41 (m, 1H), 7.34-7.17 (m, 4H), 6.89-6.85 (m, 1H), 6.67-6.65 (m, 1H), 4.38-4.36 (m, 2H), 3.62-3.60 (m, 4H), 2.60-2.58 (m, 6H), 2.05-1.99 (m, 4H); ESI-HRMS: calcd. for $C_{22}H_{23}ClN_6O$+H: 422.16219, found 422.16225.

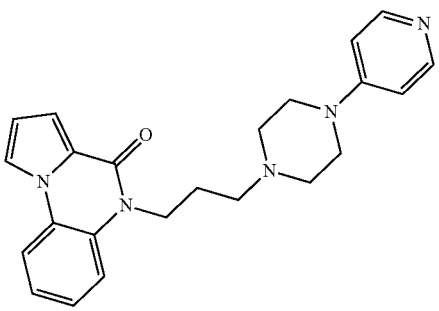 [SMILES: O=c1c2cccn2c2ccccc2n1CCCN1CCN(c2ccncc2)CC1]

Compound XIX—58% yield; ¹H NMR (400 MHz, CDCl₃): δ (ppm) 8.39-8.21 (m, 2H), 7.77-7.72 (m, 2H), 7.43-7.27 (m, 4H), 6.74-6.68 (m, 3H), 4.43-4.39 (m, 2H), 3.50-3.42 (m, 4H), 2.64-2.57 (m, 6H), 2.08-2.06 (m, 2H); ESI-HRMS: calcd. for $C_{23}H_{25}N_5O$+H: 388.21319, found 388.21314.

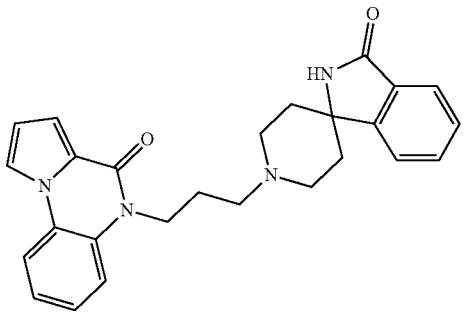 [SMILES: O=C1NC2(CCN(CCCn3c(=O)c4cccn4c4ccccc43)CC2)c2ccccc21]

Compound XX—73% yield; $^1$H NMR (400 MHz, CDCl$_3$): δ (ppm) 8.02 (s, 1H), 7.80-7.78 (m, 1H), 7.73-7.72 (m, 1H), 7.69-7.68 (m, 1H), 7.59-7.57 (m, 1H), 7.46-7.43 (m, 3H), 7.36-7.35 (m, 1H), 7.25-7.23 (m, 2H), 6.69-6.68 (m, 1H), 4.40 (t, J=8 Hz, 2H), 3.18-3.16 (m, 2H), 2.78-2.76 (m, 2H), 2.46-2.43 (m, 2H), 2.34-2.28 (m, 2H), 2.12-2.09 (m, 2H), 1.59-1.57 (m, 2H); ESI-HRMS: calcd. for $C_{26}H_{26}N_4O_2$+H: 427.21285, found 427.21289.

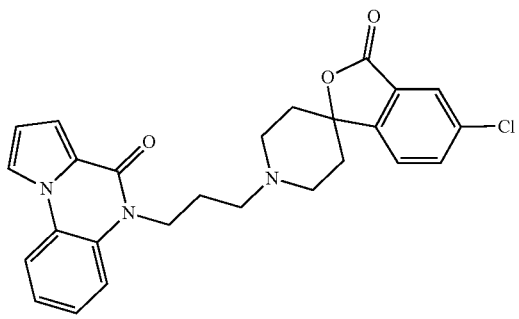 [SMILES: O=C1OC2(CCN(CCCn3c(=O)c4cccn4c4ccccc43)CC2)c2ccc(Cl)cc21]

Compound XXI—74% yield; $^1$H NMR (400 MHz, CDCl$_3$): δ (ppm) 7.83-7.82 (m, 1H), 7.74-7.72 (m, 1H), 7.65-7.63 (m, 1H), 7.47-7.45 (m, 1H), 7.41-7.39 (m, 1H), 7.37-7.34 (m, 1H), 7.28-7.25 (m, 1H), 7.24-7.23 (m, 1H), 6.69-6.68 (m, 1H), 4.38 (t, J=8 Hz, 2H), 3.32-3.28 (m, 2H), 2.94-2.90 (m, 2H), 2.84-2.77 (m, 2H), 2.60-2.52 (m, 2H), 2.20-2.14 (m, 2H), 1.76-1.73 (m, 2H); ESI-HRMS: calcd. for $C_{26}H_{24}ClN_3O_3$+H: 462.15790, found 462.15780.

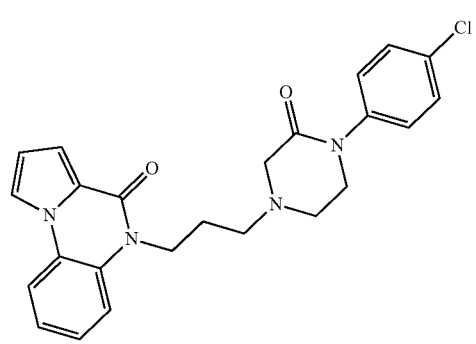 [SMILES: O=C1CN(CCCn2c(=O)c3cccn3c3ccccc32)CCN1c1ccc(Cl)cc1]

Compound XXII—77% yield; $^1$H NMR (400 MHz, CDCl$_3$): δ (ppm) 7.72-7.71 (m, 1H), 7.67-7.66 (m, 1H), 7.40-7.32 (m, 4H), 7.26-7.22 (m, 4H), 6.68-6.67 (m, 1H), 4.39 (t, J=8 Hz, 2H), 3.67 (t, J=6 Hz, 2H), 3.31 (s, 2H), 2.83 (t, J=6 Hz, 2H), 2.63 (t, J=8 Hz, 2H), 2.02-1.98 (m, 2H); ESI-HRMS: calcd. for $C_{24}H_{23}ClN_4O_2$+H: 435.15878, found 435.15888.

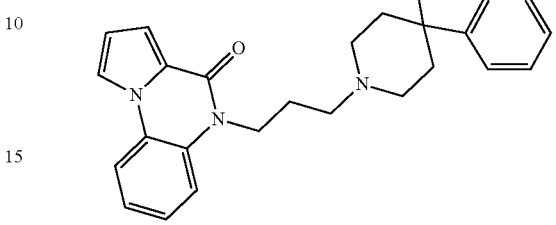

Compound XXVI—65% yield; $^1$H NMR (400 MHz, CDCl$_3$): δ (ppm) 7.71-7.63 (m, 2H), 7.48-7.44 (m, 1H), 7.32-7.11 (m, 7H), 6.68-6.65 (m, 1H), 5.06 (s, 2H), 4.39-4.33 (m, 2H), 2.91-2.86 (m, 2H), 2.63-2.56 (m, 2H), 2.46-2.38 (m, 2H), 2.04-1.91 (m, 4H), 1.79-1.74 (m, 2H); ESI-HRMS: calcd. for $C_{26}H_{27}N_3O_2$+H: 414.21760, found 414.21761.

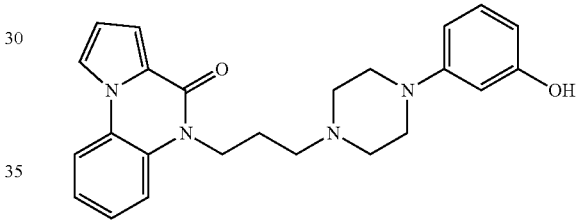

Compound XXVIII—67% yield; $^1$H NMR (300 MHz, CDCl$_3$): δ (ppm) 9.10 (s, 1H), 8.21-8.11 (m, 2H), 7.64-7.61 (m, 1H), 7.42-7.37 (m, 1H), 7.32-7.27 (m, 1H), 7.07-7.04 (m, 1H), 7.00-6.74 (m, 1H), 6.71-6.88 (m, 1H), 6.37-6.18 (m, 3H), 4.29 (t, J=6 Hz, 2H), 3.05-2.98 (m, 4H), 2.51-2.42 (m, 6H), 1.86-1.79 (m, 2H); ESI-HRMS: calcd. for $C_{24}H_{27}N_4O_2$+H: 403.21285, found 403.21262.

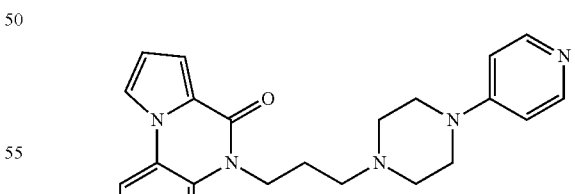

Compound XXIX—57% yield; $^1$H NMR (500 MHz, CDCl$_3$): δ (ppm) 8.17-8.08 (m, 4H), 7.63-7.61 (m, 1H), 7.26-7.21 (m, 1H), 7.05-7.03 (m, 1H), 6.79-6.77 (m, 2H), 6.69-6.68 (m, 1H), 4.25 (t, J=5 Hz, 2H), 3.24-3.21 (m, 3H), 2.42-2.39 (m, 4H), 1.89-1.86 (m, 5H); ESI-HRMS: calcd. for $C_{23}H_{25}FN_5O$+H: 406.20377, found 406.20410.

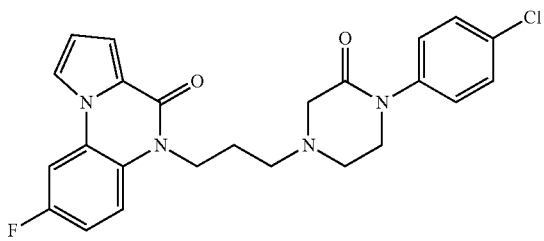 [SMILES: O=C1CN(CCCn2c(=O)c3cccn3c3cc(F)ccc32)CCN1c1ccc(Cl)cc1]

Compound XXXII—71% yield; $^1$H NMR (300 MHz, CDCl$_3$): δ (ppm) 8.22-8.20 (m, 1H), 8.17-8.12 (m, 1H), 7.67-7.62 (m, 1H), 7.46-7.43 (m, 2H), 7.38-7.34 (m, 2H), 7.29-7.23 (m, 1H), 7.07-7.05 (m, 1H), 6.73-6.71 (m, 1H), 4.28 (t, J=9 Hz, 2H), 3.59 (t, J=6 Hz, 2H), 3.17 (s, 3H), 2.76 (t, J=6 Hz, 2H), 2.53 (t, J=9 Hz, 2H), 1.89-1.81 (m, 2H); ESI-HRMS: calcd. for C$_{24}$H$_{23}$FN$_4$O$_2$+H: 453.14881, found 453.14914.

Compound XXXVI—51% yield; H NMR (500 MHz, CDCl$_3$): δ (ppm) 8.53 (s, 1H), 8.44-8.43 (m, 1H), 8.16-8.14 (m, 1H), 7.83-7.80 (m, 1H), 7.74-7.70 (m, 1H), 7.12-7.10 (m, 1H), 6.82-6.78 (m, 2H), 6.75-6.73 (m, 1H), 4.32 (t, J=6 Hz, 2H), 3.24-3.20 (m, 3H), 2.52-2.50 (m, 2H), 2.46-2.42 (m, 5H), 1.88-1.82 (m, 2H); ESI-HRMS: calcd. for C$_{24}$H$_{25}$F$_3$N$_5$O+H: 456.20057, found 456.20054.

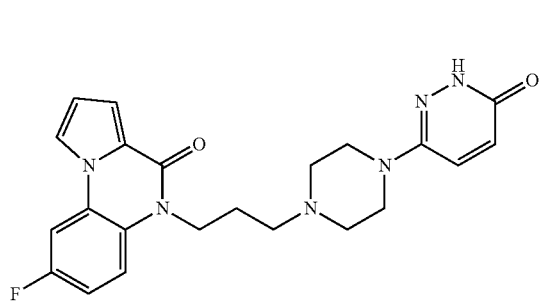 [SMILES: O=c1ccc(N2CCN(CCCn3c(=O)c4cccn4c4cc(F)ccc43)CC2)n[nH]1]

Compound XXXIII—51% yield; $^1$H NMR (500 MHz, CDCl$_3$): δ (ppm) 8.22-8.21 (m, 1H), 8.16-8.13 (m, 1H), 7.66-7.63 (m, 1H), 7.50-7.48 (m, 1H), 7.27-7.23 (m, 1H), 7.06-7.05 (m, 1H), 6.78-6.76 (m, 1H), 6.72-6.71 (m, 1H), 4.27 (t, J=9 Hz, 2H), 3.23-3.14 (m, 4H), 2.52-2.45 (m, 6H), 1.84-1.83 (m, 2H); ESI-HRMS: calcd. for C$_{22}$H$_{23}$FN$_6$O$_2$+H: 423.19448, found 423.19447.

Compound XXXVIII—48% yield; $^1$H NMR (500 MHz, CDCl$_3$): δ (ppm) 12.32 (s, 1H), 8.32-8.26 (m, 2H), 7.65-7.62 (m, 1H), 7.50-7.40 (m, 2H), 7.07-7.05 (m, 1H), 6.78-6.70 (m, 2H), 4.26 (t, J=9 Hz, 2H), 3.14-3.10 (m, 4H), 2.44-2.40 (m, 6H), 1.86-1.78 (m, 2H); ESI-HRMS: calcd. for C$_{23}$H$_{23}$F$_3$N$_6$O$_2$+H: 473.19128, found 473.19133.

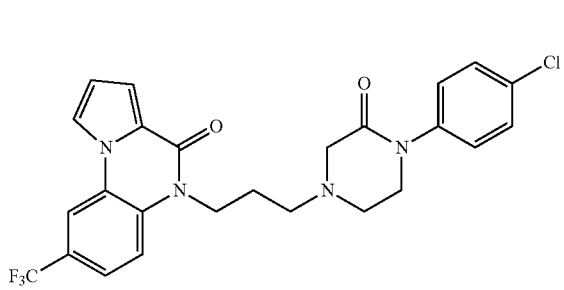 [SMILES: O=C1CN(CCCn2c(=O)c3cccn3c3cc(C(F)(F)F)ccc32)CCN1c1ccc(Cl)cc1]

Compound XXXV—63% yield; $^1$H NMR (300 MHz, CDCl$_3$): δ (ppm) 8.54 (s, 1H), 8.44-8.43 (m, 1H), 7.81-7.78 (m, 1H), 7.73-7.69 (m, 1H), 7.46-7.43 (m, 2H), 7.37-7.34 (m, 2H), 7.12-7.10 (m, 1H), 6.75-6.73 (m, 1H), 4.34 (t, J=9 Hz, 2H), 3.59 (t, J=6 Hz, 2H), 3.18 (s, 2H), 2.76 (t, J=6 Hz, 2H), 2.55 (t, J=9 Hz, 2H), 1.90-1.85 (m, 2H); ESI-HRMS: calcd. for C$_{25}$H$_{23}$F$_3$N$_4$O$_2$+H: 503.14561, found 503.14571.

Compound XXXIX—71% yield; $^1$H NMR (500 MHz, CDCl$_3$): δ (ppm) 7.94-7.90 (m, 1H), 7.68-7.63 (m, 1H), 7.34-7.32 (m, 2H), 7.30-7.25 (m, 1H), 7.22-7.19 (m, 2H), 7.02-7.01 (m, 1H), 6.51-6.49 (m, 1H), 4.27 (t, J=9 Hz, 2H), 2.96-2.91 (m, 2H), 2.82 (s, 3H), 2.51-2.44 (m, 3H), 2.02-1.96 (m, 2H), 1.85-1.80 (m, 2H), 1.70-1.64 (m, 2H), 1.53-1.44 (m, 2H); ESI-HRMS: calcd. for C$_{26}$H$_{28}$FClN$_3$O+H: 452.18994, found 452.18997.

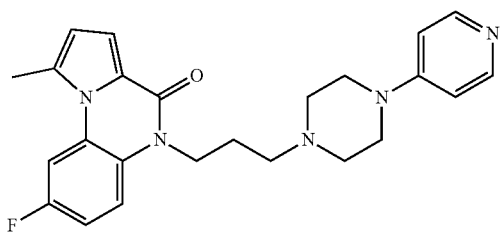 [SMILES: Cc1ccc2c(=O)n(CCCN3CCN(c4ccncc4)CC3)c3ccc(F)cc3n12]

Compound XL—53% yield; $^1$H NMR (500 MHz, CDCl$_3$): δ (ppm) 7.88-7.85 (m, 2H), 7.64-7.59 (m, 1H), 7.39-7.34 (m, 1H), 7.02-6.96 (m, 1H), 6.73-6.71 (m, 1H), 6.52-6.49 (m, 2H), 6.20-6.18 (m, 1H), 3.98 (t, J=6 Hz, 2H), 3.01-2.96 (m, 4H), 2.59-2.55 (m, 2H), 2.52 (s, 3H), 2.23-2.21 (m, 1H), 2.17-2.12 (m, 5H); ESI-HRMS: calcd. for C$_{24}$H$_{27}$FN$_5$O+H: 420.21942, found 420.21969.

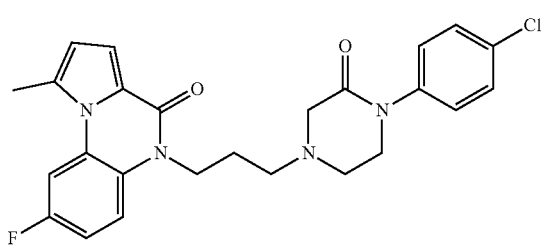 [SMILES: Cc1ccc2c(=O)n(CCCN3CCN(c4ccc(Cl)cc4)C(=O)C3)c3ccc(F)cc3n12]

Compound XLI—63% yield; $^1$H NMR (500 MHz, CDCl$_3$): δ (ppm) 7.93-7.88 (m, 1H), 7.66-7.61 (m, 1H), 7.46-7.43 (m, 2H), 7.38-7.35 (m, 2H), 7.31-7.24 (m, 1H), 7.02-7.00 (m, 1H), 6.49-6.47 (m, 1H), 4.28 (t, J=9 Hz, 2H), 3.60 (t, J=6 Hz, 2H), 3.17 (s, 2H), 2.81 (s, 2H), 2.75 (t, J=6 Hz, 2H), 2.53 (t, J=9 Hz, 2H), 1.88-1.80 (m, 2H); ESI-HRMS: calcd. for C$_{25}$H$_{25}$FClN$_4$O$_2$+H: 467.16446, found 467.16472.

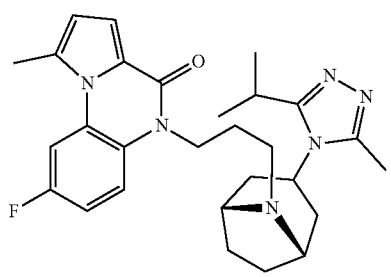 [SMILES: Cc1nnc(C(C)C)n1C1C[C@H]2CC[C@@H](C1)N2CCCn1c(=O)c2ccc(C)n2c2cc(F)ccc21]

Compound XLII—64% yield; $^1$H NMR (500 MHz, CDCl$_3$): δ (ppm) 7.95-7.90 (m, 1H), 7.69-7.64 (m, 1H), 7.32-7.25 (m, 1H), 7.02-7.00 (m, 1H), 6.49-6.48 (m, 1H), 4.32 (t, J=9 Hz, 2H), 4.28-4.20 (m, 1H), 3.19-3.10 (m, 2H), 2.52-2.45 (m, 3H), 2.40 (s, 3H), 2.17-2.08 (m, 2H), 1.96-1.92 (m, 2H), 1.88 (s, 3H), 1.80-1.74 (m, 2H), 1.72-1.68 (m, 4H), 1.25 (d, J=3 Hz, 6H); ESI-HRMS: calcd. for C$_{28}$H$_{36}$FClN$_6$O+H: 491.29291, found 491.29290.

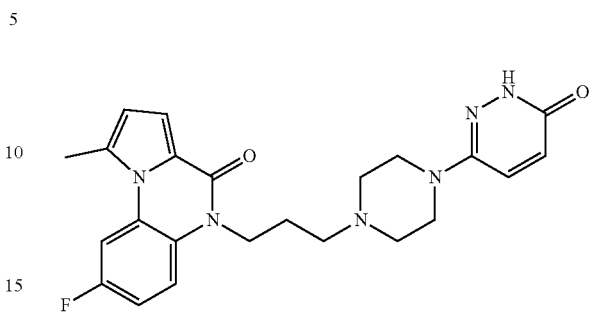

Compound XLII—54% yield; $^1$H NMR (500 MHz, CDCl$_3$): δ (ppm) 7.84-7.79 (m, 1H), 7.44-7.38 (m, 1H), 7.19-7.16 (m, 2H), 7.08-7.00 (m, 1H), 6.90-6.86 (m, 1H), 6.42-6.39 (m, 1H), 4.33 (t, J=9 Hz, 2H), 3.28-3.25 (m, 4H), 2.82 (s, 3H), 2.58-2.54 (m, 6H), 1.98-1.92 (m, 2H); ESI-HRMS: calcd. for C$_{23}$H$_{25}$FClN$_6$O$_2$+H: 437.21013, found 437.21018.

Example 7: Synthesis of CX$_3$CR1 Small Molecule Fluorescent Probes

In certain embodiments, CX$_3$CR1 small molecule fluorescent probes are useful tools that target CX$_3$CR1 expressing tumor cells and have significant potential clinical impact on the diagnosis, treatment and monitoring of biomarkers for metastatic disease. Such probes can be synthesized by methods analogous to the methods described below.

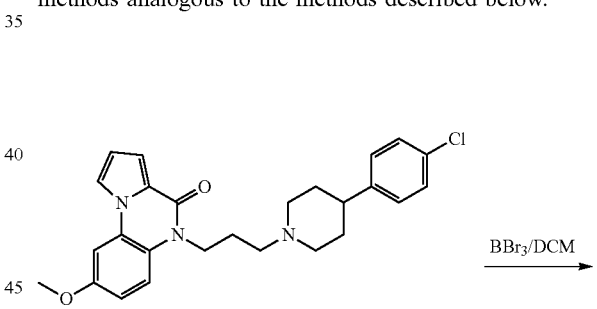

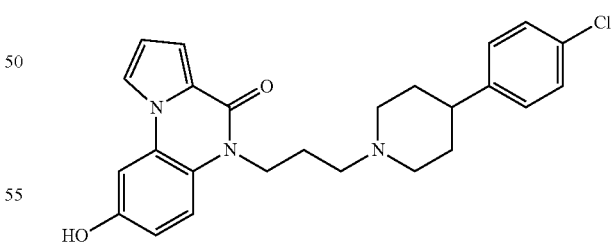

A solution of the methoxy compound (1 eq) in DCM was stirred at −40° C. under nitrogen atmosphere. BBr$_3$ (4 eq) was added slowly to this mixture, which was then heated to RT for 3 h. The reaction was monitored by TLC analysis. MeOH was added to this mixture at 0° C. The mixture was diluted with DCM, washed with 1N HCl, dried over Na$_2$SO$_4$ and concentrated. The residue was purified by flash chromatography on silica gel (DCM/MeOH=10:1) gave the hydroxy product as a yellow solid (71% yield).

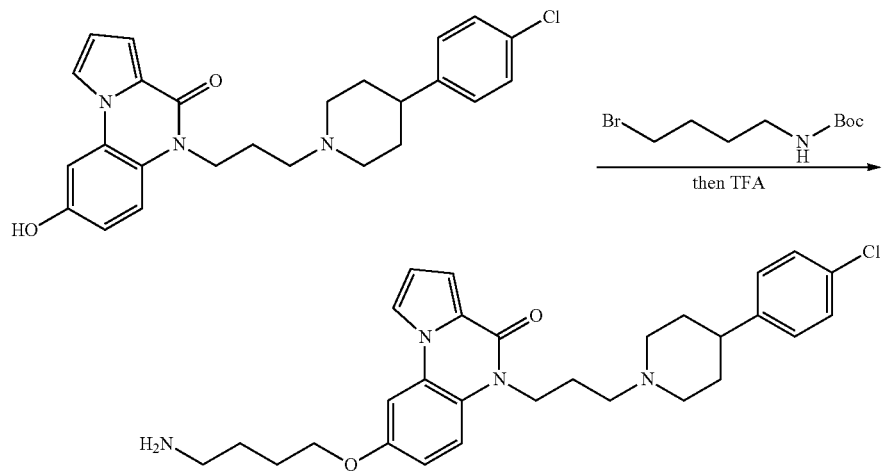

To a solution of the hydroxy compound (1 eq) and N-Boc-4-bromo-1-amino-butane (1.2 eq) in DMF was added $K_2CO_3$ (2 eq) at 50° C. After overnight, the mixture was diluted with EtOAc, washed with brine, dried over $Na_2SO_4$ and concentrated. The residue was purified by flash chromatography on silica gel (DCM/MeOH=10:1) to give compound the Boc protected product as a yellow solid. The solid was dissolved in DCM, TFA was added to this mixture, which was stirred for 2 hours. The reaction was monitored by TLC analysis. The residue was purified by flash chromatography on silica gel (DCM/MeOH=10:1) to give product as a yellow solid.

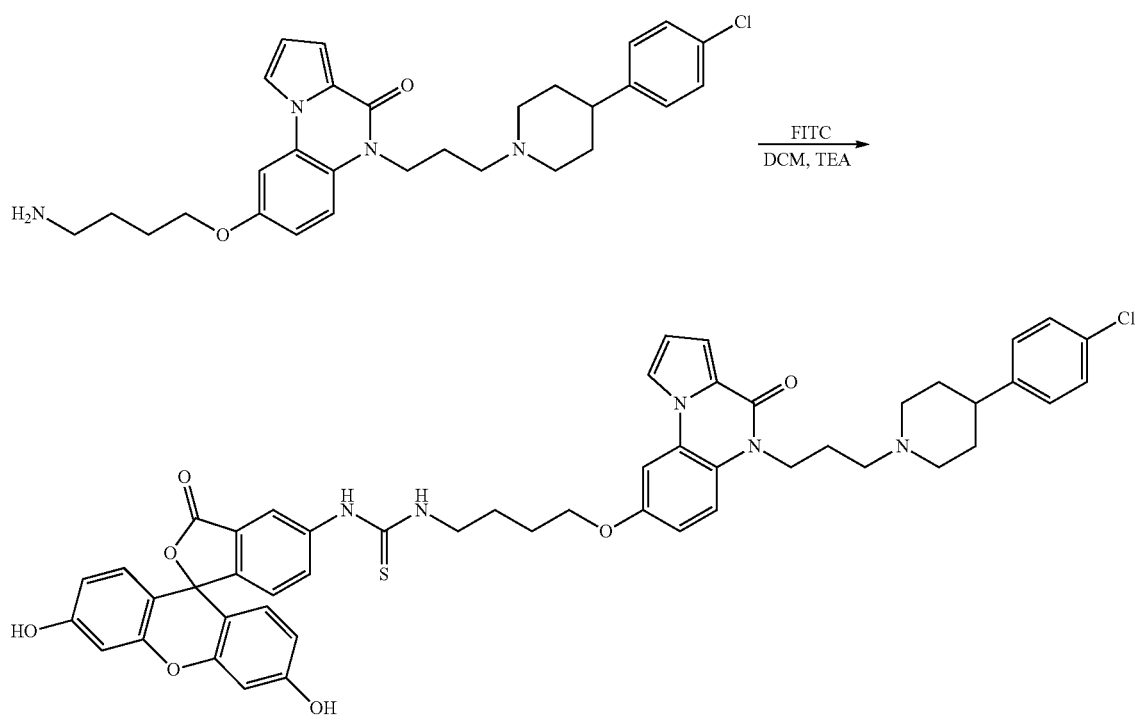

A solution of the primary amine compound (1 eq) and TEA (3 eq) in DCM was stirred at rt under nitrogen atmosphere. FITC (1.2 eq) was added slowly to this mixture, the reaction was monitored by TLC analysis. The residue was purified by flash chromatography on silica gel (DCM/MeOH=10:1) gave product as a yellow solid (31% yield), ESI-HRMS: calcd. for $C_{50}H_{46}ClN_5O_7S$+H: 896.28847, found 896.28855.

Example 8: Effect of Compound XXII on Tumor Seeding and Progression

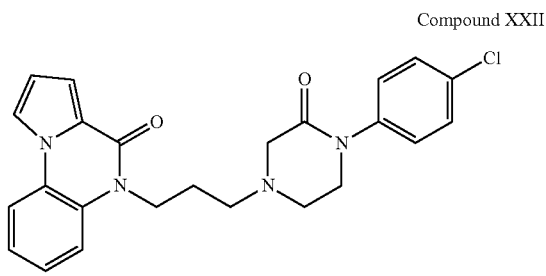 [SMILES: O=C1CN(CCCn2c(=O)c3cccn3c3ccccc32)CCN1c1ccc(Cl)cc1]

Compound XXII

Figure 7A:
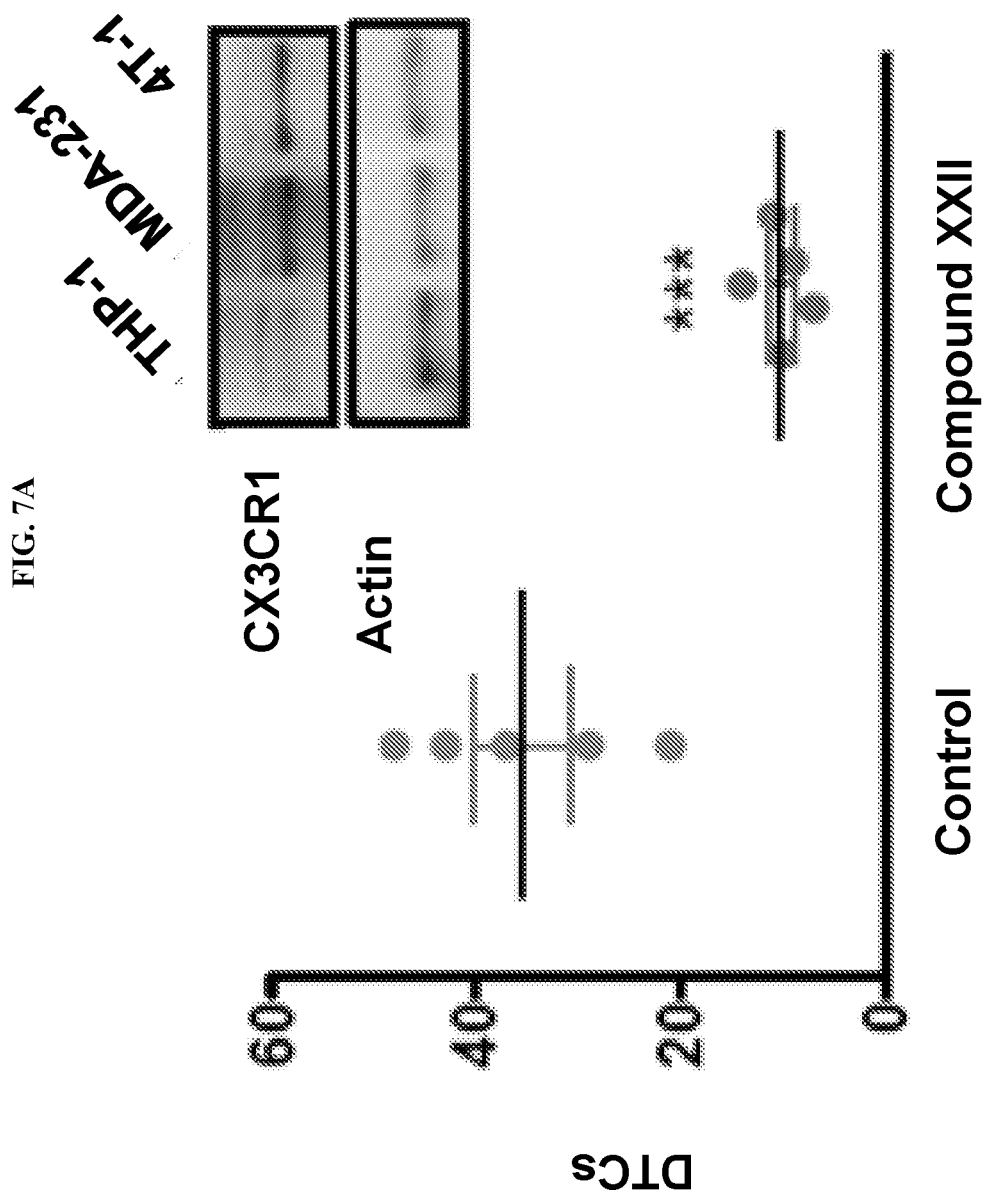
FIGS. 7A-7F comprise graphs and images showing impaired metastatic seeding and progression by pharmacologic antagonism of CX3CR1. Murine 4T-1 (FIG. 7A) and human MDA-231 (FIG. 7B) breast cancer cells, both expressing CX3CR1 (FIG. 7A inset) were significantly impaired in seeding the skeleton of mice treated with Compound XXII. In contrast, the CXCR4 antagonists AMD-3100 had no effect on tumor seeding in similar experiments ( P=0.0058; * P=0.0009, unpaired t-test).
Figure 7B:
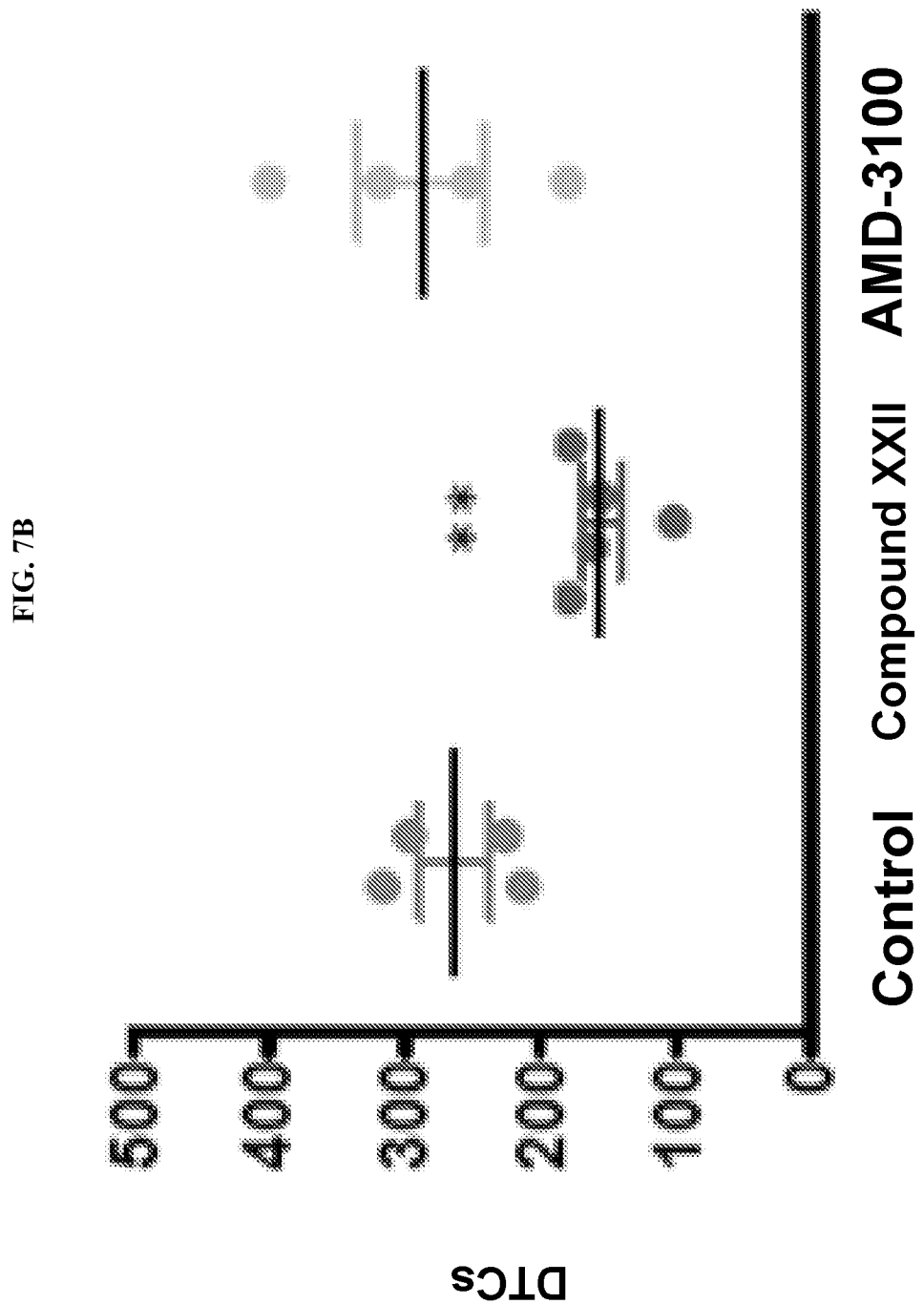
Figure 7C:
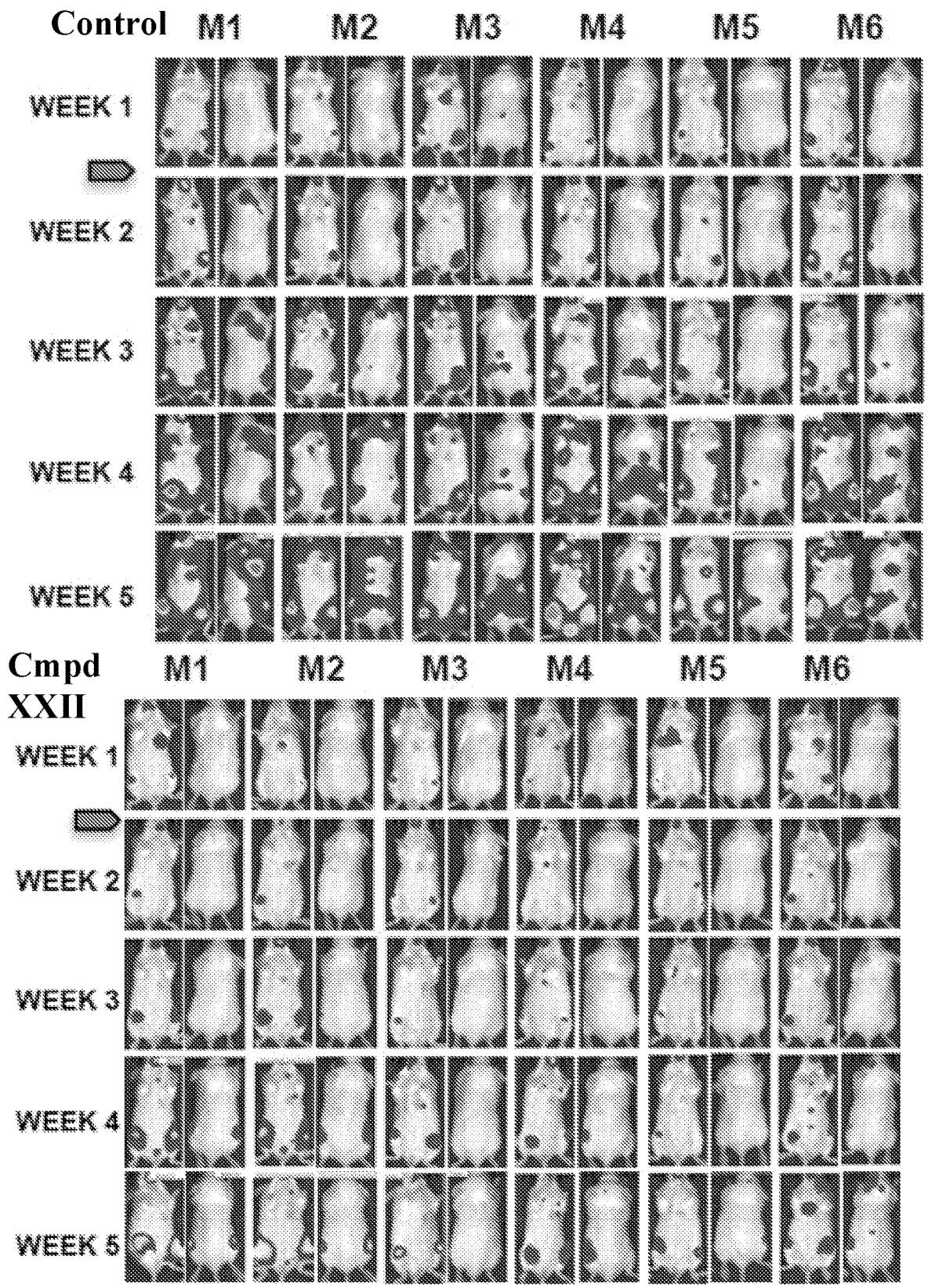
Figure 7D:
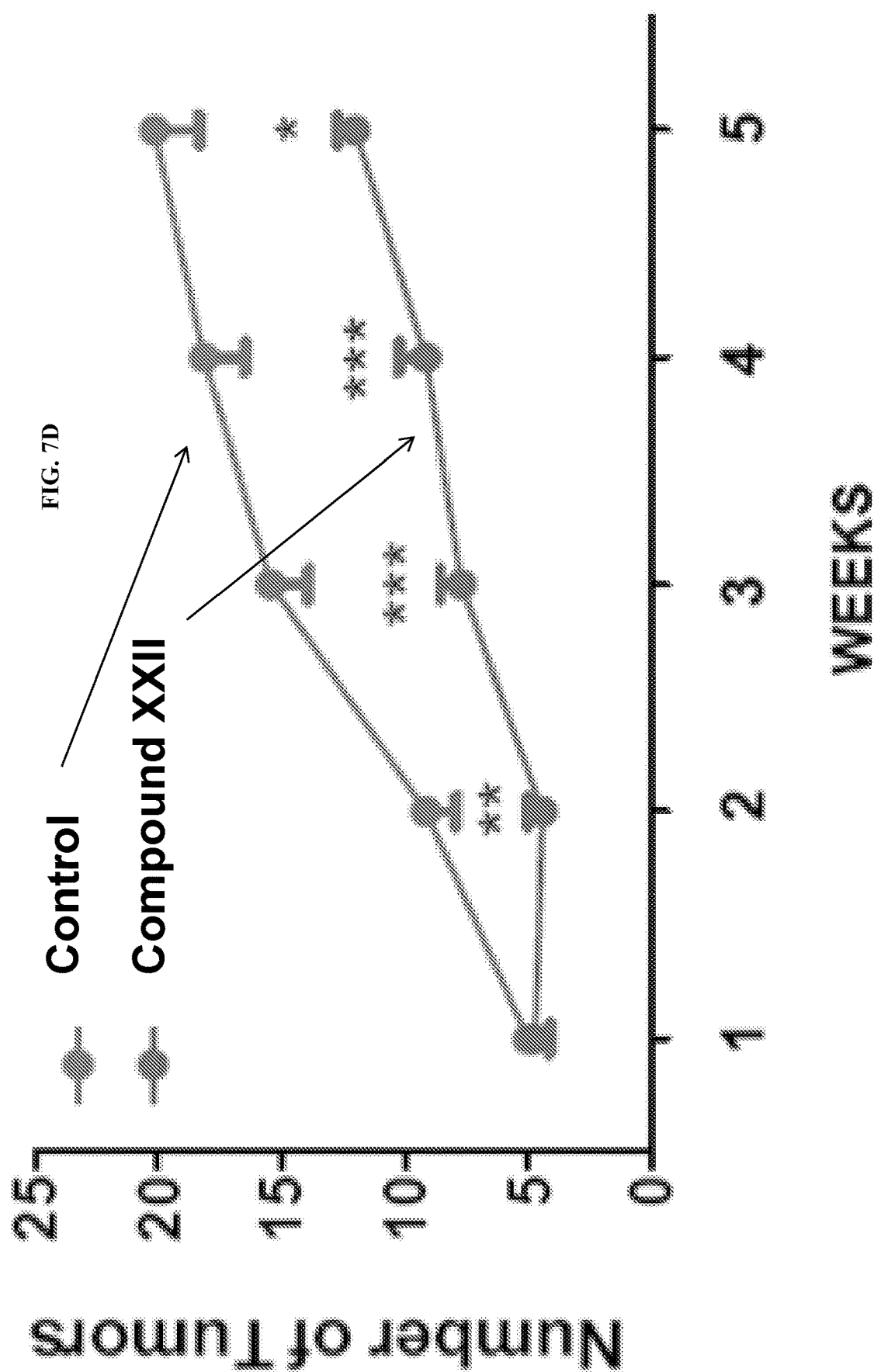
Figure 7E:
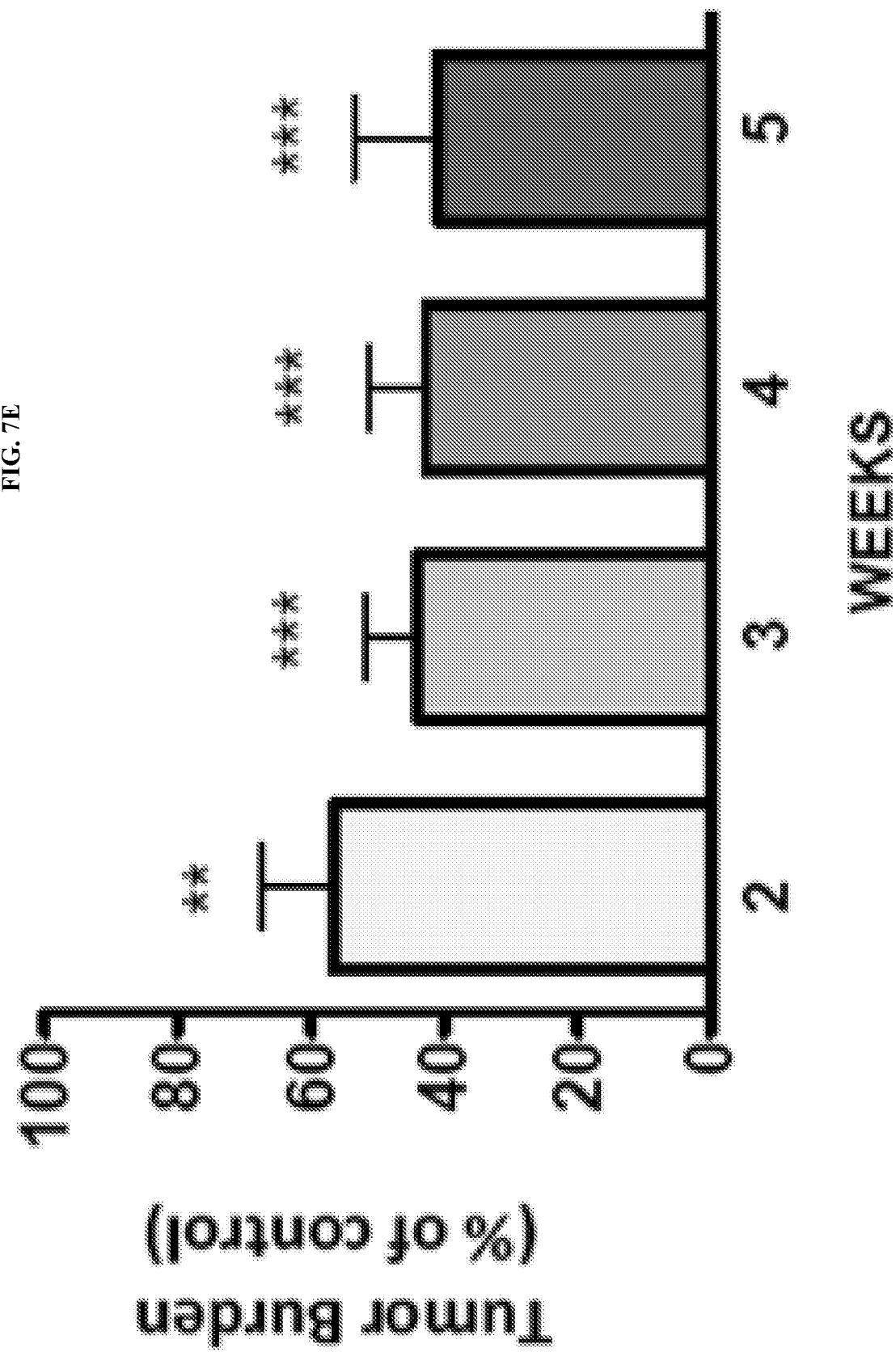
Figure 7F:
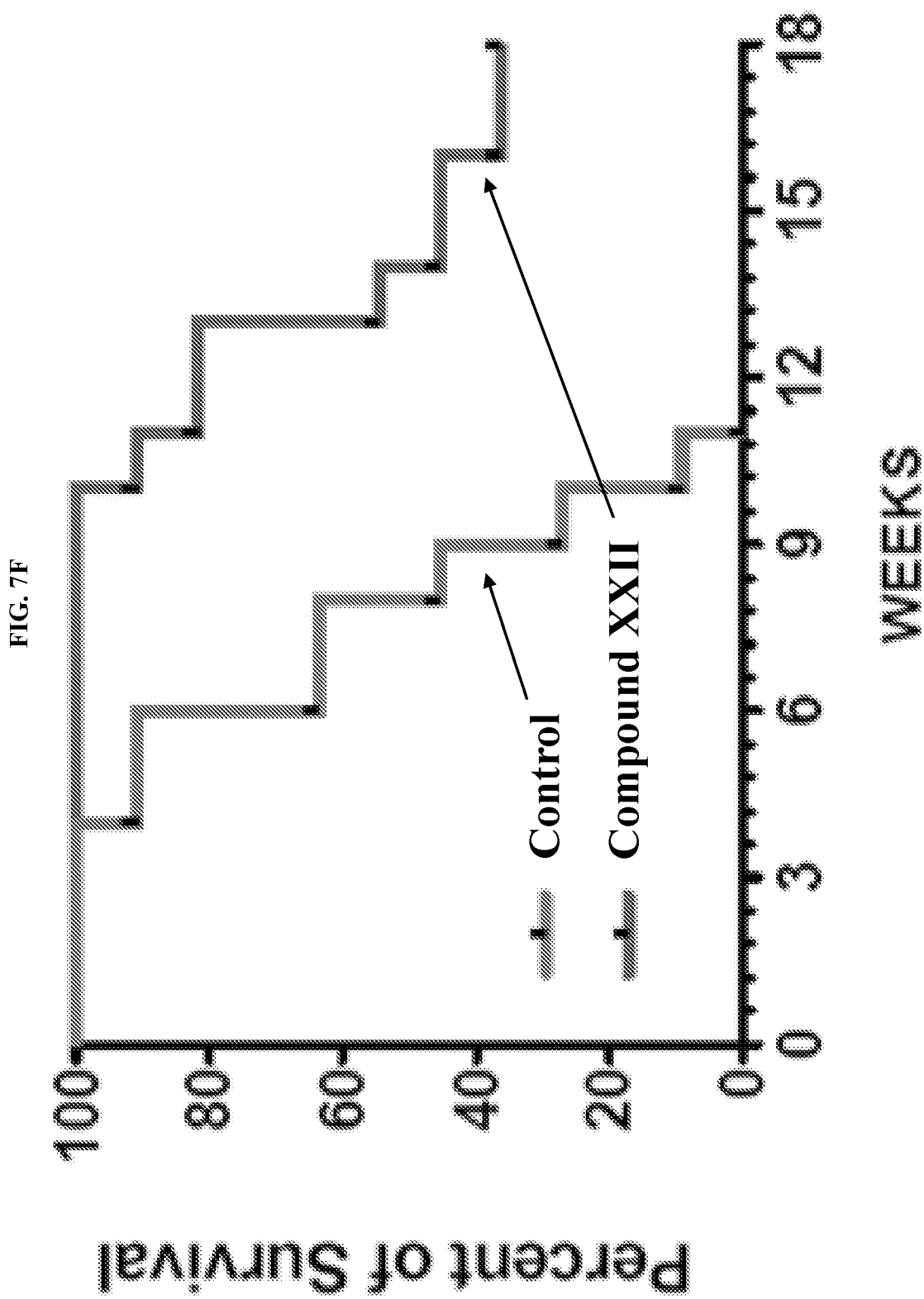

Compound XXII was tested for its ability to interfere with the seeding of circulating breast cancer cells by antagonizing CX3CR1. Human (MDA-MB-231) or murine (4T-1) breast cancer cells—both expressing CX3CR1 when compared to THP-1 human monocytic cell line as control (FIG. 7A) were grafted via the left cardiac ventricle into immuno-compromised (SCID) or immunocompetent (Balb-C) mice, respectively, to allow unbiased tumor spreading to different organs. Animals were administered with Compound XXII (10 mg/kg) or vehicle via intraperitoneal route (i.p.) one hour before and 3 hours after the inoculation of cancer cells. The effects of Compound XXII closely matched those found using Compound I. Treatment with Compound XXII severely impaired both MDA-231 and 4T-1 cell types from seeding the skeleton in treated animals (FIGS. 7A-7B). When the same experiment was conducted by administering animals with AMD-3100, a well characterized and widely used small-molecule inhibitor of the chemokine receptor CXCR4 12, the seeding of breast cancer cells was unaffected (FIG. 7B). In animals grafted with MDA-231 cells as described above, small tumors were detected by bioluminescence imaging in the skeleton and soft-tissues at one-week post-inoculation, providing a valuable pre-clinical model of early metastatic disease (FIG. 7C). Following randomization of inoculated animals into control and treated groups, it was found that targeting CX3CR1 both limited the progressive expansion in tumor numbers typically observed in untreated animals (FIG. 7D), and contained the overall tumor burden below 50% of the levels assessed in the control group (FIG. 7E). These effects translated into a dramatic extension of overall survival induced by the CX3CR1 antagonist as compared to control animals treated with vehicle (FIG. 7F). Taken together, these observations further corroborated the implication of the chemokine receptor CX3CR1 in the metastatic behavior of breast cancer cells, and indicate that the numerical expansion of early tumors into additional metastatic sites could be effectively counteracted by pharmacologically targeting this chemokine receptor.

Example 9: Effects of Compound XXII on CTCs in Blood

Figure 8A:
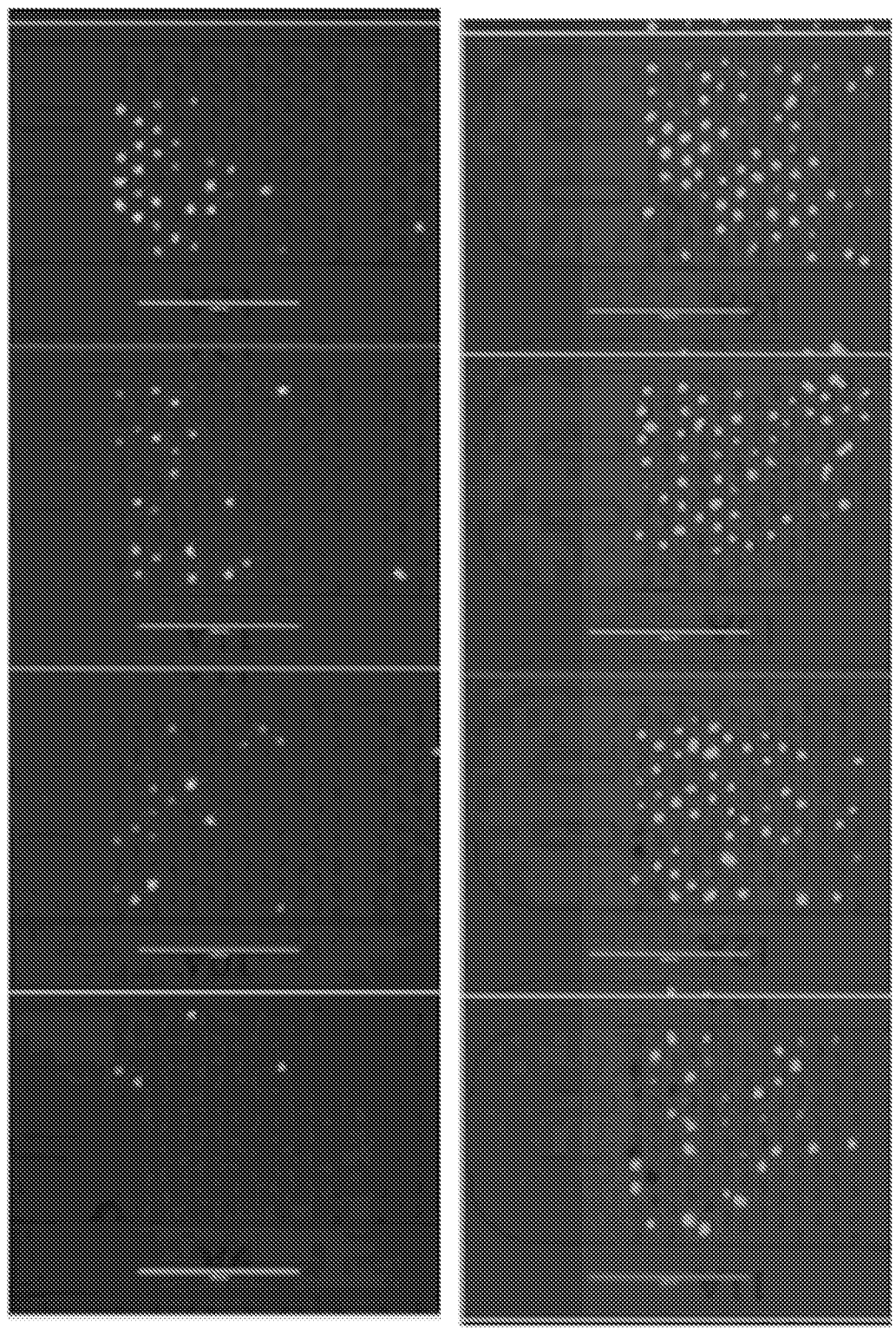
FIGS. 8A-8E comprise images and graphs showing that CX3CR1 antagonism retains CTCs in the blood and promotes apoptosis.
Figure 8B:
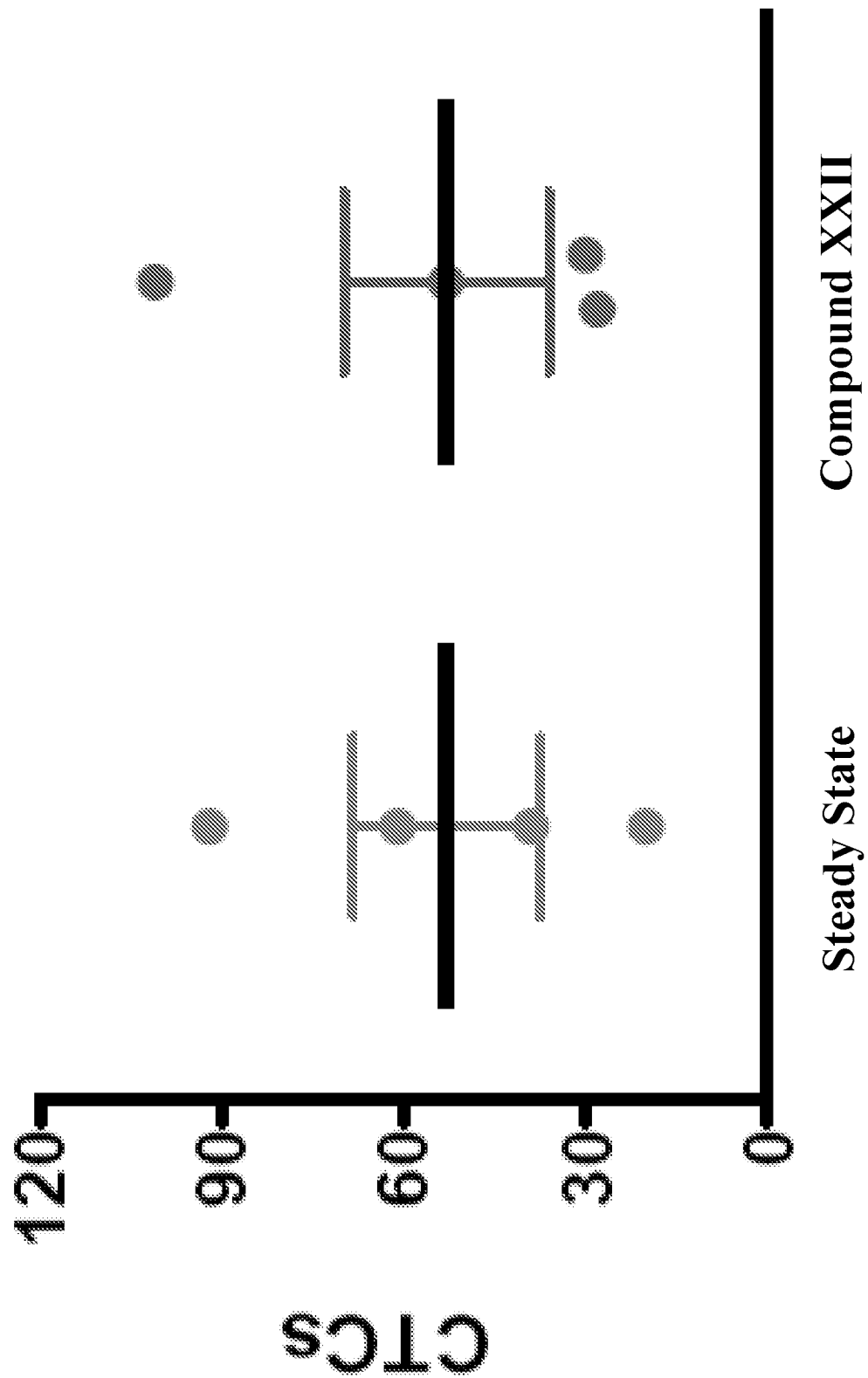
Figure 8C:
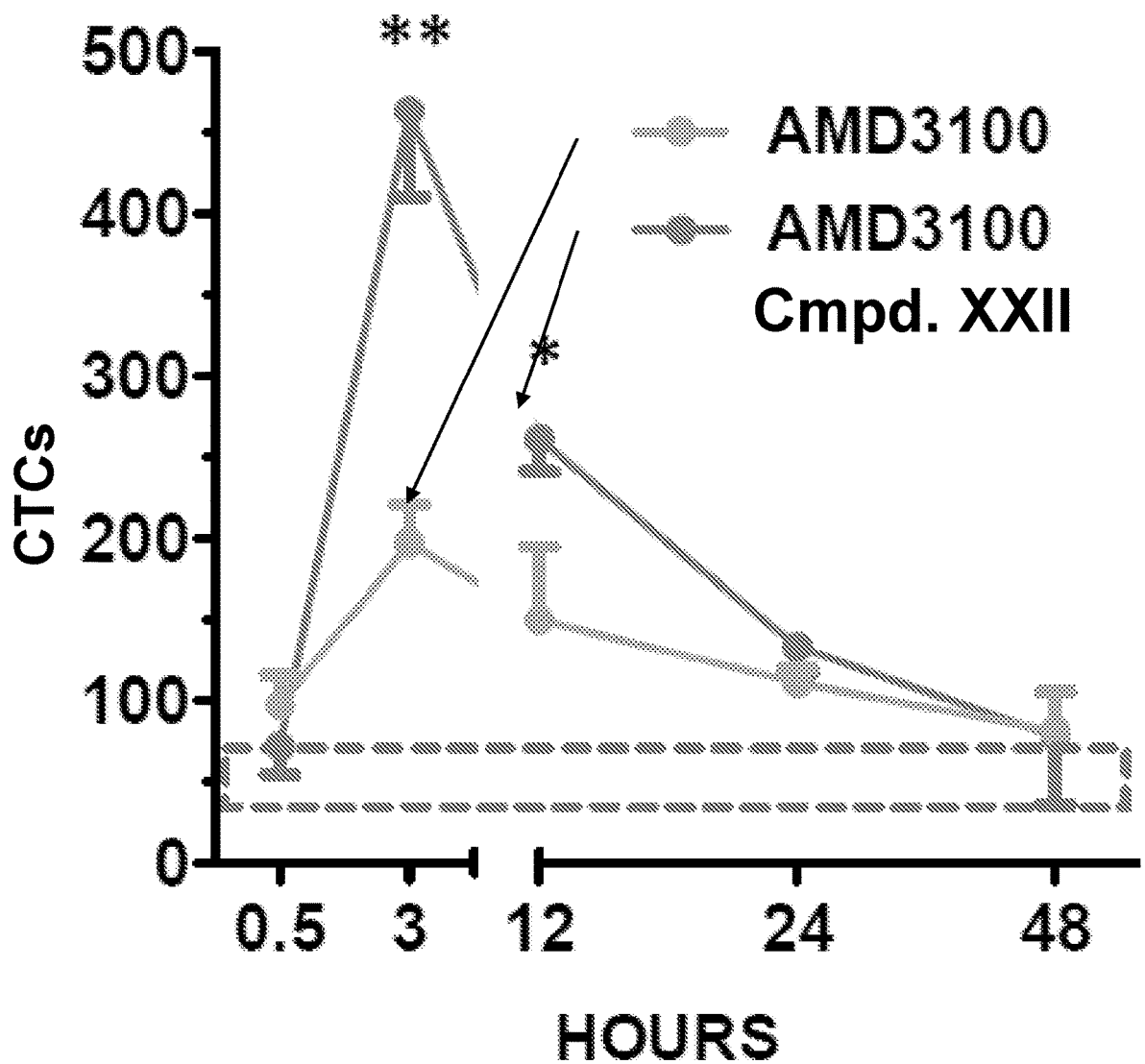
Figure 8D:
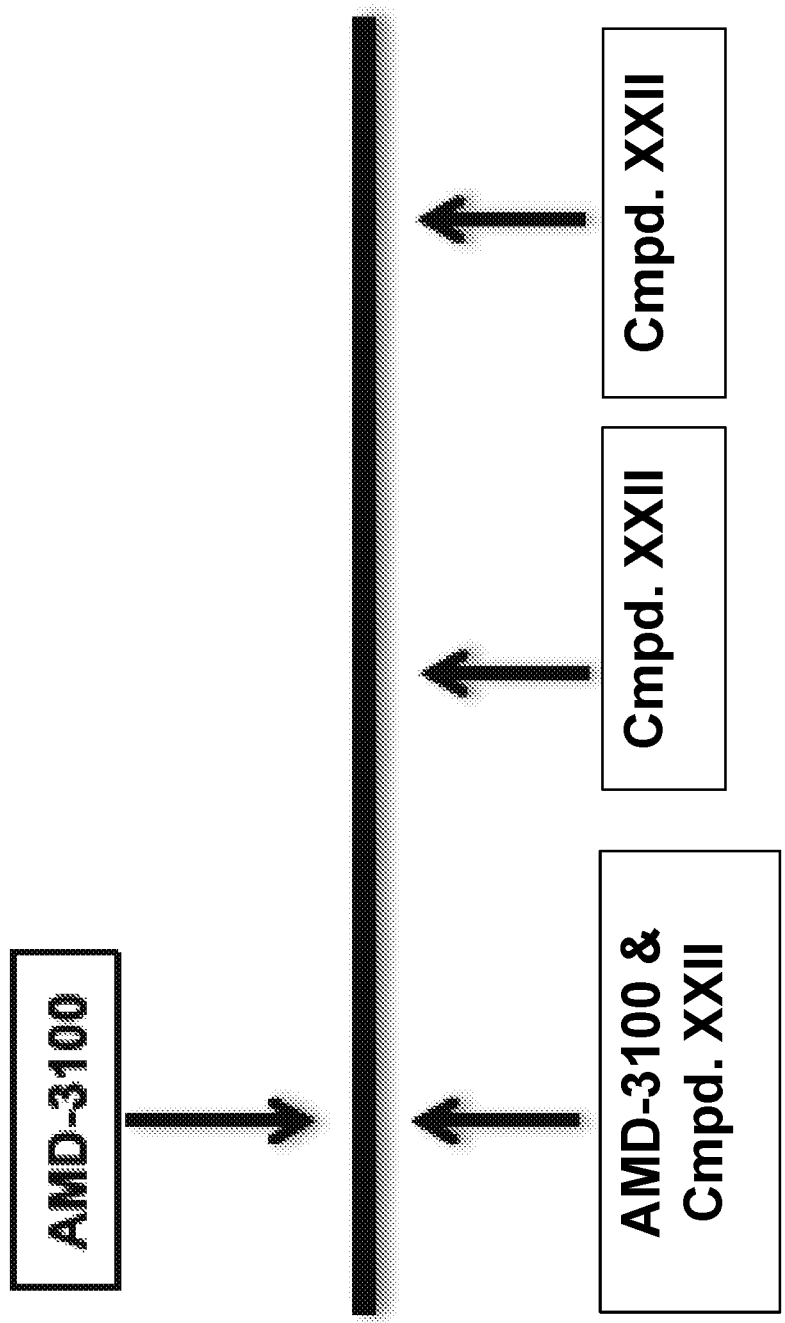
Figure 8E:
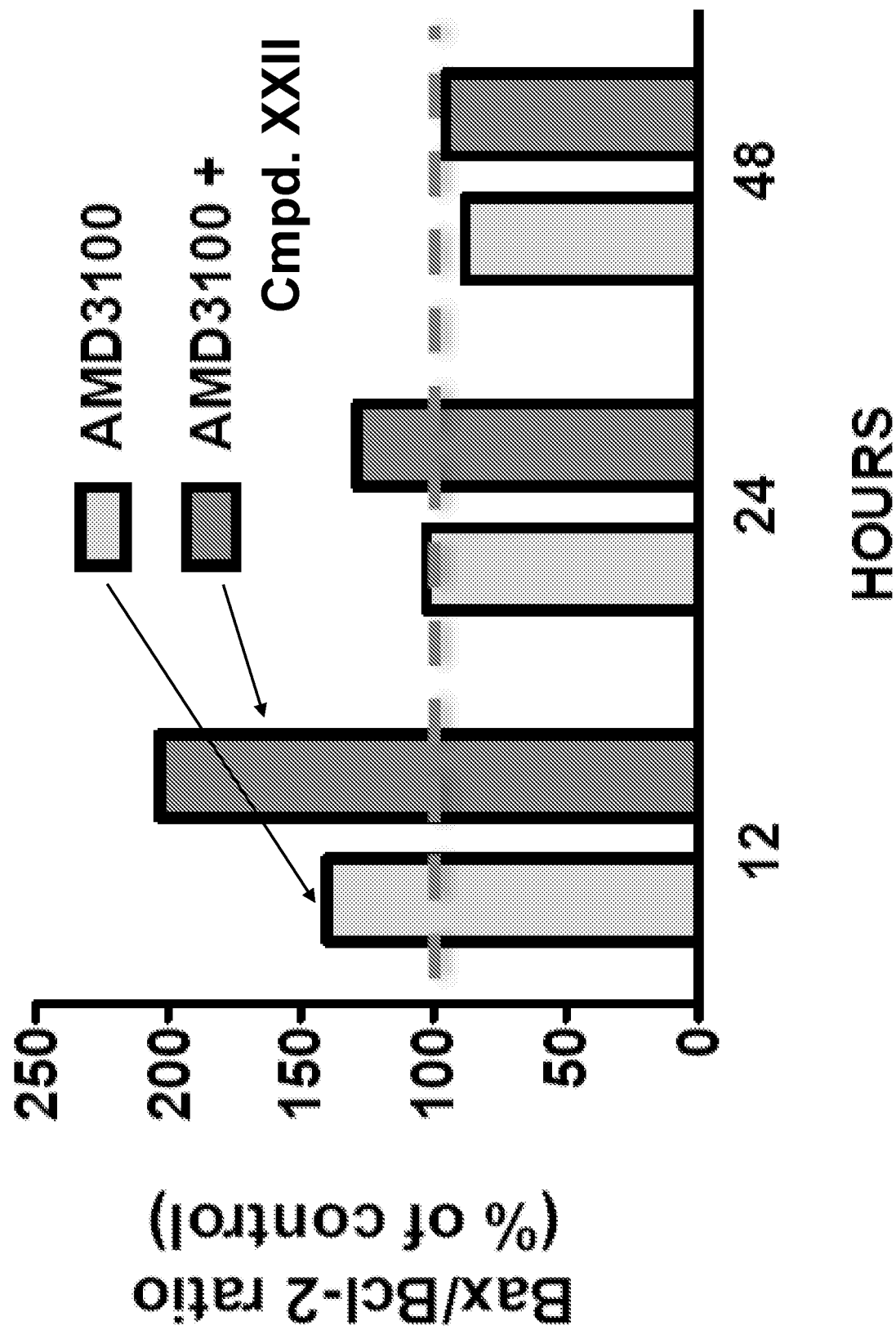

Compound XXII was then tested to see if targeting CX3CR1 contained the emergence of additional tumors by directly preventing CTCs from reseeding skeleton and soft-tissues. Cancer cells in the blood are a dynamic pool that constantly fluctuates as cells enter circulation upon being dislodged from tumors, reseed additional sites or perish to anoikis if they fail to do so. This makes determining the time spent by cancer cells in the blood problematic. A major hurdle for these types of studies is the limited ability to monitor the timing of CTCs' entry into and egress from the blood during steady-state conditions. To circumvent these issues, cancer cells were acutely mobilized from tumors in the skeleton and soft-tissues in mice—above steady-state counts—and then thereafter the blood was sampled at specific intervals, reasoning that a time-dependent decline of the number of CTCs in the blood would result from cancer cells seeding back to tissues and dying in circulation. Mice were grafted via the left cardiac ventricle with MDA-231 cells to generate unbiased tumor spreading and reproduce the clinical scenario of metastatic disease; after three weeks animals developed large tumors in skeleton and soft-tissues (FIGS. 7A-7F) and were treated with a single dose (5 mg/kg) of AMD3100, an antagonist of the CXCR4 receptor. This compound mobilizes hematopoietic stem cells and multiple myeloma cells from the bone marrow of humans and mice and has been also used to dislodge Disseminated Tumor Cells (DTCs) from the skeleton of mice. Following AMD-3100, CTCs were isolated from the blood of tumor-bearing mice and it was found that administration of the CXCR4 antagonist induced a rapid increase in the number of CTCs. The number of CTCs post-treatment peaked at 3 hours and subsequently declined, and after 48 hrs returned to the steady-state counts observed in untreated animals (FIGS. 8A, 8C). In contrast to AMD-3100, Compound XXII does not mobilize cancer cells back in the blood (FIG. 8B). By targeting CX3CR1 Compound XXII held CTCs longer in circulation by preventing reseeding to the skeleton and possibly soft-tissues. When Compound XXII was co-administered with AMD-3100, and then alone twice/day thereafter (FIG. 8D), animals showed a rapid increase in CTCs counts that occurred at the same time-point as with AMD-3100 alone, but of a magnitude more than two-fold higher than without the CX3CR1 antagonist. Return of CTC counts to steady-state levels was clearly prolonged when Compound XXII was combined with AMD-3100 (AUC=731) as compared to AMD-3100 alone (AUC=345) (FIG. 2B), suggesting that targeting CX3CR1 delays the egress of CTCs from the blood circulation. When spreading via the systemic circulation, cancer cells become susceptible to anoikis and extending the time spent in the blood increases the odds of incurring this form of apoptotic cell death. Without being limited to any particular theory, by counteracting reseeding by targeting CX3CR1 the viability of cancer cells would also be affected. To test this hypothesis, CTCs were recovered from mice harboring 3-week tumors at 12, 24 and 48 hours following a dose of AMD-3100 alone or in combination with Compound XXII, which was successively administered alone twice/day for the duration of the experiment, as described above. The fraction of apoptotic CTCs in the two treated groups was assessed by measuring the Bax/Bcl-2 ratio (Perlman, H., et al. *Cell Death Differ* 6, 48-54 (1999)) and compared to the percentage of spontaneously apoptotic CTCs collected from untreated tumor-bearing mice. As shown in FIG. 8E, targeting CX3CR1 increased the percentage of apoptotic CTCs collected at 12 and 24 hours as compared to cells mobilized by AMD-3100 in the absence of Compound XXII.

Figure 9A:
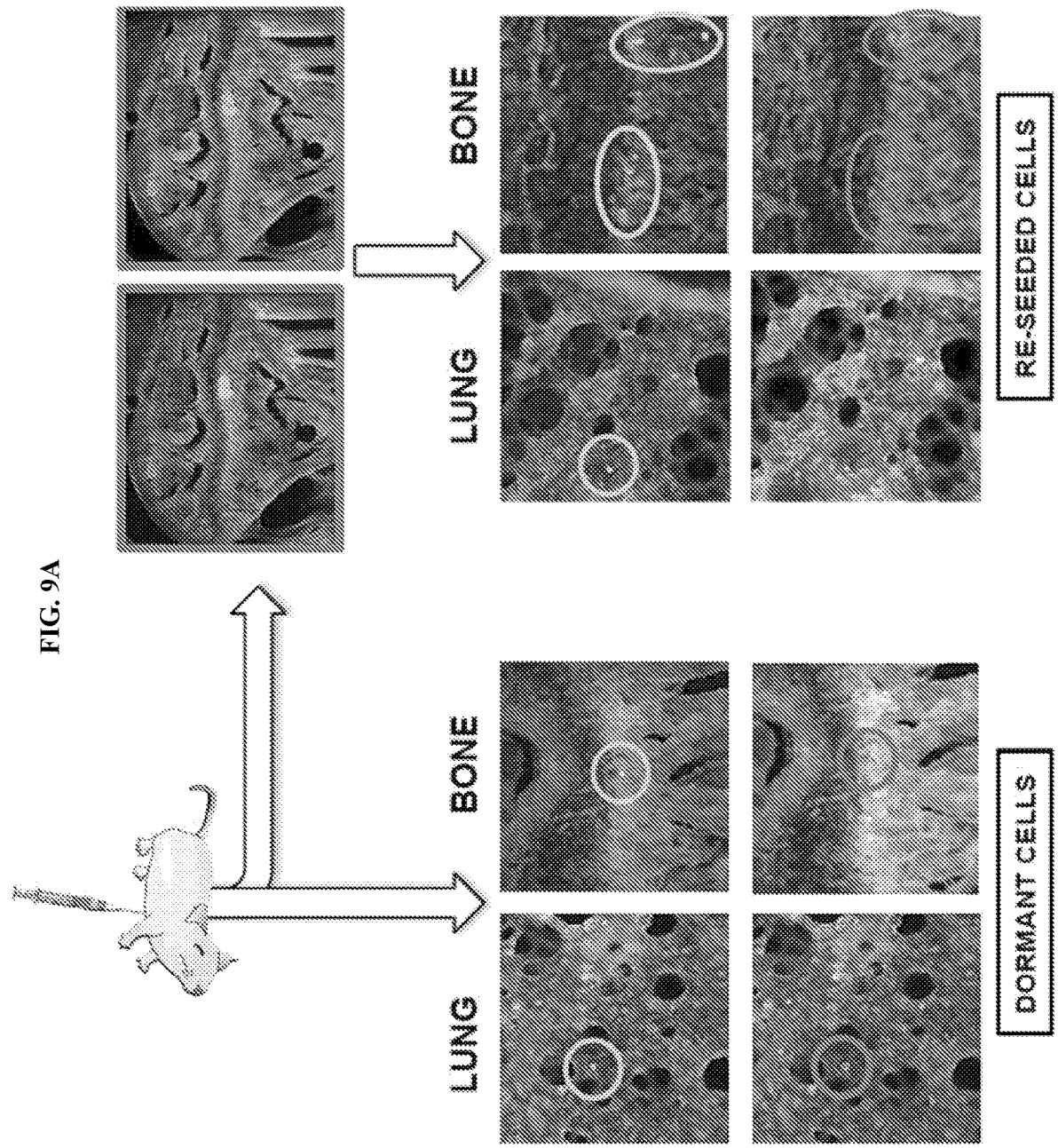
FIGS. 9A-9B comprise images of compromised reseeding of CTCs to bone and lungs.
Figure 9B:
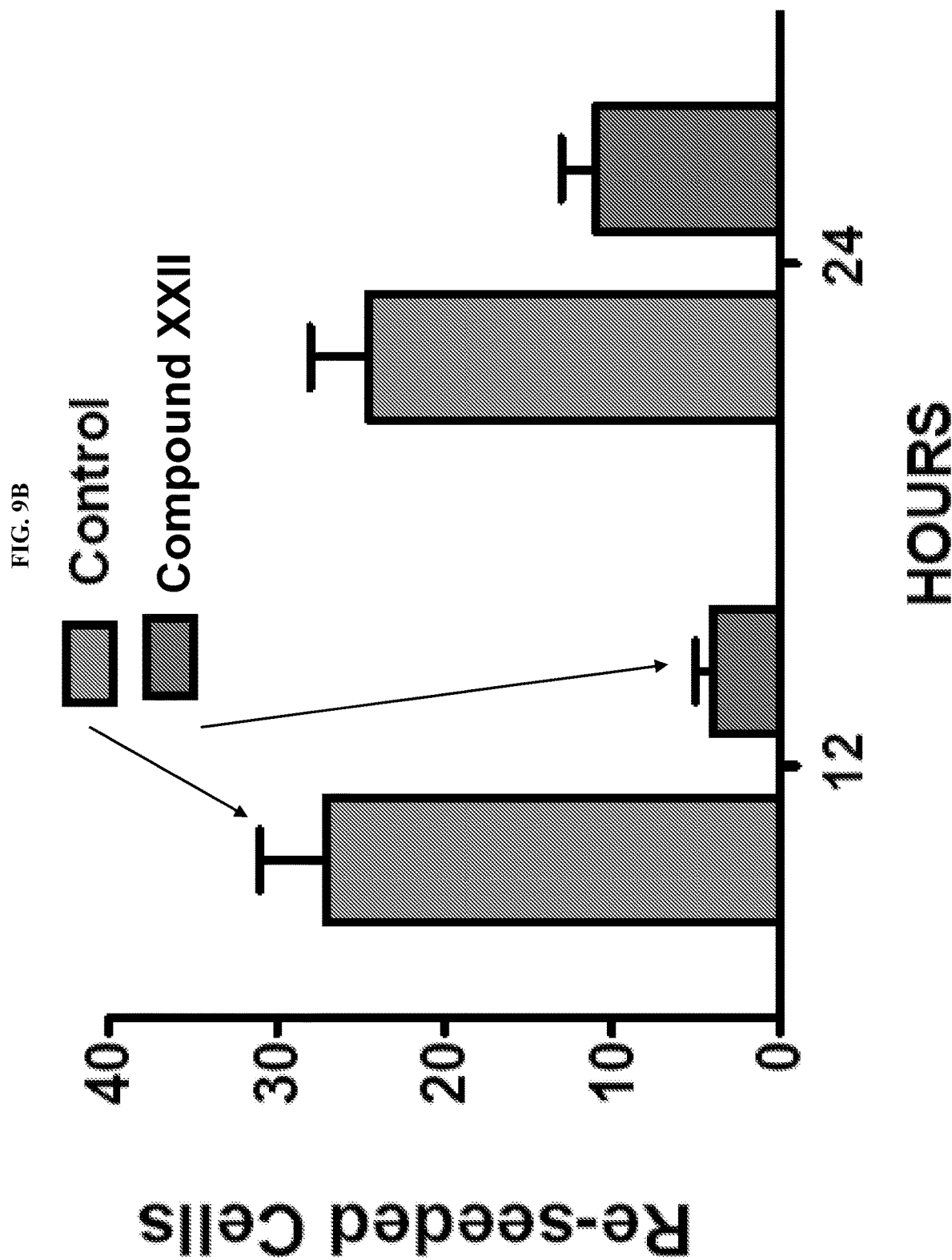

Example 10: Correlation Between CTCs in Blood Stream and Reseeded Cancer Cells Green-fluorescent MDA-231 cells were labeled with the cell-tracker CM-Dil, a widely validated red-fluorescent dye that, while being stably retained by non-dividing cells, is transferred to daughter cells upon mitosis and eventually becomes too diluted and undetectable in rapidly dividing cell populations. Based on these features, GFP/CM-DiI double-labeled cancer cells, when reseeding from established tumors would emit green fluorescence but lack red fluorescence, as the results of high proliferation during tumor growth and consequential dilution of the CM-DiI dye. Cancer cells that became dormant upon seeding different tissues following intracardiac injection would retain the CM-DiI dye, thereby emitting signals in both green and red fluorescent spectra (FIG. 9A). For these experiments, mice were grafted with double-labeled cancer cells in the left cardiac ventricle and allowed to develop tumors for two weeks. After two weeks, animals were then treated with AMD-3100 with or without Compound XXII (10 mg/Kg, i.p., 1 hr prior and 3 hrs after AMD-3100) and killed 12 or 24 hours later. Lung and knee-joints were harvested and inspected for fluorescent cancer cells using a Multispectral Imaging System. FIG. 9B shows that cancer cells with features of reseeded cells were identified at both time points and their numbers were dramatically reduced by the systemic administration of the CX3CR1 antagonist as compared to untreated animals.

Figure 10A:
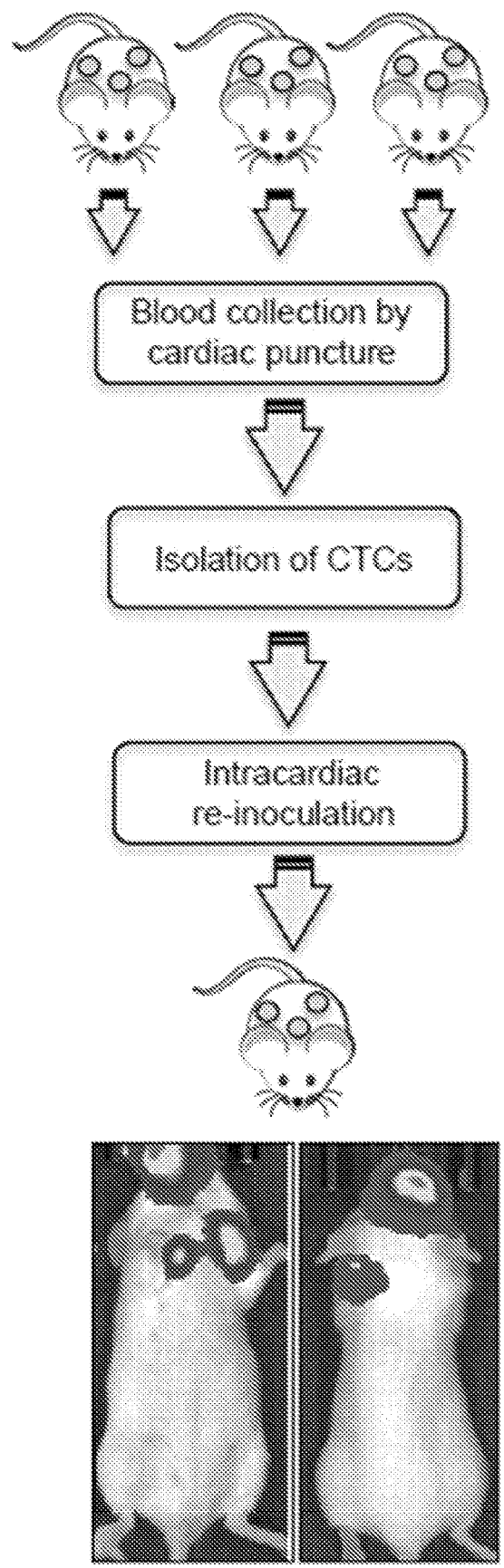
FIGS. 10A-10D comprise that CTCs from metastases have tumor-forming ability and can re-seed to generate additional lesions.

Example 11: CTCs Retain Metastatic Potential after Departing Secondary Tumors The results reported in Examples 8-10 indicate that cancer cells can effectively seed different tissues upon departing from existing disseminated tumors and this process can be countered by the pharmacological targeting of CX3CR1. It was then tested whether CTCs—in addition to reseeding—retained full metastatic behavior as defined by the ability to colonize and grow into detectable tumor foci. A label-free microfluidic system was used to isolate CTCs at steady state from nine mice inoculated with 4T-1 cells, which generated multiple tumors in skeleton and soft-tissues. CTCs were collected, counted, pooled into one cell suspension and re-inoculated into three mice at <100 CTCs/animal. Despite the extremely low number of inoculated cancer cells, one out of three mice showed multiple lesions by bioluminescence in vivo imaging at 2 weeks post-grafting and larger tumors at the fourth week (FIG. 10A). This result demonstrates the first available pre-clinical evidence of full metastatic potential retained by CTCs departed from multiple tumors reproducing metastatic disease in humans.

Figure 10B:
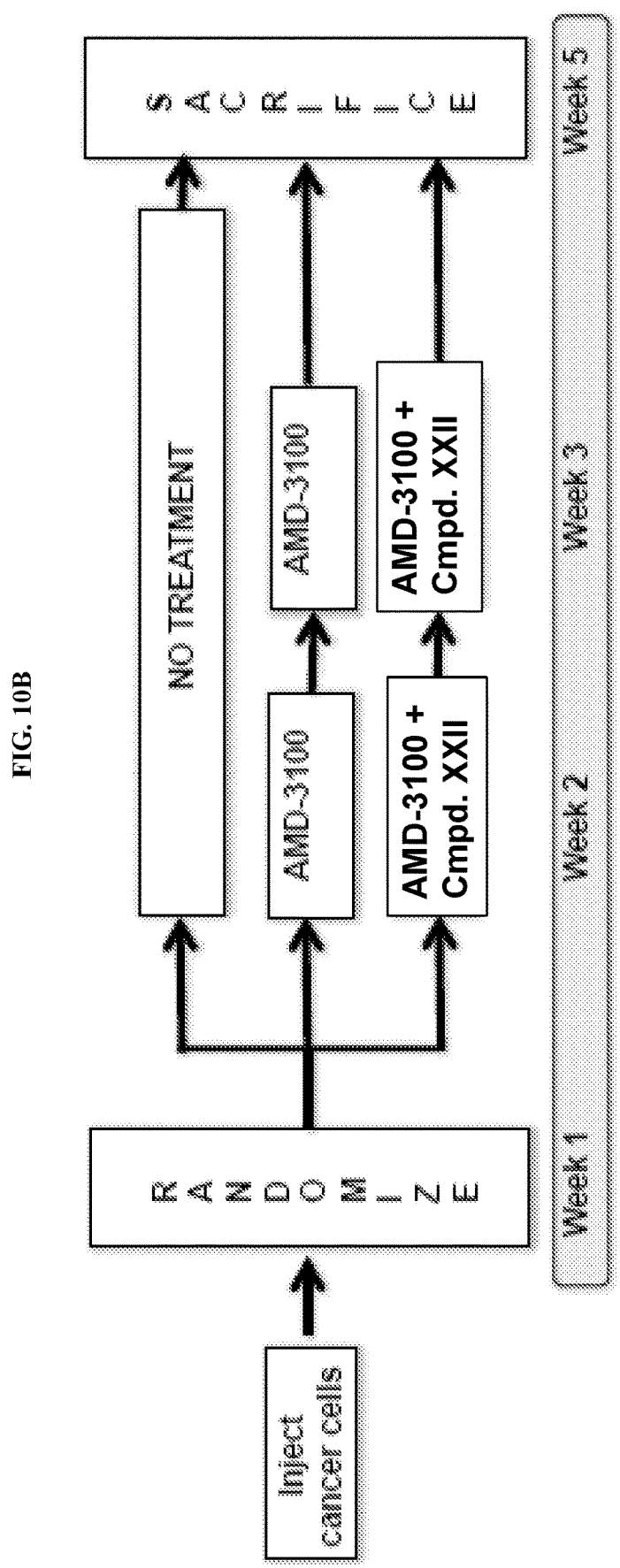
Figure 10C:
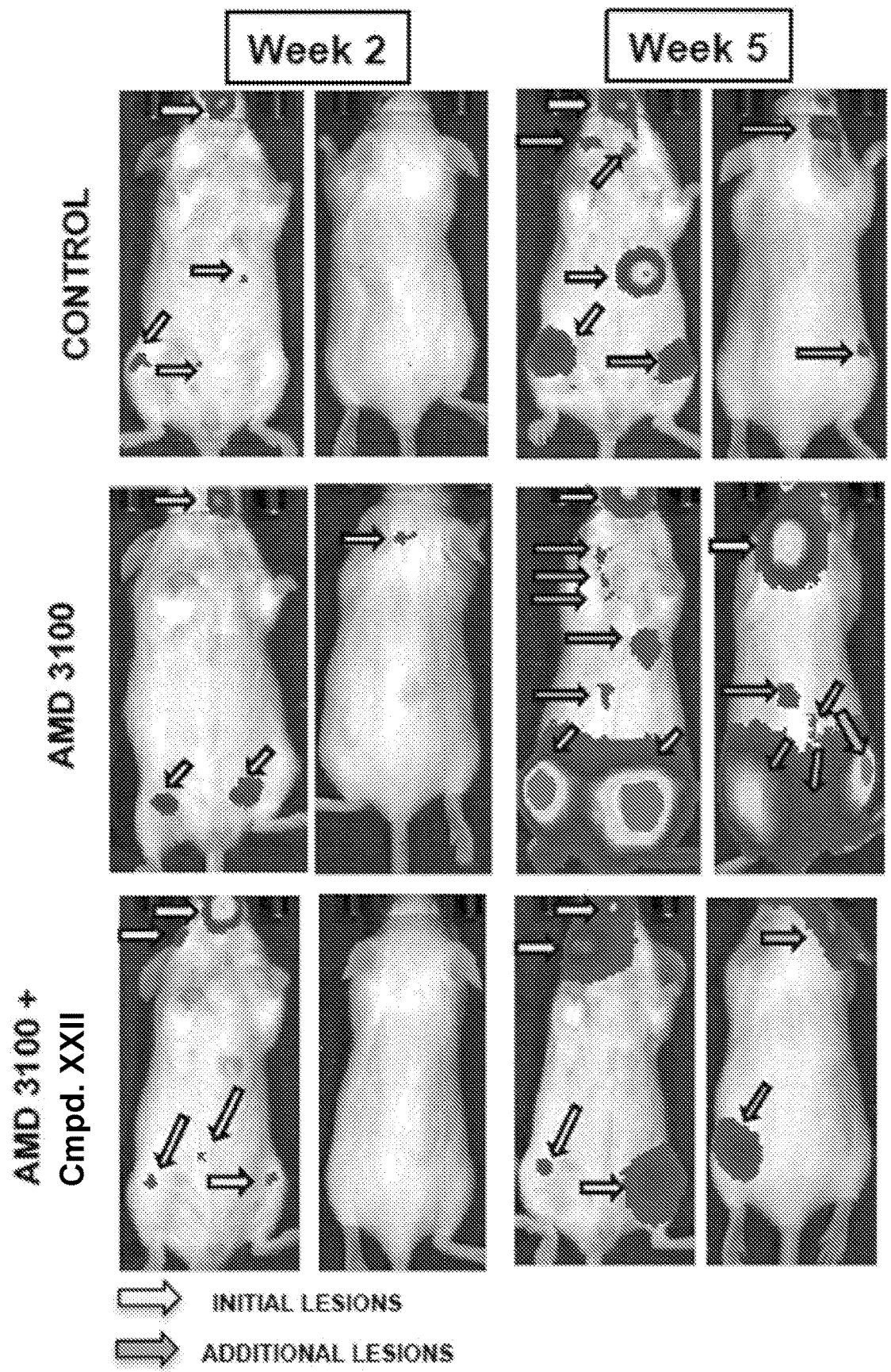
Figure 10D:
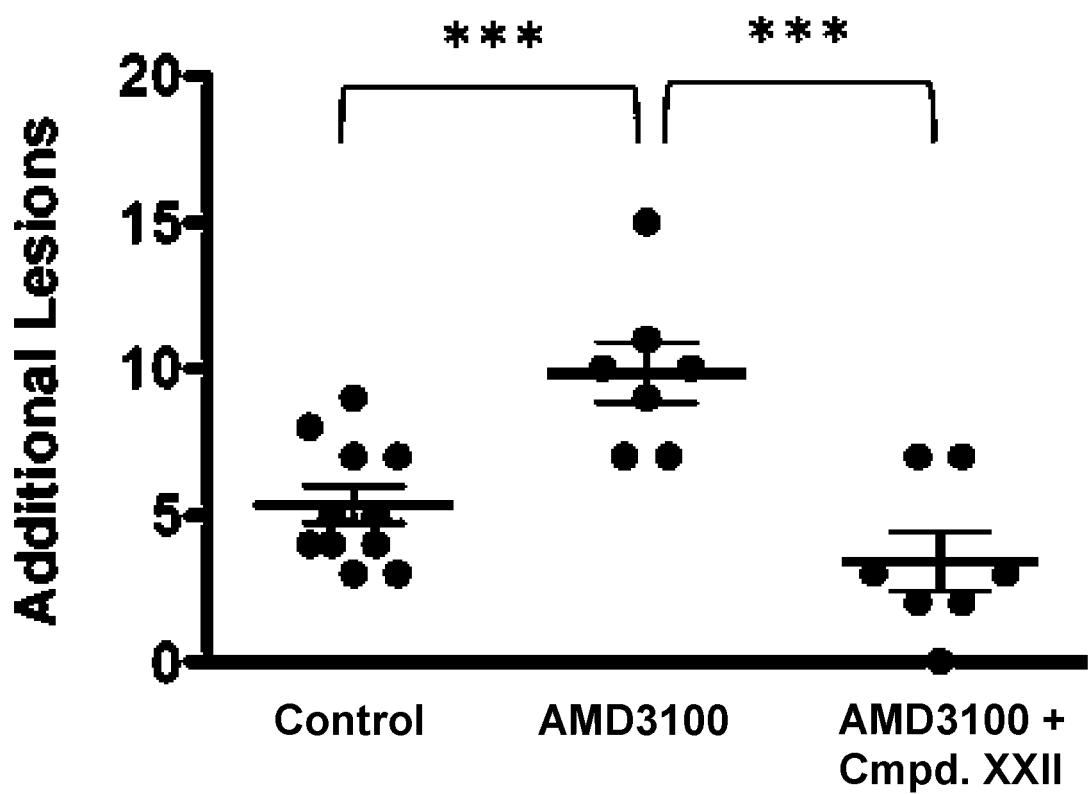

Complementary studies were conducted in mice harboring experimental metastases as detected at one week post-grafting, and left either untreated or treated at the second and third week with AMD-3100, alone or in combination with Compound XXII (FIG. 10B). All lesions identified at the fifth week that had not been previously detected at the second week of the experiment were counted and compared among treatment groups. It was found that mice receiving AMD-3100 showed a doubled number of additional lesions as compared to untreated animals, an effect that was ablated by co-administration of the CX3CR1 antagonist (FIGS. 10C-10D). These results provide evidence that cancer cells departing from secondary tumors in bone and soft-tissues retain the potential to colonize different tissues and generate additional metastases, incidentally explaining why prolonged treatment with AMD-3100 alone did not extend overall survival of mice with experimental lung metastases.

Example 12: Prevention of CTC Reseeding Prolongs Exposure to Doxorubicin

Figure 11B:
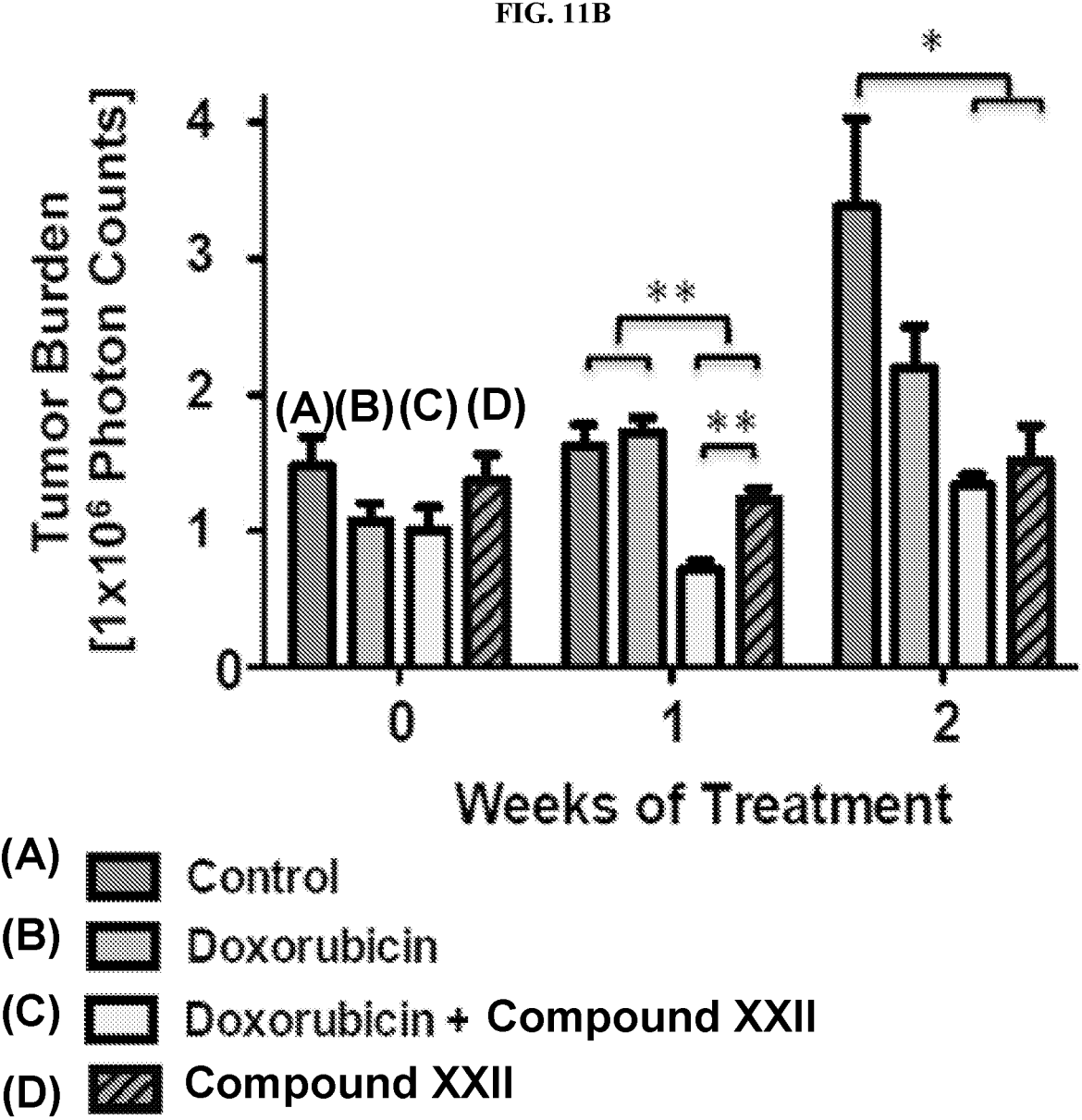
Figure 11C:
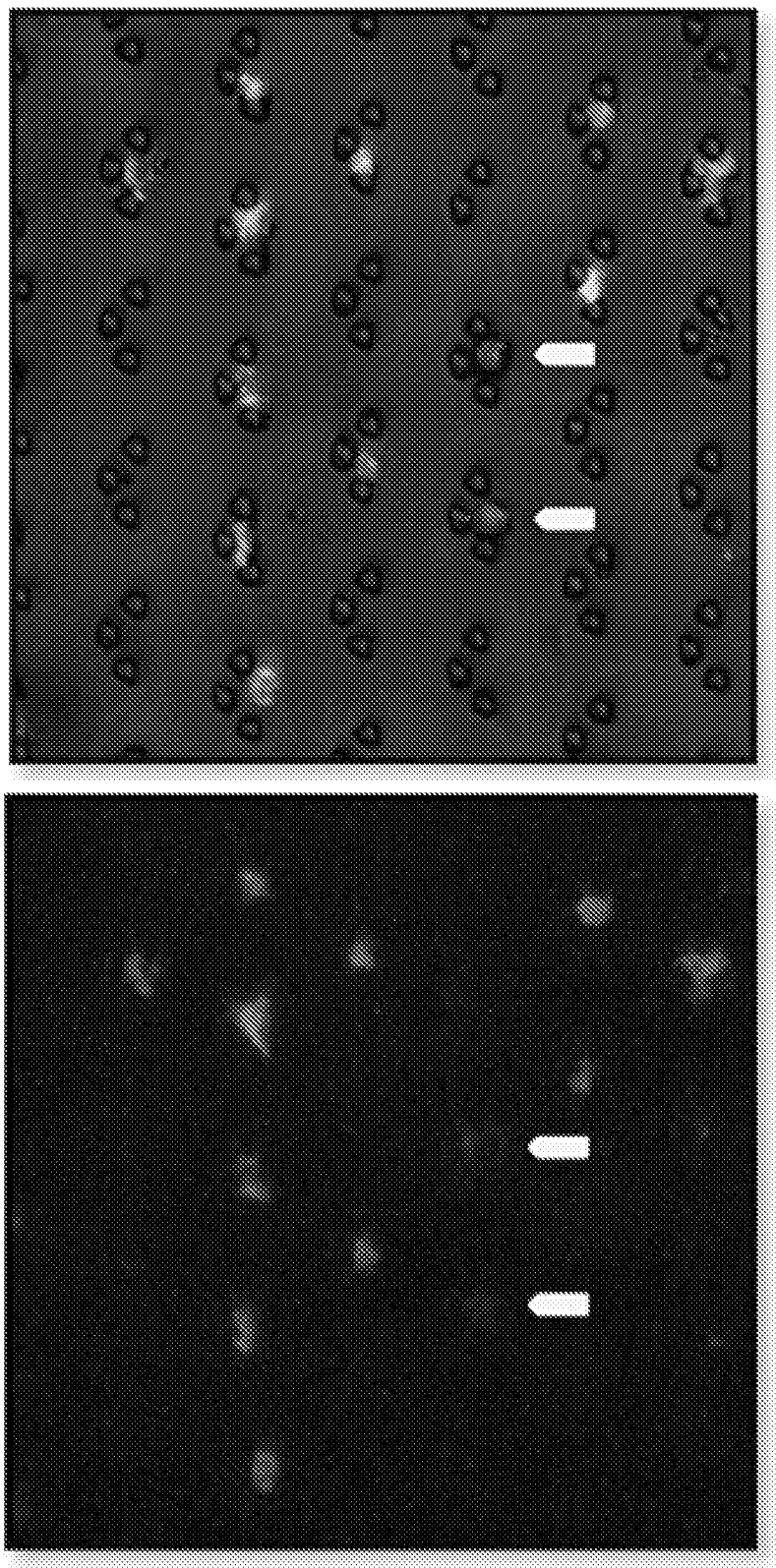
Figure 11D:
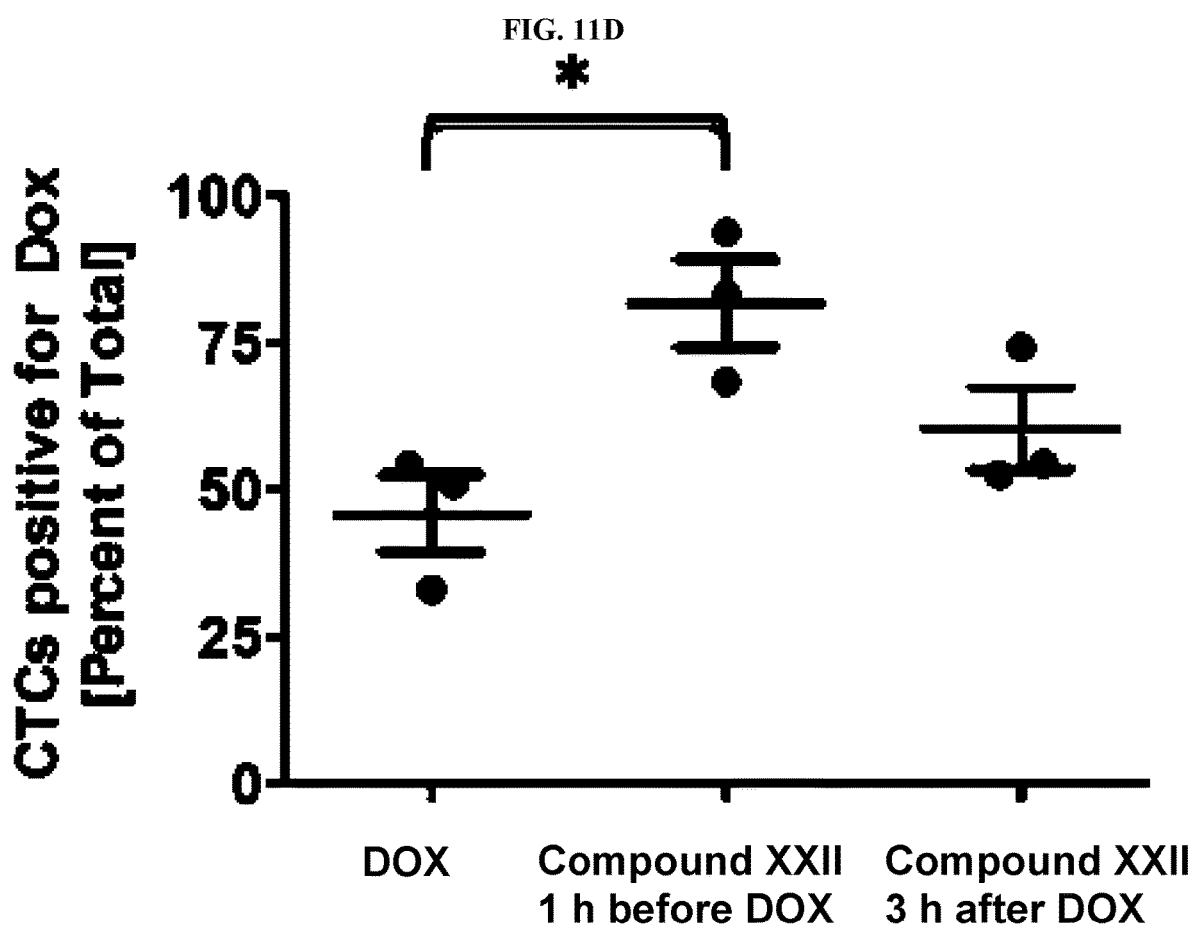

Mice harboring 1-week disseminated tumors were treated with the anthracycline antibiotic Doxorubicin (5 mg/Kg, i.p., q.w.), alone or in combination with Compound XXII (10 mg/Kg, i.p., b.i.d.) for the entire duration of the study. After two weeks of treatment animals showed significant toxicity from the Doxorubicin and had to be euthanized. When the effects on both number of tumors and tumor burden were examined, Doxorubicin failed to show any significant effect as compared to control (FIGS. 11A-11B). Furthermore, when Doxorubicin was used in combination with Compound XXII, the containment of tumor numbers and mitigation of tumor burden were comparable to Compound XXII alone, except for the tumor burden measured after one week of treatment, which showed a significantly superior effect. The data suggest that—at least over a short period of time—interfering with CX3CR1 functioning exerts a superior anti-tumor effect than Doxorubicin. It could be argued that this lack of effect shown by the chemotherapeutic drug was likely attributable to the short length of treatment, shorter than common protocols used in oncology practice. Synergistic effects were minimal with the exception of a significant reduction in tumor burden observed at 1 week—induced by combining Doxorubicin with Compound XXII. The acute toxicity of Doxorubicin precluded longer experiments. In order to test whether retaining cancer cells in the blood circulation by targeting CX3CR1 could extend their exposure to chemotherapeutics, the fluorescent properties of Doxorubicin were utilized and the red-spectrum emitted fluorescence of CTCs was collected at steady state from mice harboring disseminated tumors which were treated with Doxorubicin (alone, one hour after or three hours prior to administration of Compound XXII). CTCs were collected—independently of the type of treatment—four hours after Doxorubicin administration. The uptake of Doxorubicin was assessed by fluorescence microscopy (FIG. 11C) and the analysis showed that a prior administration of the CX3CR1 antagonist caused a significant increase in the number of CTCs positive for intracellular Doxorubicin as compared to mice exposed to the drug either alone or followed by Compound XXII. These results imply that impairing reseeding also increases the drug exposure of CTCs, which could thereby improve the efficacy of cytotoxic and targeted therapeutics by increasing their cellular bioavailability.

Example 13: Prevention of CTC Reseeding Prolongs Exposure to Docetaxel

Figure 11E:
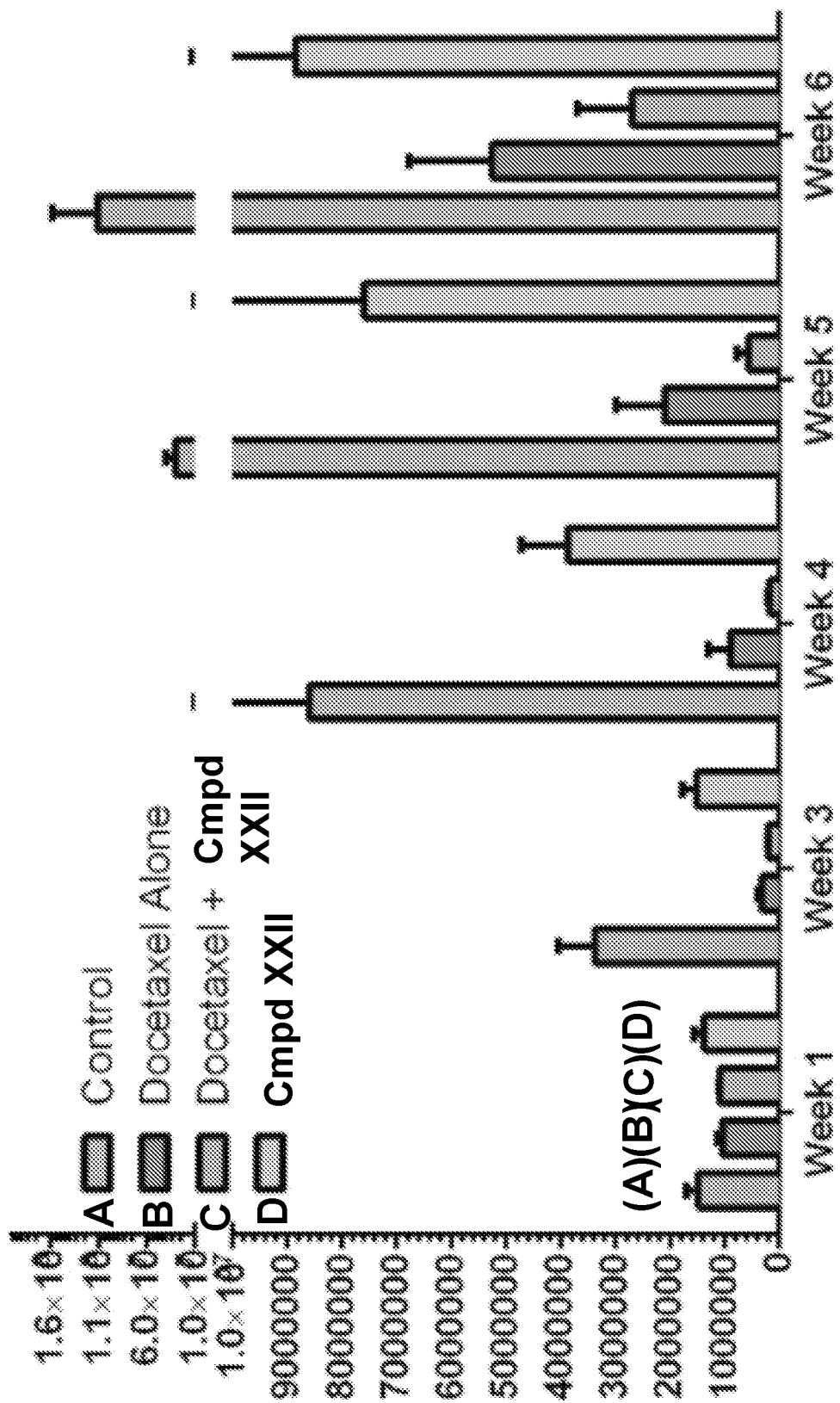
Figure 11F:
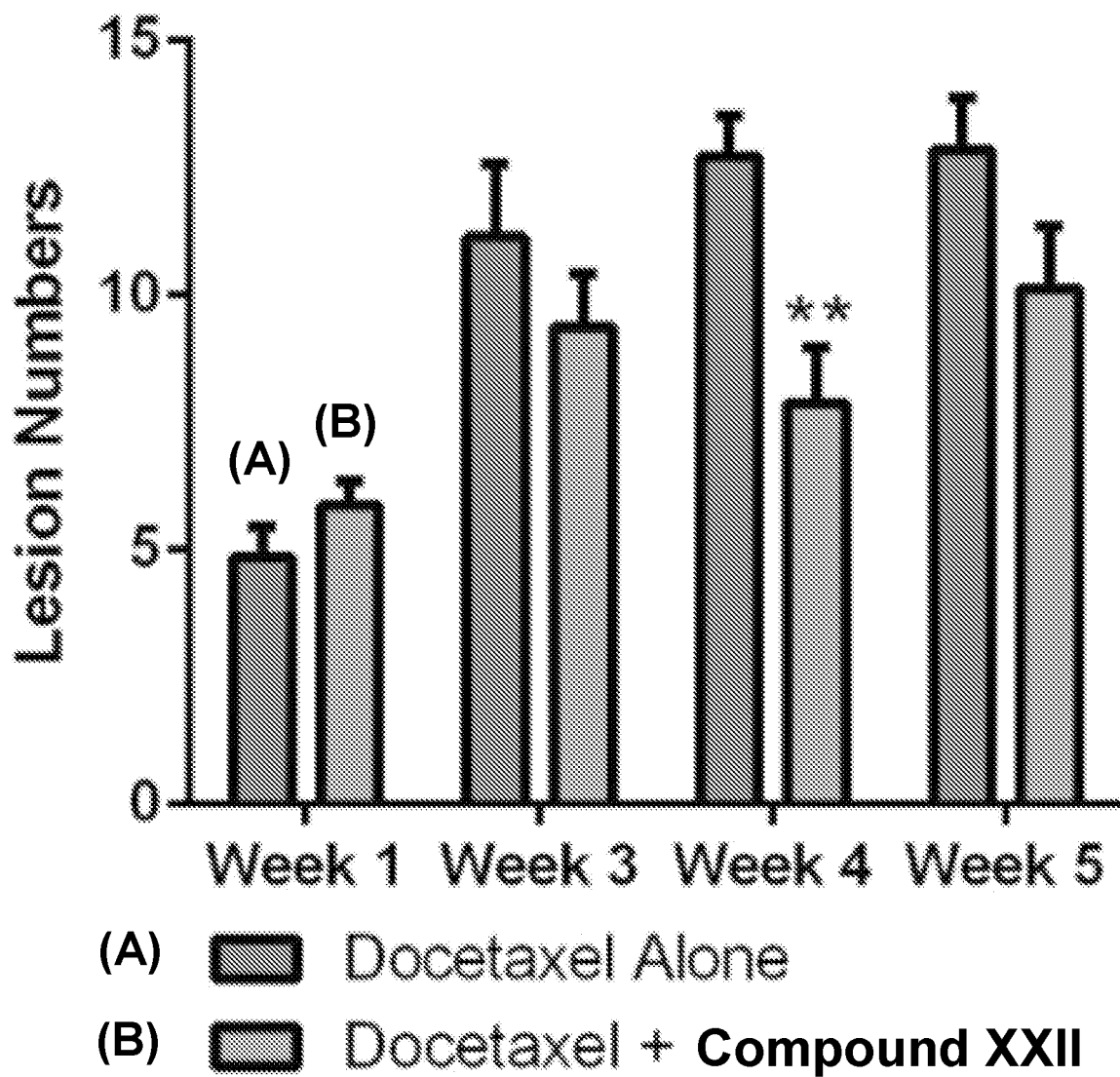
Figure 11G:
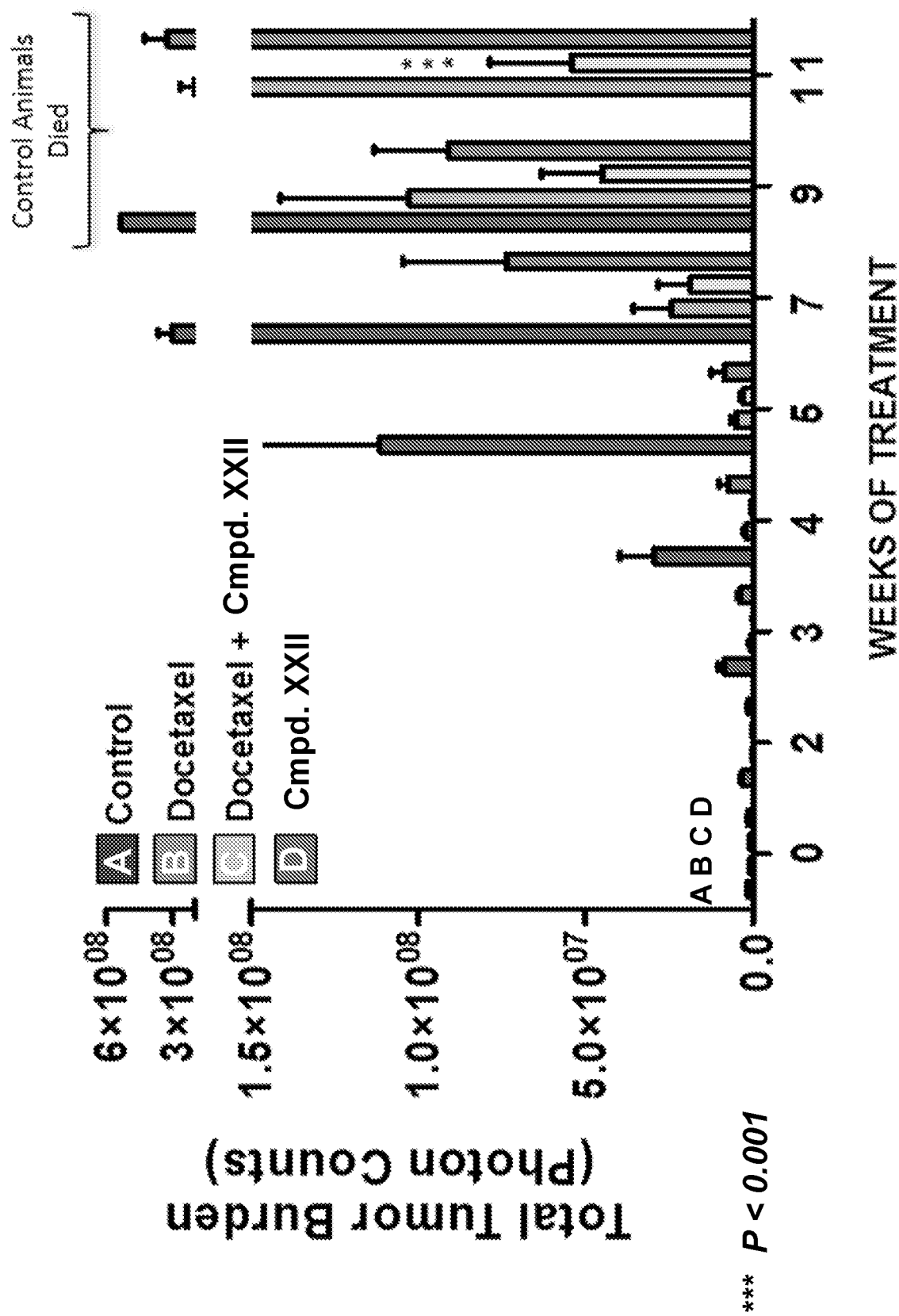

Animals bearing disseminated tumors were treated with Docetaxel (2 mg/Kg, i.p., bis in 7 d.) either alone or in combination with Compound XXII (10 mg/Kg i.p., q12 h) and compared to Compound XXII alone (FIGS. 11E-11G). The combined therapy was found to increase therapeutic effect while minimizing the cytotoxic effect of Docetaxel. Synergistic effects were observed in the combined therapies, especially after 11 days of treatment. It was noted that the overall efficacy of Compound XXII alone for lowering total tumor burden was comparable to the current standard of care, docetaxel alone, at each time point observed during the course of treatment.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A compound of Formula (I):

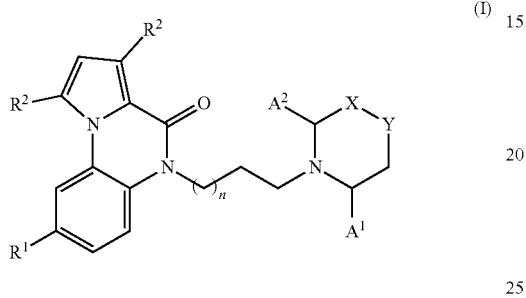

or a pharmaceutically acceptable salt thereof, wherein:

(i) $A^1$ is H or $C_1$-$C_6$ alkyl; and
$A^2$ is H or $C_1$-$C_6$ alkyl; or (ii) $A^1$, together with the carbon atom to which it is bound, forms —C(O)—; and
$A^2$ is H or $C_1$-$C_6$ alkyl; or (iii) $A^2$, together with the carbon atom to which it is bound, forms —C(O)—; and
$A^1$ is H or $C_1$-$C_6$ alkyl; or (iv) $A^1$ and $A^2$, together with the carbon atoms to which they are bound, form —CH$_2$—, —CH$_2$CH$_2$—, or —CH$_2$CH$_2$CH$_2$—;

X is —CH$_2$— or —C(O)—;

Y is —CR$^3$R$^4$— or —NR$^3$—;

$R^1$ is H, halogen, $C_1$-$C_3$ haloalkyl, or OR$^5$;

each $R^2$ is independently H, halogen, or CH$_3$;

$R^3$ is phenyl or heteroaryl, wherein the phenyl or heteroaryl is optionally substituted with one or more substituents independently selected from the group consisting of halogen, NO$_2$, $C_1$-$C_6$ alkyl, $C_1$-$C_6$ haloalkyl, NH$_2$, NHC(O)CH$_3$, OH, and OC$_1$-$C_6$ alkyl;

$R^4$ is H or OH; or $R^3$ and $R^4$, together with the carbon atom to which they are bound, form a 5- or 6-membered heterocyclyl, wherein the 5- or 6-membered heterocyclyl is optionally substituted with one or more substituents independently selected from the group consisting of oxo, halogen, NO$_2$, $C_1$-$C_6$ alkyl, $C_1$-$C_6$ haloalkyl, NH$_2$, NHC(O)CH$_3$, OH, OC$_1$-$C_6$ alkyl, and aryl, and further wherein each aryl substituent is optionally and independently substituted with one or more independently selected halogen substituents;

$R^5$ is H, $C_1$-$C_6$ alkyl, or (CH$_2$)$_{2-5}$NH$_2$; or $R^5$ is:

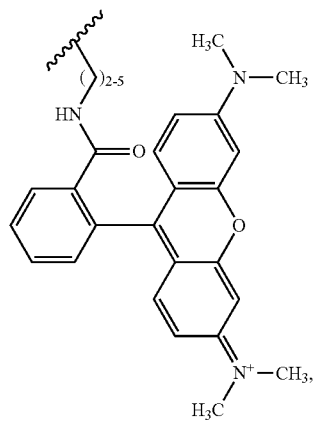

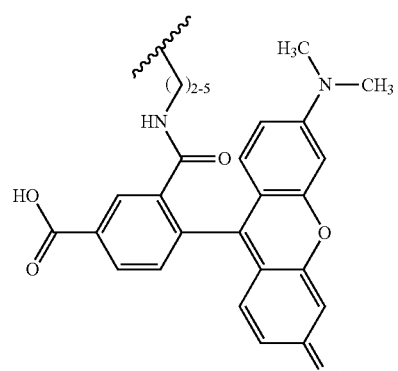

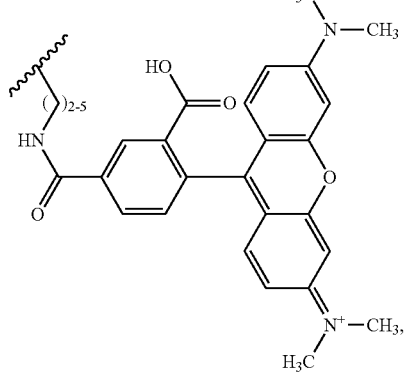

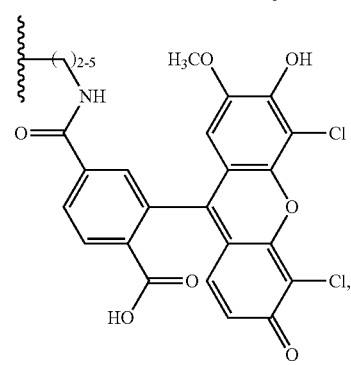

-continued

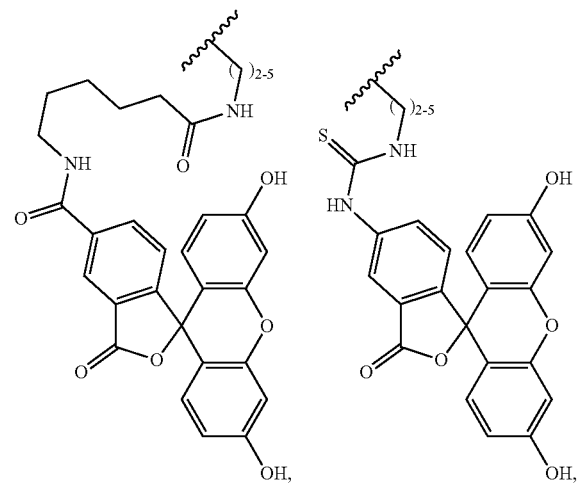

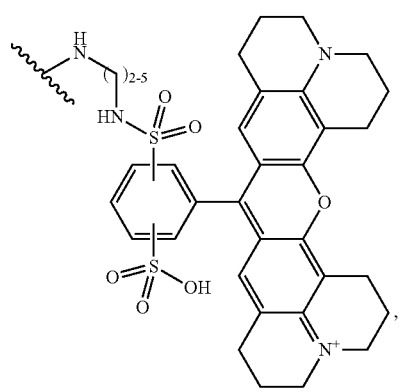

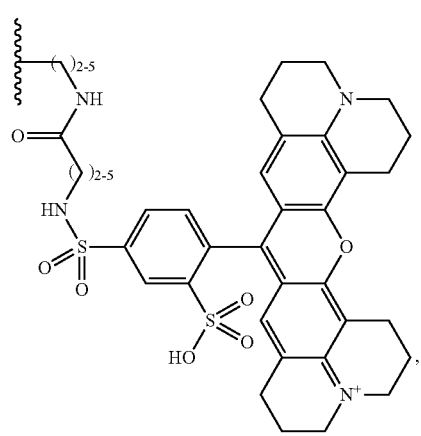

-continued

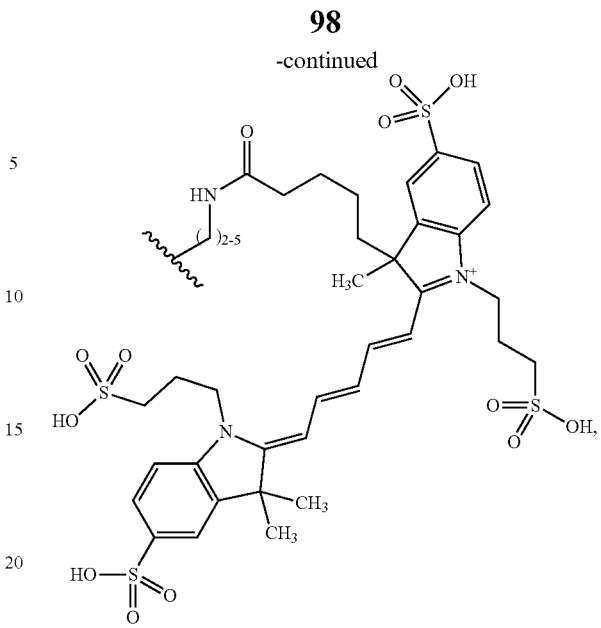

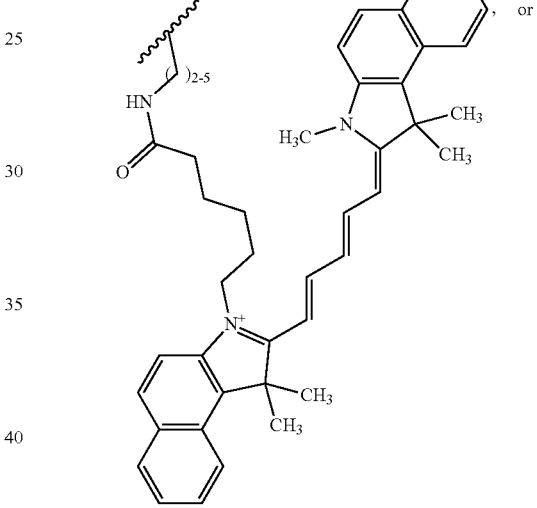

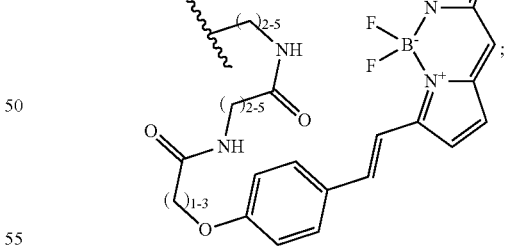

and n is 1, 2, or 3;

with the proviso that if Y is —CR$^3$R$^4$— and X is —CH$_2$—, then R$^3$ and R$^4$, together with the carbon atom to which they are bound, form a 5- or 6-membered heterocyclyl, wherein the 5- or 6-membered heterocyclyl is optionally substituted with one or more substituents independently selected from the group consisting of halogen, NO$_2$, C$_1$-C$_6$ alkyl, C$_1$-C$_6$ haloalkyl, NH$_2$, NHC(O)CH$_3$, OH, and OC$_1$-C$_6$ alkyl.

2. The compound of claim 1, or a pharmaceutically acceptable salt thereof, wherein:
$A^1$ is H; and
$A^2$ is H.

3. The compound of claim 1, or a pharmaceutically acceptable salt thereof, wherein:
(i) X is —$CH_2$—; and
Y is —$CR^3R^4$—; or
(ii) X is —$CH_2$—; and
Y is —$NR^3$—; or
(iii) X is —C(O)—; and
Y is —$CR^3R^4$—; or
(iv) X is —C(O)—; and
Y is —$NR^3$—.

4. The compound of claim 1, or a pharmaceutically acceptable salt thereof, wherein $R^3$ is:

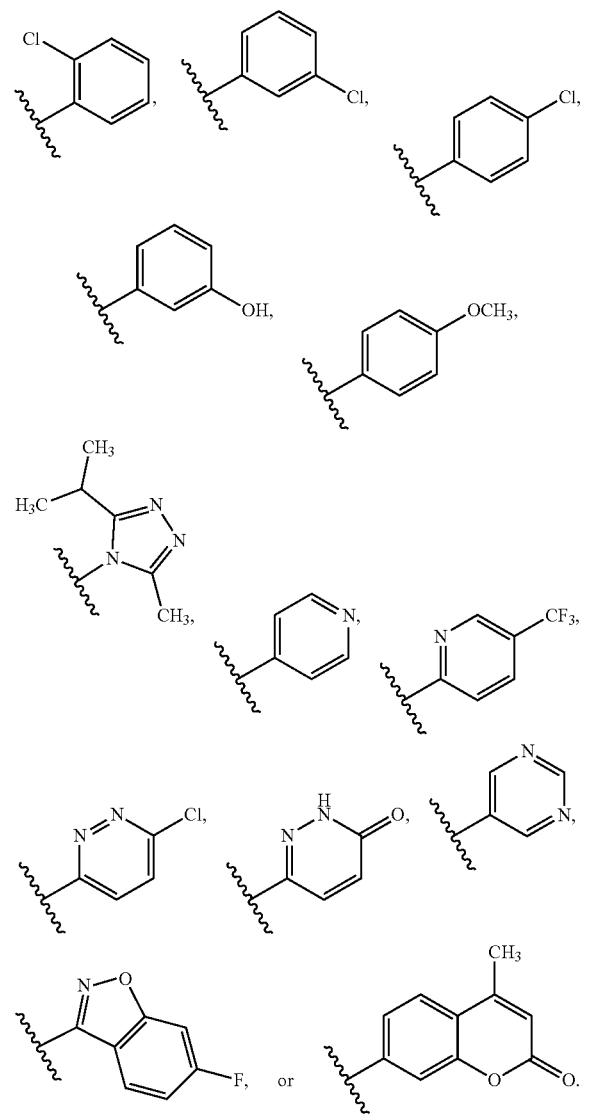

5. The compound of claim 1, or a pharmaceutically acceptable salt thereof, wherein:
Y is —$NR^3$—; and
$R^3$ is phenyl or heteroaryl, wherein the phenyl or heteroaryl is optionally substituted with one or more substituents independently selected from the group consisting of halogen, $NO_2$, $C_1$-$C_6$ alkyl, $C_1$-$C_6$ haloalkyl, $NH_2$, $NHC(O)CH_3$, OH, and $OC_1$-$C_6$ alkyl.

6. The compound of claim 1, or a pharmaceutically acceptable salt thereof, wherein:
X is —C(O)—;
Y is —$CR^3R^4$—; and
$R^3$ is phenyl or heteroaryl, wherein the phenyl or heteroaryl is optionally substituted with one or more substituents independently selected from the group consisting of halogen, $NO_2$, $C_1$-$C_6$ alkyl, $C_1$-$C_6$ haloalkyl, $NH_2$, $NHC(O)CH_3$, OH, and $OC_1$-$C_6$ alkyl.

7. The compound of claim 6, or a pharmaceutically acceptable salt thereof, wherein $R^3$ is 2-oxo-2H-chromen-7-yl, wherein the 2-oxo-2H-chromen-7-yl is optionally substituted with one or more substituents independently selected from the group consisting of halogen, $NO_2$, $C_1$-$C_6$ alkyl, $C_1$-$C_6$ haloalkyl, $NH_2$, $NHC(O)CH_3$, OH, and $OC_1$-$C_6$ alkyl.

8. The compound of claim 1, or a pharmaceutically acceptable salt thereof, wherein:

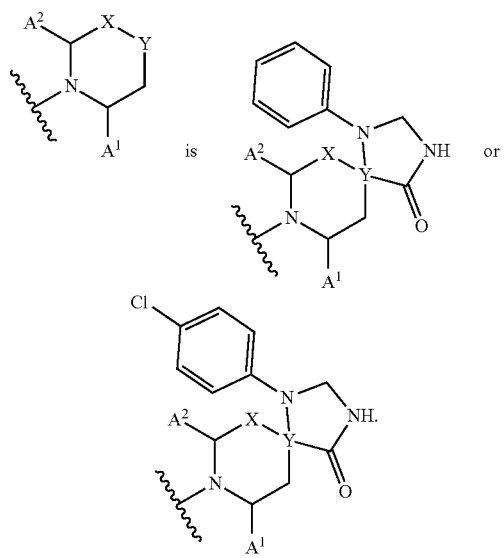

9. The compound of claim 1, wherein the compound is selected from the group consisting of:

101
-continued
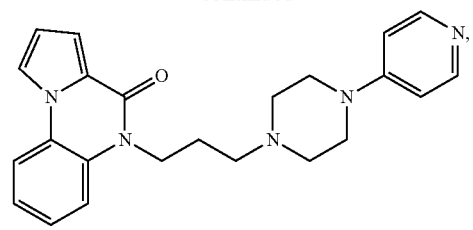
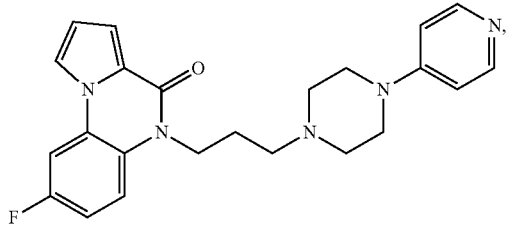
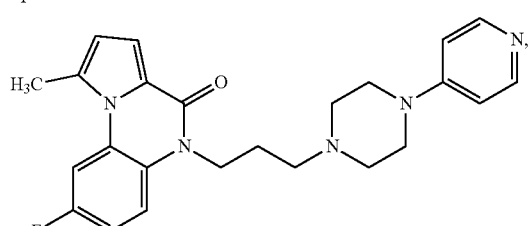
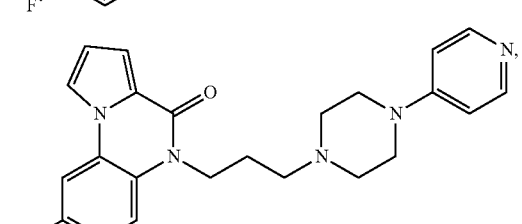
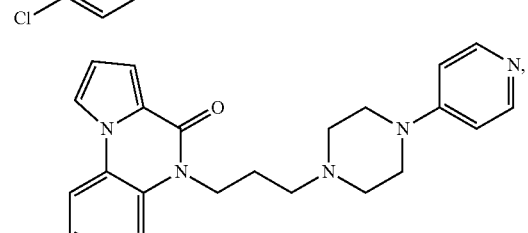
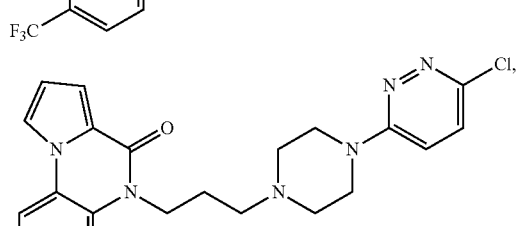
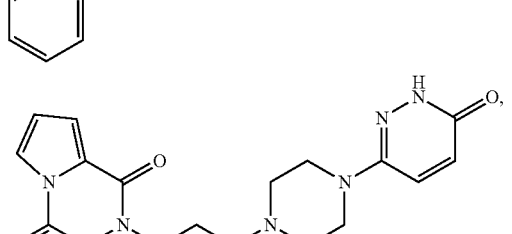
102
-continued
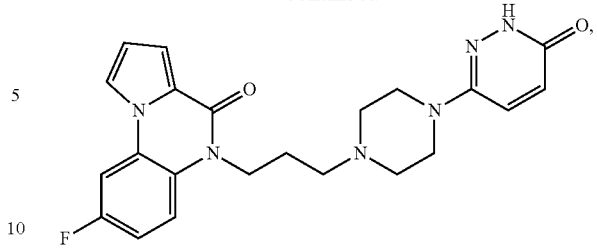
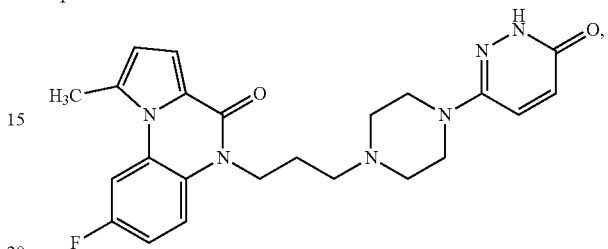
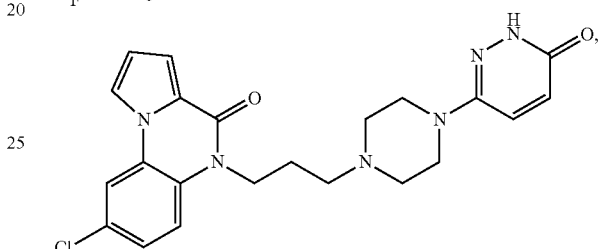
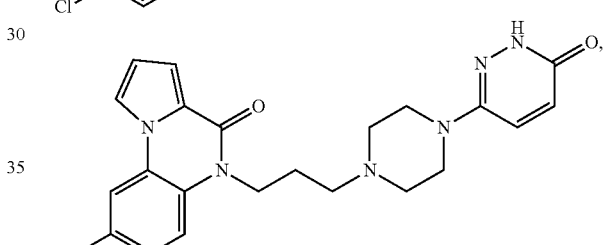
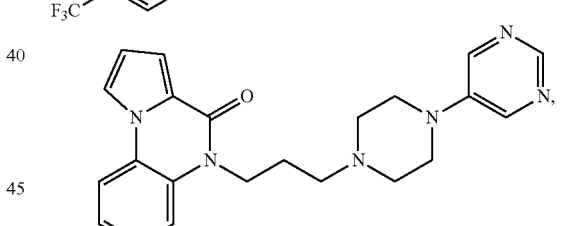
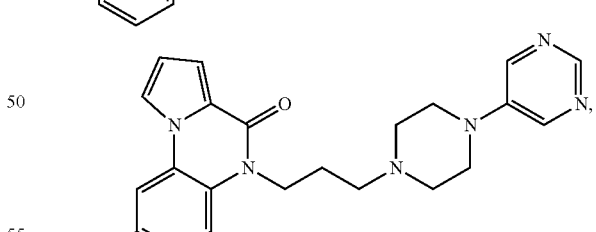
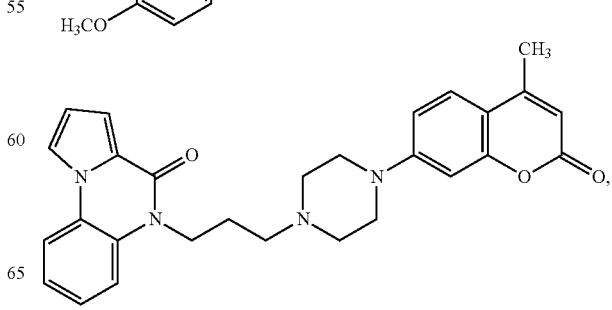

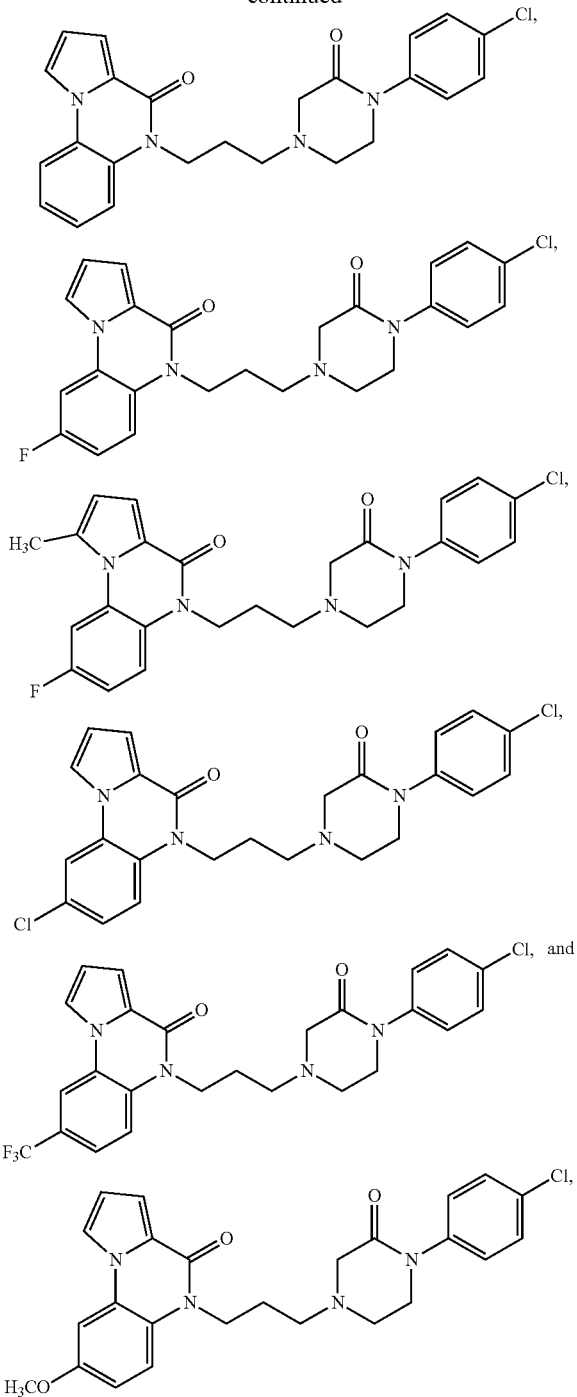

or a pharmaceutically acceptable salt thereof.

10. A pharmaceutical composition comprising at least one pharmaceutically acceptable carrier and at least one compound of claim 1, or a pharmaceutically acceptable salt thereof.

11. A kit comprising at least one compound of claim 1, or a pharmaceutically acceptable salt thereof, and instructional material describing a method for identifying a subject diagnosed with cancer that is to be administered a therapeutically effective amount of at least one CX3C chemokine receptor 1 antagonist for treating metastasis in the subject diagnosed with cancer.

12. A method for detecting a CX3C chemokine receptor 1-expressing cell in a biological sample of a subject diagnosed with cancer, wherein the method comprises:
(a) contacting the biological sample of the subject diagnosed with cancer with at least one compound of claim 1, or a pharmaceutically acceptable salt thereof;
wherein the at least one compound of claim 1, or a pharmaceutically acceptable salt thereof, is fluorescent; and
wherein the at least one compound of claim 1, or a pharmaceutically acceptable salt thereof, binds to any CX3C chemokine receptor 1-expressing cell present in the biological sample of the subject diagnosed with cancer, forming a first system;
(b) removing any unbound compound of claim 1, or a pharmaceutically acceptable salt thereof, from the first system; and
(c) detecting any compound of claim 1, or a pharmaceutically acceptable salt thereof, bound to the CX3C chemokine receptor 1-expressing cell present in the biological sample of the subject diagnosed with cancer.

13. The method of claim 12, wherein the CX3C chemokine receptor 1-expressing cell is a circulating tumor cell.

14. The method of claim 12, wherein the biological sample of the subject diagnosed with cancer is blood or lymphatic fluid.

15. The method of claim 12, wherein the biological sample of the subject diagnosed with cancer is in vitro, in vivo, or ex vivo.

16. A method for identifying a subject diagnosed with cancer that is to be treated for metastasis in the subject diagnosed with cancer, wherein the method comprises:
(a) contacting a biological sample of the subject diagnosed with cancer with at least one compound of claim 1, or a pharmaceutically acceptable salt thereof;
wherein the at least one compound of claim 1, or a pharmaceutically acceptable salt thereof, is fluorescent; and
wherein the at least one compound of claim 1, or a pharmaceutically acceptable salt thereof, binds to any CX3C chemokine receptor 1-expressing cell present in the biological sample of the subject diagnosed with cancer, forming a first system;
(b) removing any unbound compound of claim 1, or a pharmaceutically acceptable salt thereof, from the first system;
(c) detecting any compound of claim 1, or a pharmaceutically acceptable salt thereof, bound to the CX3C chemokine receptor 1-expressing cell present in the biological sample of the subject diagnosed with cancer; and
(d) providing instruction material for the subject diagnosed with cancer to be administered a therapeutically effective amount of at least one CX3C chemokine receptor 1 antagonist for treating metastasis in the subject diagnosed with cancer.

17. The method of claim 16, wherein the CX3C chemokine receptor 1-expressing cell is a circulating tumor cell.

18. The method of claim 16, wherein the biological sample of the subject diagnosed with cancer is blood or lymphatic fluid.

19. The method of claim 16, wherein the biological sample of the subject diagnosed with cancer is in vitro, in vivo, or ex vivo.

20. The method of claim 16, wherein at least one CX3C chemokine receptor 1 antagonist is a compound of claim 1, or a pharmaceutically acceptable salt thereof.

21. The method of claim 16, wherein the method further comprises administering to the subject diagnosed with cancer a therapeutically effective amount of at least one CX3C chemokine receptor 1 antagonist for treating metastasis in the subject diagnosed with cancer.

22. A method for treating metastasis in a subject diagnosed with cancer, wherein the method comprises administering to the subject in need thereof a therapeutically effective amount of at least one compound of claim 1, or a pharmaceutically acceptable salt thereof.

23. The method of claim 22, wherein the metastasis is bone metastasis.

24. The method of claim 22, wherein the cancer is selected from the group consisting of breast cancer and prostate cancer.

25. The method of claim 22, wherein the subject is a mammal.

26. The method of claim 25, wherein the mammal is a human.

27. The method of claim 22, wherein the subject is subjected to primary surgery related to cancer.

28. The method of claim 27, wherein the method further comprises administering to the subject in need thereof a therapeutically effective amount of at least one compound of claim 1, or a pharmaceutically acceptable salt thereof, over a time period selected from the group consisting of:
   (a) before the primary surgery related to cancer;
   (b) during the primary surgery related to cancer; and
   (c) after the primary surgery related to cancer.

29. The method of claim 28, wherein the method further comprises administering to the subject in need thereof a therapeutically effective amount of at least one compound of claim 1, or a pharmaceutically acceptable salt thereof, over a time period selected from the group consisting of:
   (a) at least one month before the primary surgery related to cancer;
   (b) at least three months before the primary surgery related to cancer;
   (c) at least six months before the primary surgery related to cancer; and
   (d) within one week after the primary surgery related to cancer.

30. The method of claim 22, wherein the method further comprises administering to the subject a therapeutically effective amount of at least one compound of claim 1, or a pharmaceutically acceptable salt thereof, via a route of administration selected from the group consisting of buccal, inhalation, intranasal, intrathecal, intravenous, ophthalmic, oral, parenteral, pulmonary, rectal, topical, transdermal, and vaginal.

31. A method for treating cardiovascular disease in a subject in need thereof, wherein the method comprises administering to the subject a therapeutically effective amount of at least one compound of claim 1, or a pharmaceutically acceptable salt thereof.

32. The method of claim 31, wherein the cardiovascular disease is selected from the group consisting of atherosclerosis, coronary artery disease, coronary vascular endothelial dysfunction, and undesired vascular smooth muscle proliferation.

33. A method for treating a central nervous system disease in a subject in need thereof, wherein the method comprises administering to the subject a therapeutically effective amount of at least one compound of claim 1, or a pharmaceutically acceptable salt thereof.

34. The method of claim 33, wherein the central nervous system disease is selected from the group consisting of Alzheimer's disease and human immunodeficiency virus associated neurocognitive disorder.

35. A method for treating inflammation in a subject in need thereof, wherein the method comprises administering to the subject a therapeutically effective amount of at least one compound of claim 1, or a pharmaceutically acceptable salt thereof.

36. The method of claim 35, wherein the inflammation is arthritis.

37. A method for treating multiple sclerosis in a subject in need thereof, wherein the method comprises administering to the subject a therapeutically effective amount of at least one compound of claim 1, or a pharmaceutically acceptable salt thereof.

38. A method for treating pain in a subject in need thereof, wherein the method comprises administering to the subject a therapeutically effective amount of at least one compound of claim 1, or a pharmaceutically acceptable salt thereof.

39. A compound of Formula (II):

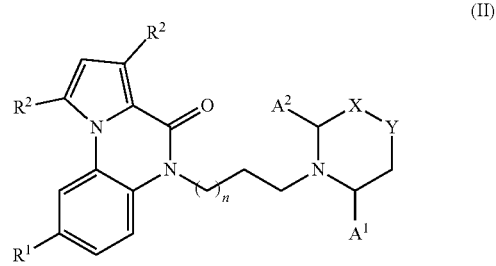

or a pharmaceutically acceptable salt thereof,
wherein:
(i) $A^1$ is H; and
   $A^2$ is H; or
(ii) $A^1$ and $A^2$, together with the carbon atoms to which they are bound, form —$CH_2$—, —$CH_2CH_2$—, or —$CH_2CH_2CH_2$—;
X is —$CH_2$—;
Y is —$CR^3R^4$—;
$R^1$ is H, halogen, $C_1$-$C_3$ haloalkyl, or $OR^5$;
each $R^2$ is independently H, Cl, or $CH_3$;
$R^3$ is phenyl or heteroaryl, wherein the phenyl or heteroaryl is optionally substituted with one or more substituents independently selected from the group consisting of halogen, $NO_2$, $C_1$-$C_6$ alkyl, $C_1$-$C_6$ haloalkyl, $NH_2$, $NHC(O)CH_3$, OH, and $OC_1$-$C_6$ alkyl;
$R^4$ is H or OH;
$R^5$ is H or $(CH_2)_{2-5}NH_2$; or R⁵ is:
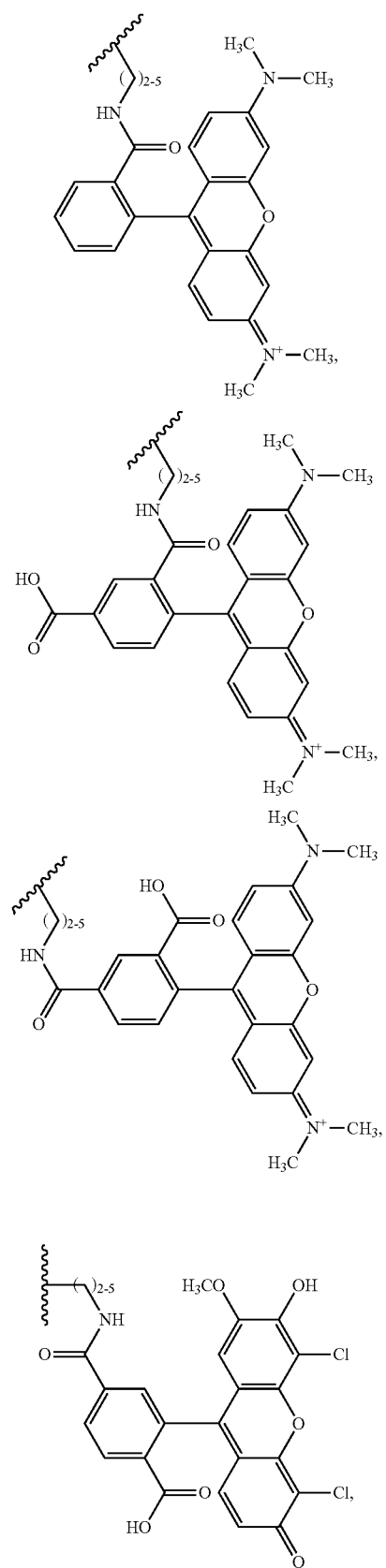
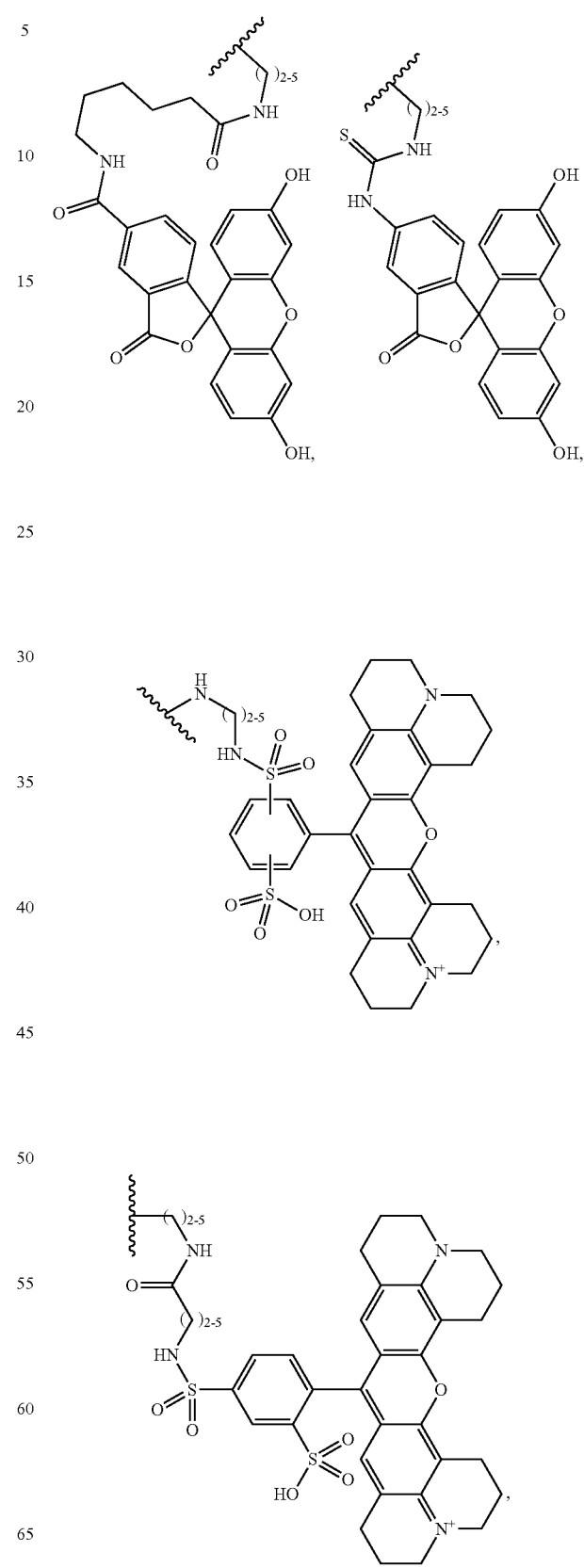

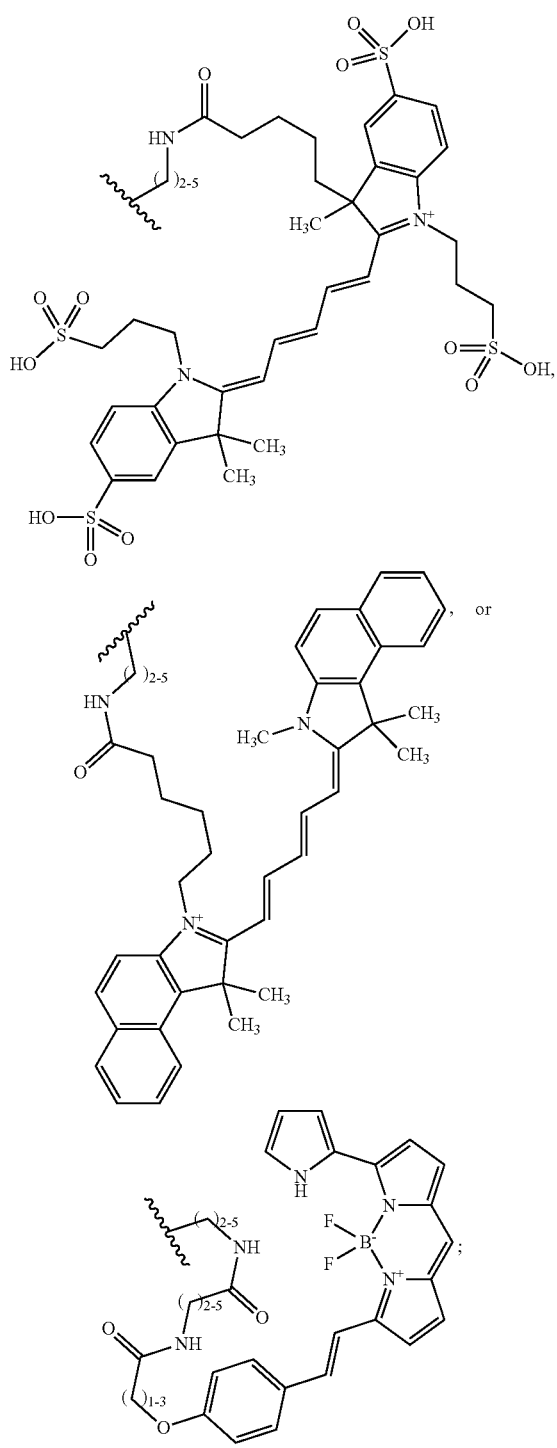

and
n is 1, 2, or 3;
with the proviso that if each $R^2$ is independently H, then $R^1$ is $OR^5$ and $R^5$ is not H.

40. The compound of claim 39, or a pharmaceutically acceptable salt thereof, wherein:
$A^1$ is H; and
$A^2$ is H.

41. The compound of claim 39, or a pharmaceutically acceptable salt thereof, wherein $R^3$ is phenyl or heteroaryl, wherein the phenyl or heteroaryl is optionally substituted with one or more substituents independently selected from the group consisting of halogen, $C_1$-$C_6$ alkyl, and $C_1$-$C_6$ haloalkyl.

42. The compound of claim 41, or a pharmaceutically acceptable salt thereof, wherein $R^3$ is 2-oxo-2H-chromen-7-yl, wherein the 2-oxo-2H-chromen-7-yl is optionally substituted with one or more substituents independently selected from the group consisting of halogen, $C_1$-$C_6$ alkyl, and $C_1$-$C_6$ haloalkyl.

43. The compound of claim 39, or a pharmaceutically acceptable salt thereof, wherein $R^3$ is:

44. The compound of claim 39, wherein the compound is selected from the group consisting of:

111 112
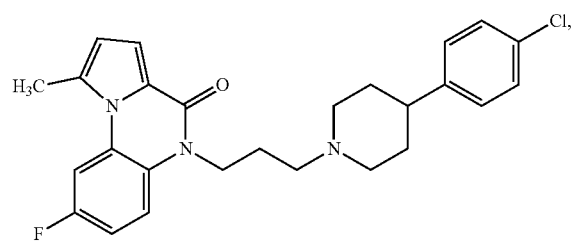
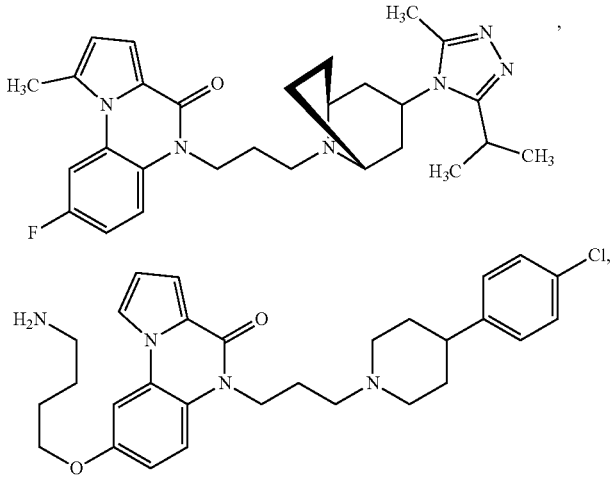
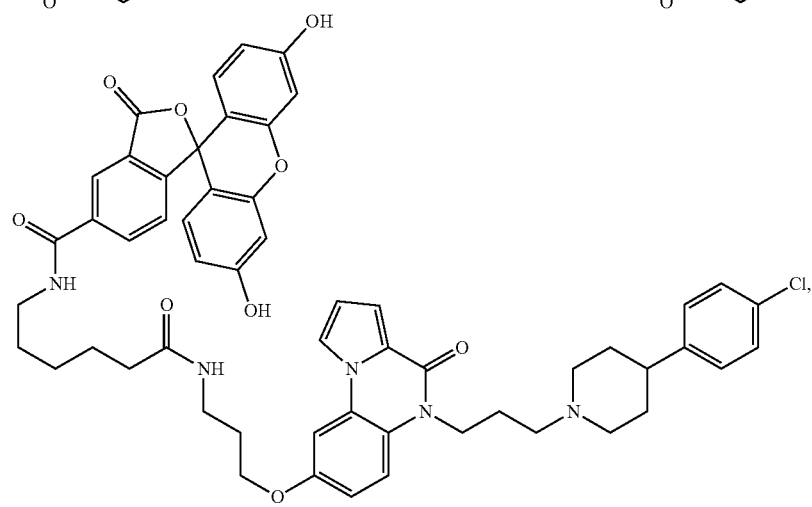
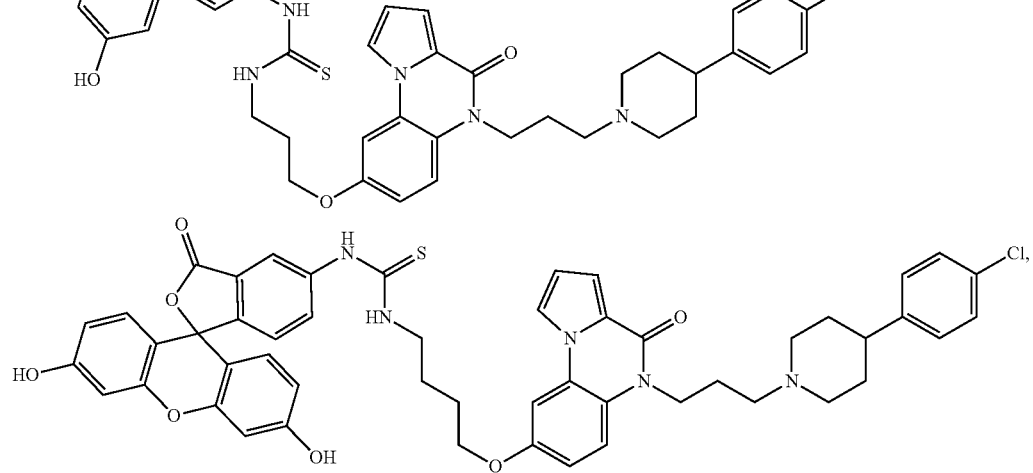
or a pharmaceutically acceptable salt thereof.

45. A pharmaceutical composition comprising at least one pharmaceutically acceptable carrier and at least one compound of claim 39, or a pharmaceutically acceptable salt thereof.

46. A kit comprising at least one compound of claim 39, or a pharmaceutically acceptable salt thereof, and instructional material describing a method for identifying a subject diagnosed with cancer that is to be administered a therapeutically effective amount of at least one CX3C chemokine receptor 1 antagonist for treating metastasis in the subject diagnosed with cancer.

47. A pharmaceutical composition comprising at least one pharmaceutically acceptable carrier and a compound of Formula (XXII):

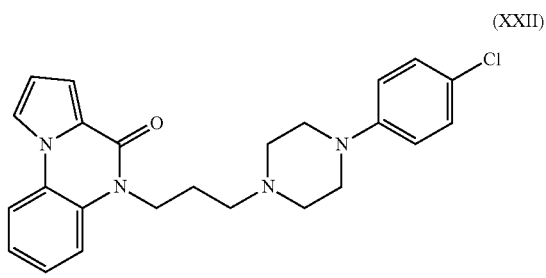 [SMILES: O=c1c2cccn2c2ccccc2n1CCCN1CCN(c2ccc(Cl)cc2)CC1]

(XXII)

or a pharmaceutically acceptable salt thereof.

48. The pharmaceutical composition of claim 47, wherein the pharmaceutical composition further comprises at least one chemotherapeutic agent selected from the group consisting of an anthracycline and a taxane.

49. The pharmaceutical composition of claim 48, wherein at least one anthracycline or taxane is selected from the group consisting of cabazitaxel, docetaxel, doxorubicin, epirubicin, nab-paclitaxel, and paclitaxel.

50. A method for treating metastasis in a subject diagnosed with cancer, wherein the method comprises administering to the subject in need thereof a therapeutically effective amount of:
(a) a compound of Formula (XXII):

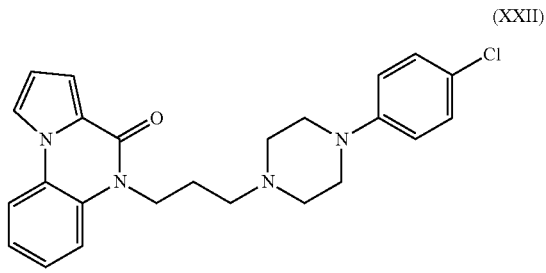 [SMILES: O=c1c2cccn2c2ccccc2n1CCCN1CCN(c2ccc(Cl)cc2)CC1]

(XXII)

or a pharmaceutically acceptable salt thereof; and
(b) at least one chemotherapeutic agent selected from the group consisting of an anthracycline and a taxane.

51. The method of claim 50, wherein the compound of Formula (XXII) and at least one chemotherapeutic agent are coformulated in a pharmaceutical composition.

52. The method of claim 50, wherein at least one anthracycline or taxane is selected from the group consisting of docetaxel, doxorubicin, epirubicin, and paclitaxel.

53. The method of claim 50, wherein the metastasis is bone metastasis.

54. The method of claim 50, wherein the cancer is selected from the group consisting of breast cancer and prostate cancer.

55. The method of claim 50, wherein the subject is a mammal.

56. The method of claim 55, wherein the mammal is a human.

57. The method of claim 50, wherein the subject is subjected to primary surgery related to cancer.

58. The method of claim 57, wherein the method further comprises administering to the subject in need thereof a therapeutically effective amount of the compound of Formula (XXII), or a pharmaceutically acceptable salt thereof, over a time period selected from the group consisting of:
(a) before the primary surgery related to cancer;
(b) during the primary surgery related to cancer; and
(c) after the primary surgery related to cancer.

59. The method of claim 58, wherein the method further comprises administering to the subject in need thereof a therapeutically effective amount of the compound of Formula (XXII), or a pharmaceutically acceptable salt thereof, over a time period selected from the group consisting of:
(a) at least one month before the primary surgery related to cancer;
(b) at least three months before the primary surgery related to cancer;
(c) at least six months before the primary surgery related to cancer; and
(d) within one week after the primary surgery related to cancer.

60. The method of claim 57, wherein the method further comprises administering to the subject in need thereof a therapeutically effective amount of at least one chemotherapeutic agent over a time period selected from the group consisting of:
(a) before the primary surgery related to cancer;
(b) during the primary surgery related to cancer; and
(c) after the primary surgery related to cancer.

61. The method of claim 60, wherein the method further comprises administering to the subject in need thereof a therapeutically effective amount of at least one chemotherapeutic agent over a time period selected from the group consisting of:
(a) at least one month before the primary surgery related to cancer;
(b) at least three months before the primary surgery related to cancer;
(c) at least six months before the primary surgery related to cancer; and
(d) within one week after the primary surgery related to cancer.

62. The method of claim 50, wherein the method further comprises administering to the subject a therapeutically effective amount of at least one compound of claim 1, or a pharmaceutically acceptable salt thereof, via a route of administration selected from the group consisting of buccal, inhalation, intranasal, intrathecal, intravenous, ophthalmic, oral, parenteral, pulmonary, rectal, topical, transdermal, and vaginal.

63. A compound selected from the group consisting of:
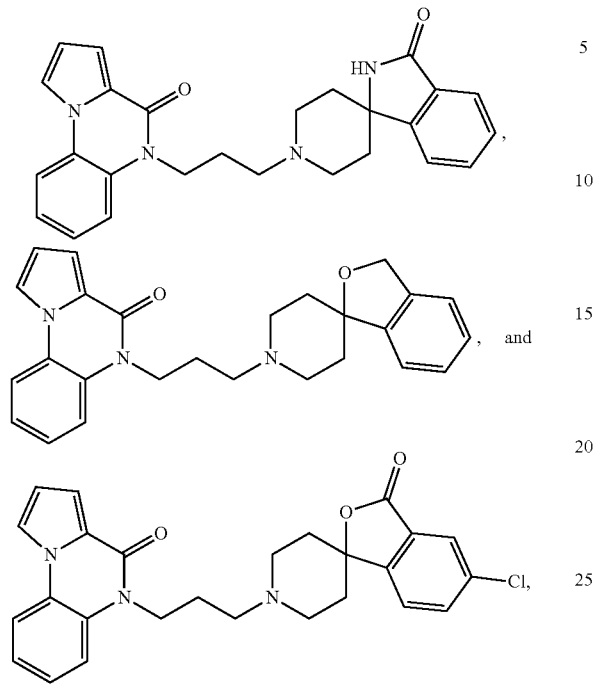
or a pharmaceutically acceptable salt thereof.
* * * * *